United States Patent
Kim et al.

(10) Patent No.: US 9,997,724 B2
(45) Date of Patent: Jun. 12, 2018

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Bitnari Kim, Cheonan (KR);
Hee-Ryong Kang, Seoul (KR);
Hyun-Ju Kang, Gwangmyeong (KR);
Jin-Ri Hong, Cheonan (KR);
Young-Mook Lim, Cheonan (KR);
Doo-Hyeon Moon, Hwaseong (KR)

(73) Assignee: Rohm and Haas Electronic Materials Korea Ltd., Cheonan (KR)

( * ) Notice: Subject to any disclaimer, the term of this patent is extended or adjusted under 35 U.S.C. 154(b) by 0 days. days.

(21) Appl. No.: 15/509,588

(22) PCT Filed: Sep. 25, 2015

(86) PCT No.: PCT/KR2015/010245
§ 371 (c)(1),
(2) Date: Mar. 8, 2017

(87) PCT Pub. No.: WO2016/052962
PCT Pub. Date: Apr. 7, 2016

(65) Prior Publication Data
US 2017/0301867 A1     Oct. 19, 2017

(30) Foreign Application Priority Data

Sep. 29, 2014  (KR) .......... 10-2014-0130061
Sep. 24, 2015  (KR) .......... 10-2015-0135881

(51) Int. Cl.
*C07D 487/16*   (2006.01)
*C07D 487/22*   (2006.01)
*C07D 471/16*   (2006.01)
*C09K 11/06*   (2006.01)
*H01L 51/54*   (2006.01)
*H05B 33/14*   (2006.01)
*H01L 51/00*   (2006.01)
*C07D 519/00*   (2006.01)
*C07D 471/22*   (2006.01)
*H01L 51/50*   (2006.01)

(52) U.S. Cl.
CPC ........ *H01L 51/0072* (2013.01); *C07D 471/22* (2013.01); *C07D 487/16* (2013.01); *C07D 487/22* (2013.01); *C07D 519/00* (2013.01); *C09K 11/06* (2013.01); *H01L 51/0061* (2013.01); *H01L 51/0073* (2013.01); *H01L 51/0074* (2013.01); *C09K 2211/1007* (2013.01); *C09K 2211/1014* (2013.01); *C09K 2211/1018* (2013.01); *C09K 2211/1022* (2013.01); *H01L 51/001* (2013.01); *H01L 51/5016* (2013.01); *H01L 51/5056* (2013.01); *H01L 51/5088* (2013.01); *H01L 2251/558* (2013.01)

(58) Field of Classification Search
CPC .. C07D 487/16; C07D 487/22; C07D 471/16; C09K 11/06; H01L 51/54; H01B 33/14
USPC ............ 540/555; 257/40, E51.046; 313/504; 428/690, 917
See application file for complete search history.

(56) References Cited

U.S. PATENT DOCUMENTS 8,174,002 B2    5/2012  Fukuzaki
9,502,667 B2 *  11/2016 Saito ................... H01L 51/0072

FOREIGN PATENT DOCUMENTS

| DE | 19808088 A1 | 8/1999 |
| JP | 2014/160813 A | 9/2014 |
| KR | 2015-0021861 A | 3/2015 |
| WO | 2011-042107 A2 | 4/2011 |
| WO | 2014/088290 A1 | 6/2014 |

OTHER PUBLICATIONS

Atzrodt et al. Angew. Chem. Int. Ed. 2007, 46, 7744-7765.*

* cited by examiner

*Primary Examiner* — Venkataraman Balasubramanian
(74) *Attorney, Agent, or Firm* — S. Matthew Cairns

(57) ABSTRACT

The present disclosure relates to an organic electroluminescent compound and an organic electroluminescent device comprising the same. The organic electroluminescent compound of the present disclosure has good color purity, solubility, and thermal stability. By comprising the organic electroluminescent compound of the present disclosure, an organic electroluminescent device showing low driving voltage, excellent current and power efficiencies, and significantly improved lifespan can be provided.

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials have been widely researched. Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, and lifespan is short. (2) The power efficiency of the organic EL device is given by [(π/voltage)×current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still required to be improved.

German Patent Application Laying-Open No. 19808088 and U.S. Pat. No. 8,174,002 disclose a compound having a structure shown in the following formula A, formed by a cross-linkage between a carbazole and a phenyl group. WO 2011-042107 discloses a compound having a structure shown in the following formula B, formed by a cross-linkage between a carbazole and an alkyl-substituted phenyl group. However, they fail to disclose a compound formed by a cross-linkage between a carbazole and a phenyl-substituted quinoline or quinoxaline group.

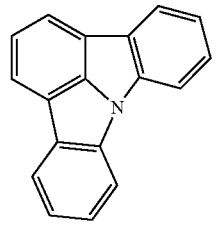

[Formula A]

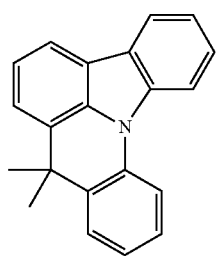

[Formula B]

DISCLOSURE OF THE INVENTION

Problems to be Solved

The objective of the present disclosure is to provide an organic electroluminescent compound, which can provide an organic electroluminescent device showing long lifespan, low driving voltage, and excellence in luminous efficiency such as current and power efficiencies, color purity, solubility, and thermal stability, and to provide an organic electroluminescent device comprising the organic electroluminescent compound.

Solution to Problems

The present inventors found that the above objective can be achieved by an organic electroluminescent compound represented by the following formula 1.

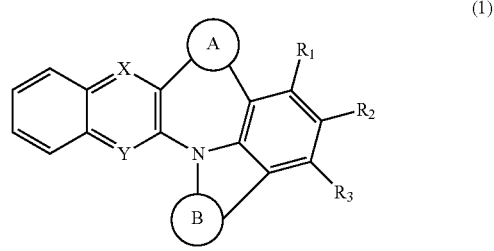

(1)

wherein ring A and ring B, each independently, represent any one of the following formulae 2-1 to 2-3:

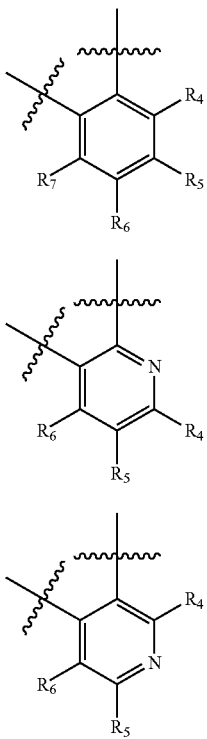

X and Y, each independently, represent —$CR_8$— or —N—; provided that both X and Y are not —$CR_8$—, simultaneously;

$R_1$ to $R_8$, each independently, represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur; and the heteroaryl contains at least one hetero atom selected from B, N, O, S, Si, and P.

Effects of the Invention

The organic electroluminescent compound of the present disclosure has good color purity, solubility, and thermal stability. By comprising the organic electroluminescent compound of the present disclosure, an organic electroluminescent device showing low driving voltage, excellent current and power efficiencies, and significantly improved lifespan can be provided.

EMBODIMENTS OF THE INVENTION

Hereinafter, the present disclosure will be described in detail. However, the following description is intended to explain the invention, and is not meant in any way to restrict the scope of the invention.

The present disclosure provides the organic electroluminescent compound represented by formula 1 above, an organic electroluminescent material comprising the organic electroluminescent compound, and an organic electroluminescent device comprising the compound.

The details of the organic electroluminescent compound of formula 1 are as follows.

Herein, "alkyl" includes methyl, ethyl, n-propyl, isopropyl, n-butyl, isobutyl, tert-butyl, etc. "Cycloalkyl" includes cyclopropyl, cyclobutyl, cyclopentyl, cyclohexyl, etc. "(3- to 7-membered)heterocycloalkyl" indicates a cycloalkyl having 3 to 7 ring backbone atoms including at least one hetero atom selected from B, N, O, S, Si, and P, preferably O, S, and N, and includes tetrahydrofuran, pyrrolidine, thiolan, tetrahydropyran, etc. Furthermore, "aryl(ene)" indicates a monocyclic or fused ring radical derived from an aromatic hydrocarbon, and includes a spiro compound in which two rings are connected through one atom. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "3- to 30-membered heteroaryl(ene)" indicates an aryl group having 3 to 30 ring backbone atoms including at least one, preferably 1 to 4, hetero atom selected from the group consisting of B, N, O, S, Si, and P, preferably O, S, and N; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, dihydroacridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. In the present disclosure, the substituents for the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino in $R_1$ to $R_8$, each independently, may be at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30) alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino, a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl; and preferably a (C1-C10)alkyl, a 5- to 18-membered heteroaryl, a 5- to 18-membered heteroaryl substituted with a (C6-C18)aryl, a (C6-C18)aryl, a (C6-C18)aryl substituted with a 5- to 18-membered heteroaryl, a di(C6-C12)arylamino, and a (C1-C10)alkyl(C5-C18)aryl.

Preferably, $R_1$ to $R_8$, each independently, may represent hydrogen, a substituted or unsubstituted (C6-C20)aryl, a substituted or unsubstituted 5- to 25-membered heteroaryl, or a substituted or unsubstituted di(C6-C20)arylamino, or may be linked to an adjacent substituent(s) to form a substituted or unsubstituted (C3-C20) mono- or polycyclic, alicyclic or aromatic ring. More preferably, $R_1$ to $R_7$, each independently, may represent hydrogen; a (C6-C20)aryl unsubstituted or substituted with a (C1-C6)alkyl, a 5- to 20-membered heteroaryl or a di(C6-C12)arylamino; or a 5- to 20-membered heteroaryl unsubstituted or substituted with a (C1-C6)alkyl, a (C6-C12)aryl or a di(C6-C12)arylamino; or may be linked to an adjacent substituent(s) to form a (C3-C20) mono- or polycyclic aromatic ring unsubstituted or substituted with a (C1-C6)alkyl; provided that $R_1$ to $R_7$ are not simultaneously hydrogen; and $R_8$ may represent hydrogen or a (C1-C6)alkyl.

Specifically, $R_1$ to $R_7$, each independently, may represent hydrogen, a (C1-C20)alkyl, or any one of the following formulae 3-1 to 3-6, or may be linked to an adjacent substituent(s) to form a benzene ring unsubstituted or substituted with a (C1-C6)alkyl or a naphthalene ring unsubstituted or substituted with a (C1-C6)alkyl, provided that $R_1$ to $R_7$ are not simultaneously hydrogen.

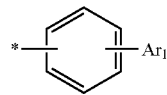

(3-1)

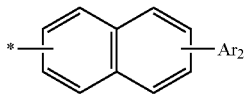

(3-2)

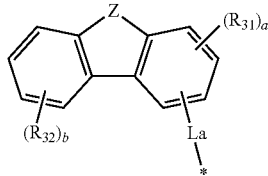

(3-3)

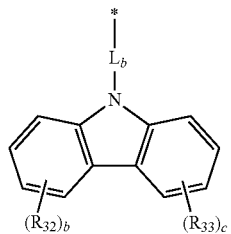

(3-4)

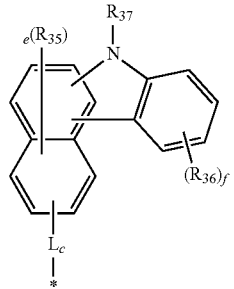

(3-5)

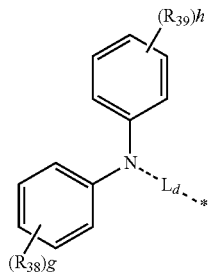

(3-6)

wherein, $Ar_1$ and $Ar_2$, each independently, represent hydrogen, a substituted or unsubstituted (C1-C30)alkyl, or a substituted or unsubstituted (C6-C30)aryl; provided that $Ar_1$ and $Ar_2$ are not fluorenyl;

$L_a$, $L_b$, $L_c$, and $L_d$, each independently, represent a single bond, a substituted or unsubstituted (C6-C30)arylene, or a substituted or unsubstituted 3- to 30-membered heteroarylene;

Z represents —S—, —O—, —$NR_{11}$—, or —$CR_{12}R_{13}$—;

$R_{11}$ to $R_{13}$, each independently, represent hydrogen, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, or a substituted or unsubstituted 3- to 7-membered heterocycloalkyl; or may be linked to an adjacent substituent(s) to form a substituted or unsubstituted 3- to 30-membered, mono- or polycyclic, alicyclic or aromatic ring;

$R_{31}$ to $R_{39}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted 3- to 7-membered heterocycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or may be linked to an adjacent substituent(s) to form a substituted or unsubstituted 3- to 30-membered, mono- or polycyclic, alicyclic or aromatic ring, whose carbon atom(s) may be replaced with at least one hetero atom selected from nitrogen, oxygen, and sulfur;

the heteroaryl(ene) and heterocycloalkyl, each independently, contain at least one hetero atom selected from nitrogen, oxygen, and sulfur;

a represents an integer of 1 to 3;

b to d and f, each independently, represent an integer of 1 to 4;

e, g, and h, each independently, represent an integer of 1 to 5; and where a, b, c, d, e, f, g, or h is an integer of 2 or more, each of $R_{31}$, $R_{32}$, $R_{33}$, $R_{34}$, $R_{35}$, $R_{36}$, $R_{37}$, $R_{38}$, or $R_{39}$ may be the same or different.

Specifically, $Ar_1$ and $Ar_2$, each independently, may represent hydrogen, a substituted or unsubstituted (C1-C20) alkyl, a substituted or unsubstituted phenyl, a substituted or unsubstituted biphenyl, a substituted or unsubstituted naphthyl, a substituted or unsubstituted anthracenyl, a substituted or unsubstituted phenanthrenyl, a substituted or unsubstituted chrysenyl, a substituted or unsubstituted tetracenyl, a substituted or unsubstituted pyrenyl, a substituted or unsubstituted triphenylenyl, or a substituted or unsubstituted fluoranthenyl.

Specifically, $L_a$ to $L_d$, each independently, may represent a single bond, or a substituted or unsubstituted (C6-C18) arylene. More specifically, $L_a$ to $L_d$, each independently, may represent a single bond, a substituted or unsubstituted phenylene, a substituted or unsubstituted biphenylene, or a substituted or unsubstituted naphthylene.

Specifically, Z may represent —$NR_{11}$—.

Specifically, $R_{11}$ to $R_{13}$, each independently, may represent hydrogen, a substituted or unsubstituted (C1-C10)alkyl, or a substituted or unsubstituted (C5-C18)aryl, or may be linked to an adjacent substituent(s) to form a substituted or unsubstituted 3- to 30-membered, mono- or polycyclic aromatic ring. More specifically, $R_{11}$ to $R_{13}$, each independently, may represent hydrogen, a unsubstituted (C1-C6) alkyl, a substituted or unsubstituted phenyl, a substituted or unsubstituted biphenyl, or a substituted or unsubstituted naphthyl.

Specifically, $R_{31}$ to $R_{39}$, each independently, may represent hydrogen, a substituted or unsubstituted (C1-C10)alkyl, a substituted or unsubstituted (C6-C18)aryl, or a substituted or unsubstituted 5- to 18-membered heteroaryl, or may be linked to an adjacent substituent(s) to form a substituted or unsubstituted 5- to 18-membered mono- or polycyclic, alicyclic or aromatic ring, whose carbon atom(s) may be replaced with one to three hetero atom(s) selected from nitrogen, oxygen, and sulfur. More specifically, $R_{31}$ to $R_{39}$, each independently, may represent hydrogen, a substituted or unsubstituted phenyl, a substituted or unsubstituted biphenyl, a substituted or unsubstituted naphthyl, a substituted or unsubstituted carbazolyl, a substituted or unsubstituted dibenzofuranyl, or a substituted or unsubstituted dibenzothiophenyl, or may be linked to an adjacent substituent(s) to form a benzene ring or any one of the following formulae 4-1 to 4-5.

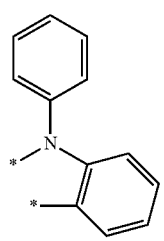

(4-1)

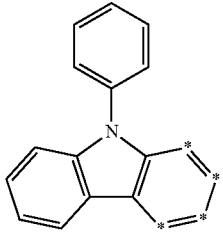

(4-2)

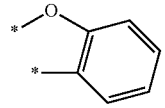

(4-3)

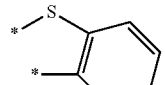

(4-4)

(4-5)

wherein, * represents a bonding site.

According to one embodiment of the present disclosure, X and Y, each independently, may represent —$CR_8$— or —N—, provided that both X and Y are not simultaneously —$CR_8$—; ring A and ring B, each independently, may represent any one of the formulae 2-1 to 2-3; $R_1$ to $R_8$, each independently, may represent hydrogen, a substituted or unsubstituted (C6-C20)aryl, a substituted or unsubstituted 5- to 25-membered heteroaryl, or a substituted or unsubstituted di(C6-C20)arylamino, or may be linked to an adjacent substituent(s) to form a substituted or unsubstituted (C3-C20) mono- or polycyclic, alicyclic or aromatic ring.

According to another embodiment of the present disclosure, X and Y, each independently, may represent —$CR_8$— or —N—, provided that both X and Y are not simultaneously —$CR_8$—; ring A and ring B, each independently, may represent any one of the formulae 2-1 to 2-3; $R_1$ to $R_7$, each independently, may represent hydrogen, a (C6-C20)aryl unsubstituted or substituted with a (C1-C6)alkyl, a 5- to 20-membered heteroaryl or a di(C6-C12)arylamino, or a 5- to 20-membered heteroaryl unsubstituted or substituted with a (C1-C6)alkyl, a (C6-C12)aryl or a di(C6-C12)arylamino, or may be linked to an adjacent substituent(s) to form a (C3-C20), mono- or polycyclic aromatic ring unsubstituted or substituted with a (C1-C6)alkyl; provided that $R_1$ to $R_7$ are not simultaneously hydrogen; and $R_8$ may represent hydrogen or a (C1-C6)alkyl.

According to another embodiment of the present disclosure, $R_1$ to $R_7$, each independently, may represent hydrogen, a (C1-C20)alkyl, or any one of the formulae 3-1 to 3-6, or may be linked to an adjacent substituent(s) to form a benzene ring unsubstituted or substituted with a (C1-C6) alkyl or a naphthalene ring unsubstituted or substituted with a (C1-C6)alkyl, provided that $R_1$ to $R_7$ are not simultaneously hydrogen; and $R_8$ may represent hydrogen or a (C1-C6)alkyl.

According to another embodiment of the present disclosure, at least one of $R_1$ to $R_7$ may be selected from formulae 3-3 to 3-5, and Z of formula 3-3 may represent —$NR_{11}$—.

More specifically, the organic electroluminescent compound of formula 1 includes the following, but is not limited thereto:
A-1
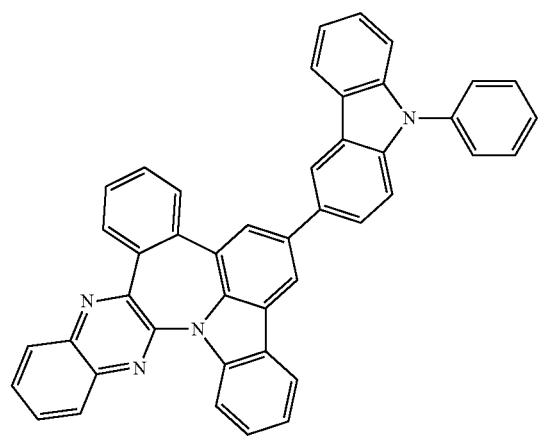
A-2
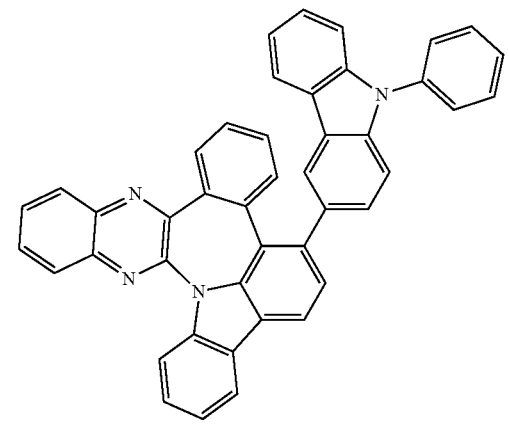
A-3
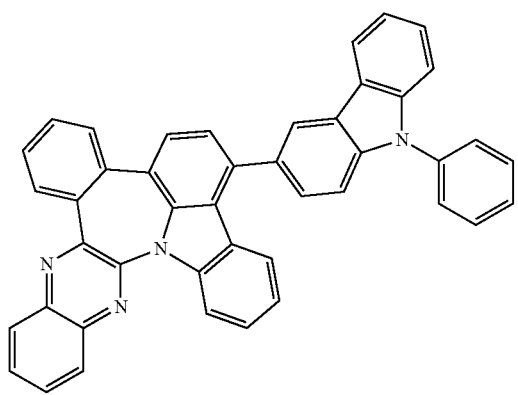
A-4
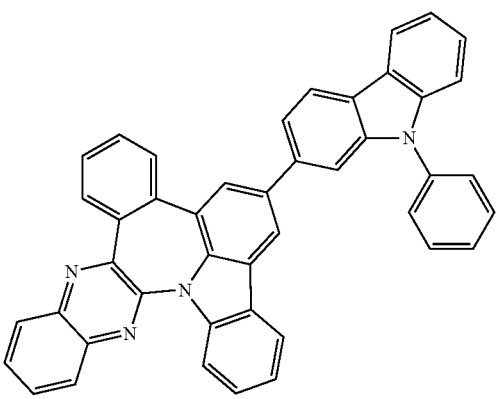
A-5
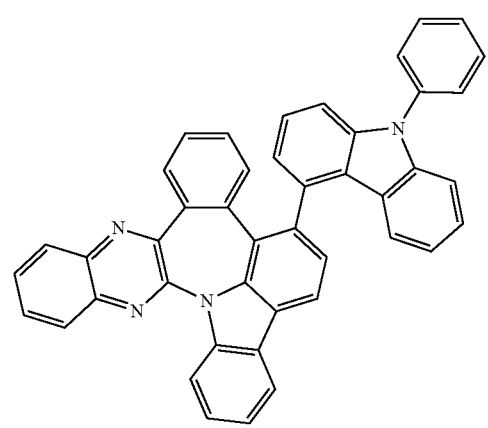
A-6
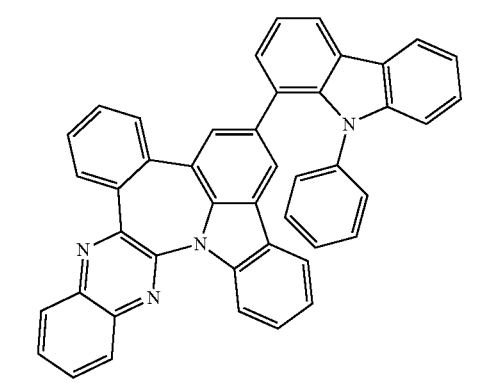
A-7
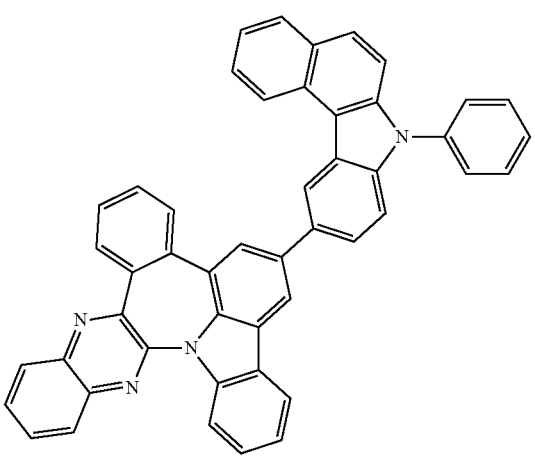

A-8
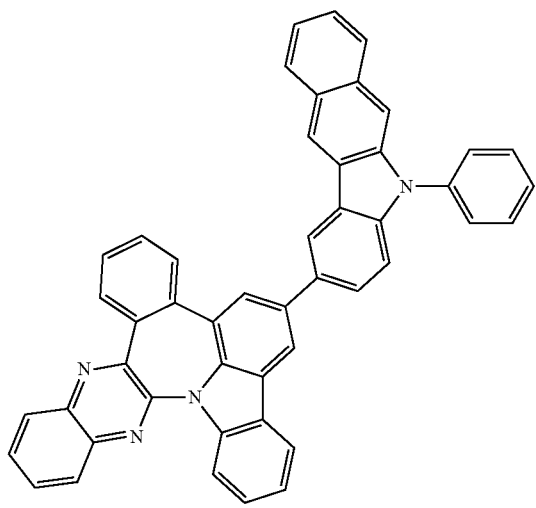
A-9
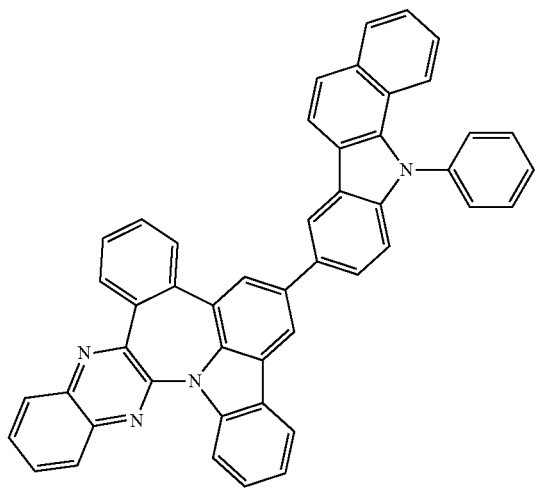
A-10
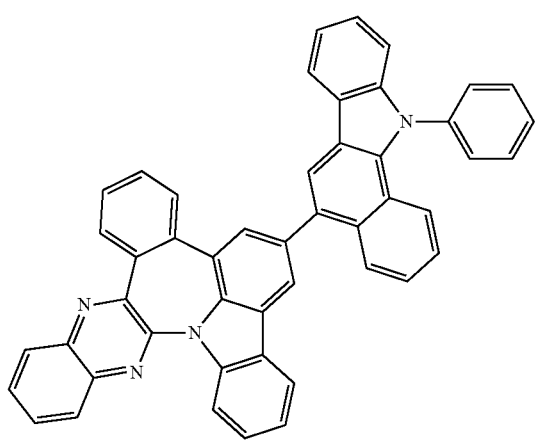
A-11
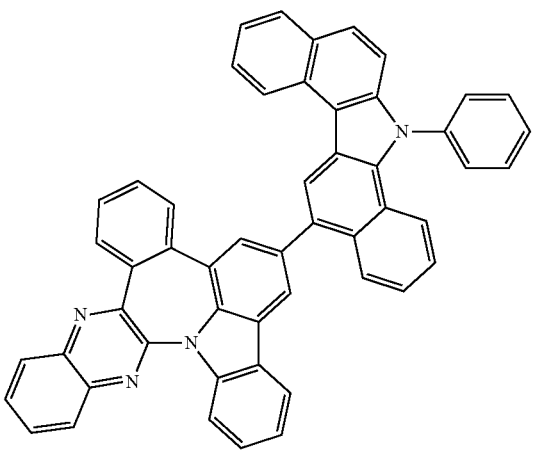
A-12
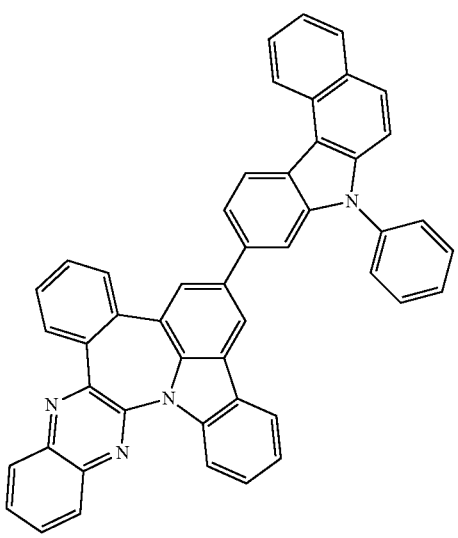
A-13
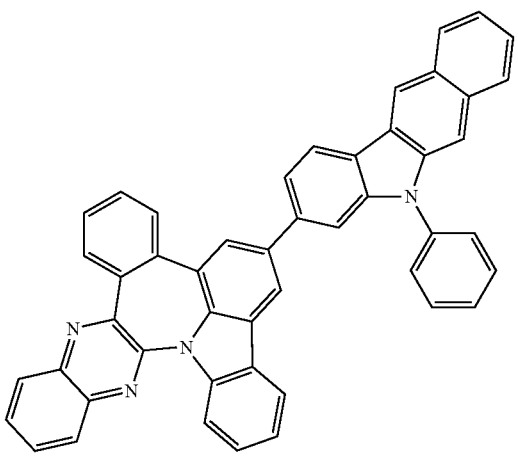

-continued
A-14
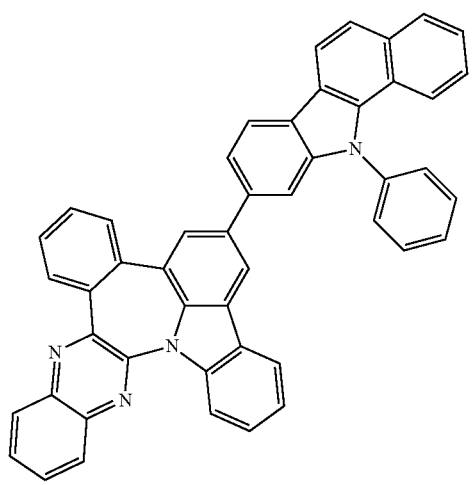
A-15
A-16
A-17
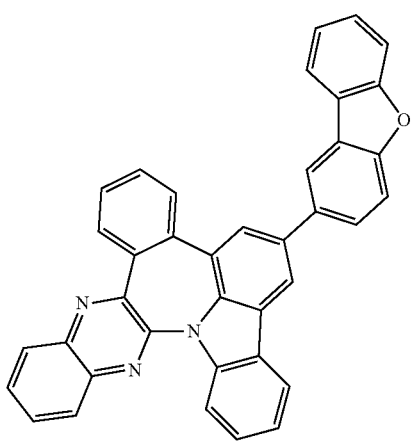
A-18
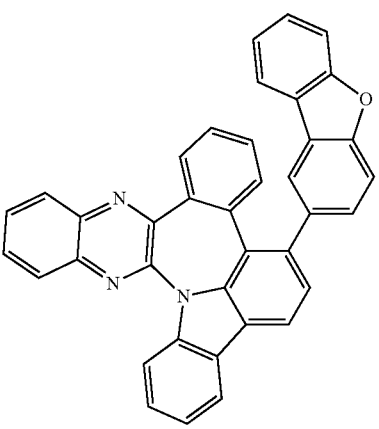
A-19
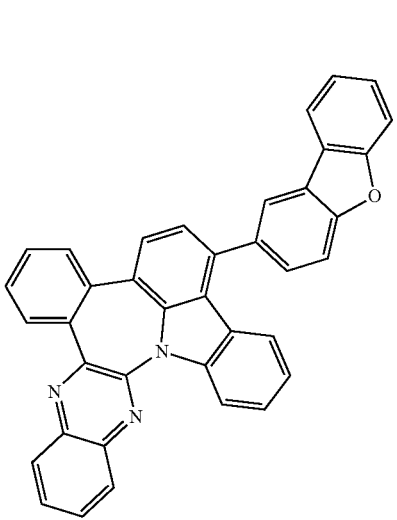

-continued
A-20
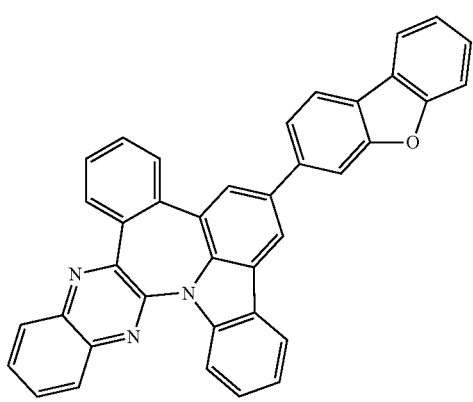
A-21
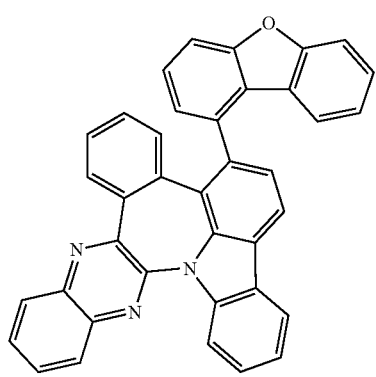
A-22
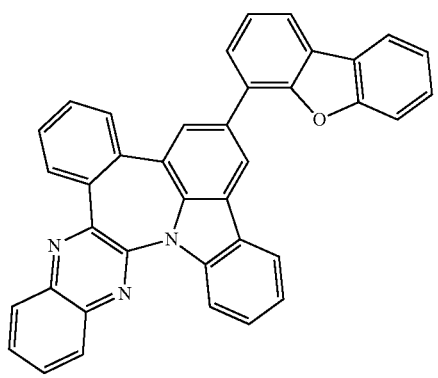
A-23
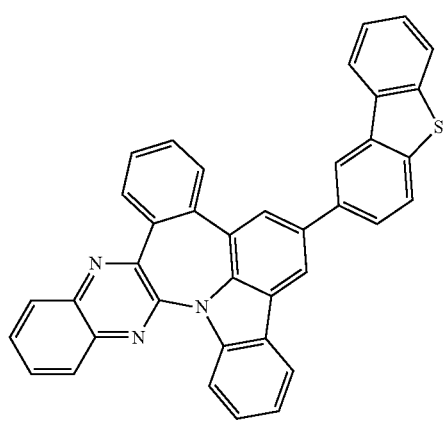
-continued
A-24
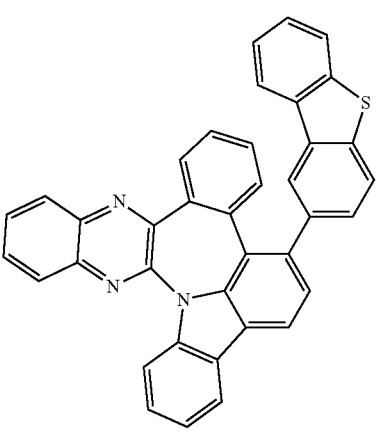
A-25
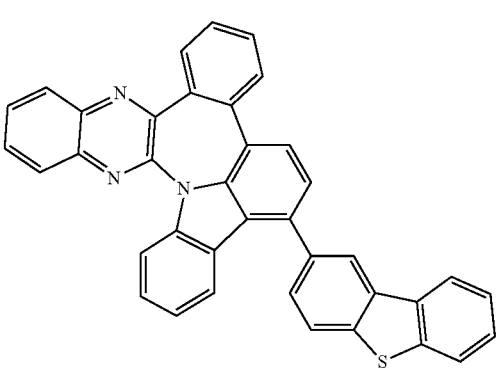
A-26
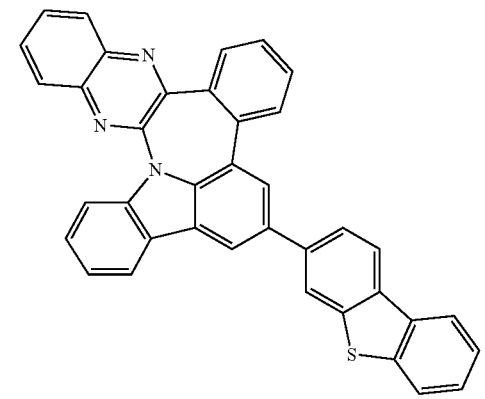
A-27
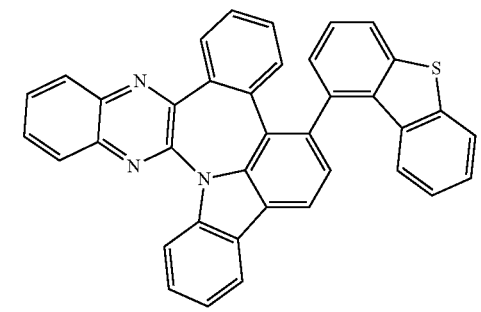

A-28
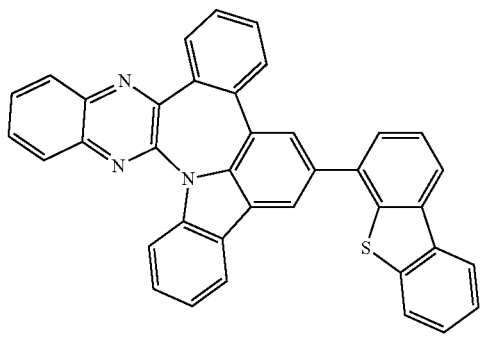
A-29
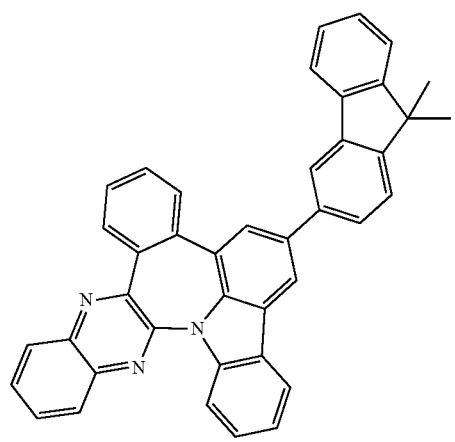
A-30
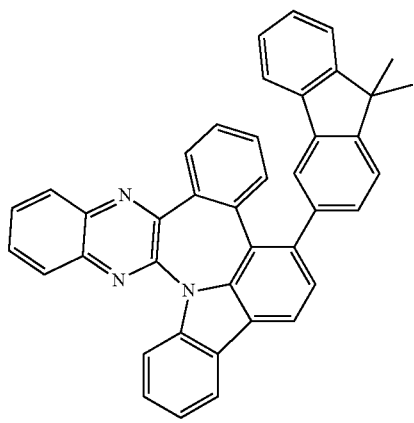
A-31
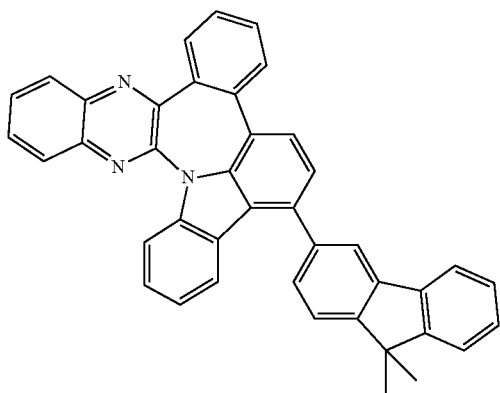
A-32
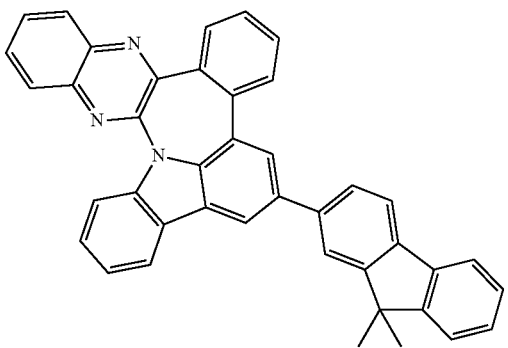
A-33
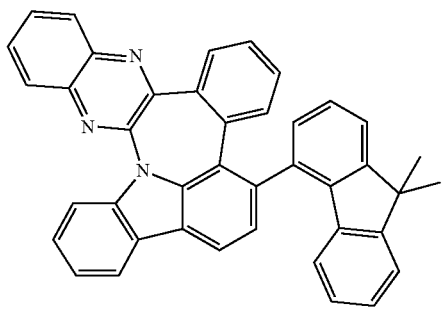
A-34
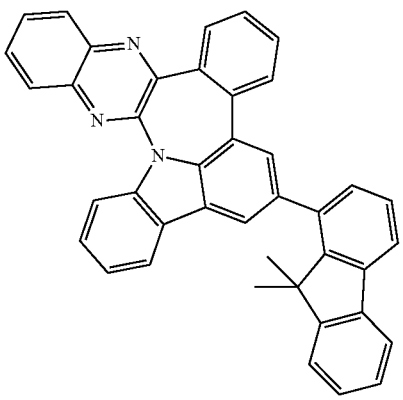
A-35
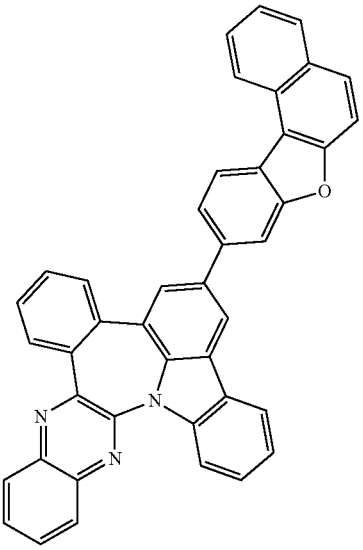

A-36
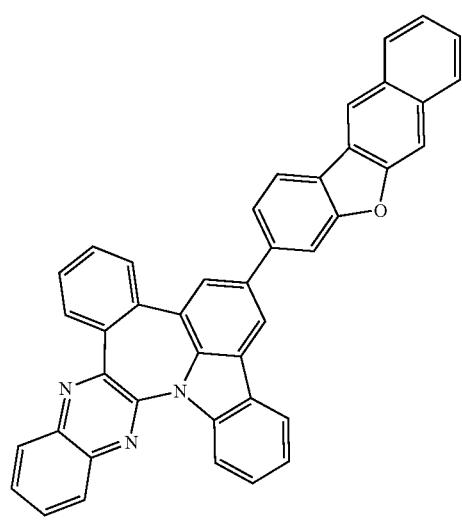
A-37
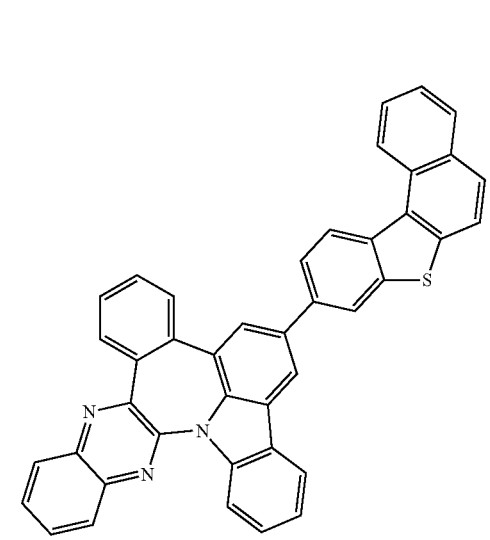
A-38
A-39
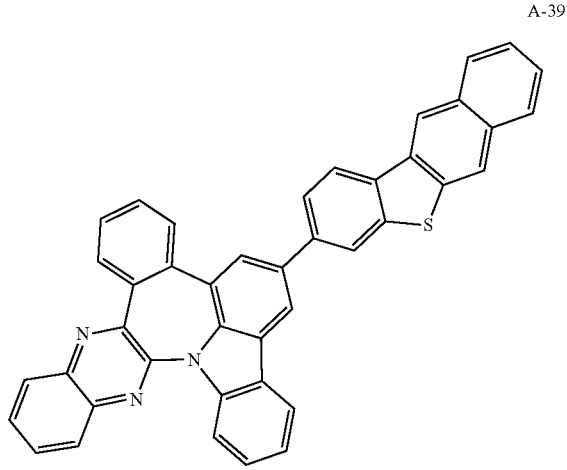
A-40
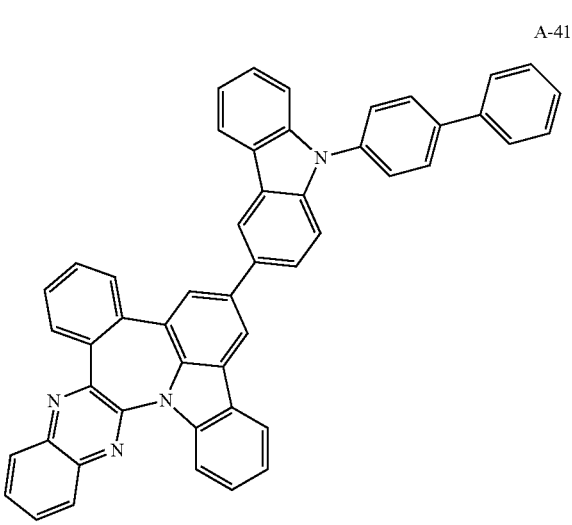
A-41

A-42
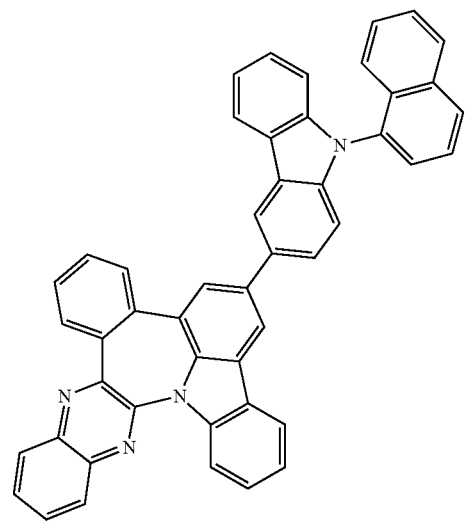
A-43
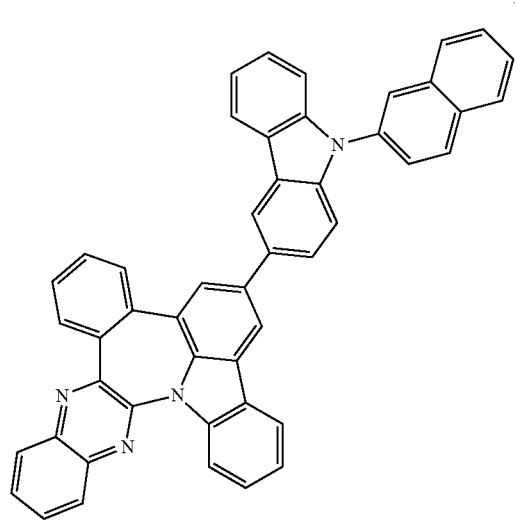
A-44
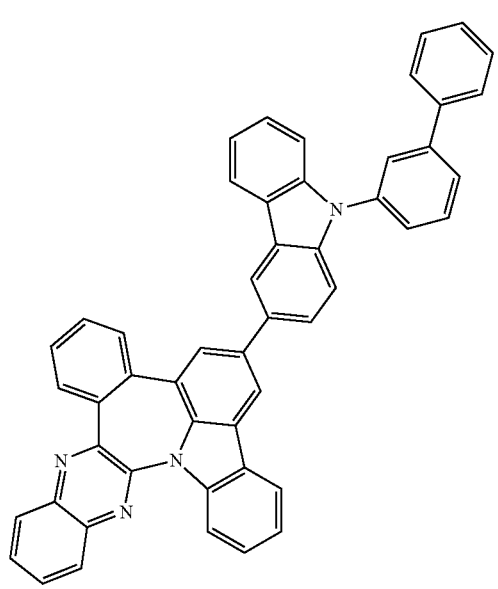
A-45
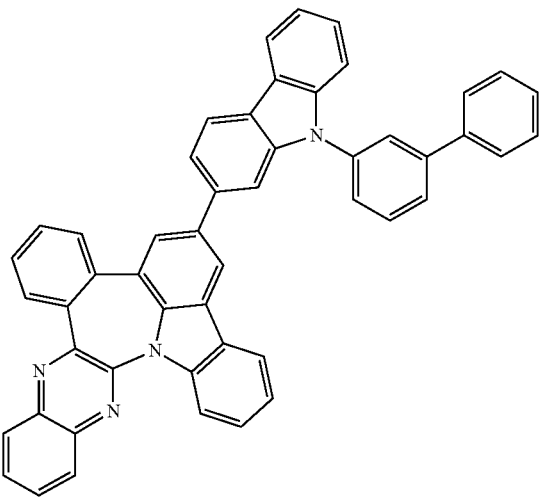
A-46
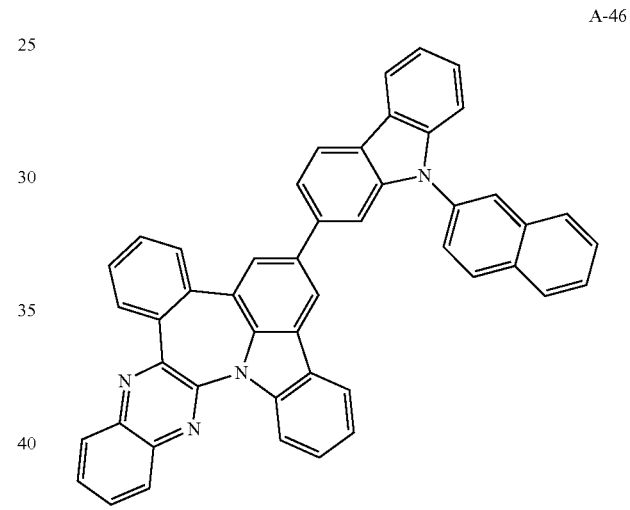
A-47
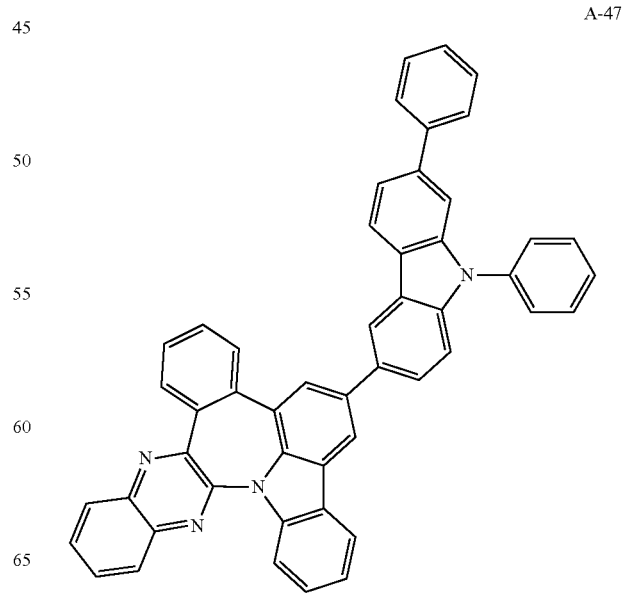

A-48
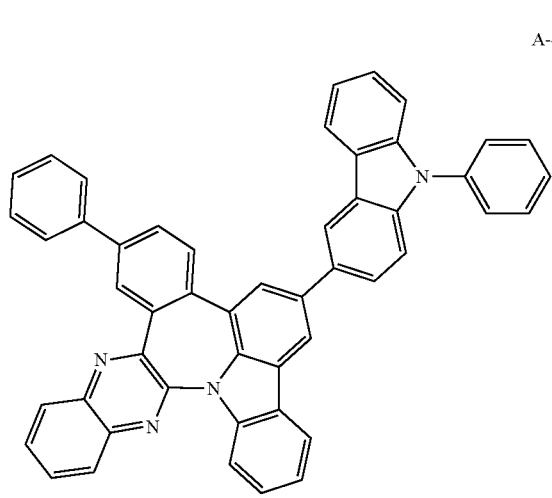
A-49
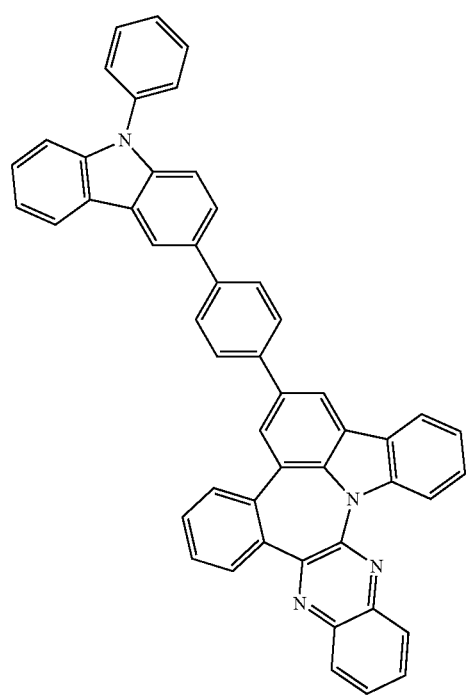
A-50
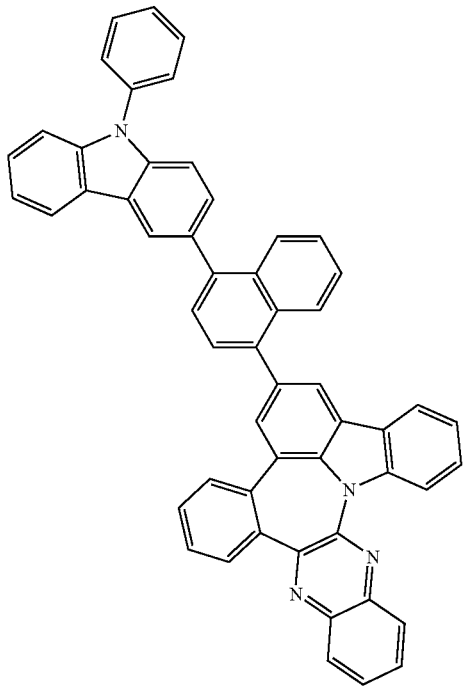
A-51
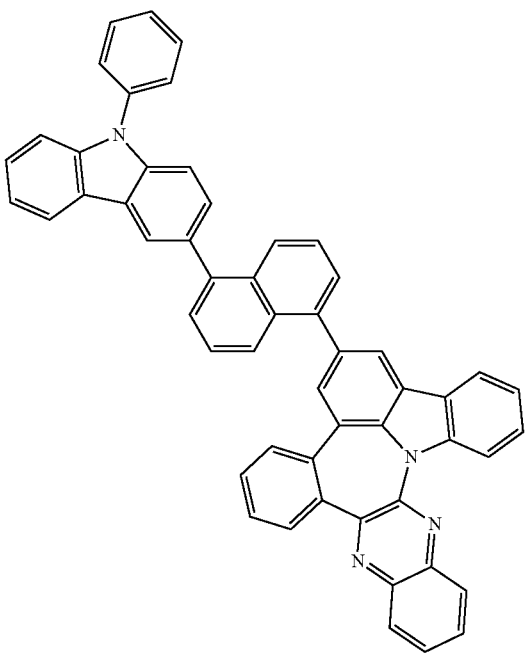

A52
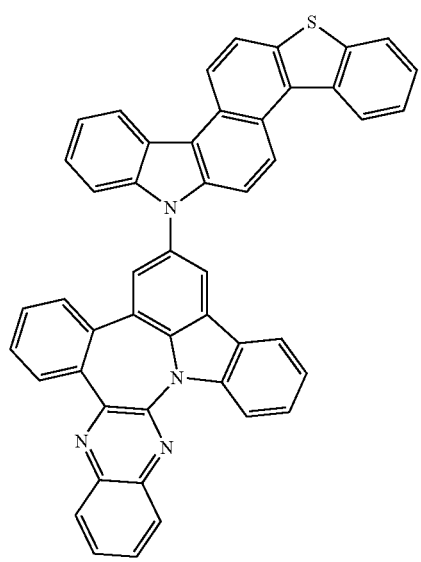
A-53
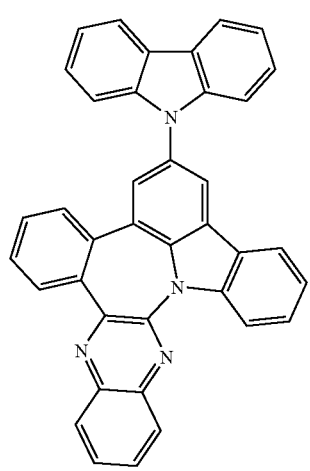
A-54
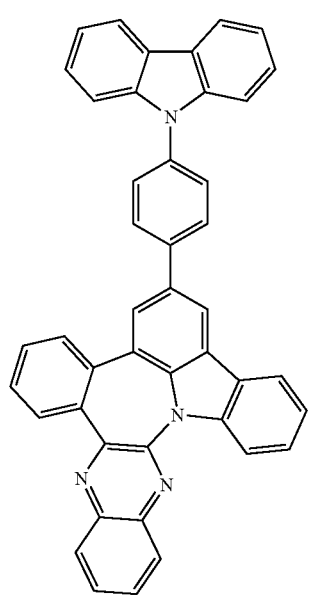
A-55
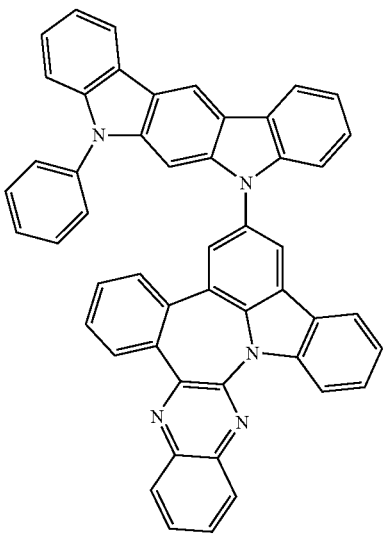
A-56
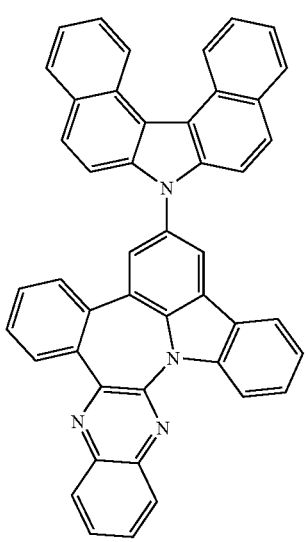
A-57
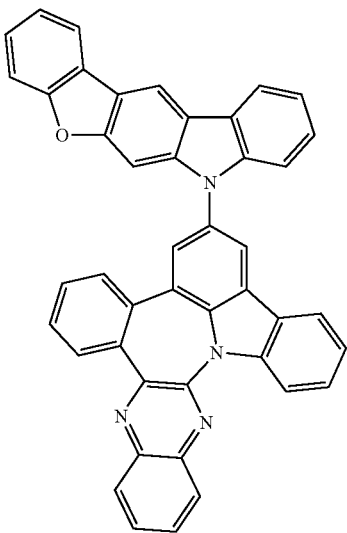

A-58
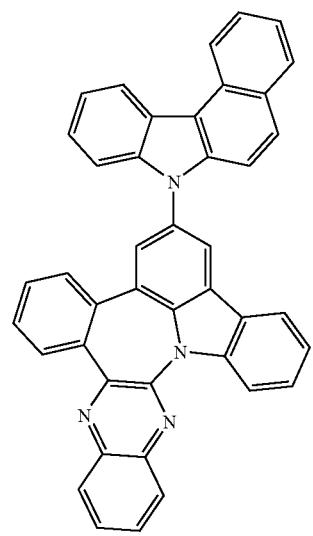
A-59
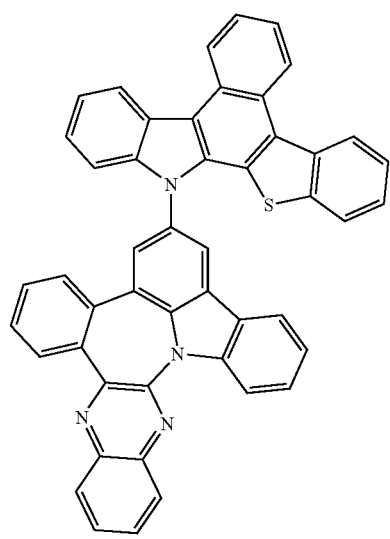
A-60
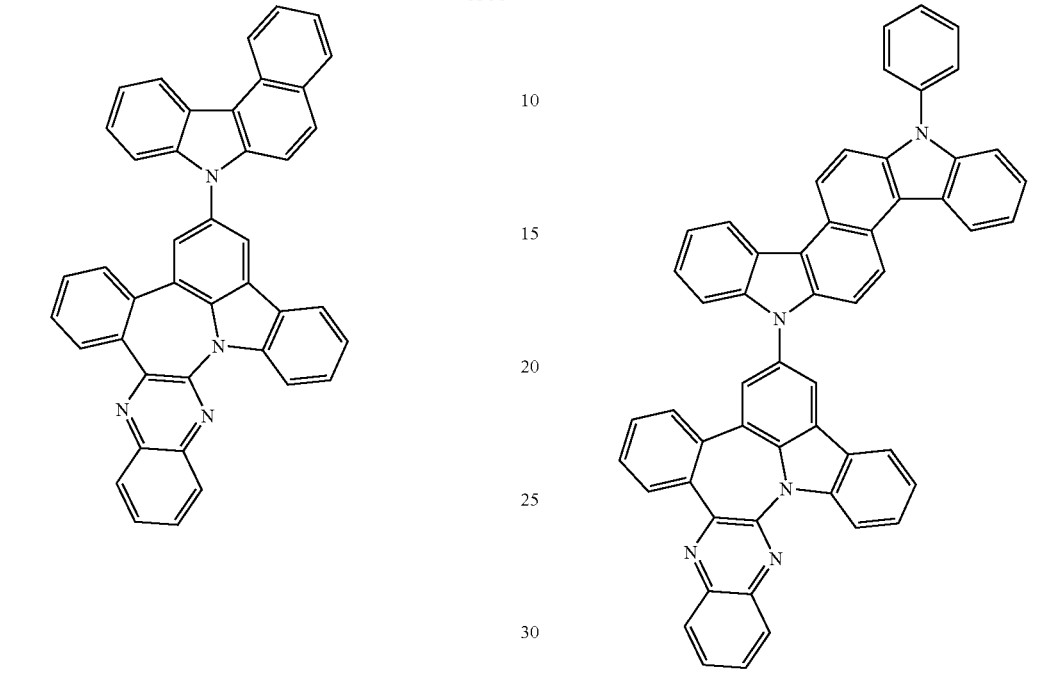
A-61
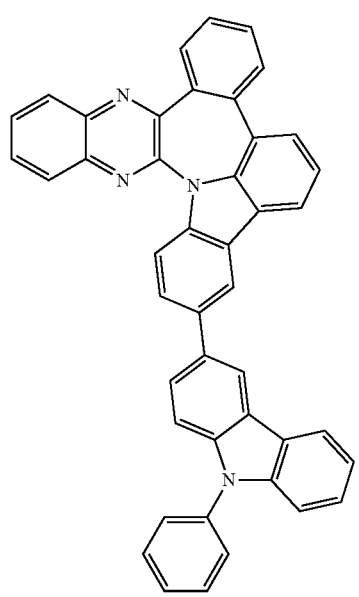

A-62
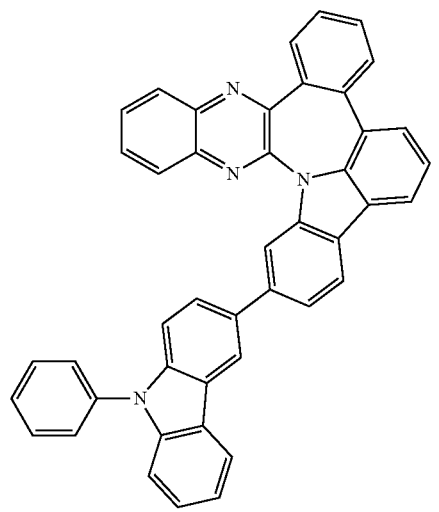
A-63
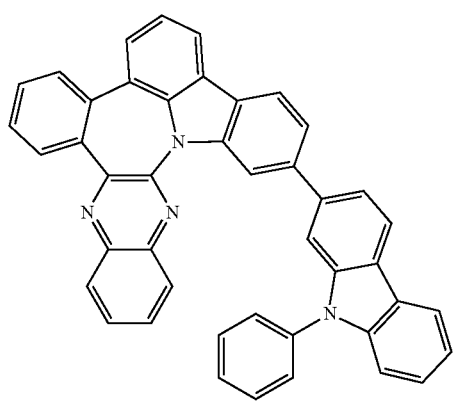
A-64
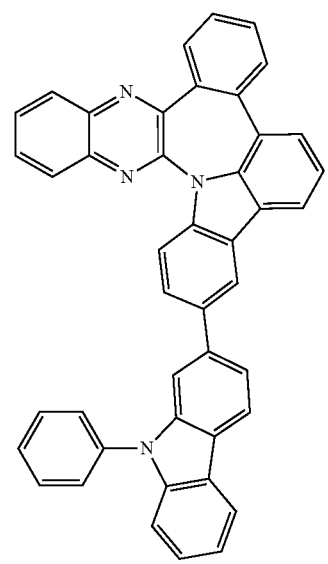
A-65
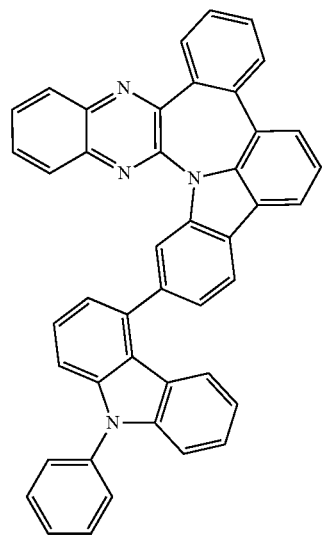
A-66
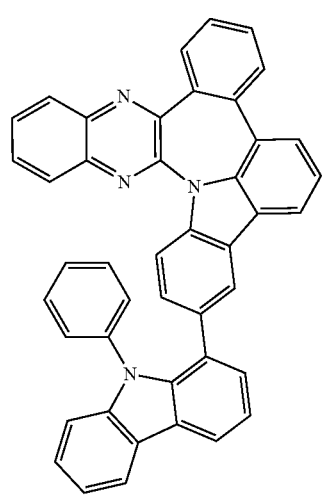
A-67
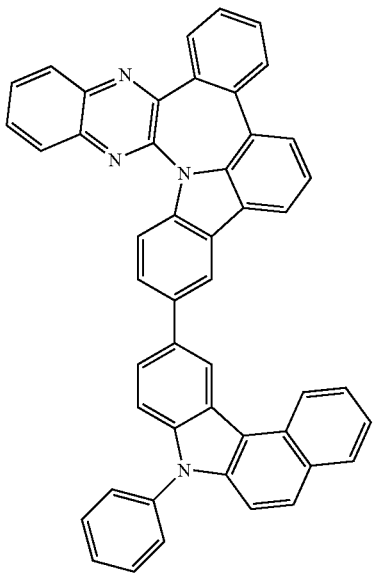

A-68
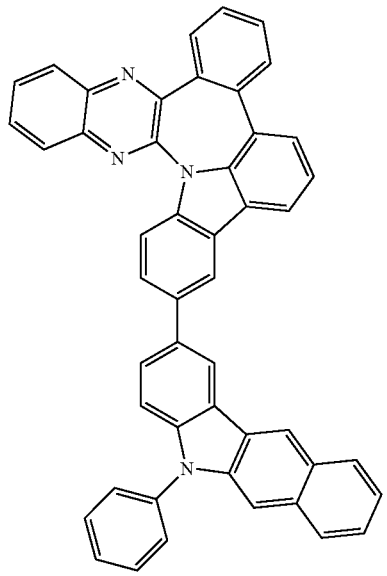
A-69
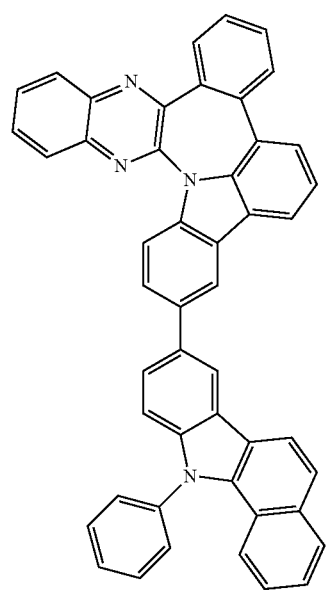
A-70
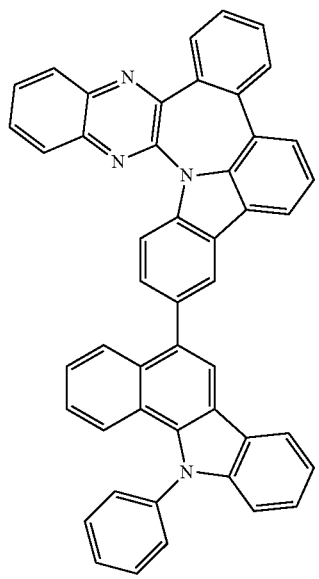
A-71
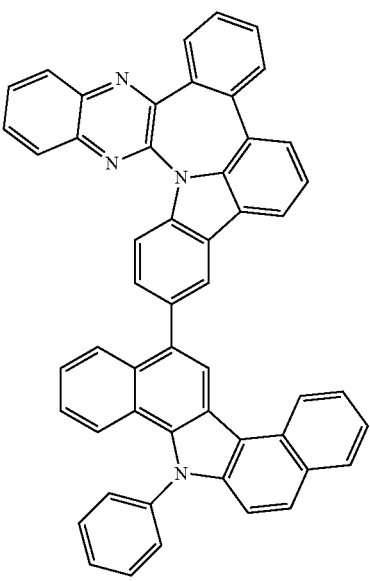

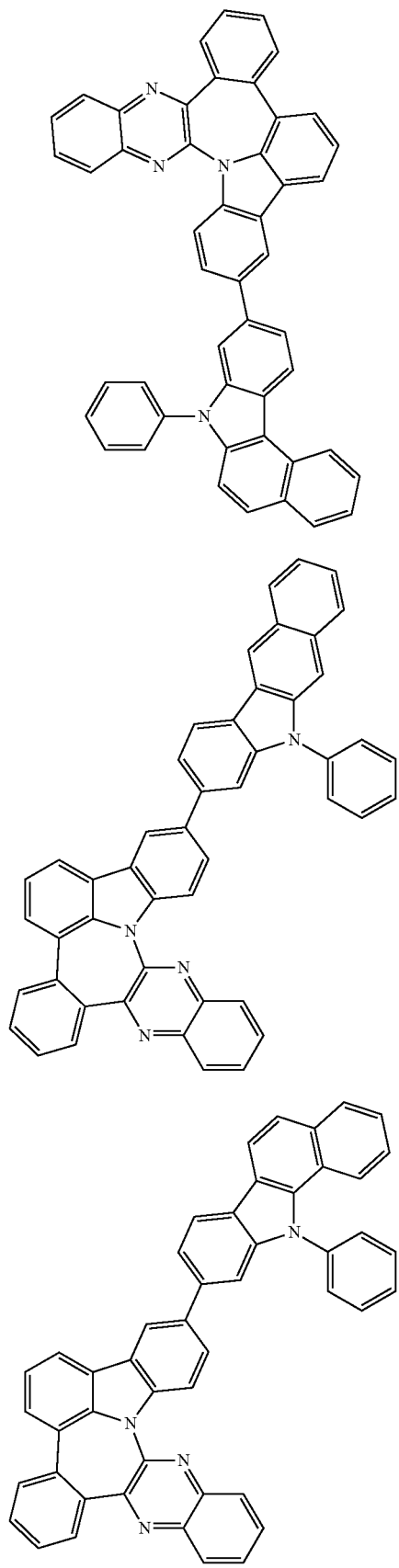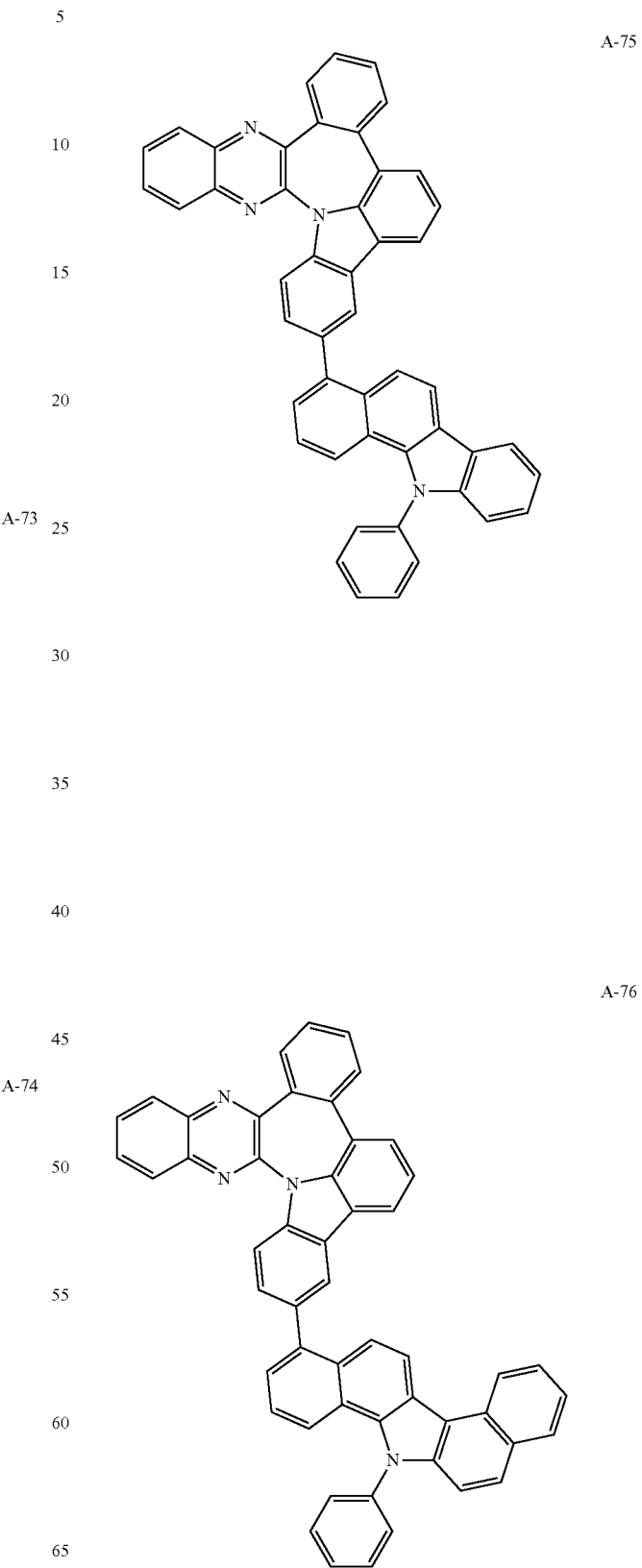

A-77
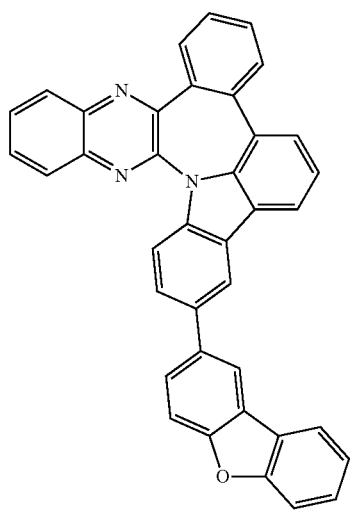
A-78
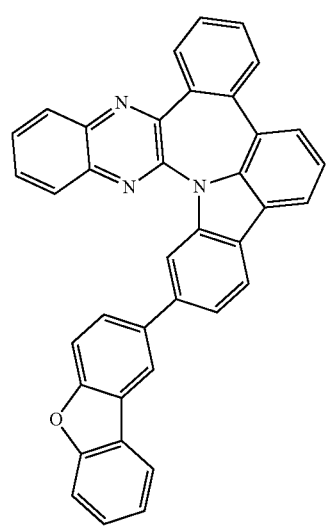
A-79
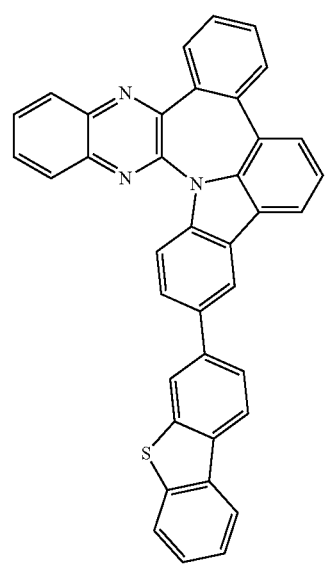
A-80
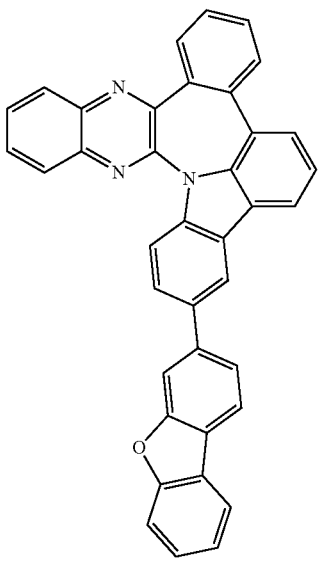
A-81
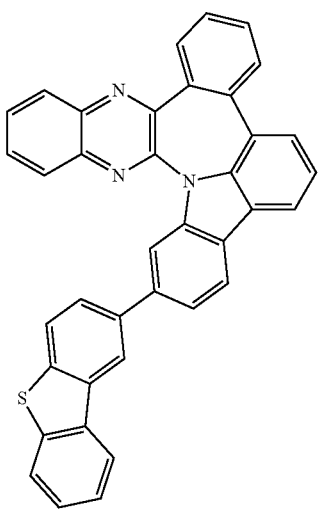
A-82
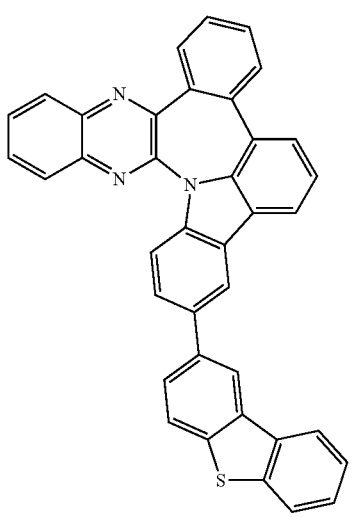

A-83
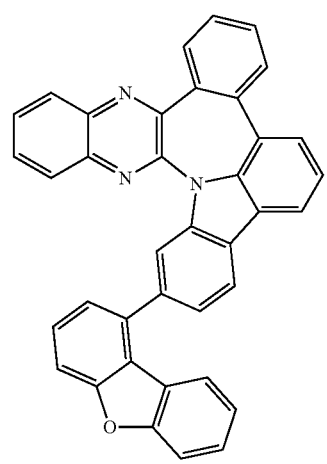
A-84
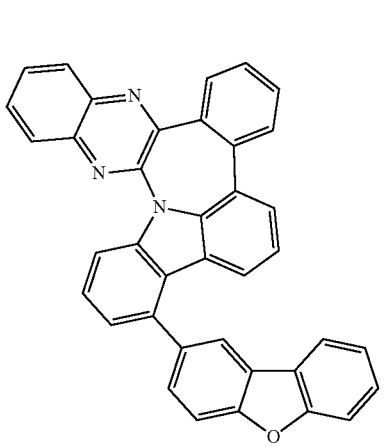
A-85
A-86
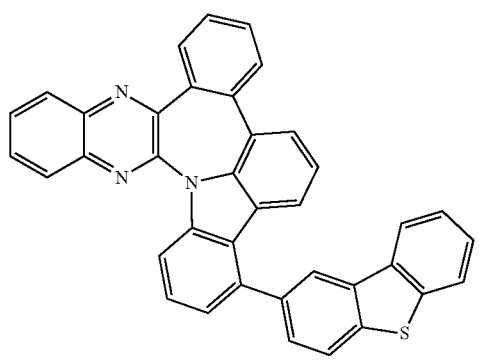
A-87
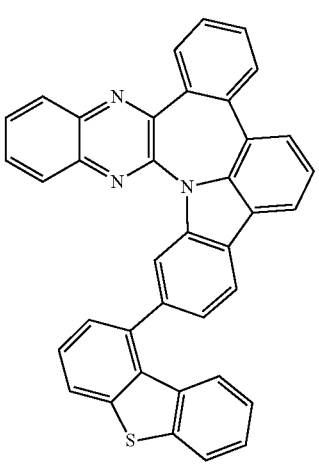
A-88
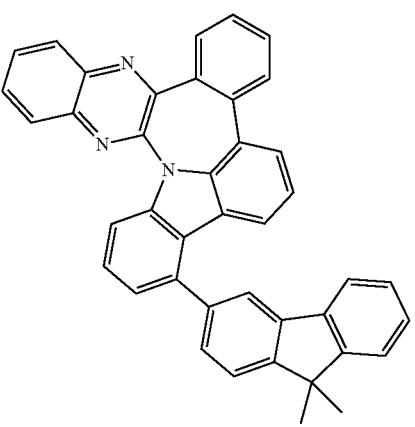

A-89
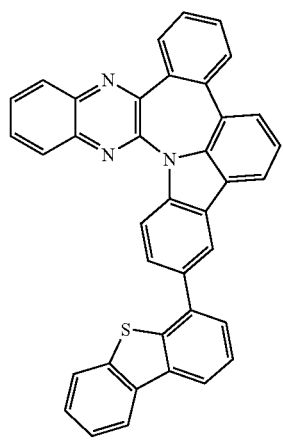
A-90
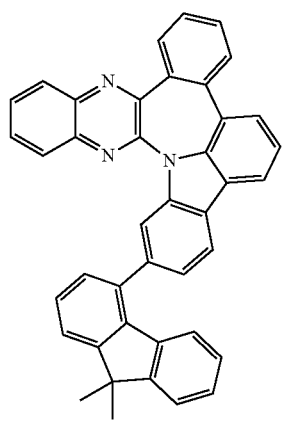
A-91
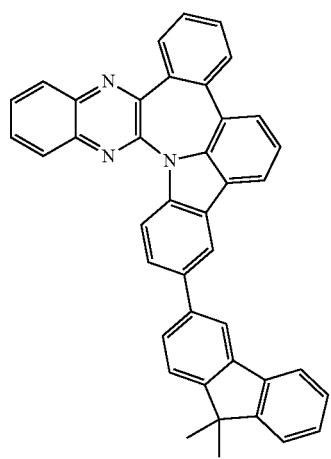
A-92
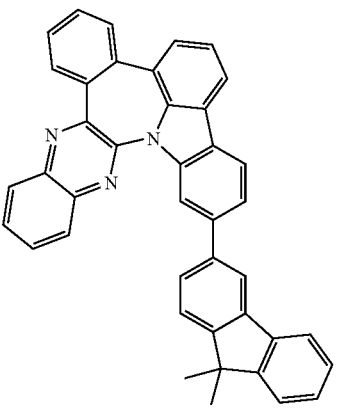
A-93
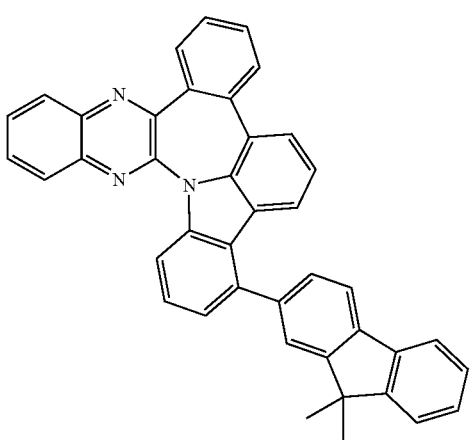
A-94
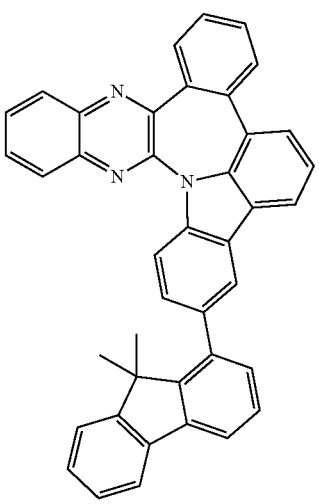

A-95
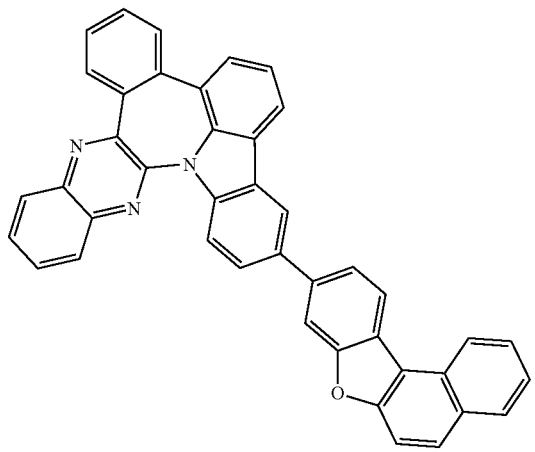
A-98
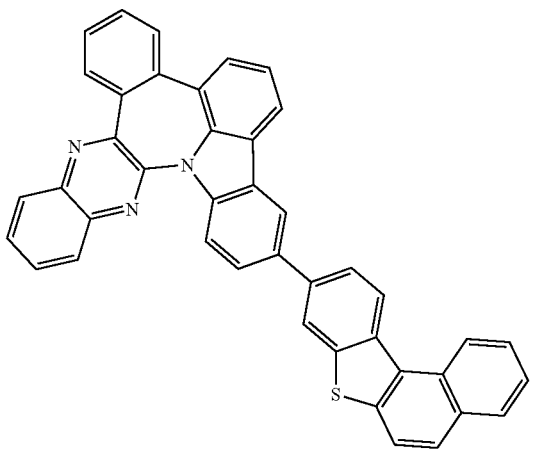
A-96
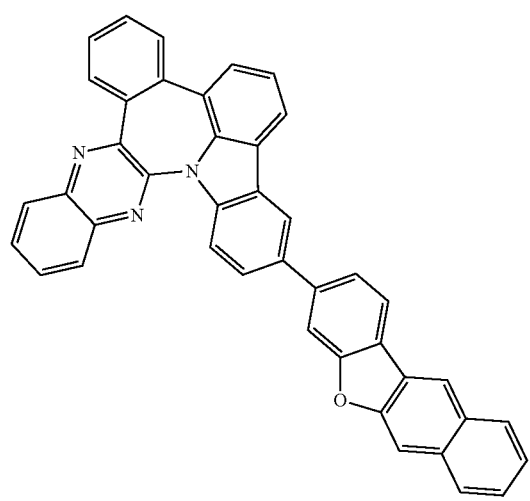
A-99
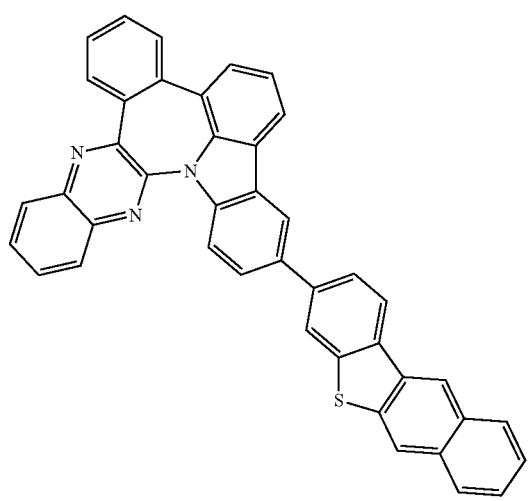
A-97
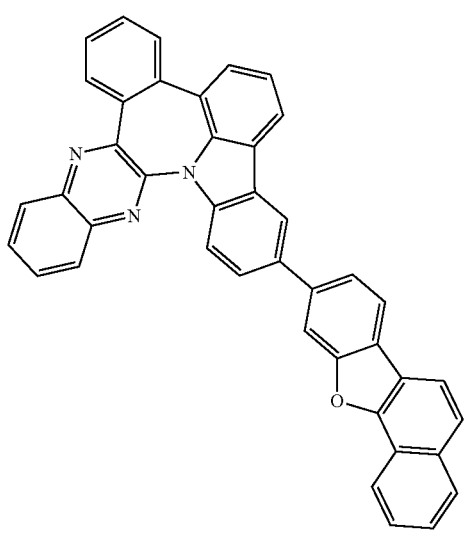
A-100
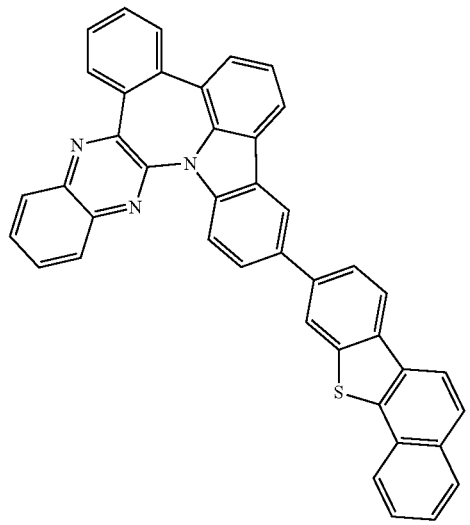

A-101
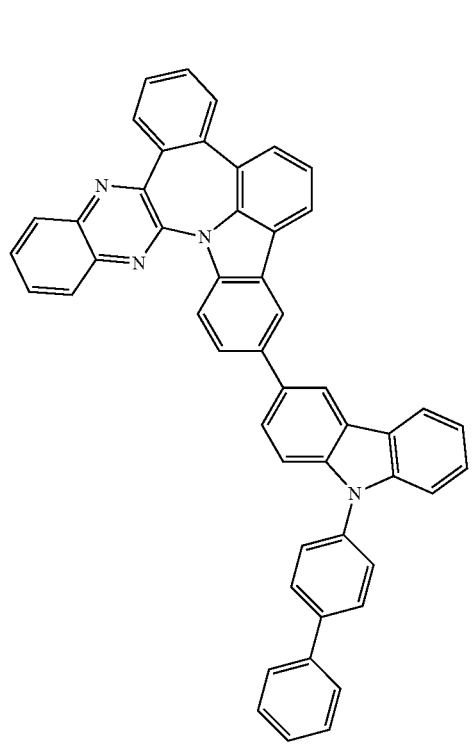
A-103
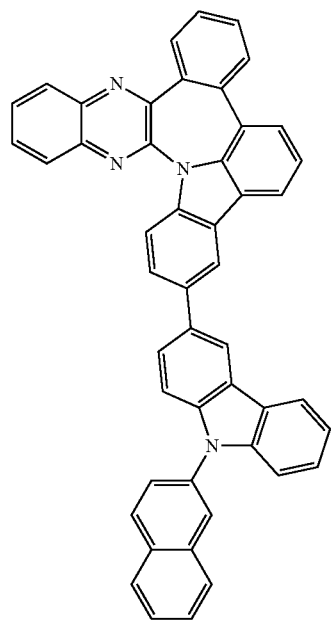
A-102
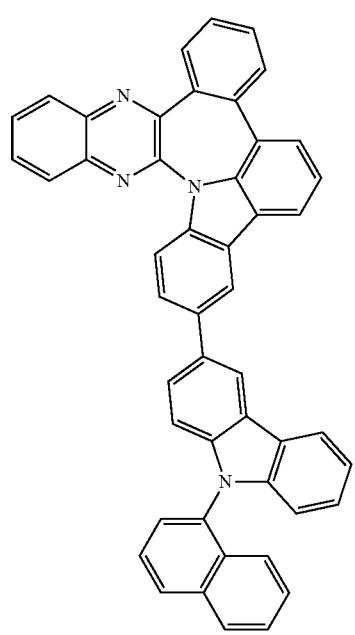
A-104
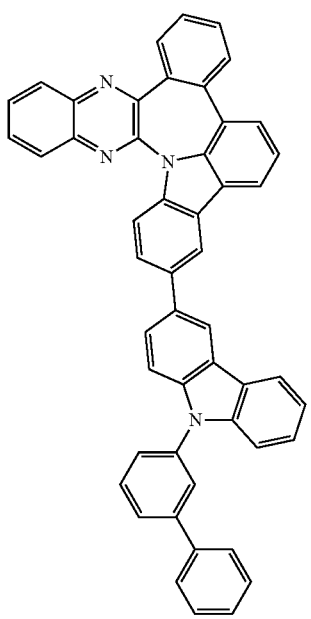

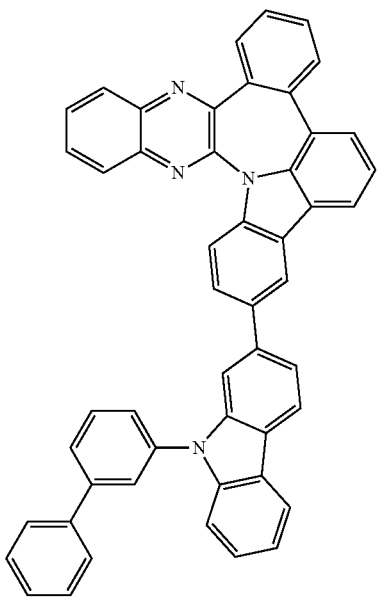
A-105
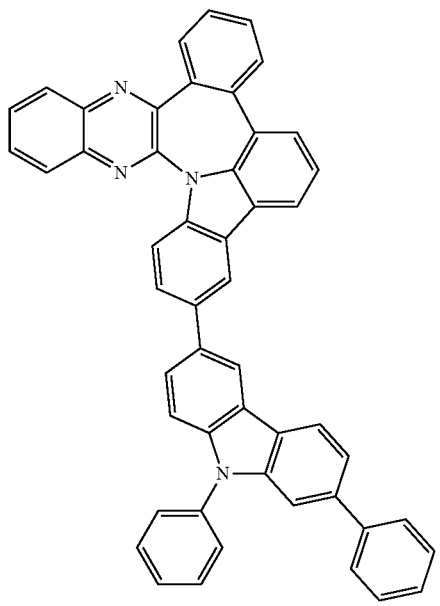
A-107
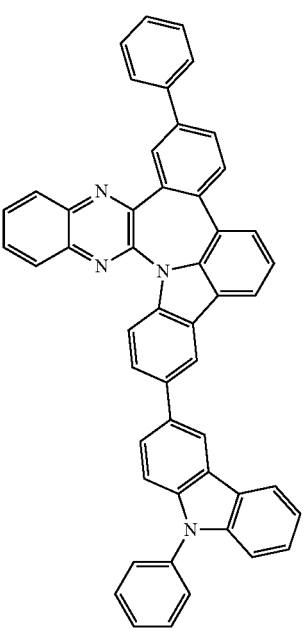
A-106
A-108

A-109
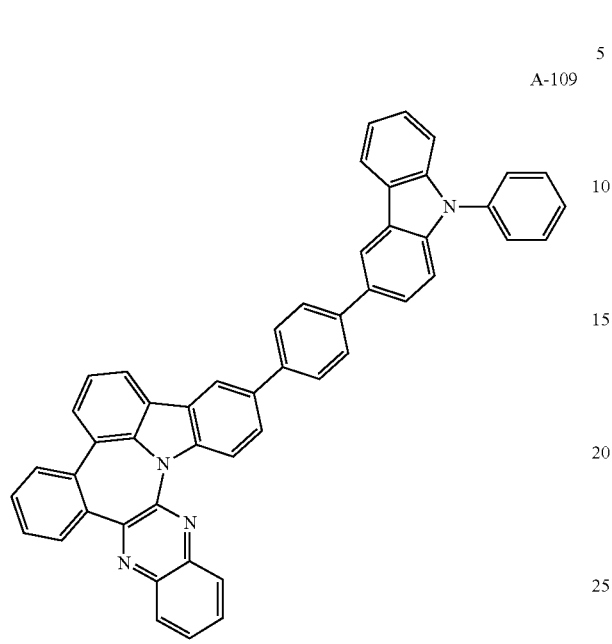
A-111
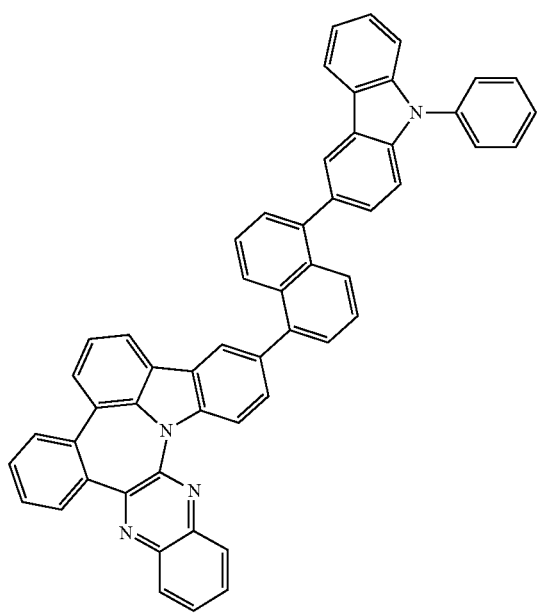
A-110
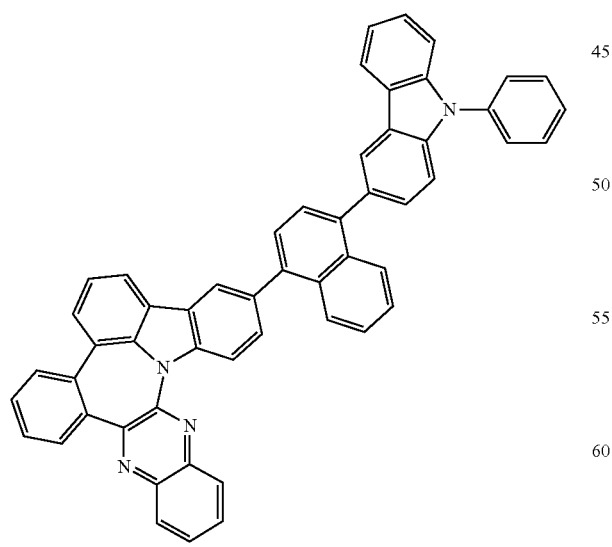
A-112
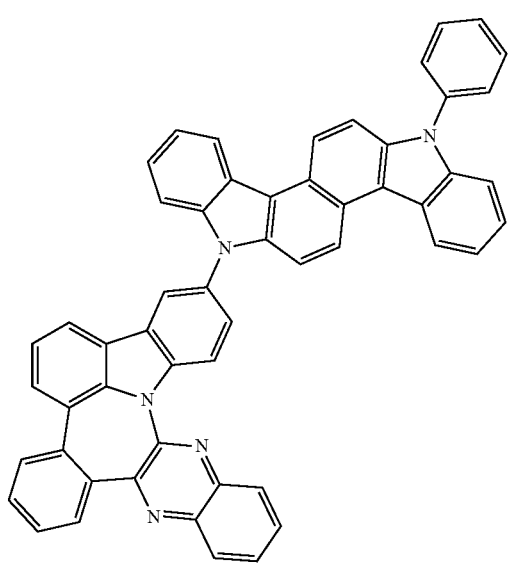

A-113
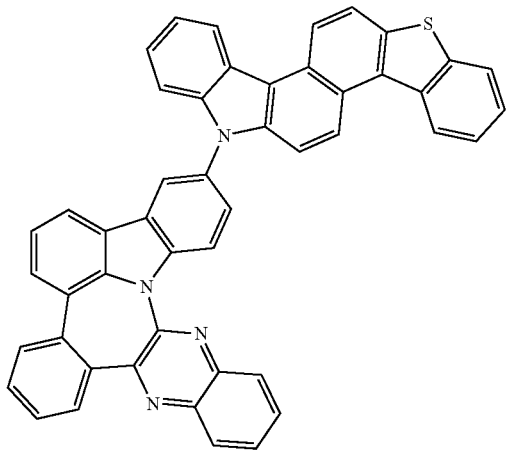
A-114
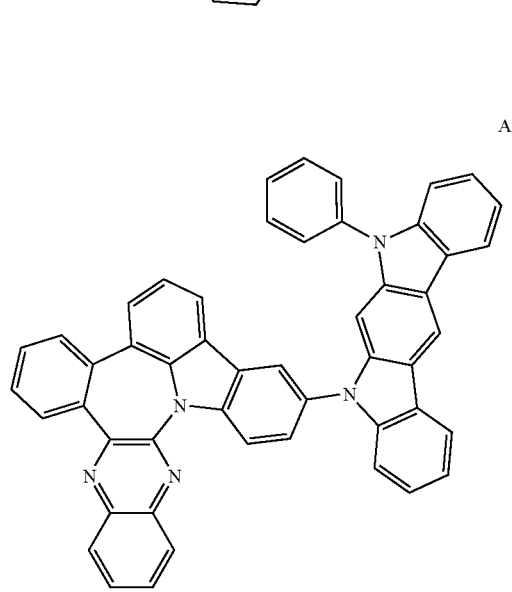
A-115
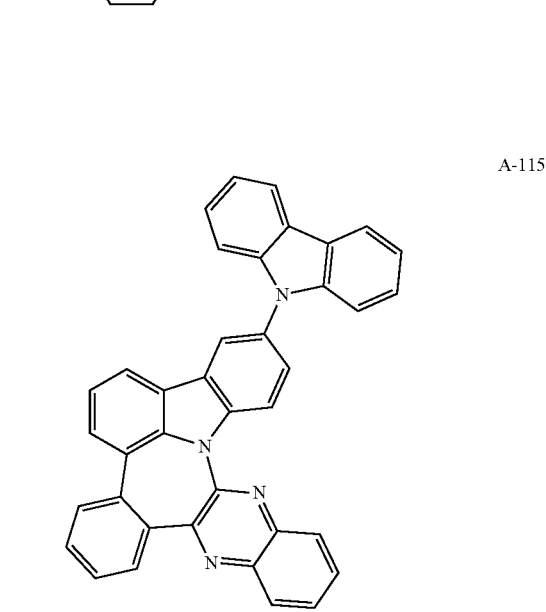
A-116
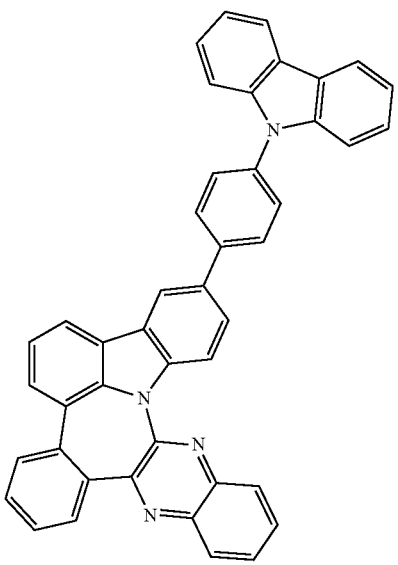
A-117
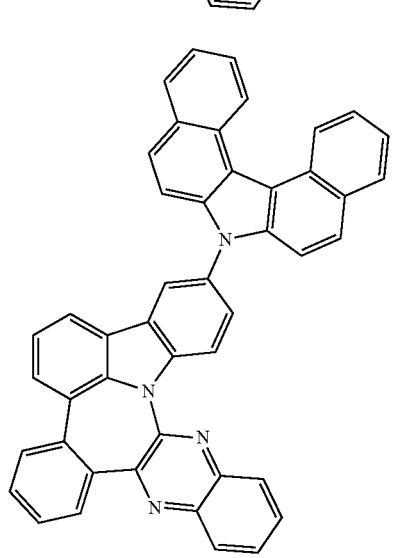
A-118
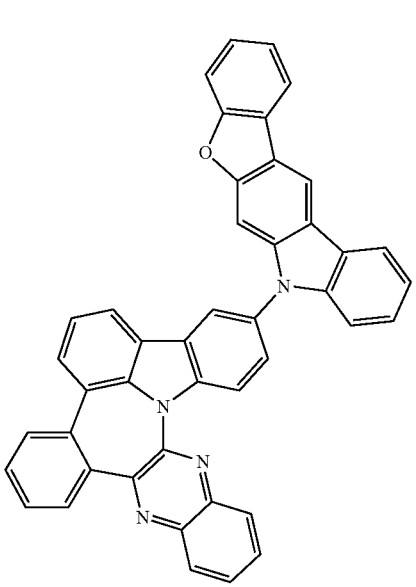

A-119
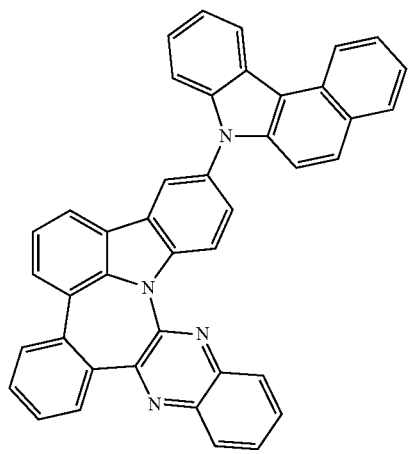
A-120
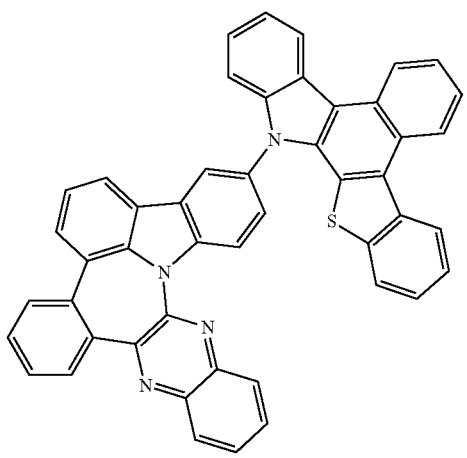
A-121
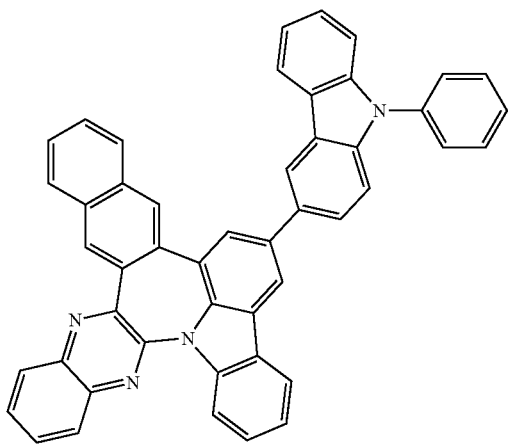
A-122
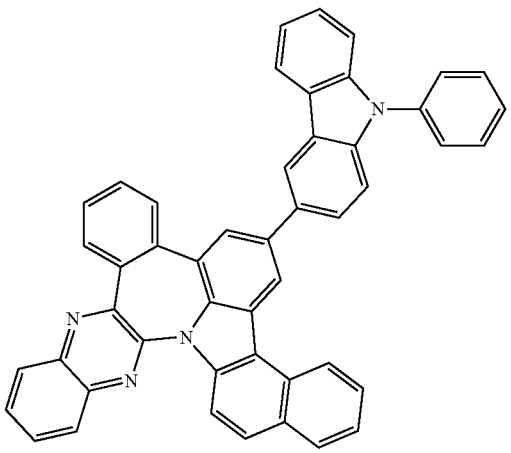
A-123
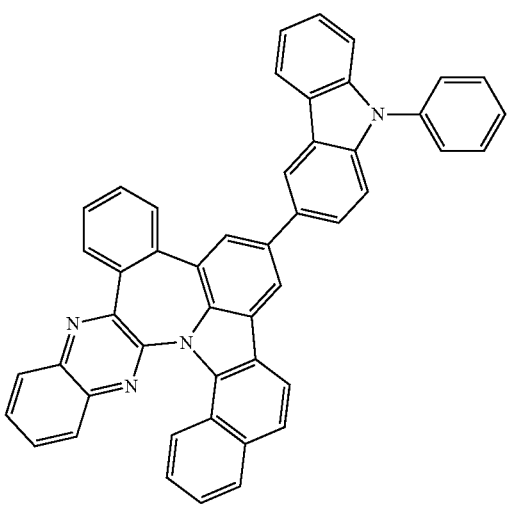
A-124
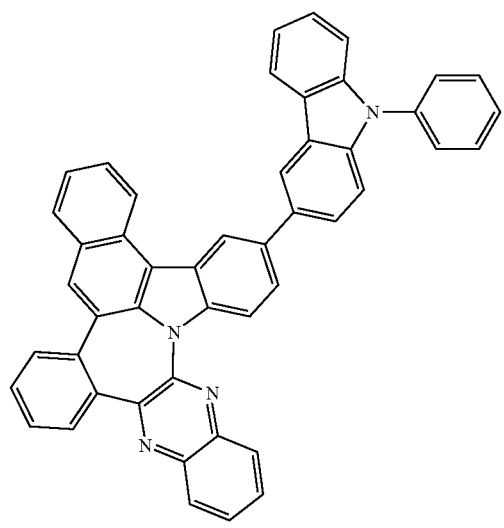

A-125
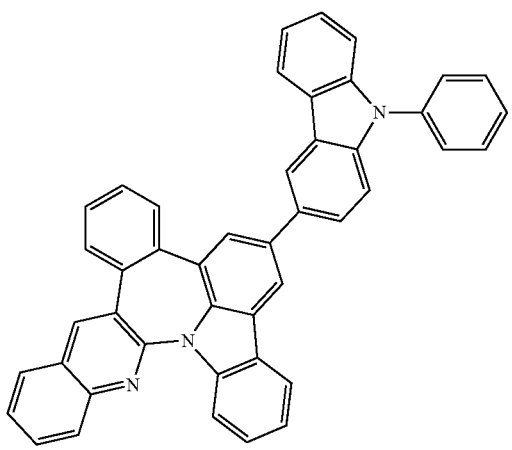
A-126
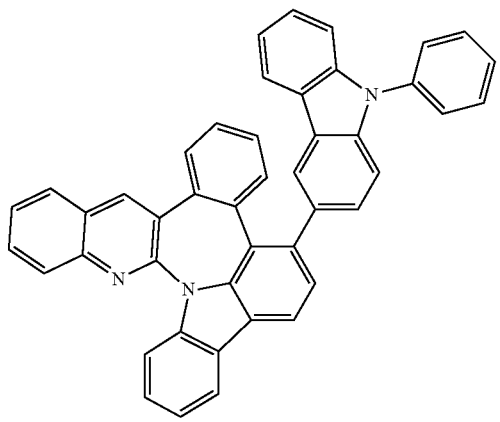
A-127
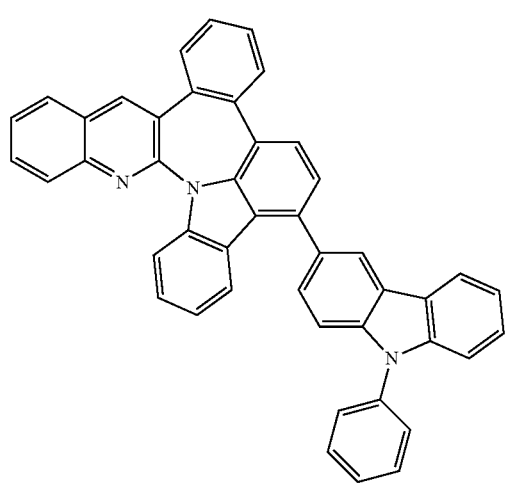
A-128
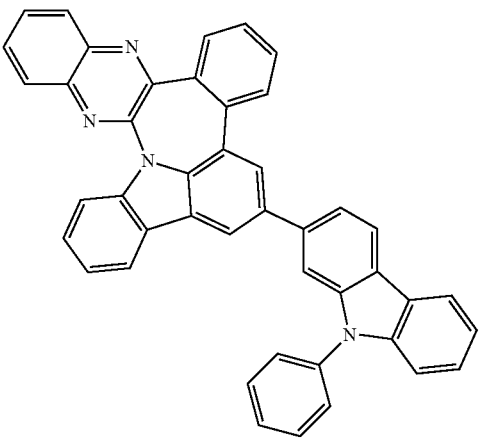
A-129
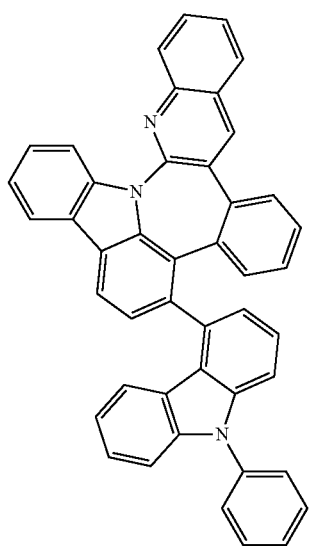
A-130
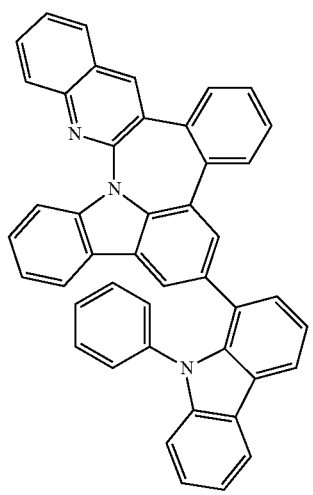

A-131
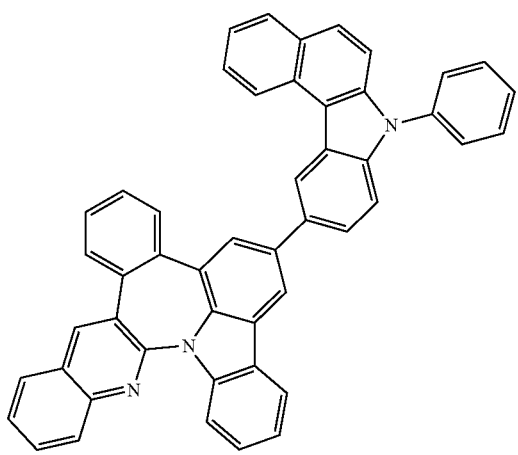
A-134
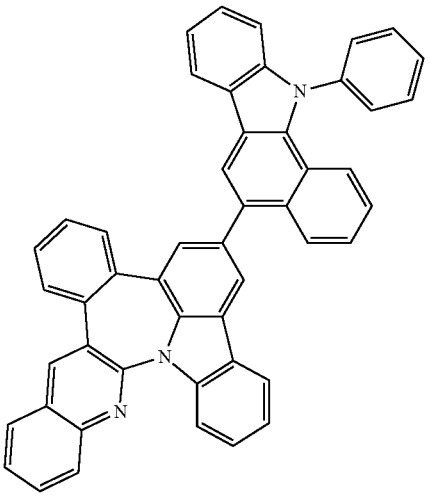
A-132
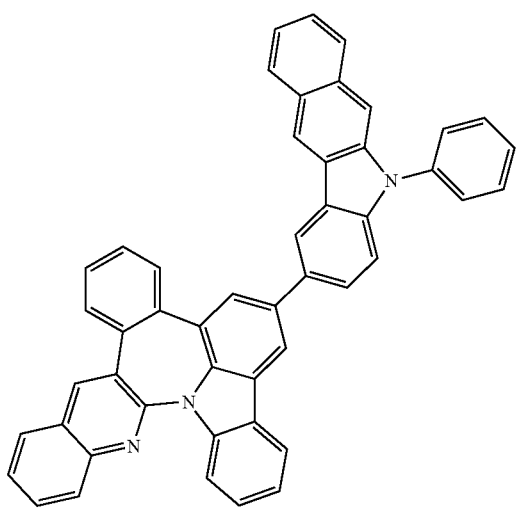
A-135
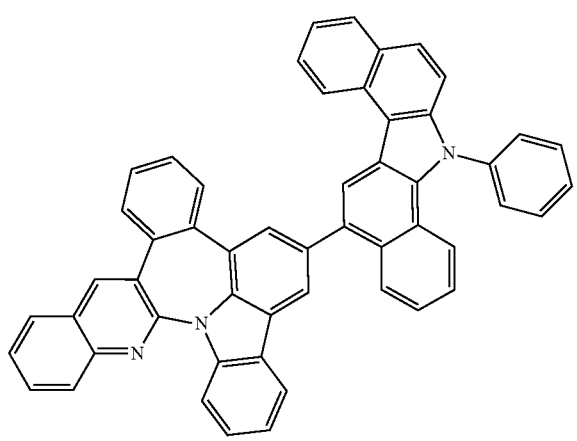
A-133
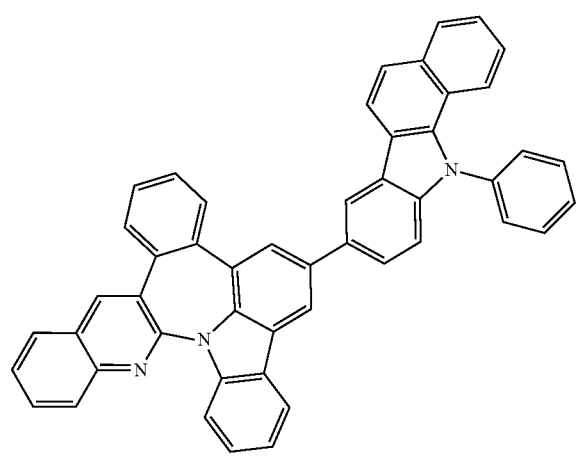
A-136
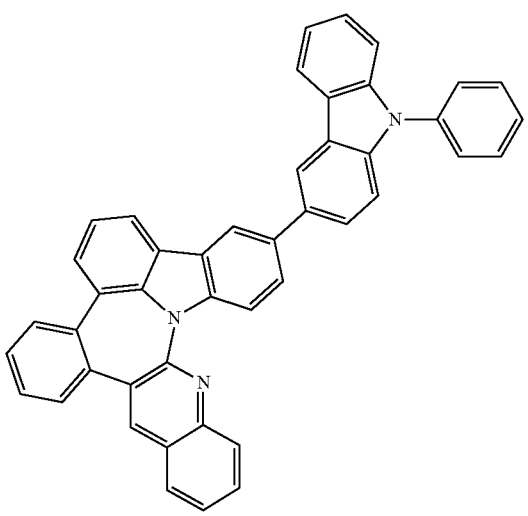

A-137
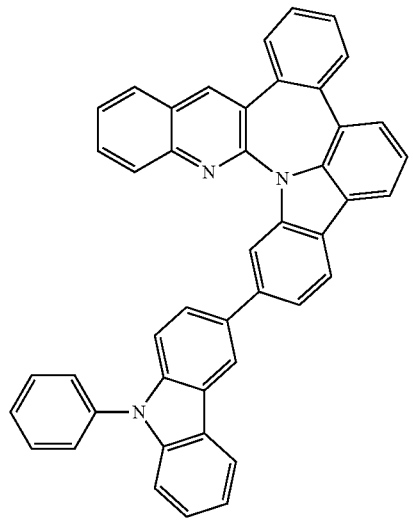
A-138
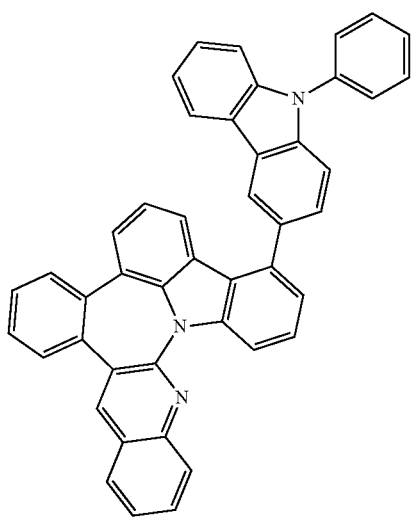
A-139
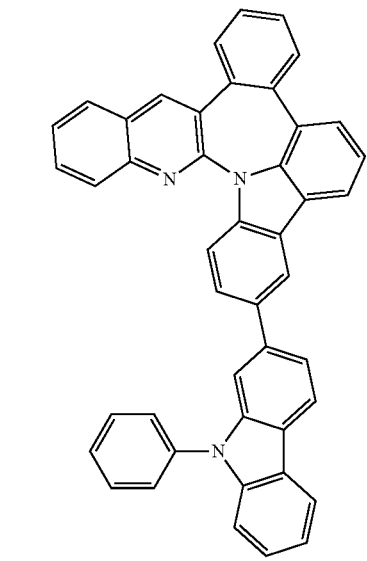
A-140
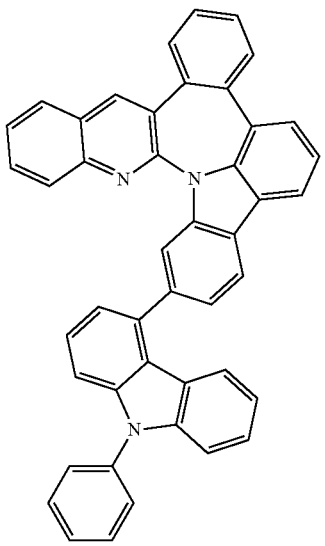
A-141
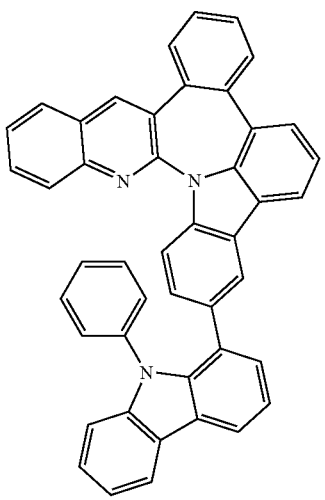
A-142
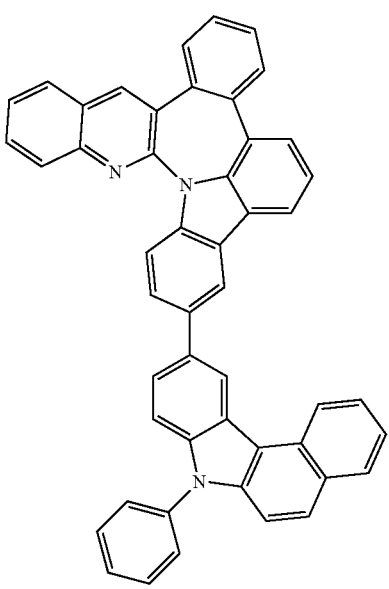

A-143
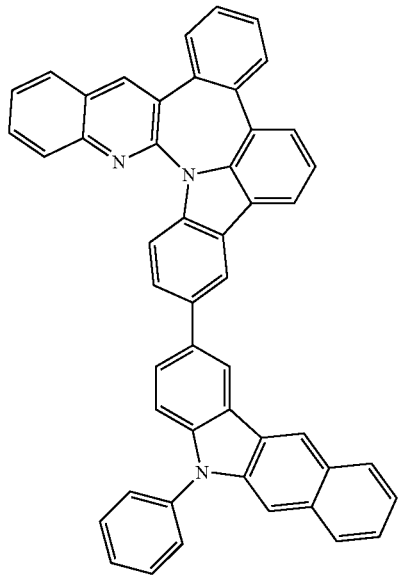
A-144
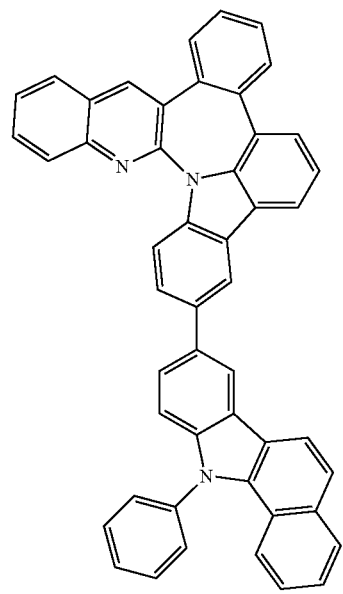
A-145
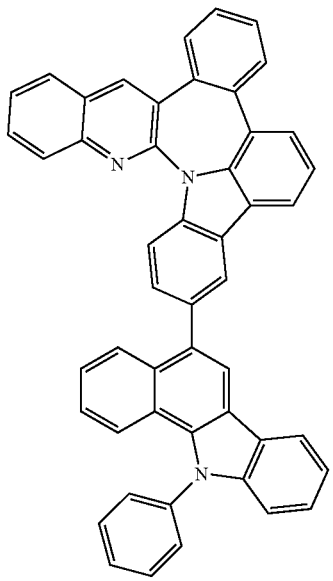
A-146
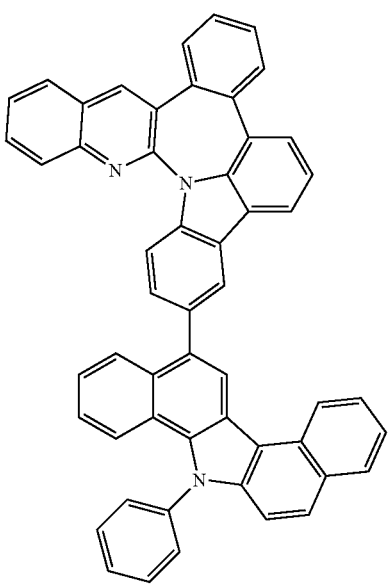
A-147
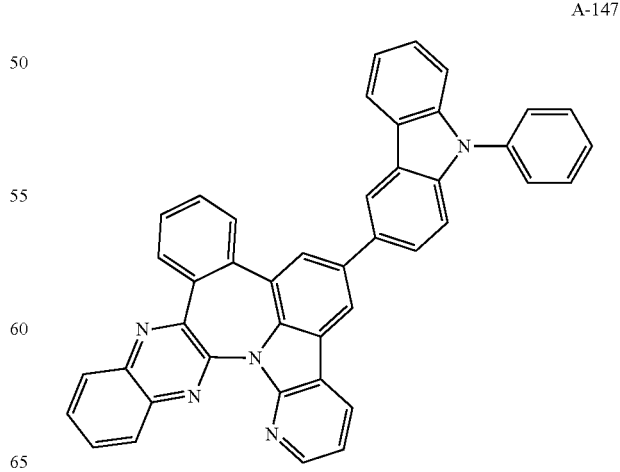

A-148
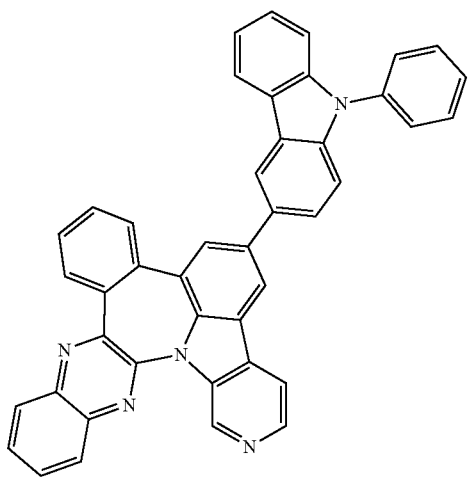
A-151
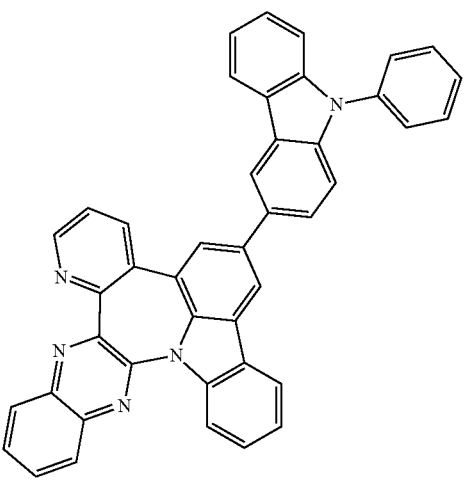
A-149
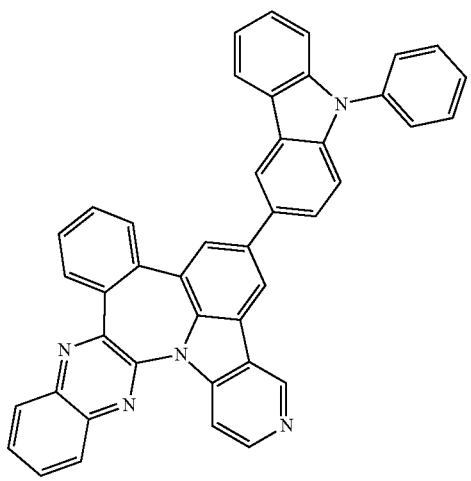
A-152
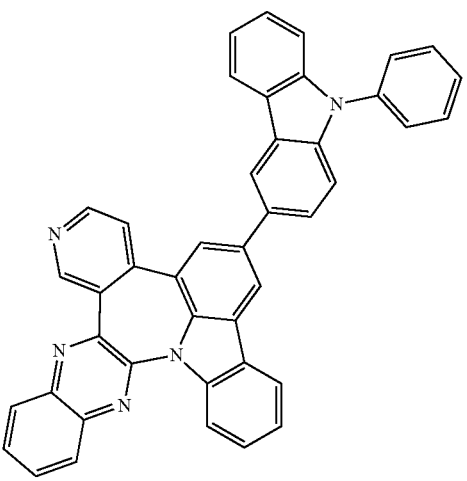
A-150
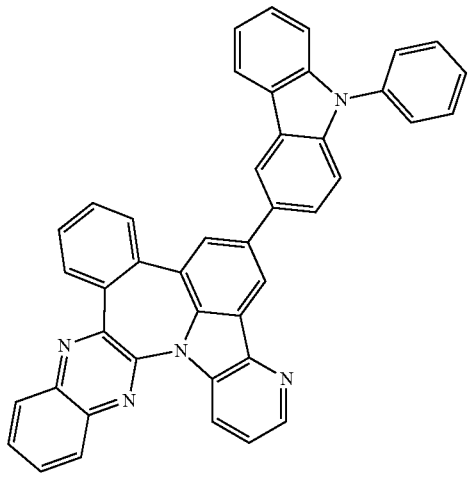
A-153
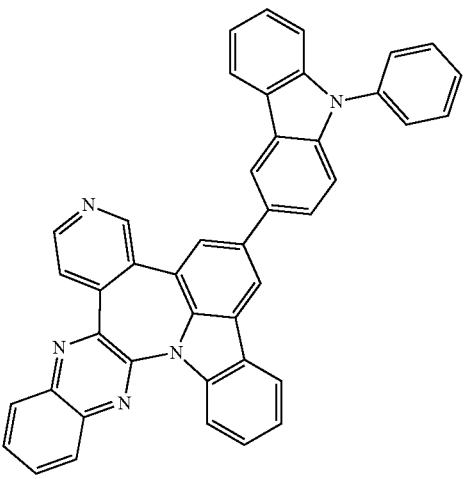

A-154
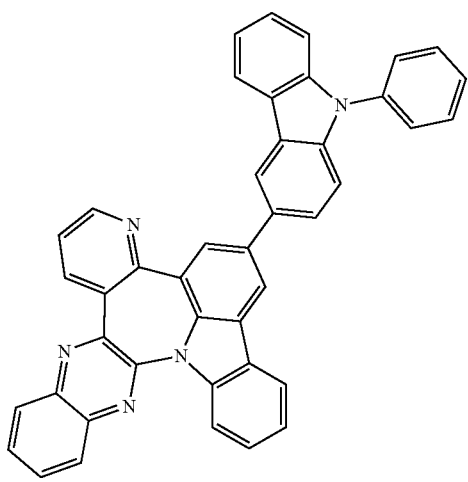
A-157
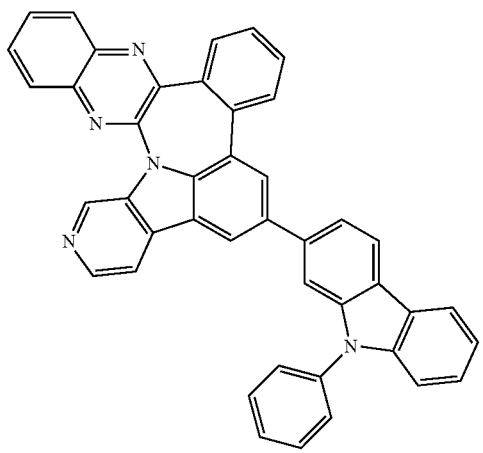
A-155
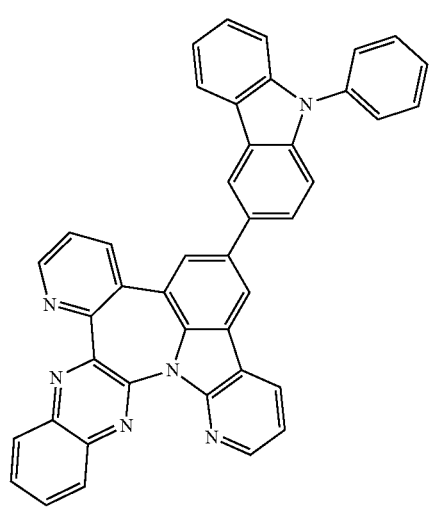
A-158
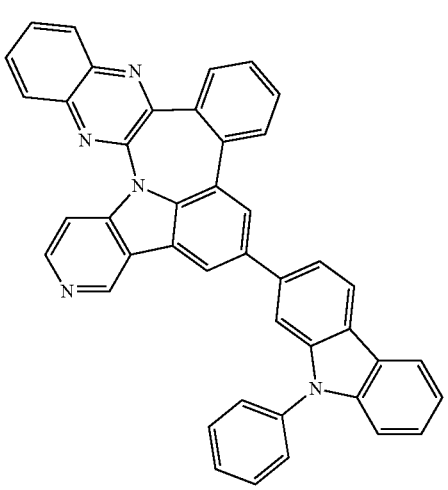
A-156
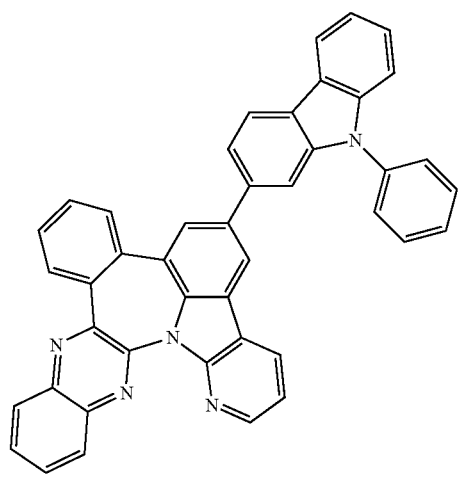
A-159
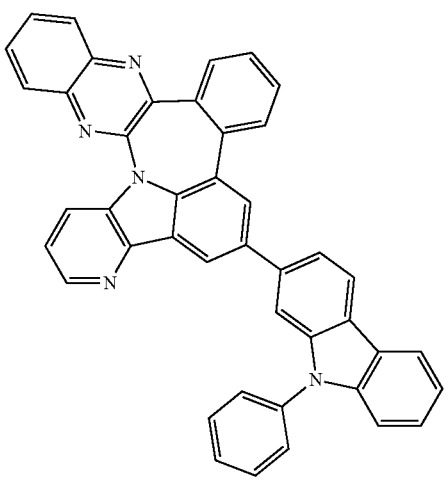

A-160
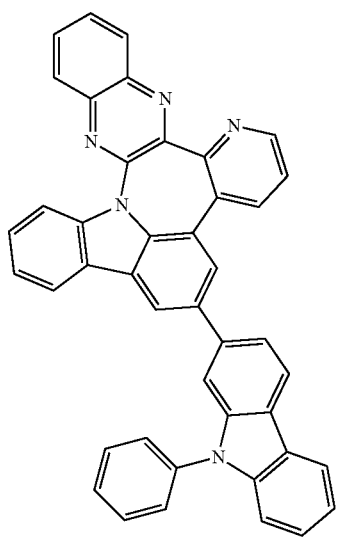
A-161
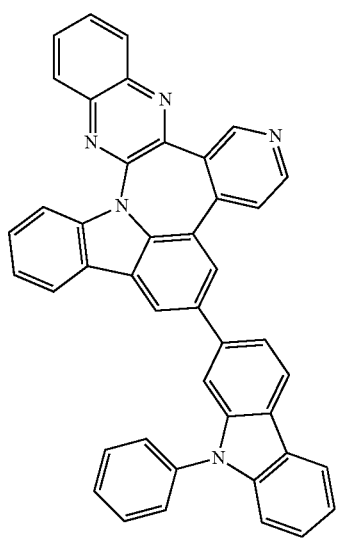
A-162
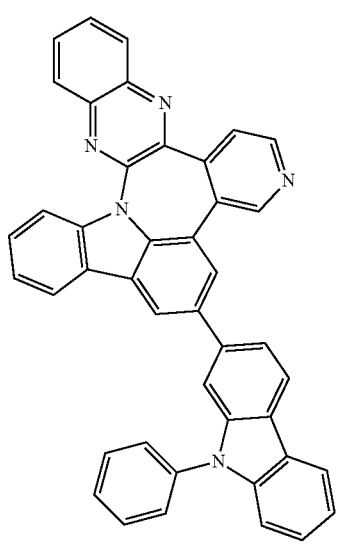
A-163
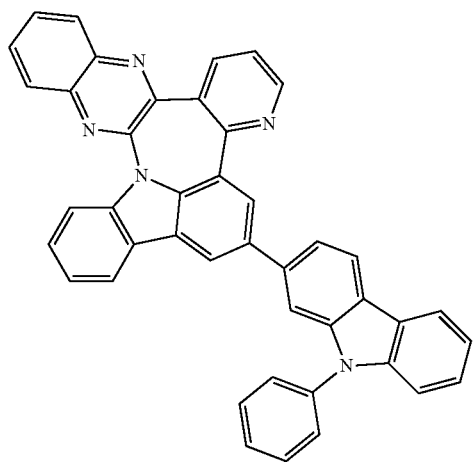
A-164
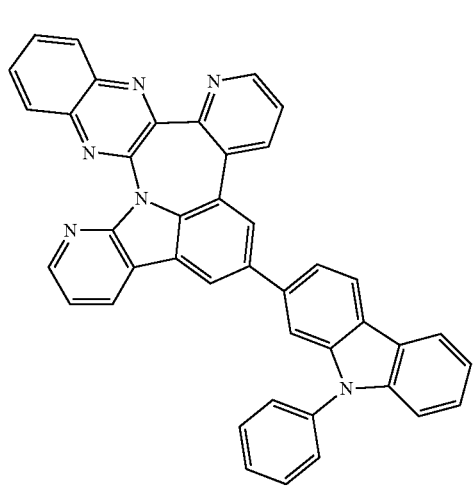
A-165
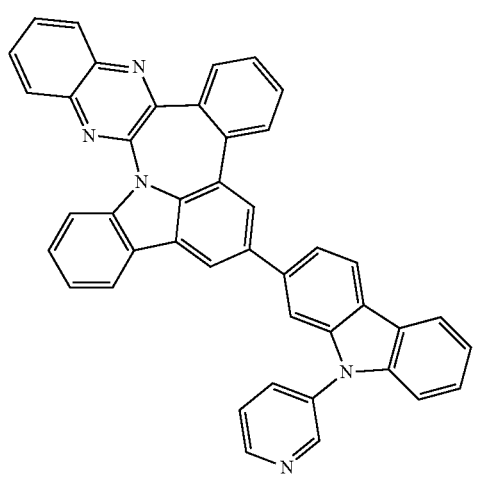

A-166
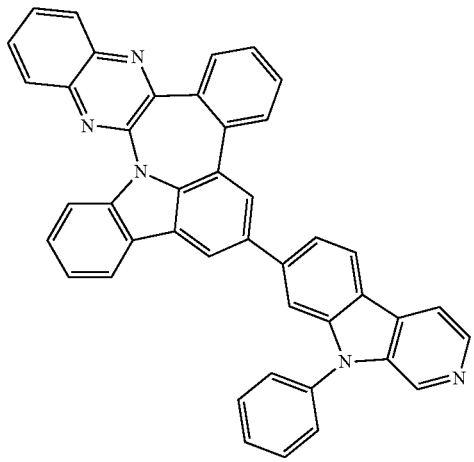
A-167
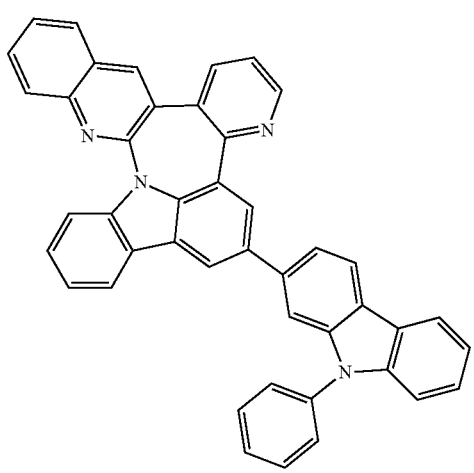
A-169
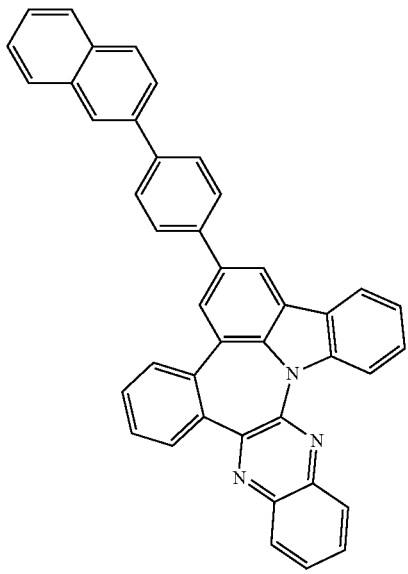
A-170
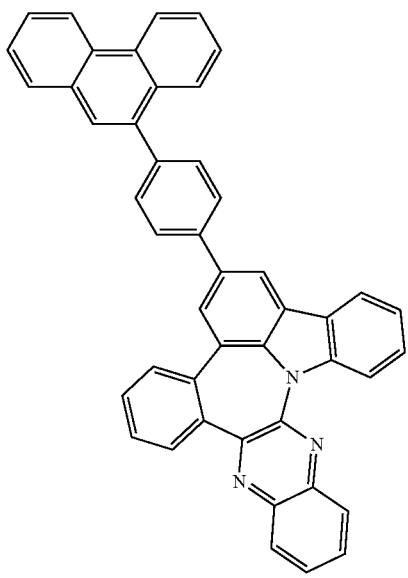
A-168

A-171
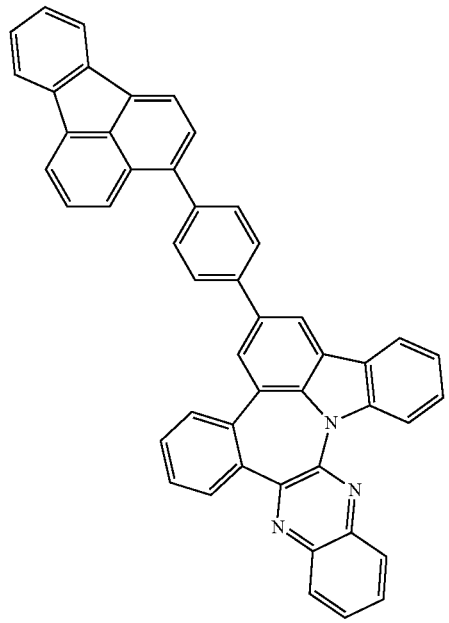
A-172
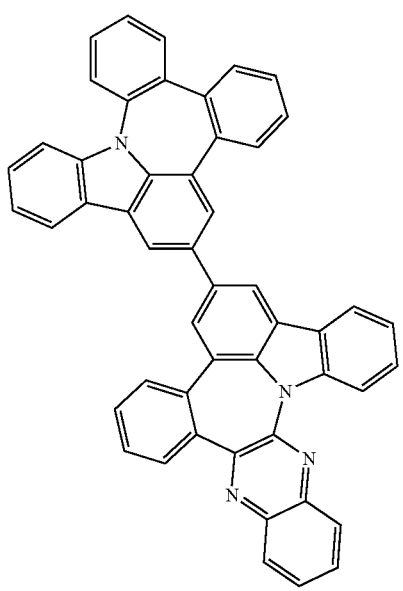
A-173
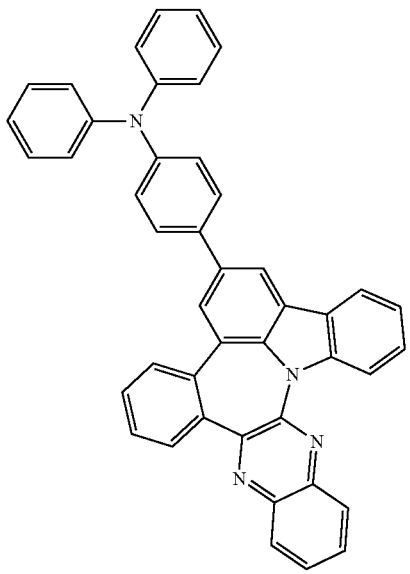
A-174
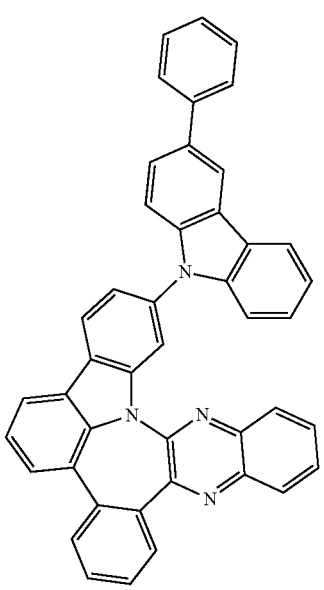
A-175
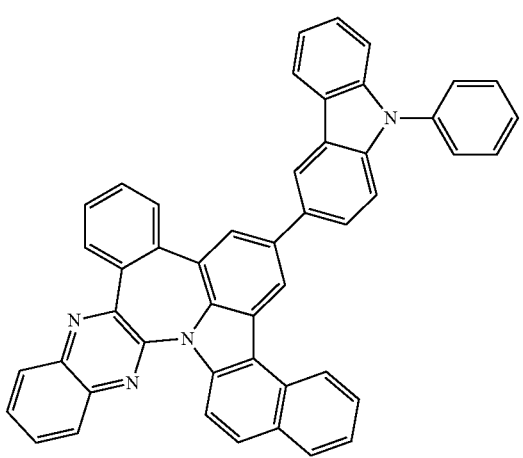

A-176
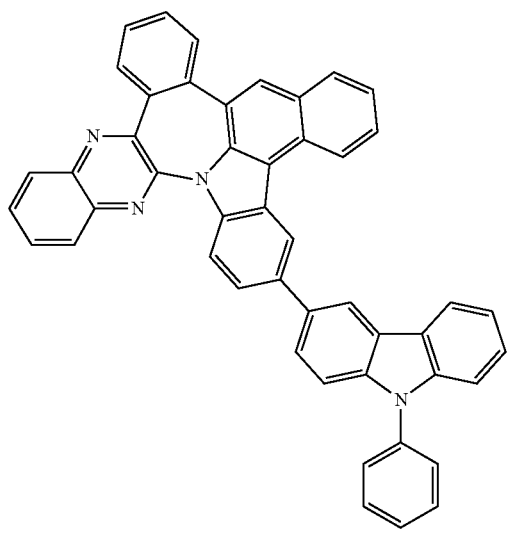
A-177
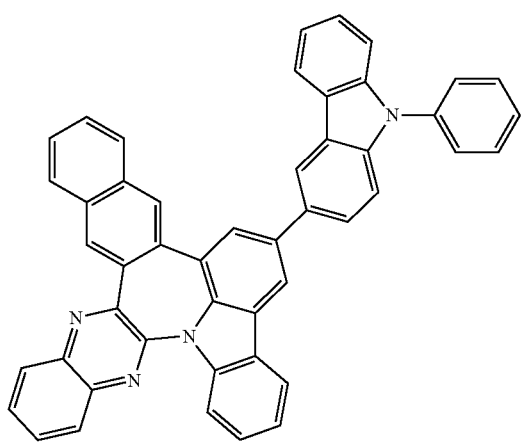
A-178
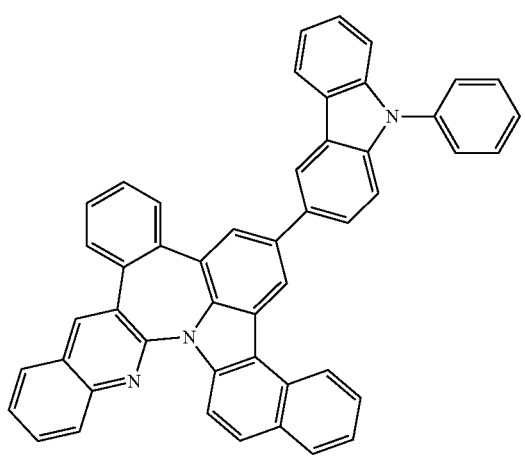
A-179
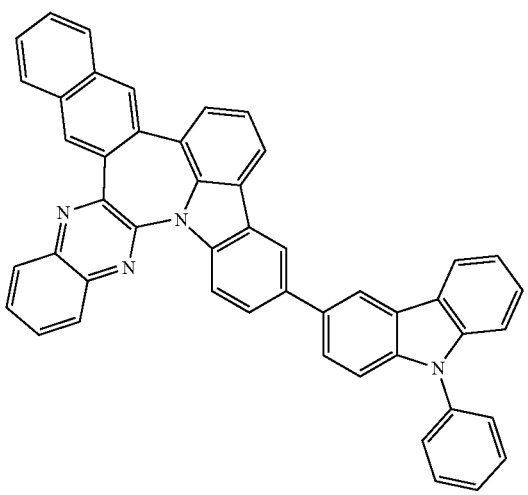
A-180
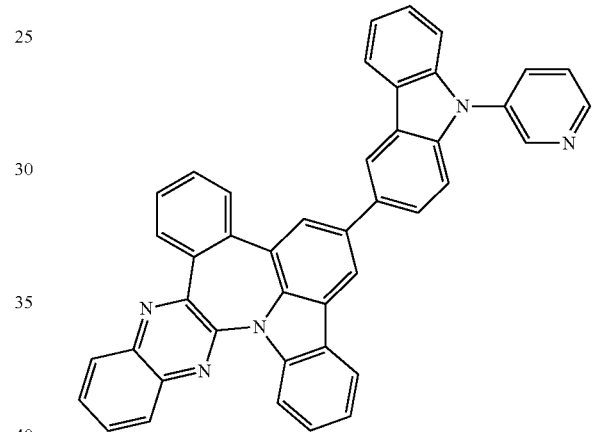
The organic electroluminescent compound of the present disclosure can be prepared by a synthetic method known to one skilled in the art. For example, it can be prepared according to the following reaction scheme 1.
[Reaction Scheme 1]
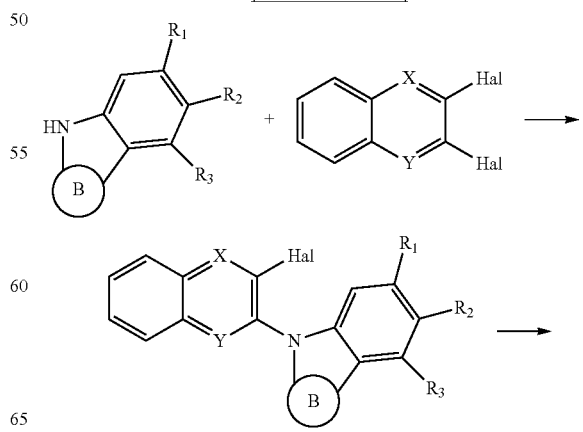

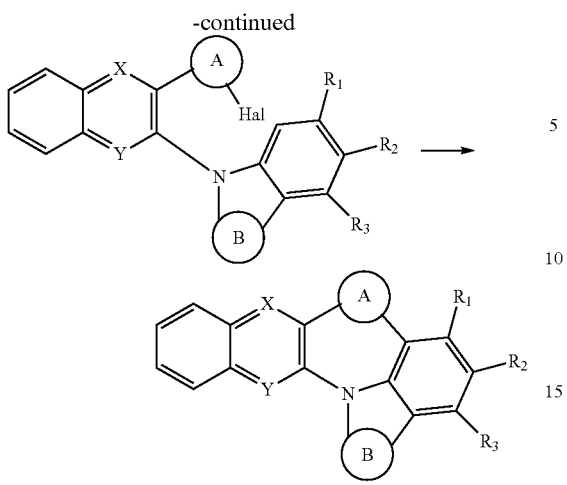

wherein $R_1$ to $R_3$, ring A, ring B, X, and Y are as defined in formula 1 above, and Hal represents a halogen.

The present disclosure provides an organic electroluminescent material comprising the organic electroluminescent compound of formula 1, and an organic electroluminescent device comprising the material.

The material may consist of the organic electroluminescent compound of the present disclosure. Otherwise, the material may further comprise a conventional compound(s) which has been comprised for an organic electroluminescent material. The organic electroluminescent material may be preferably a host material, more preferably a phosphorescent host material, and even more preferably a phosphorescent red light-emitting host material. When the organic electroluminescent material is used as a host material, it may further comprise the following second host material, in addition to the compound of formula 1.

The organic electroluminescent device of the present disclosure may comprise a first electrode, a second electrode, and at least one organic layer disposed between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron buffering layer, and an electron blocking layer.

The organic electroluminescent compound of formula 1 of the present disclosure may be comprised in the light-emitting layer. When used in the light-emitting layer, the organic electroluminescent compound of the present disclosure may be comprised as a host material, preferably a phosphorescent host material, and more preferably a phosphorescent red light-emitting host material. Preferably, the light-emitting layer may further comprise at least one or more dopants, and, if necessary, a second host material other than the compound of formula 1 of the present disclosure. The weight ratio between the first host material and the second host material is in the range of 1:99 to 99:1.

The second host material may be from any of the known phosphorescent hosts. The material selected from the group consisting of the compounds of formulae 11 to 15 is preferably the second host material in view of luminous efficiency.

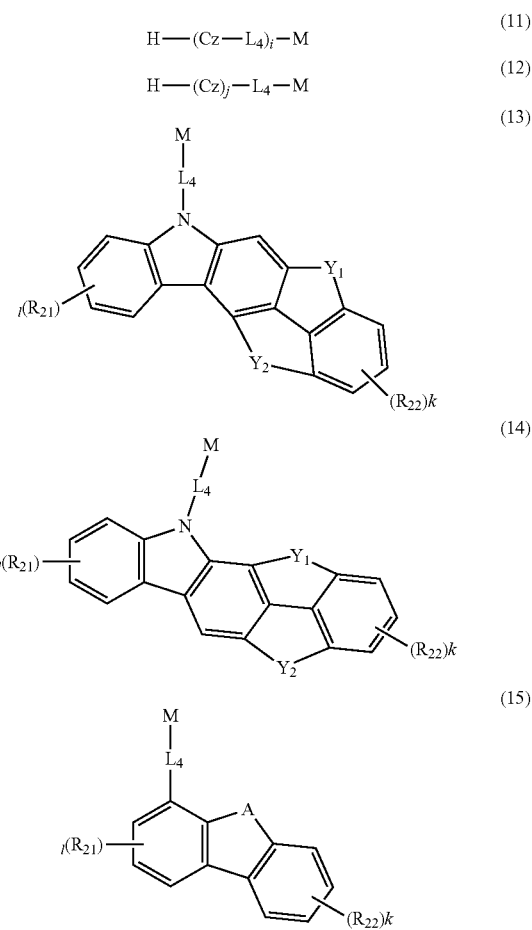

wherein Cz represents the following structure:

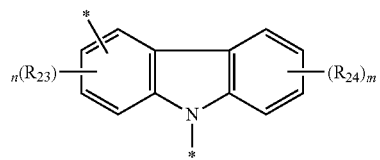

A represents —O— or —S—;
$R_{21}$ to $R_{24}$, each independently, represent hydrogen, deuterium, a halogen, a substituted or unsubstituted (C1-C30) alkyl, a substituted or unsubstituted (C6-C30)aryl, a substituted or unsubstituted 5- to 30-membered heteroaryl or —$SiR_{25}R_{26}R_{27}$; $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted 5- to 30-membered heteroarylene; M represents a substituted or unsubstituted (C6-C30)aryl, or a substituted or unsubstituted 5- to 30-membered heteroaryl; $Y_1$ and $Y_2$, each independently, represent —O—, —S—, —N($R_{41}$)—, or —C($R_{42}$)($R_{43}$)—, and $Y_1$ and $Y_2$ are not present simultaneously; $R_{41}$ to $R_{43}$, each independently, represent a substituted or unsubstituted (C1-C30)alkyl, a substituted or unsubstituted (C6-C30)aryl, or a substituted or unsubstituted 5- to 30-membered heteroaryl; $R_{42}$ and $R_{43}$ may be the same or different; i and j, each independently, represent an integer of 1 to 3; k, l, m, and n, each independently, represent an integer of 0 to 4; and where i, j, k, l, m, or n is an integer of 2 or more, each of (Cz-L$_4$), (Cz), R$_{21}$, R$_{22}$, R$_{23}$, or R$_{24}$ may be the same or different.
Specifically, the preferred second host material includes the following, but is not limited thereto.
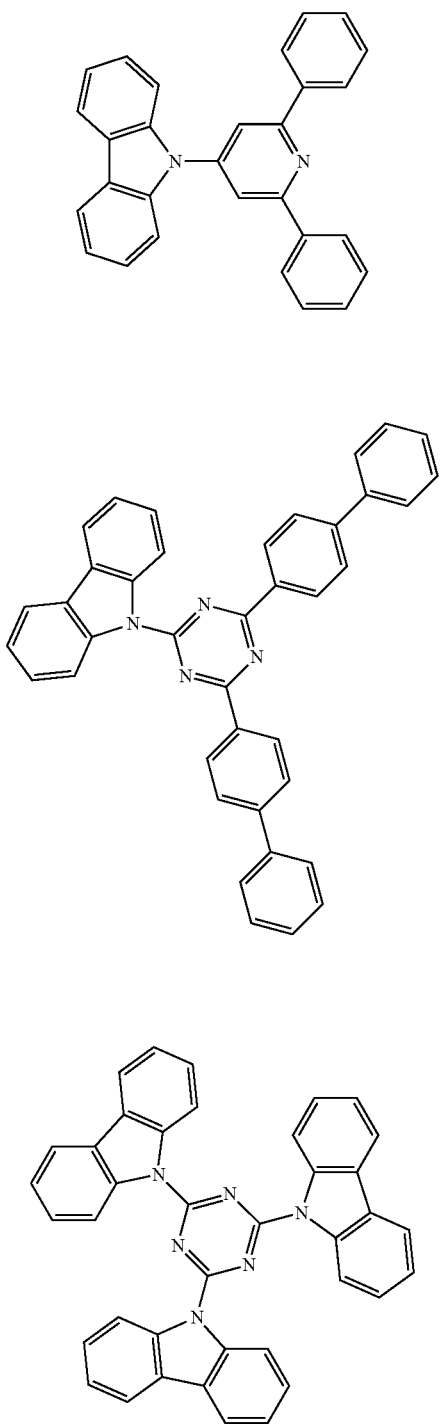
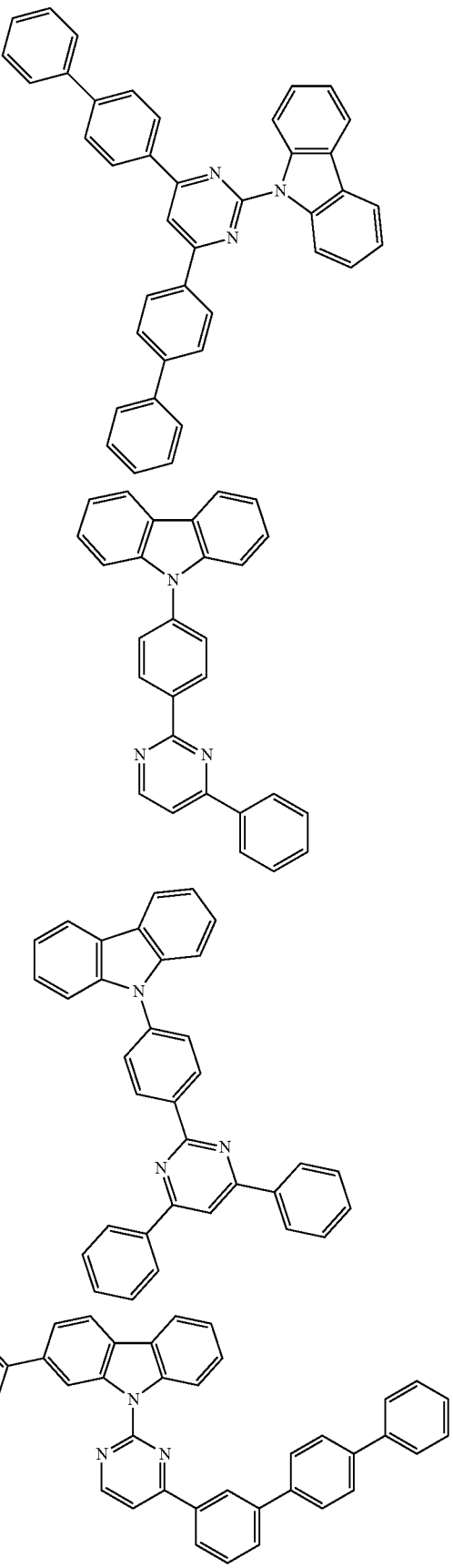

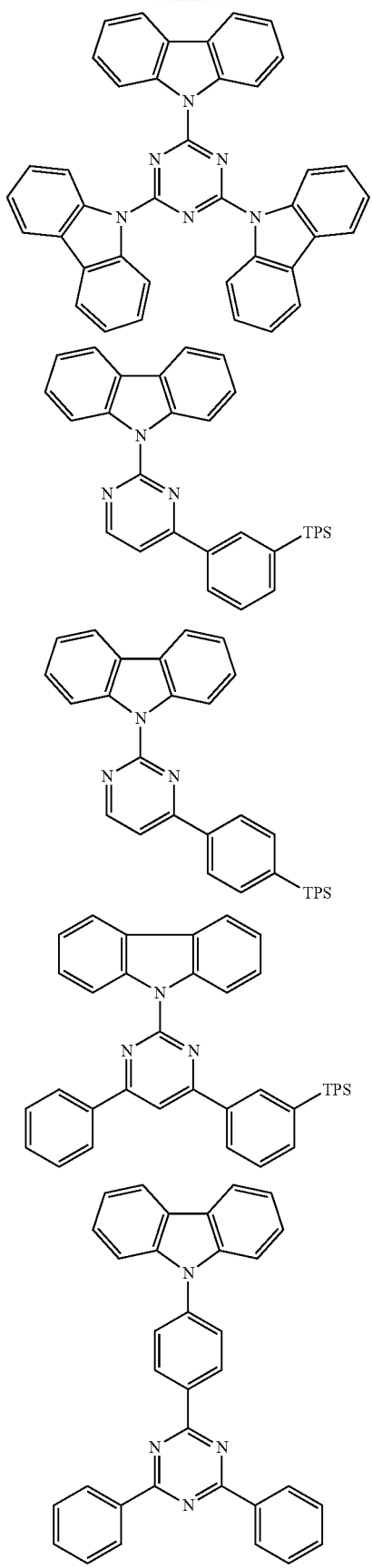
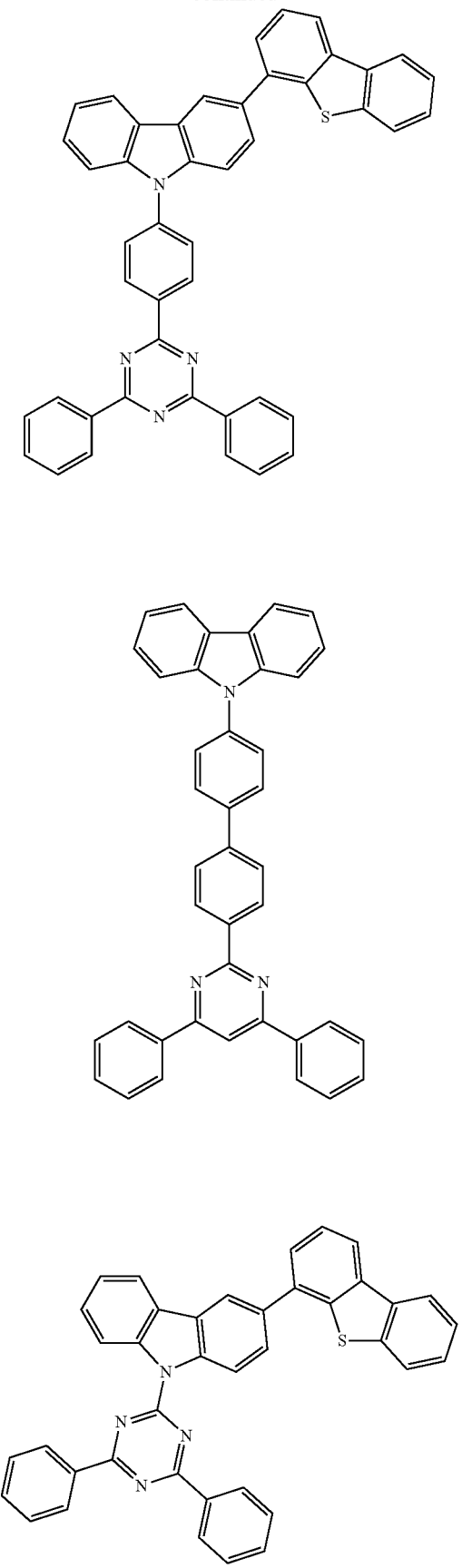

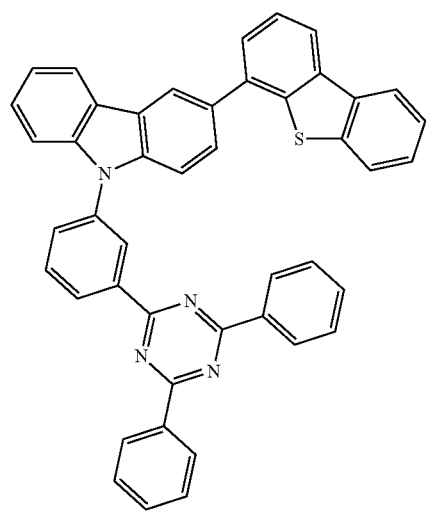
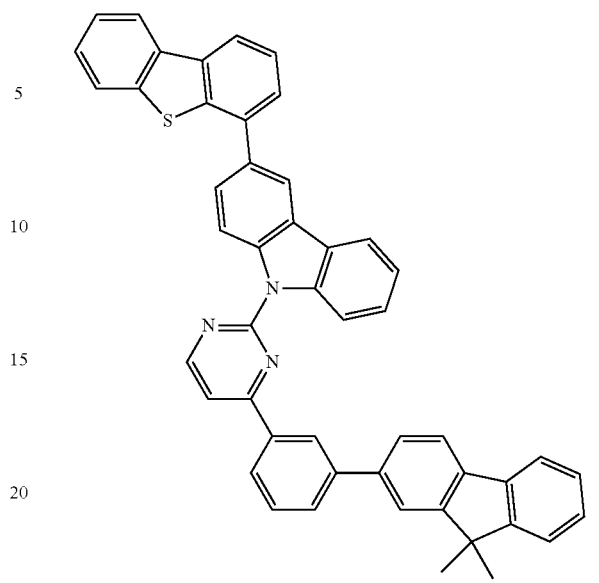
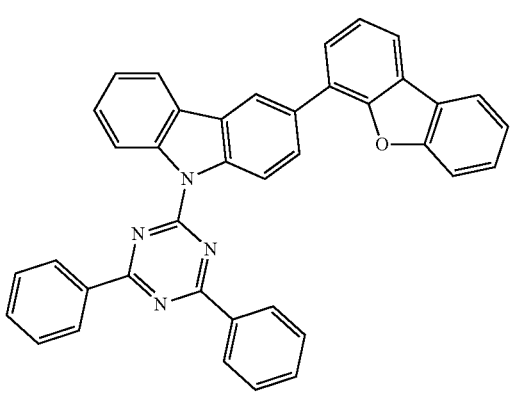
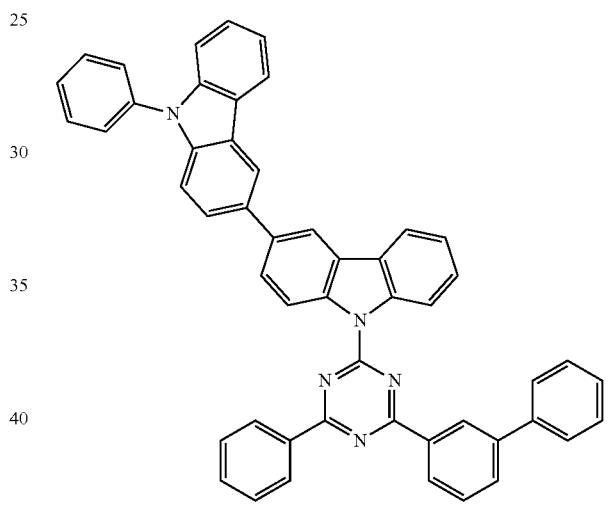
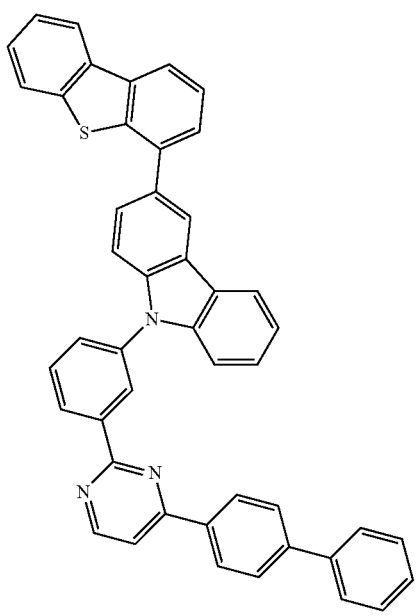
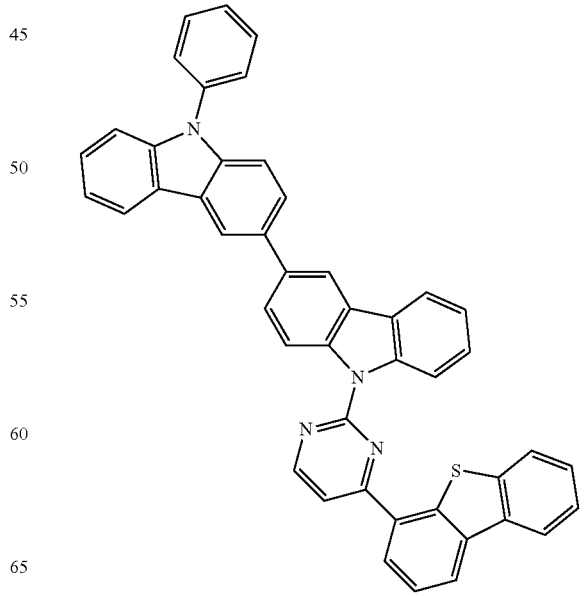

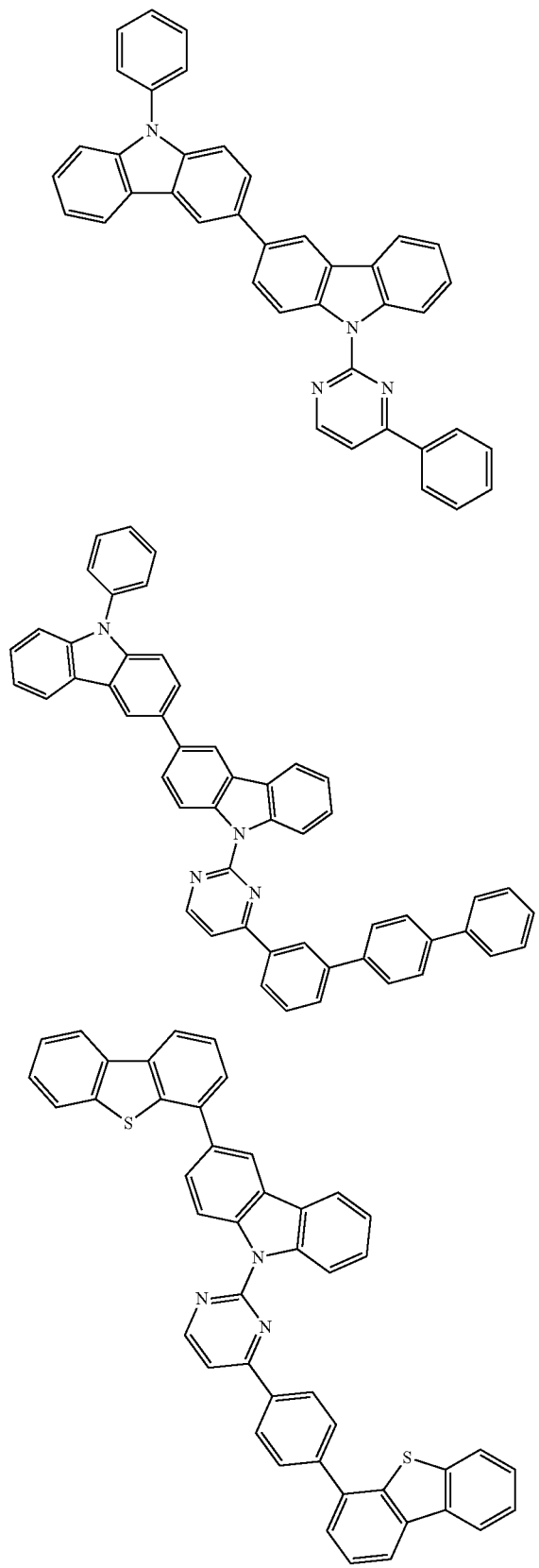
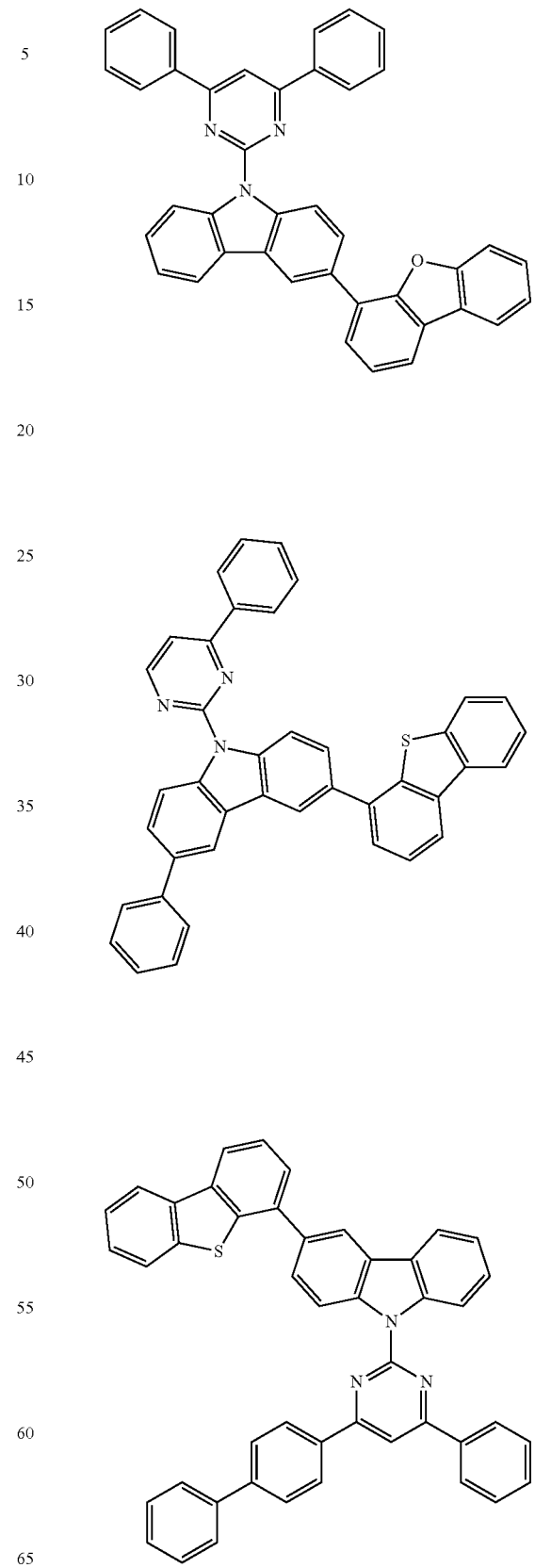

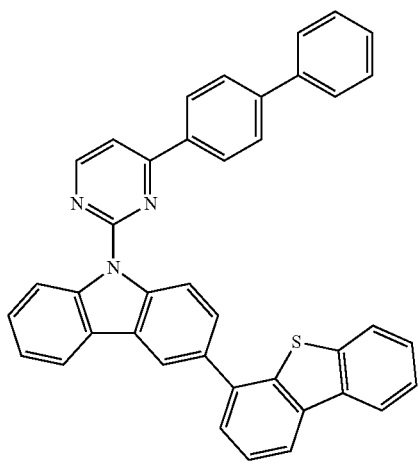
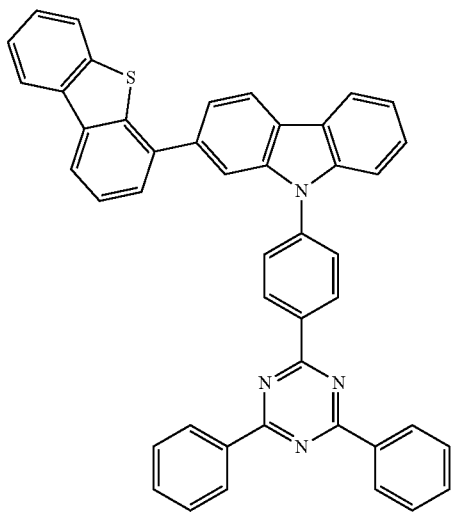
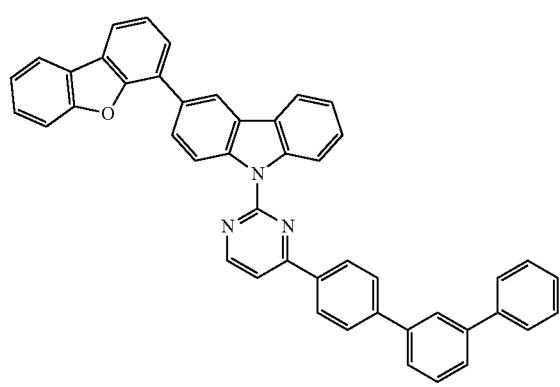
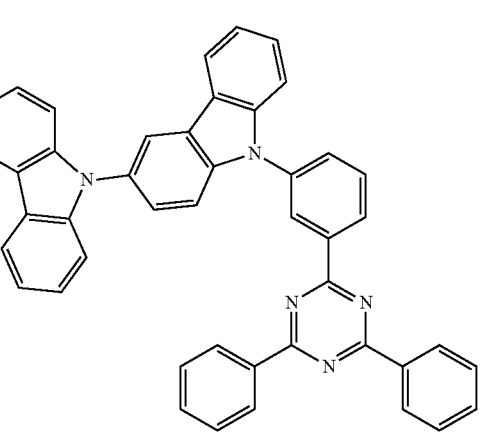
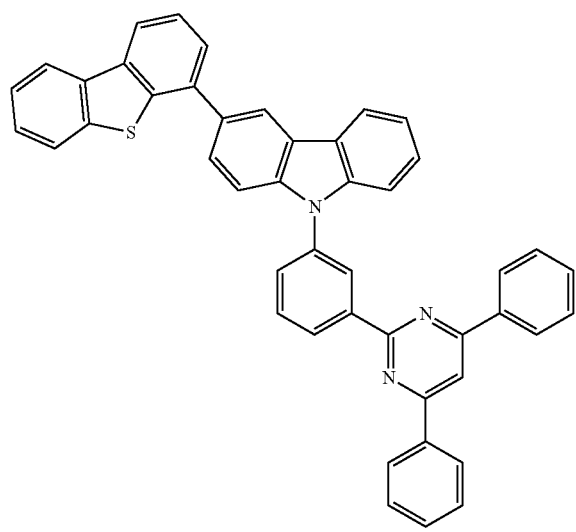
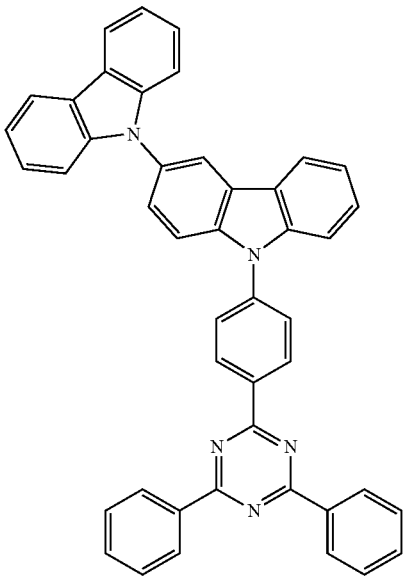

85
-continued
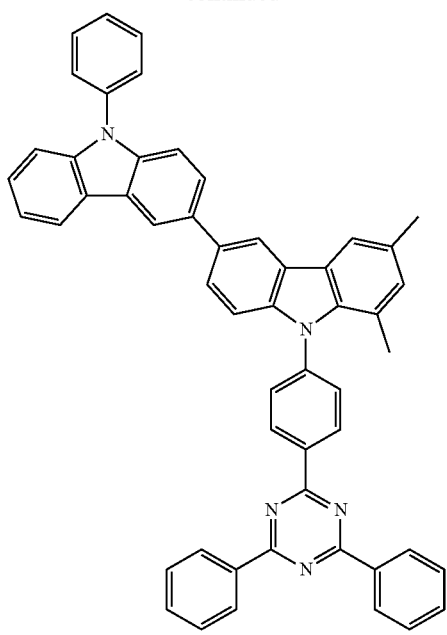
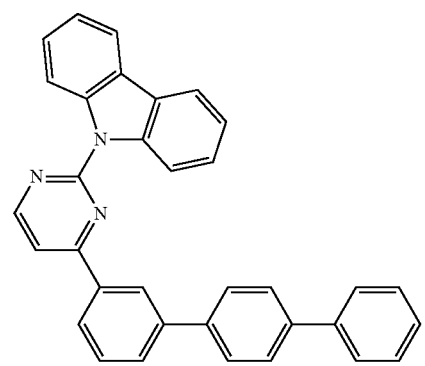
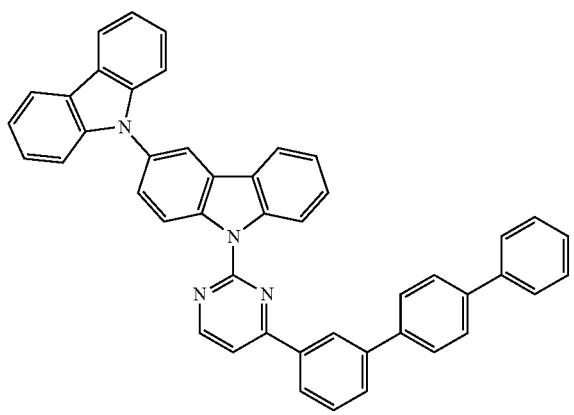
86
-continued
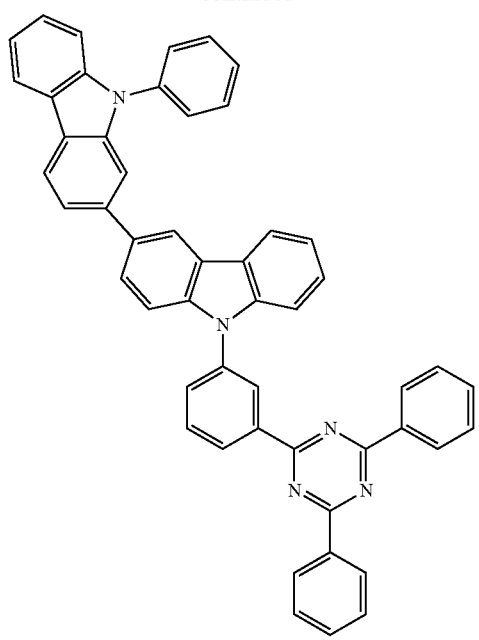
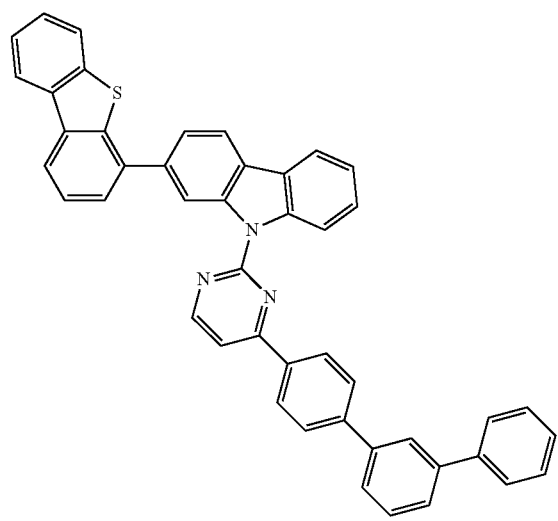
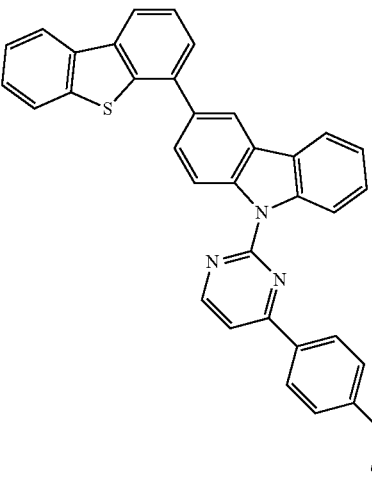

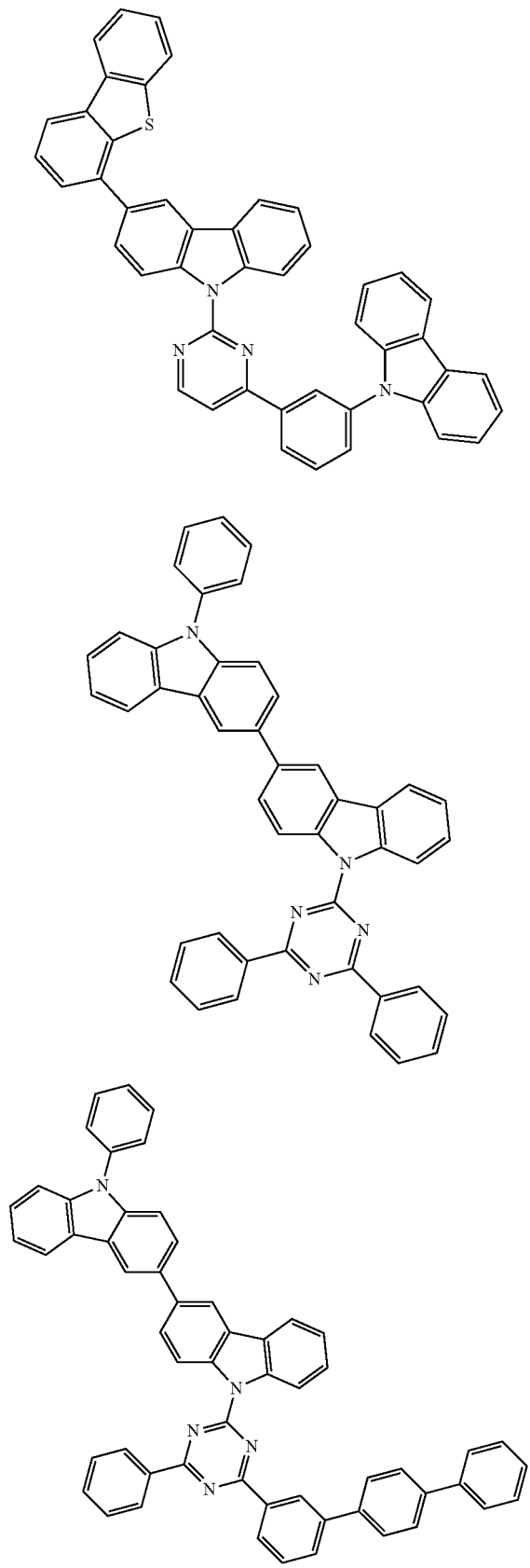
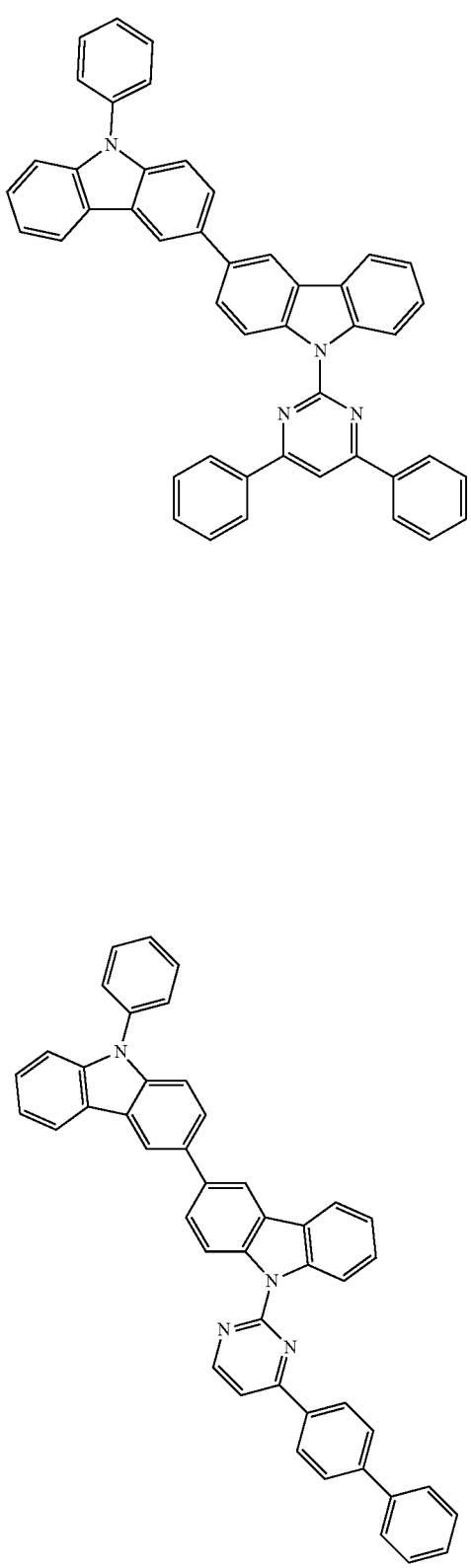

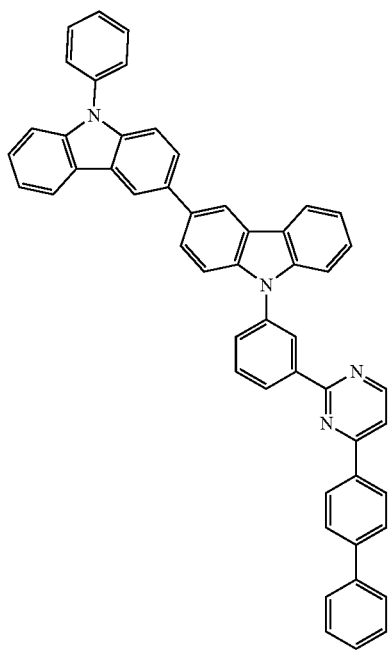
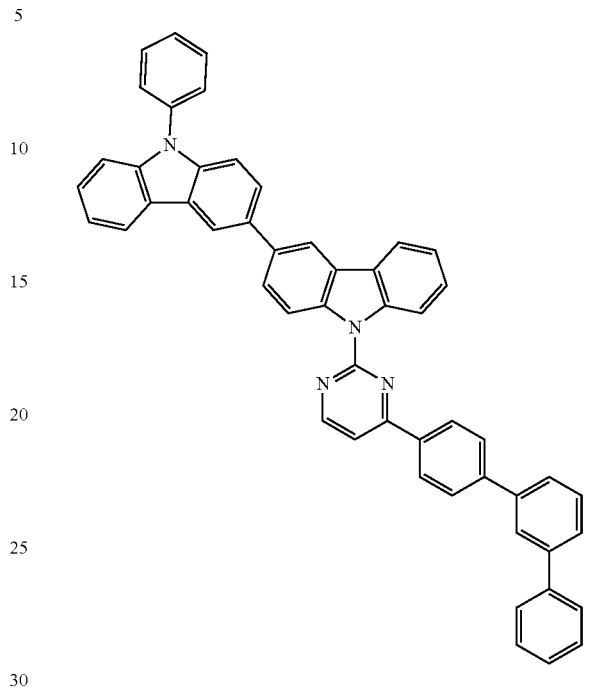
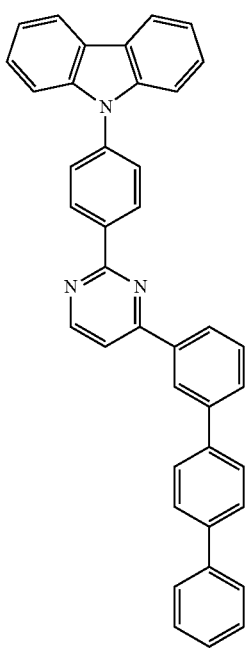
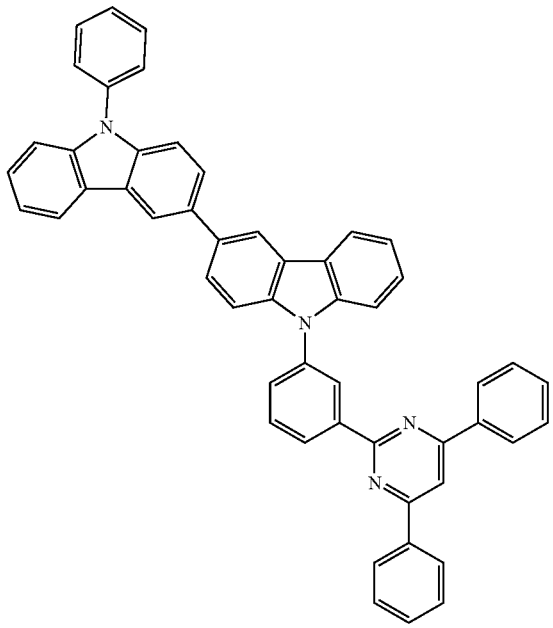

91
-continued
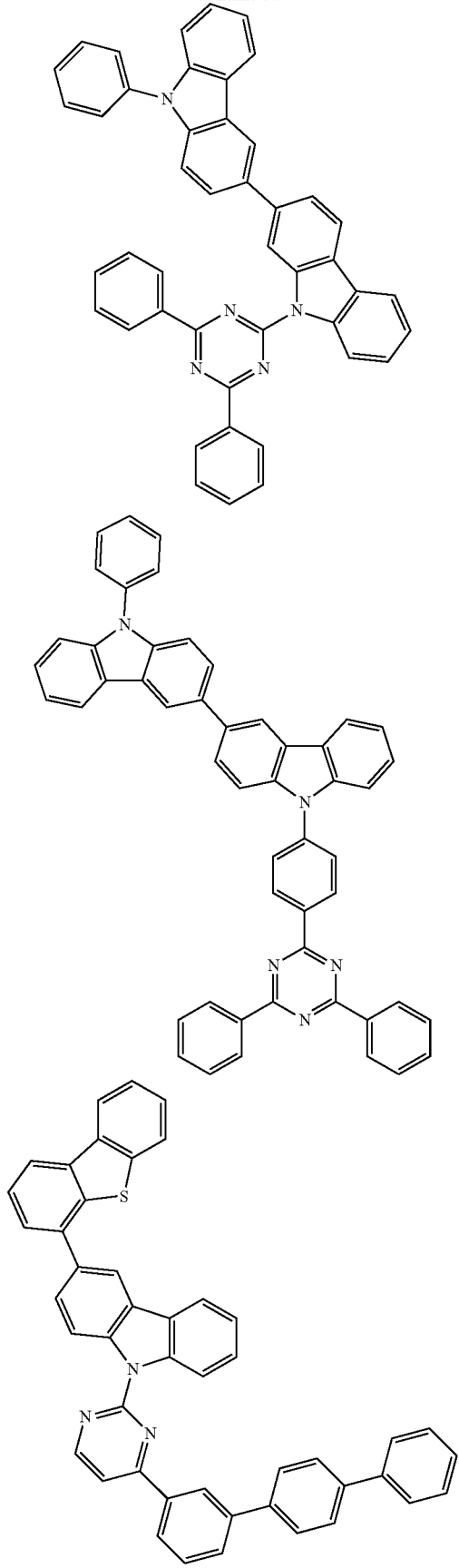
92
-continued
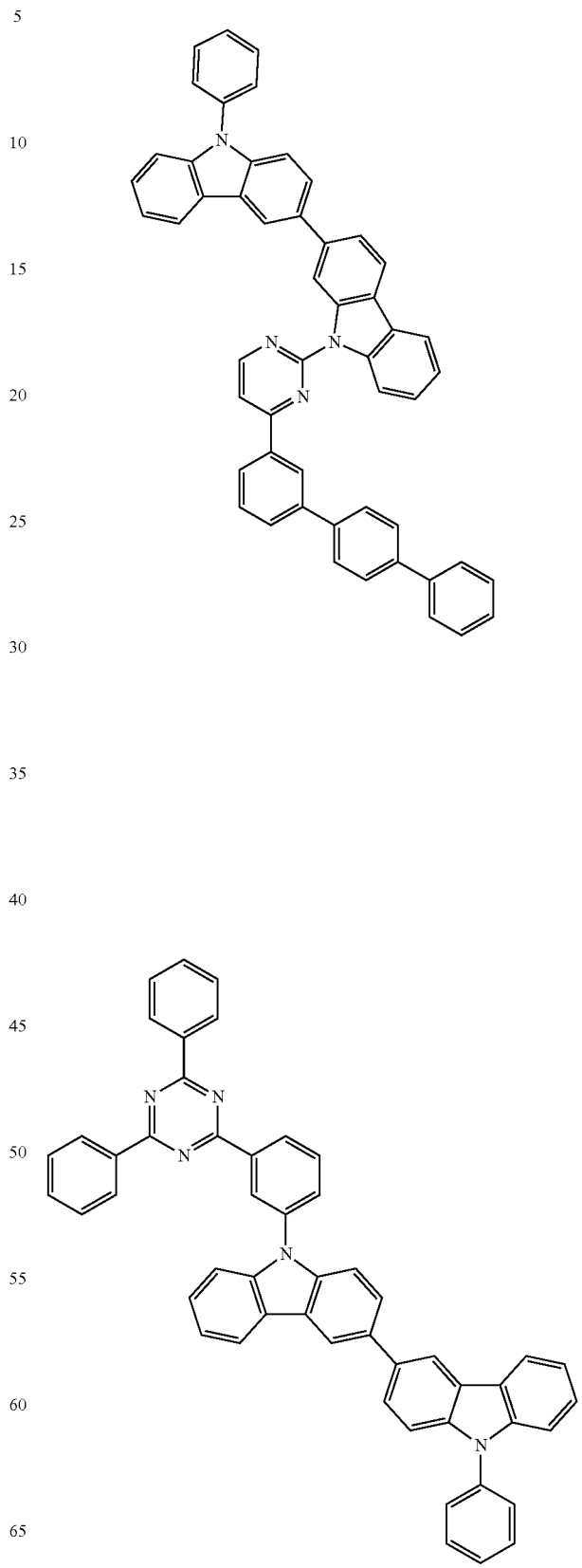

93
-continued
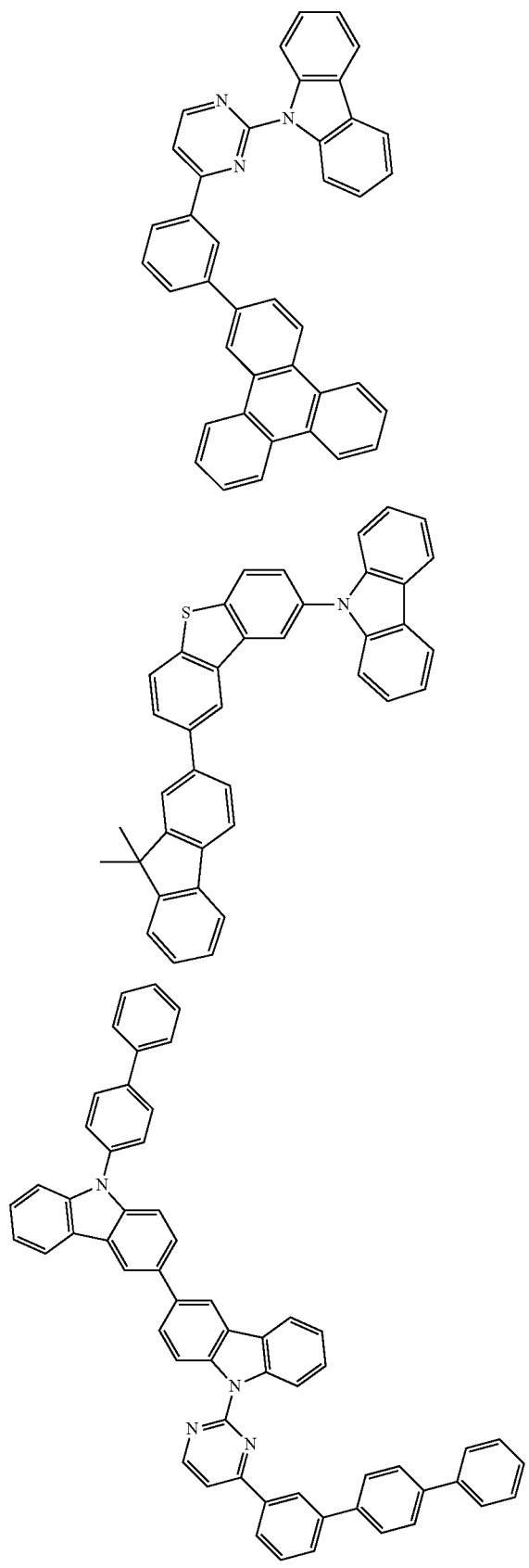
94
-continued
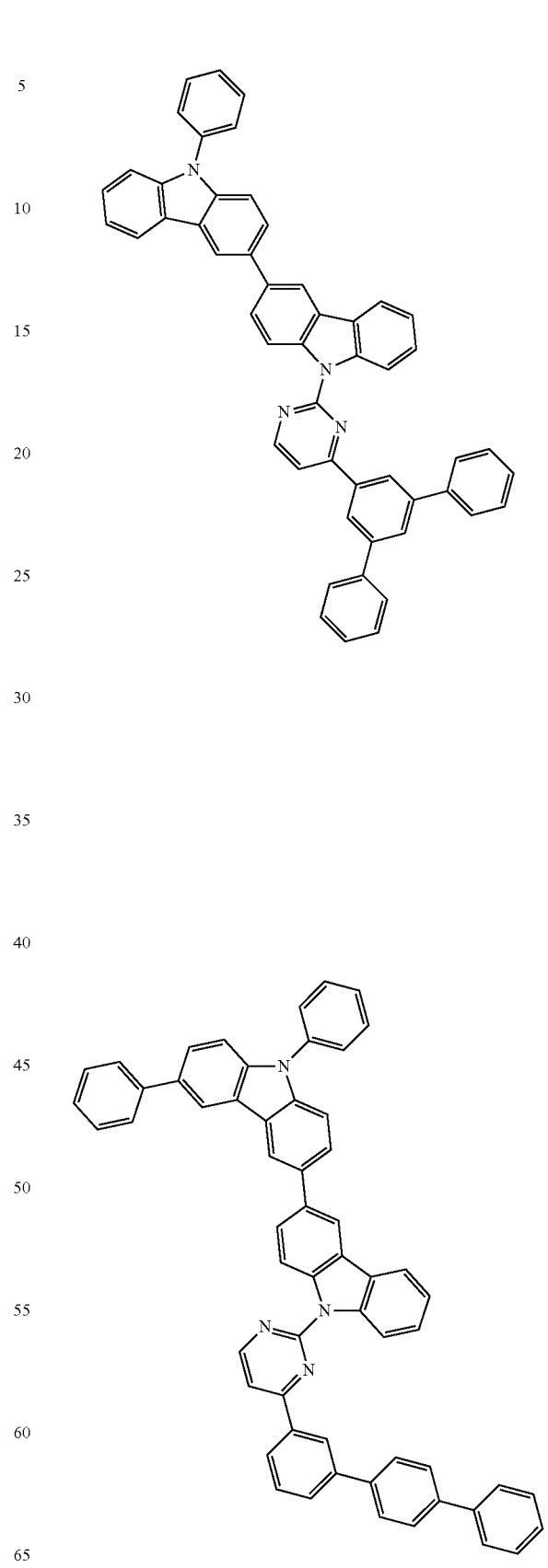

95
-continued
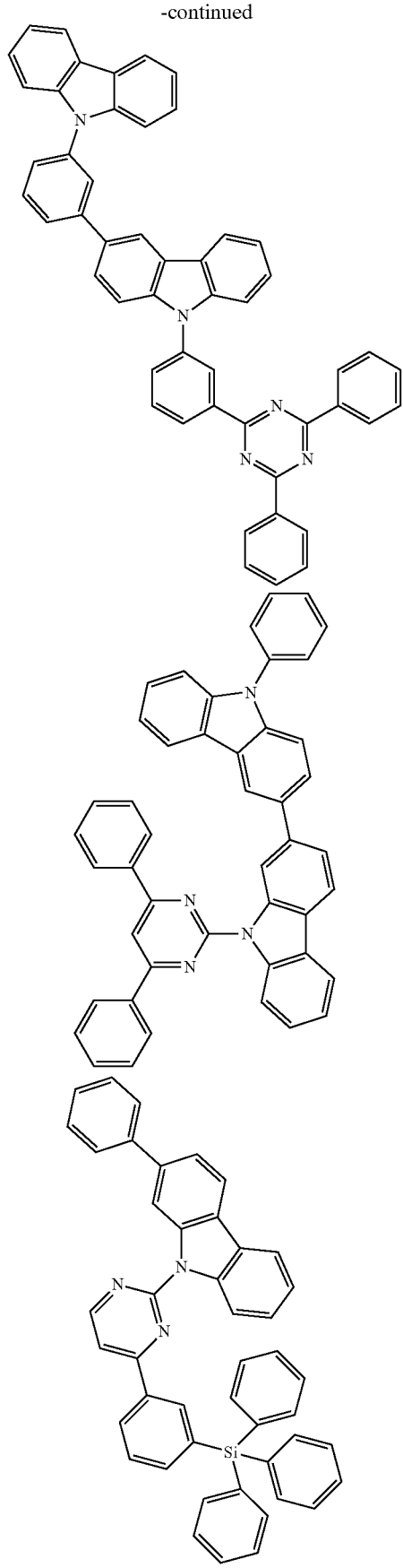
96
-continued
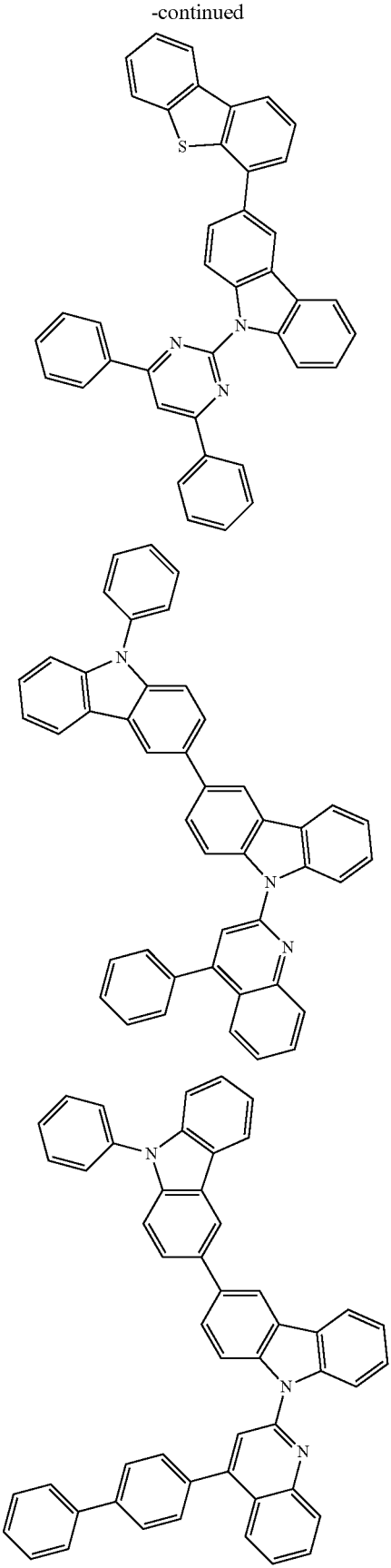

-continued
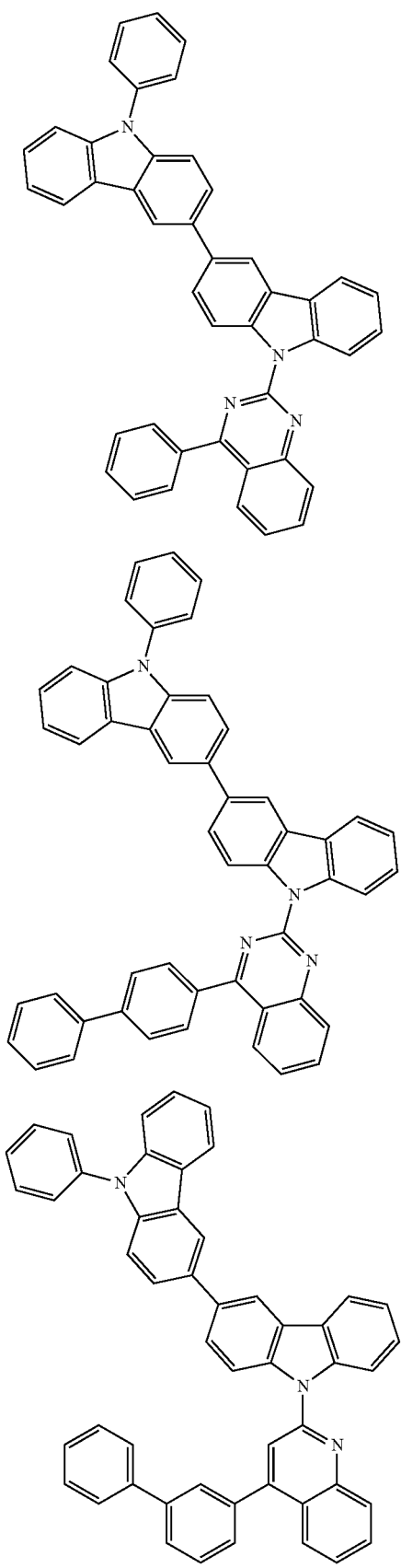
-continued
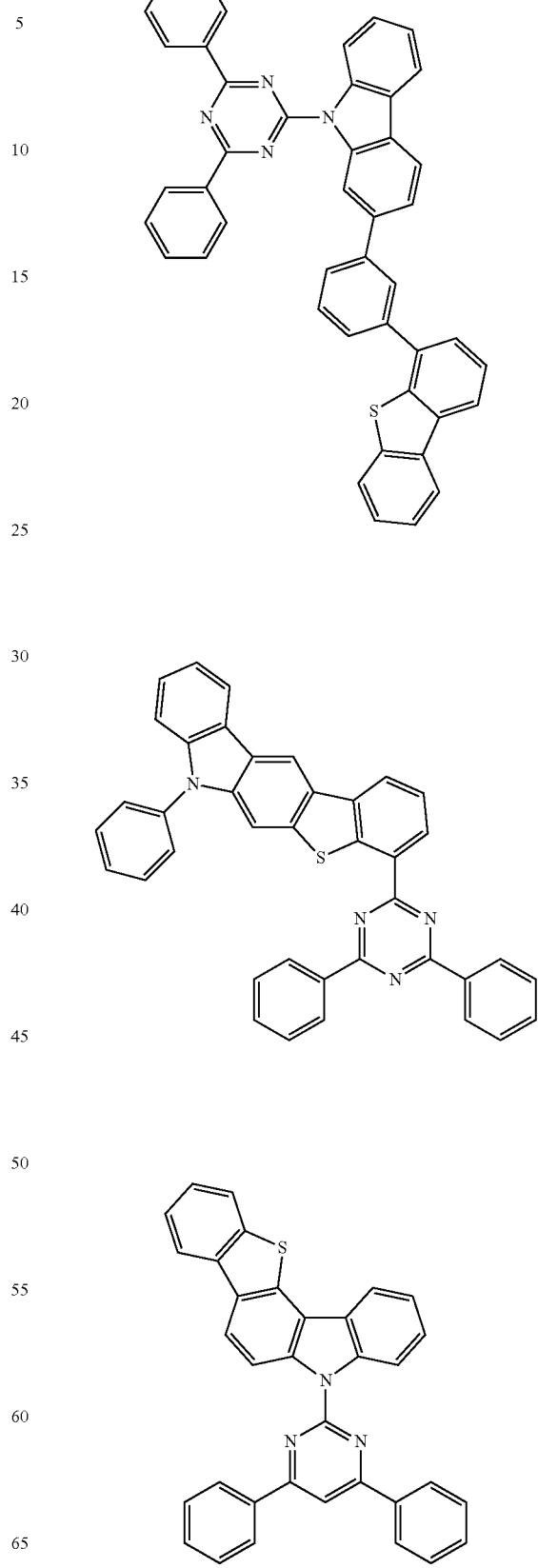

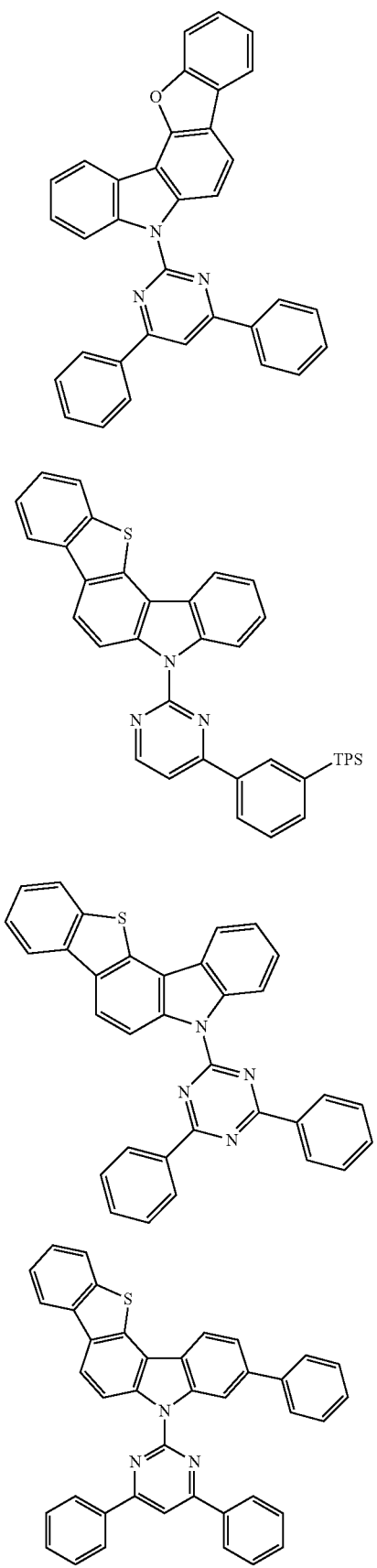
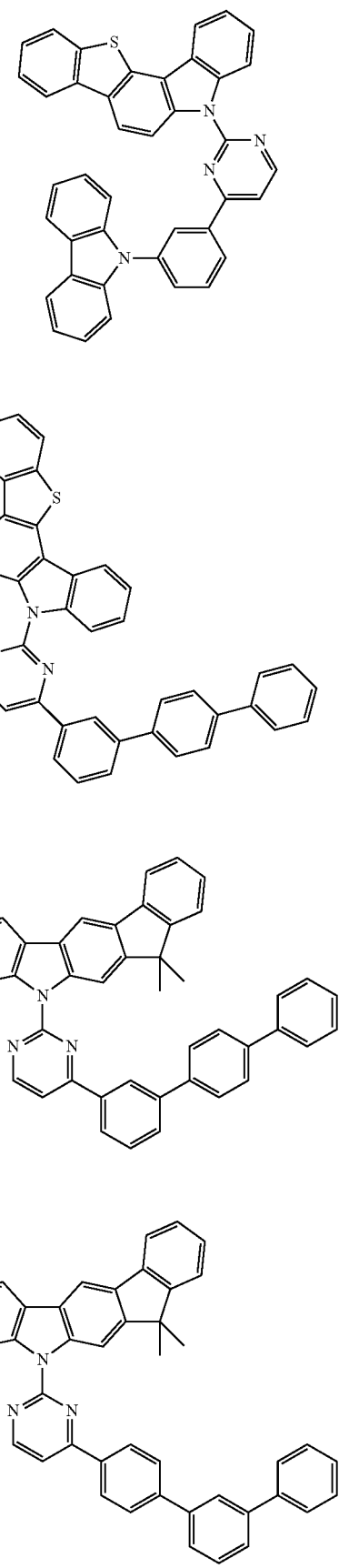

101
-continued
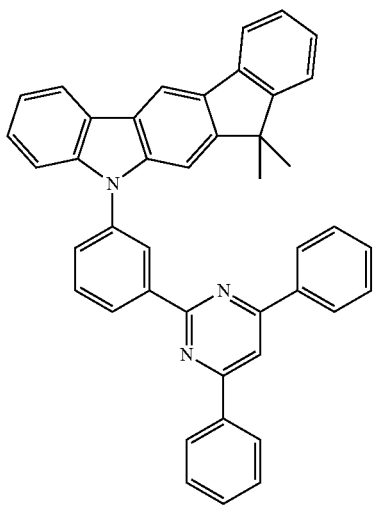
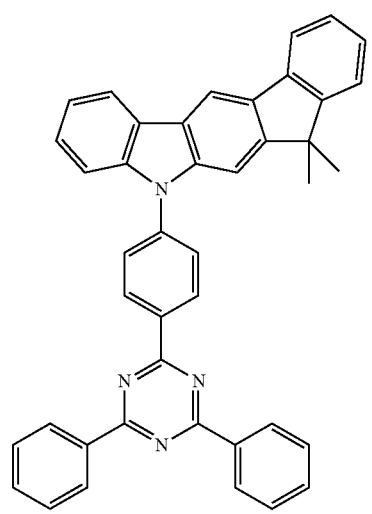
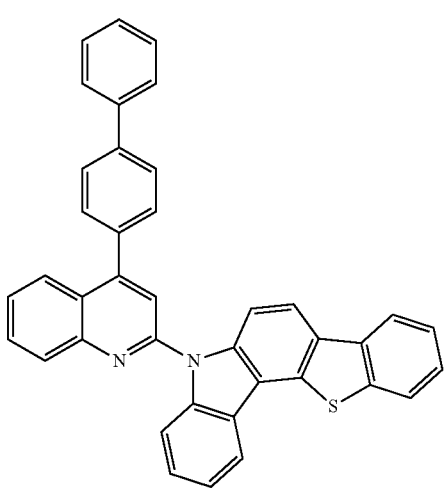
102
-continued
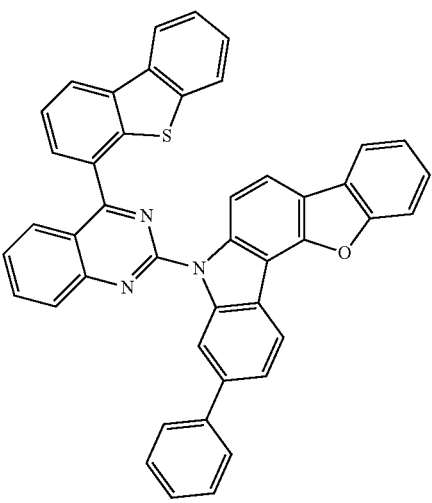
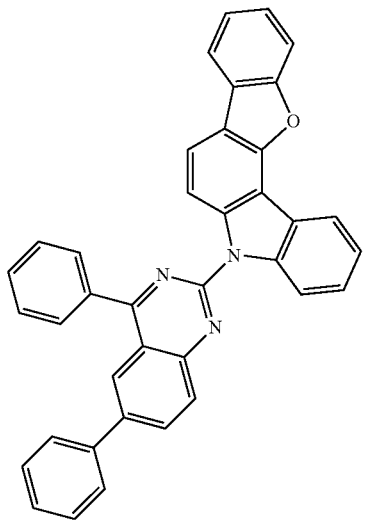
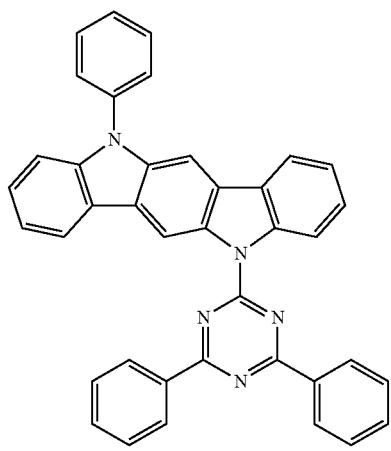

103
-continued
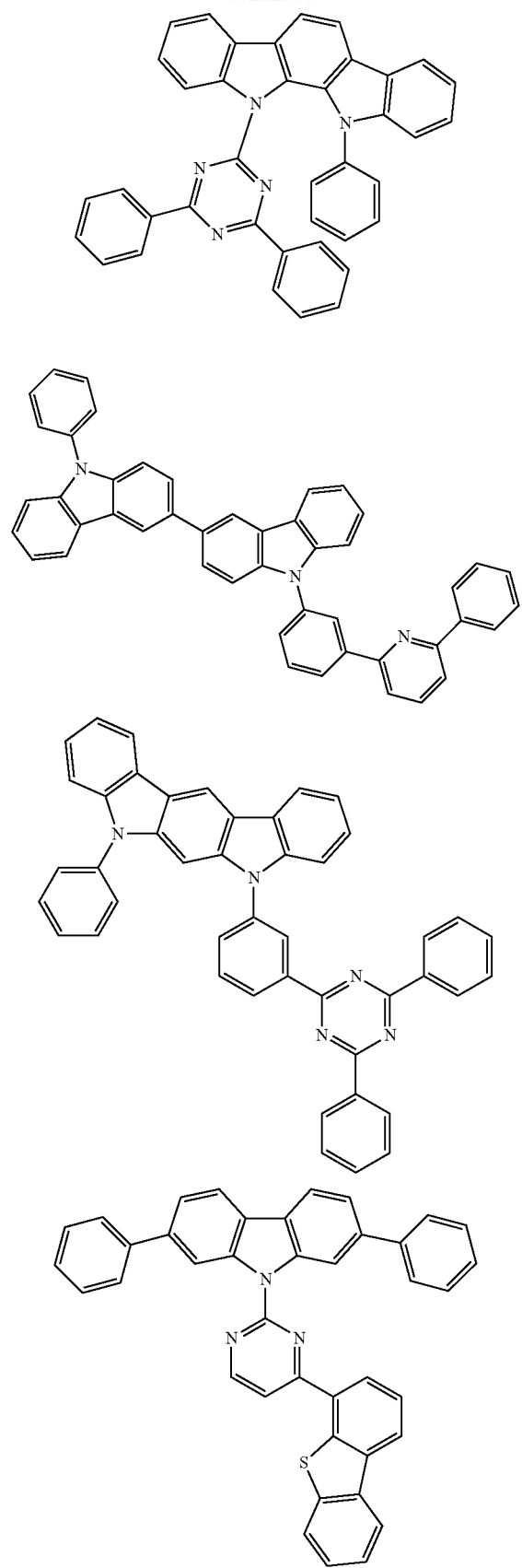
104
-continued
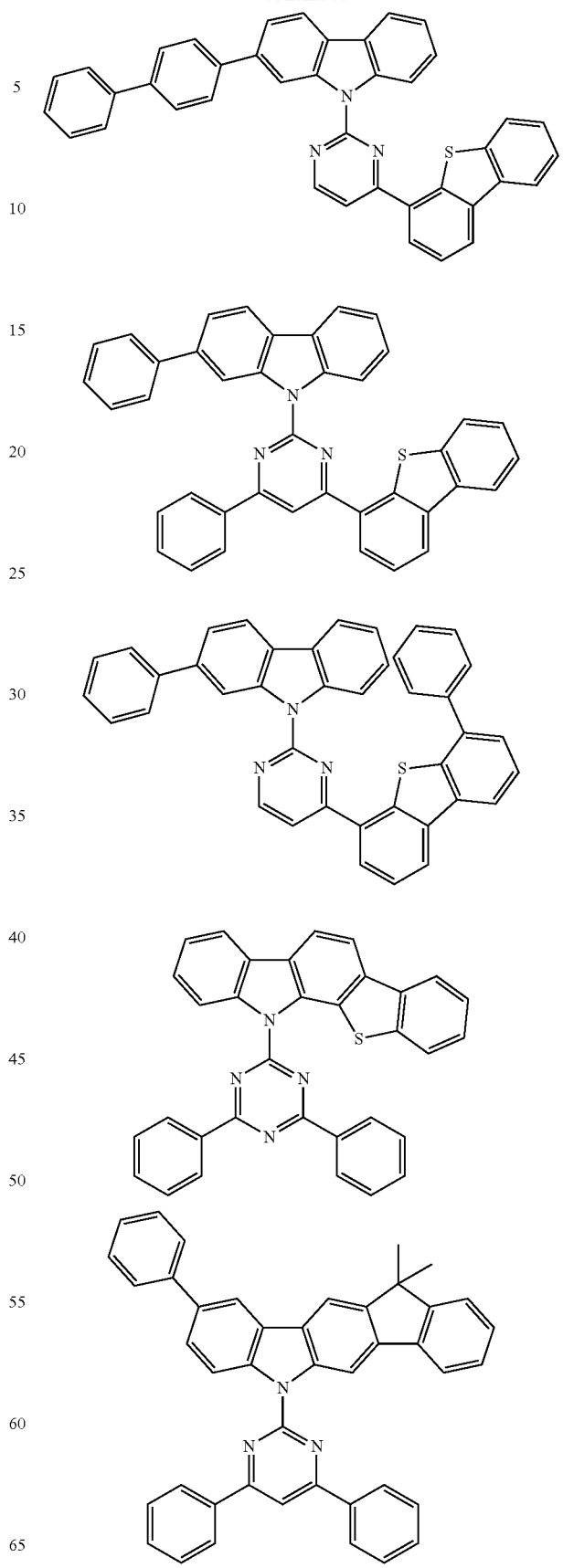

105
-continued
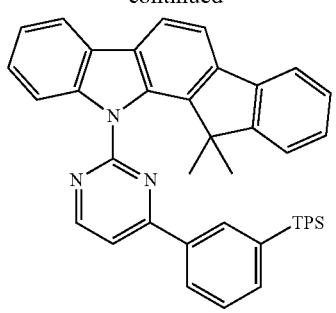
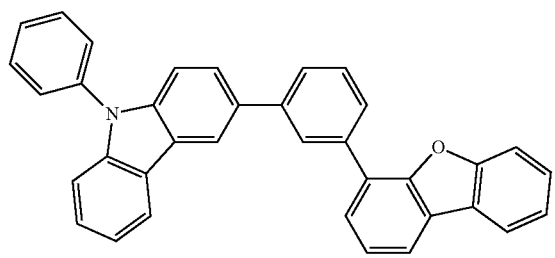
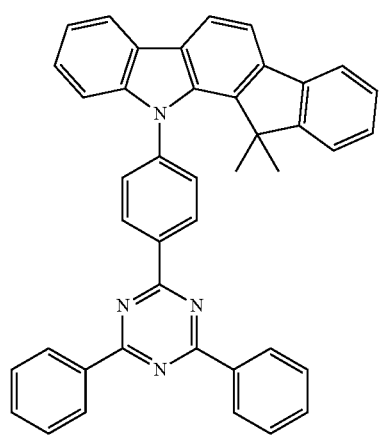
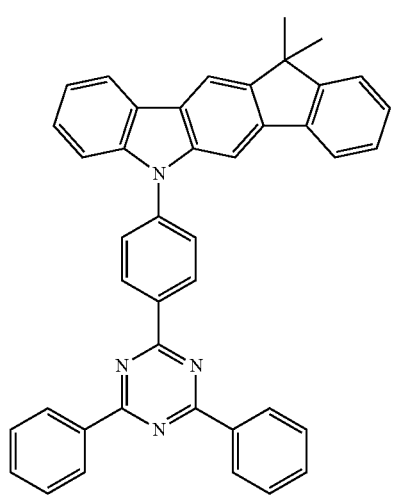
106
-continued
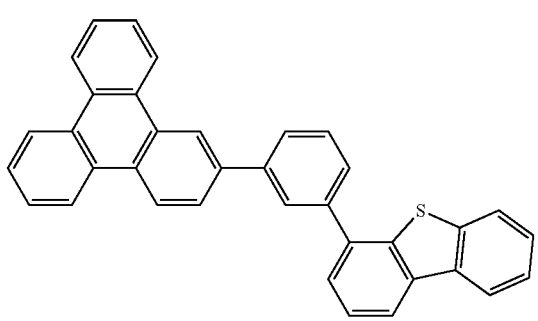
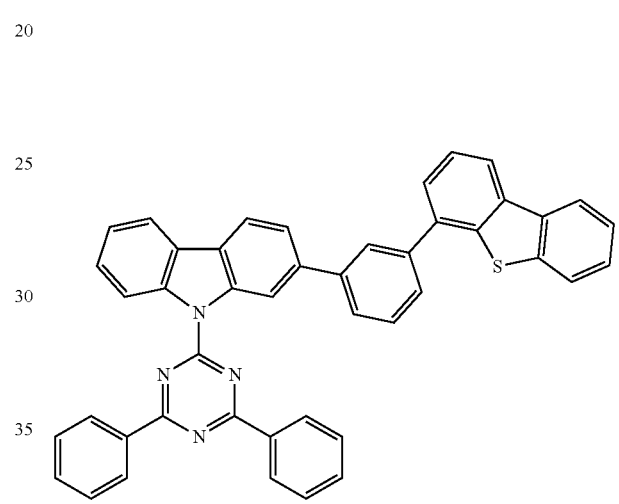
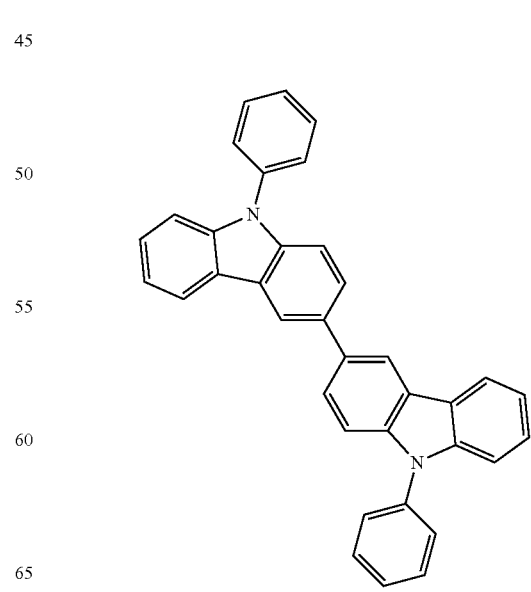

107
-continued
108
-continued
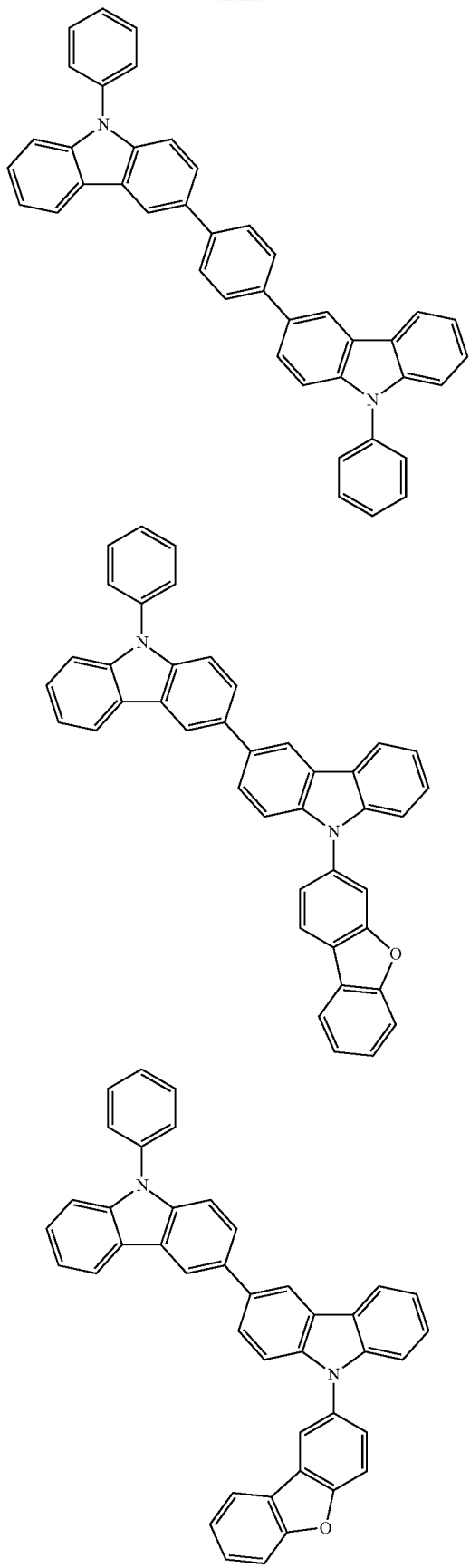
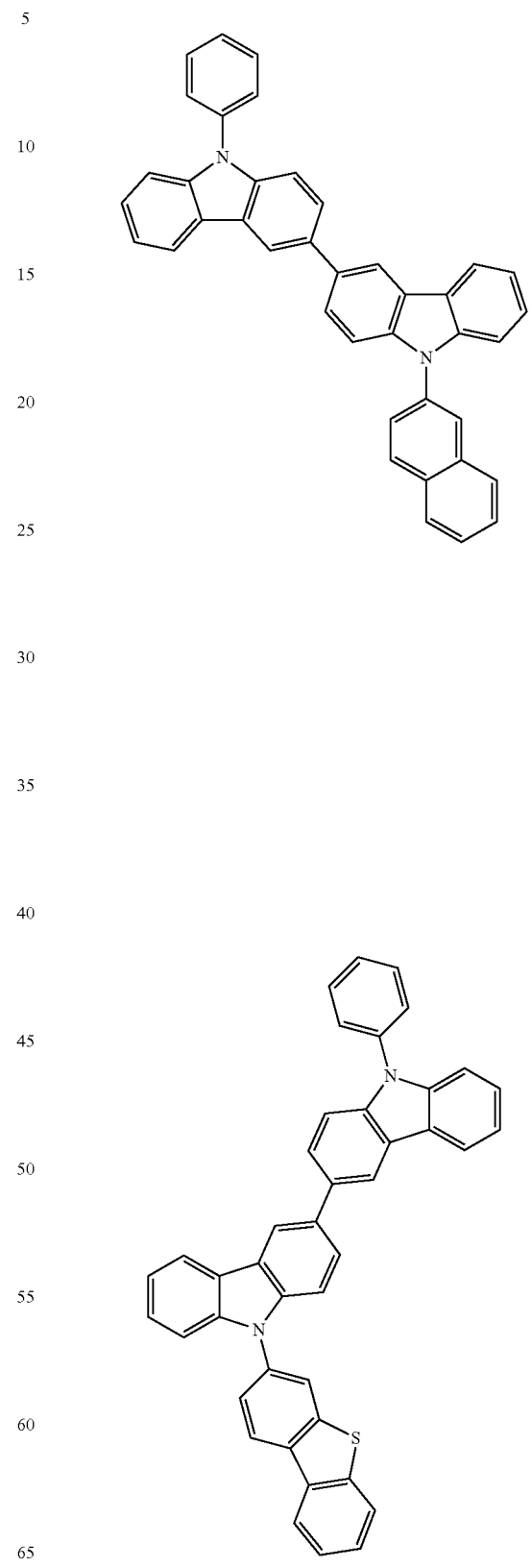

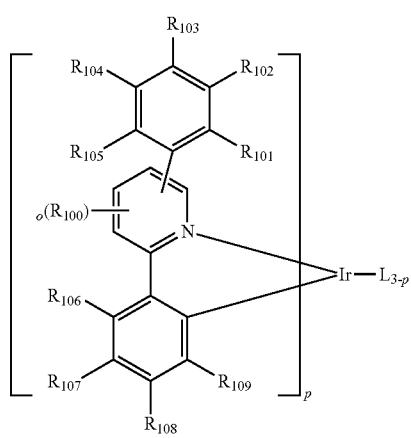

(wherein, TPS represents a triphenylsilyl group.)

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

Preferably, the dopant to be comprised in the organic electroluminescent device of the present disclosure may be selected from the group consisting of compounds represented by the following formulae 101 to 103.

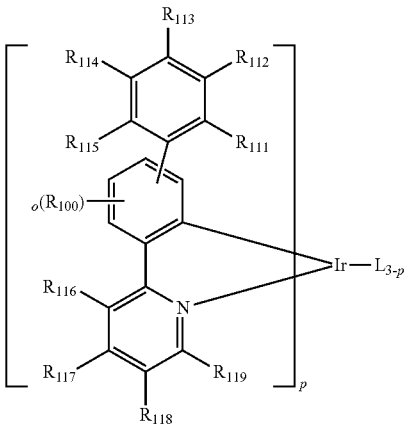
(102)

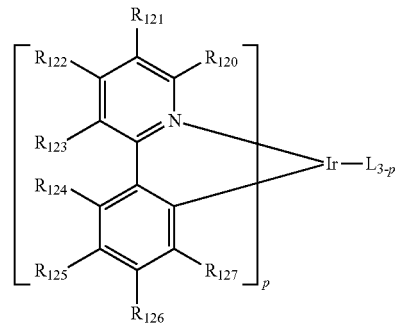
(103)

wherein L is selected from the following structures:

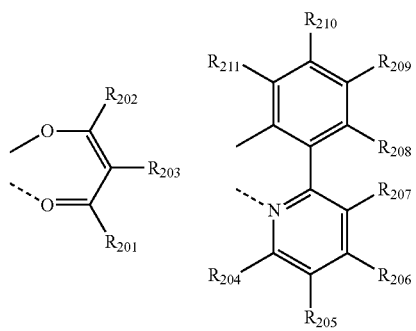

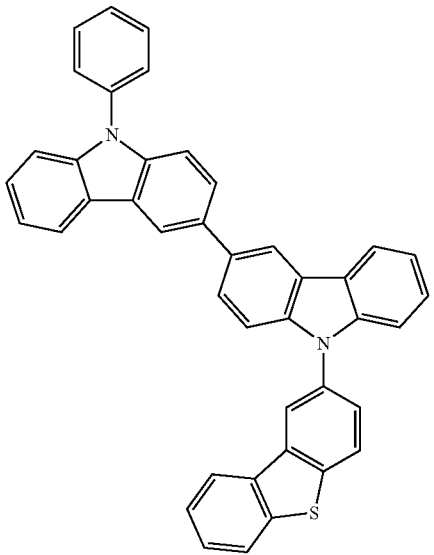 [SMILES: c1ccc(-n2c3ccccc3c3cc(-c4ccc5c(c4)c4ccccc4n5-c4ccc5sc6ccccc6c5c4)ccc32)cc1]
(101)

$R_{100}$ represents hydrogen, a substituted or unsubstituted (C1-C30)alkyl, or a substituted or unsubstituted (C3-C30) cycloalkyl; $R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{120}$ to $R_{123}$ may be linked to an adjacent substituent(s) to form a substituted or unsubstituted fused ring, for example, quinoline unsubstituted or substituted with alkyl or aryl; $R_{124}$ to $R_{127}$, each independently, represent hydrogen, deuterium, a halogen, a substituted or unsubstituted (C1-C30)alkyl, or a substituted or unsubstituted (C6-C30)aryl; $R_{124}$ to $R_{127}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; $R_{208}$ to $R_{211}$ may be linked to an adjacent substituent(s) to form a substituted or unsubstituted fused ring, for example, fluorene unsubstituted or substituted with alkyl, dibenzothiophene unsubstituted or substituted with alkyl or dibenzofuran unsubstituted or substituted with alkyl; o represents an integer of 1 to 3; where o is an integer of 2 or more, each of $R_{100}$ may be the same or different; and p represents an integer of 1 to 3.

Specifically, the dopant material includes the following, but is not limited thereto.

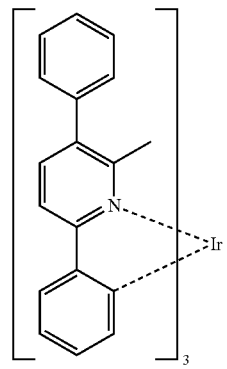

D-1

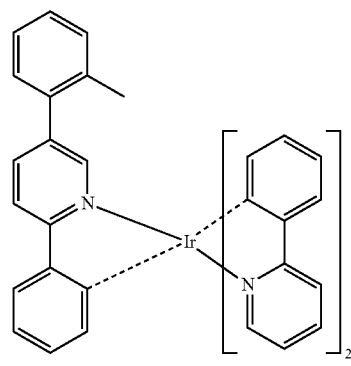

D-2

D-3

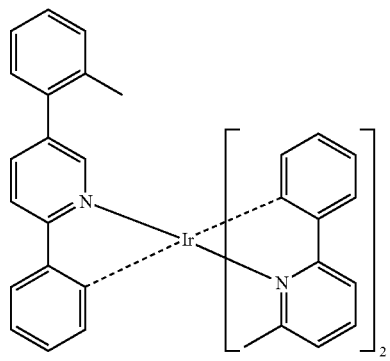

D-4

D-5

D-6

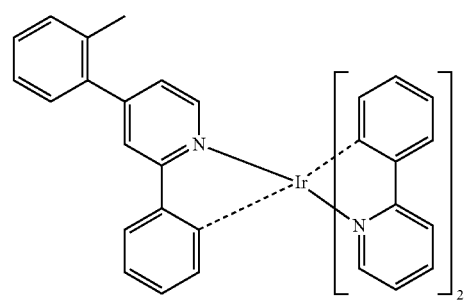

D-7

-continued
D-8
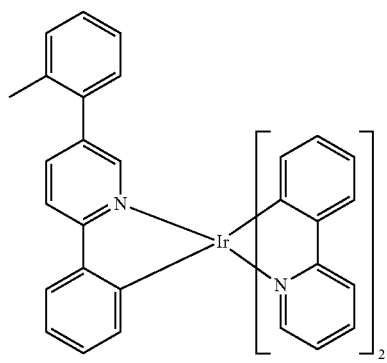
D-9
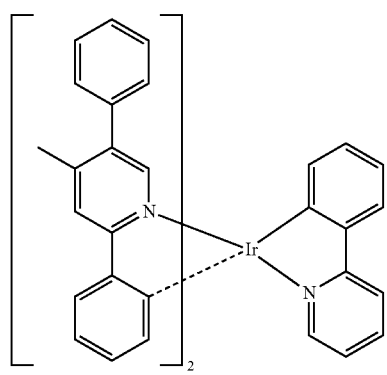
D-10
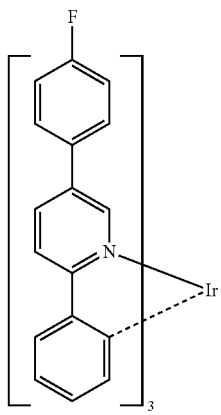
D-11
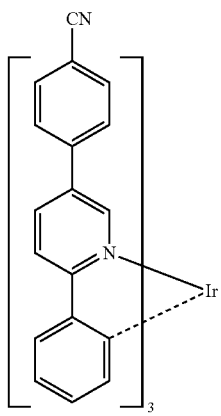
-continued
D-12
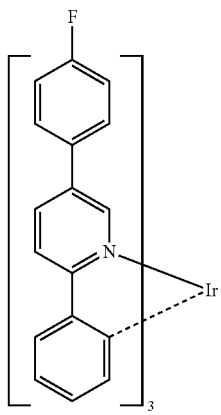
D-13
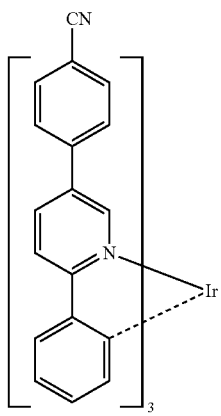
D-14
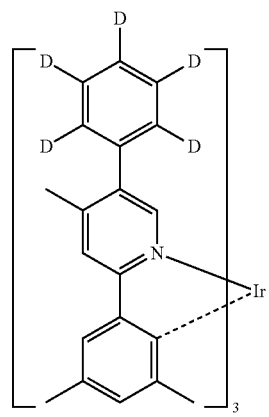
D-15
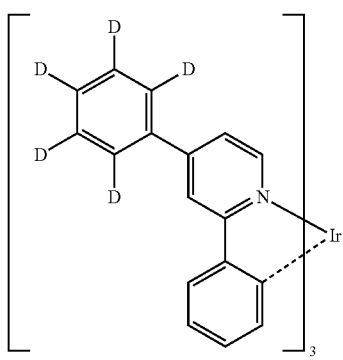

-continued
D-16
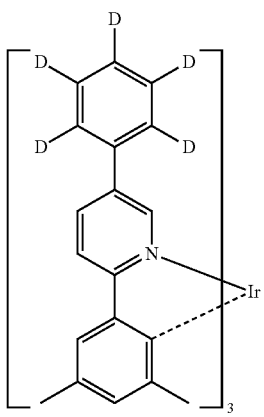
D-17
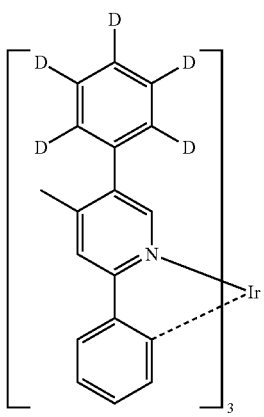
D-18
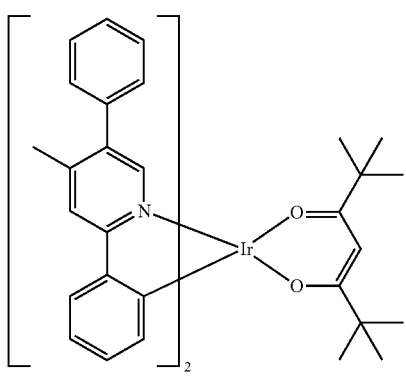
D-19
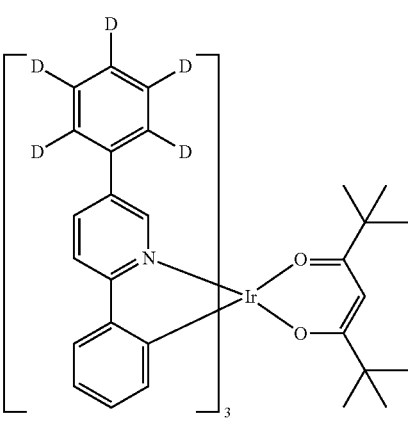
D-20
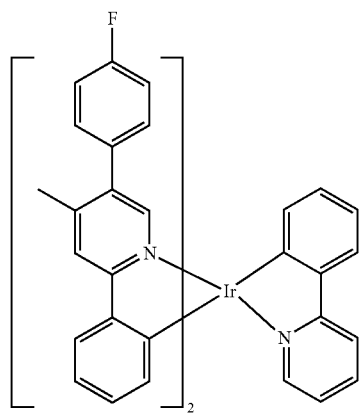
D-21
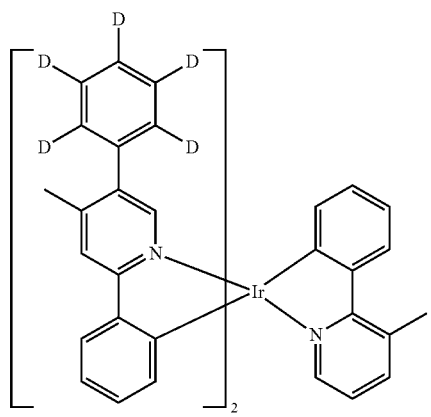
D-22
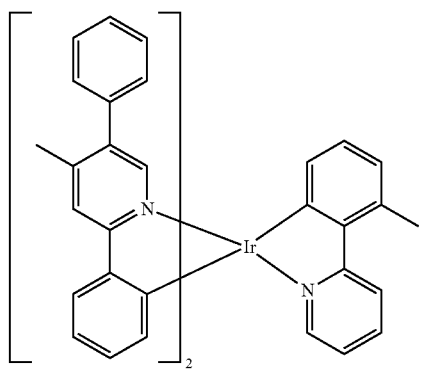
D-23
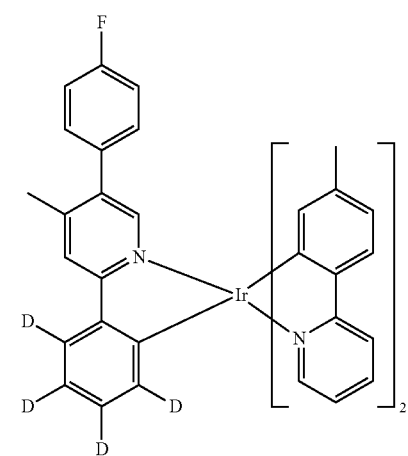

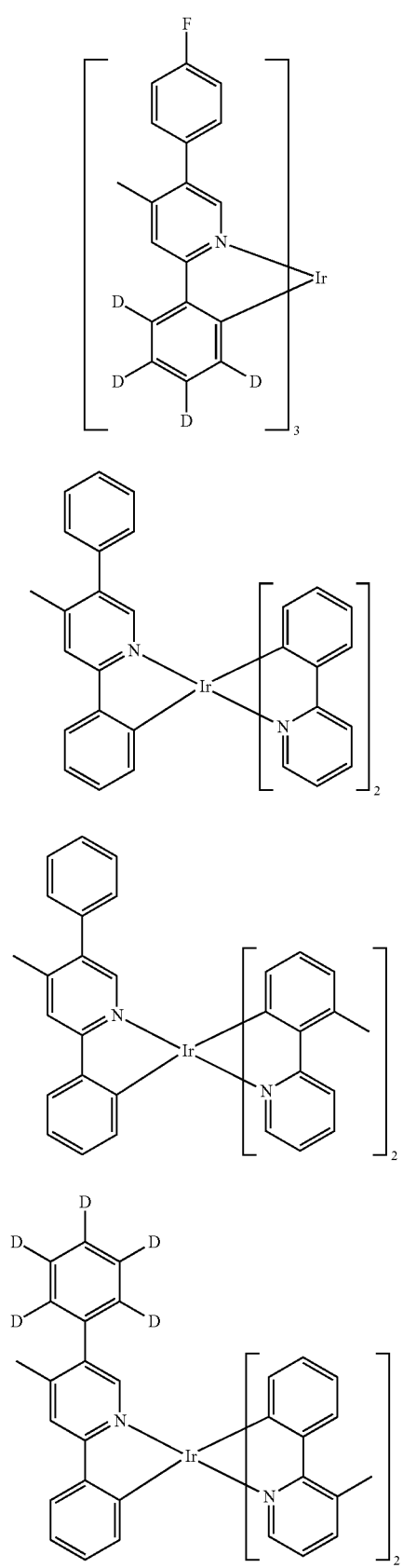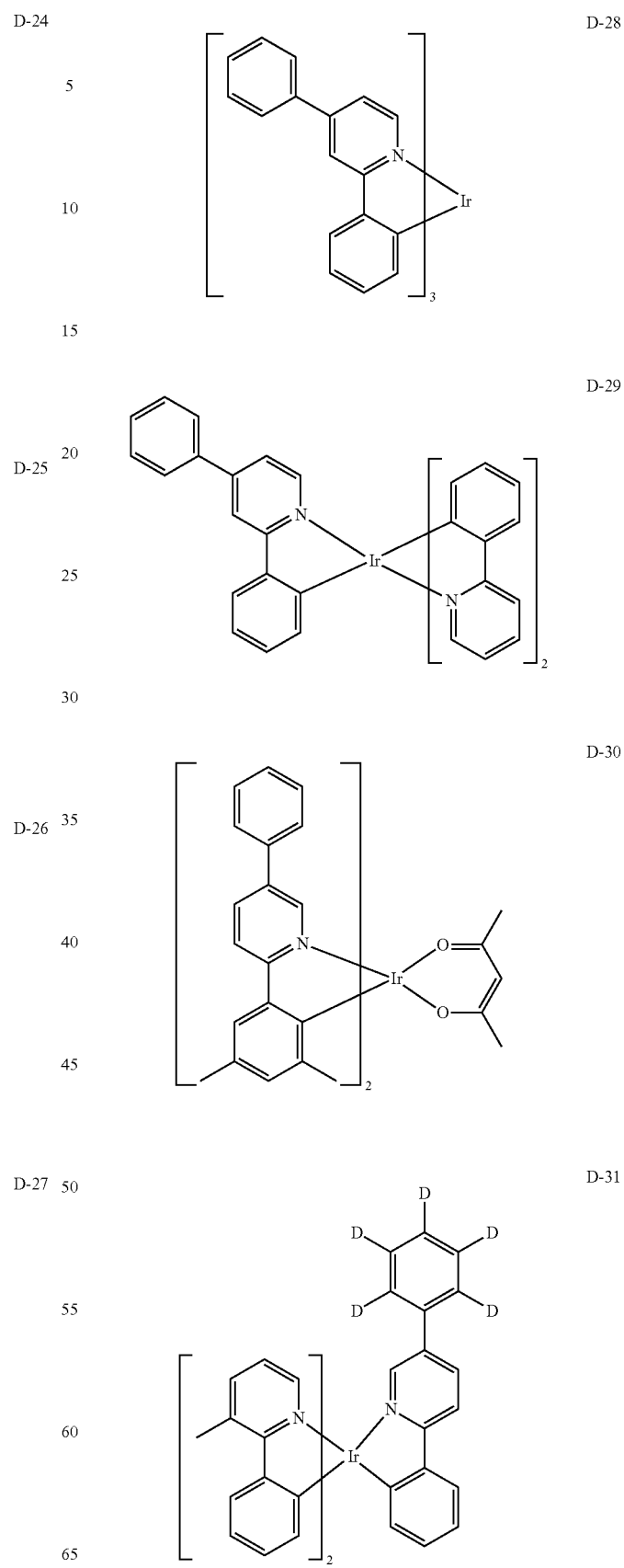

D-32 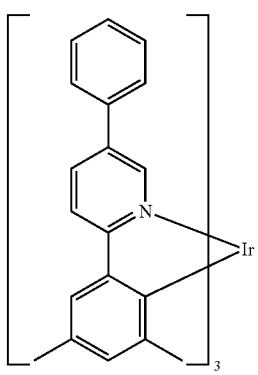
D-33 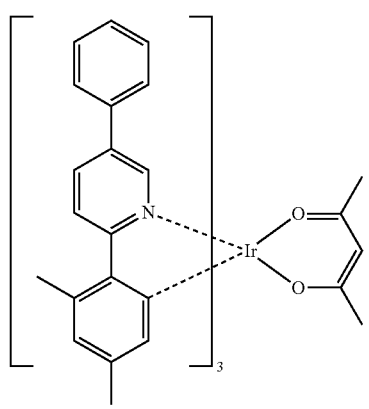
D-34 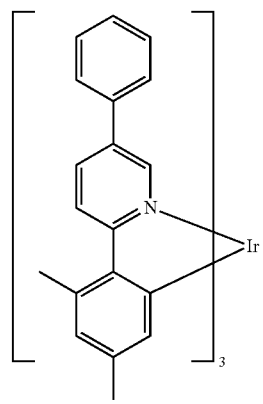
D-35 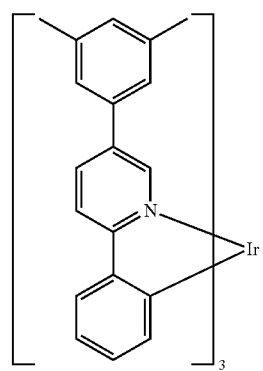
D-36 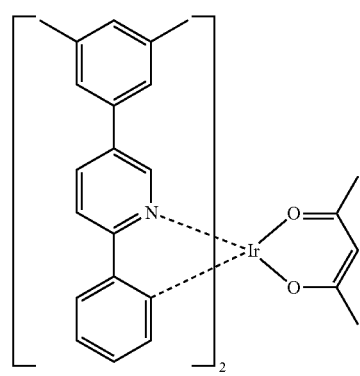
D-37 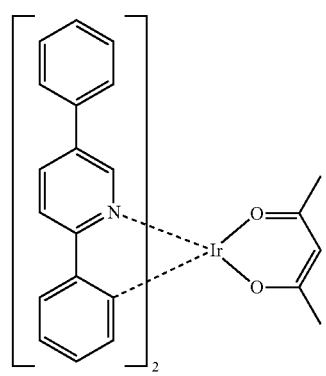
D-38 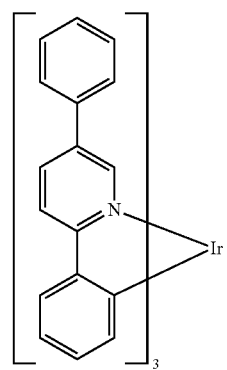
D-39 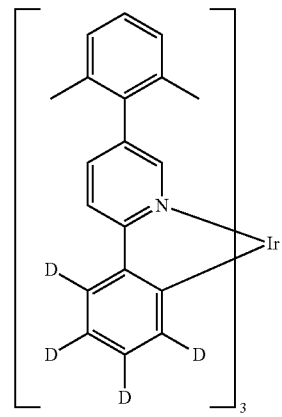

D-40 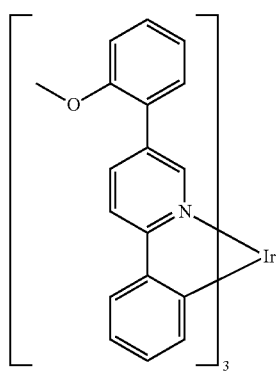
D-41 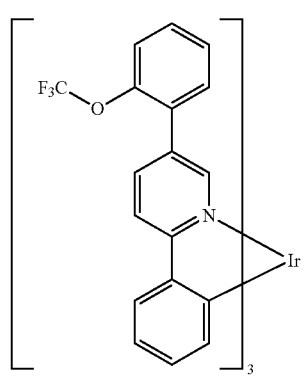
D-42 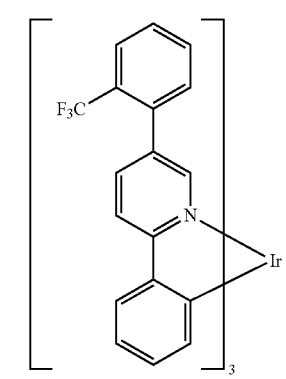
D-43 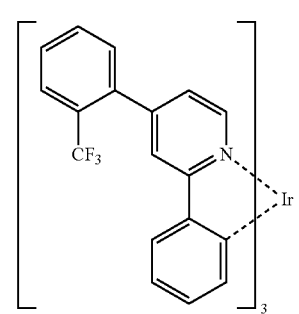
D-44 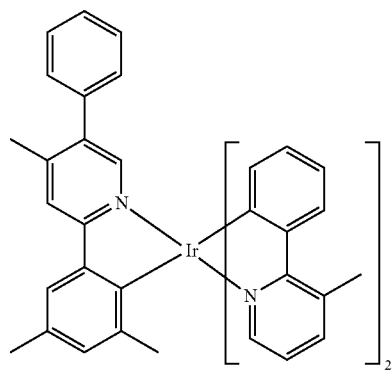
D-45 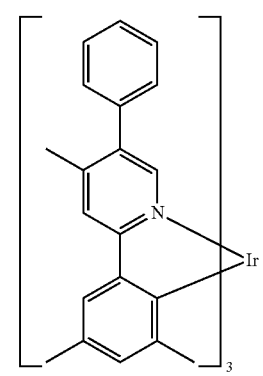
D-46 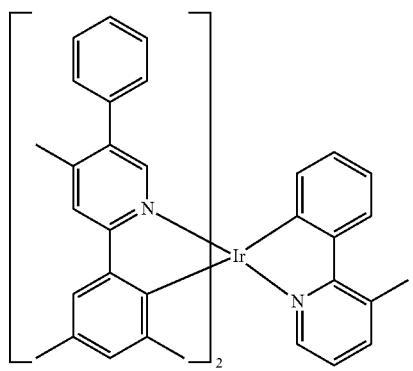
D-47 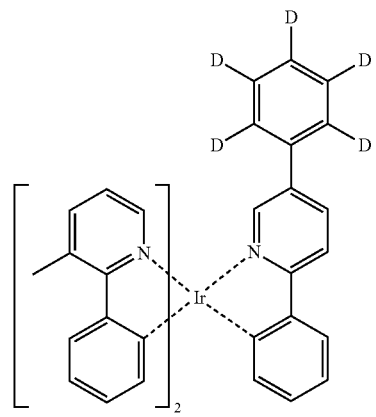

D-48
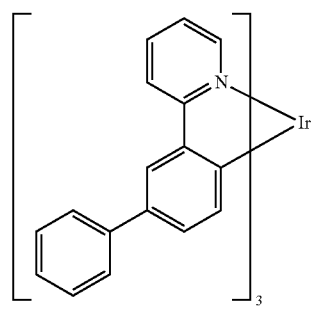
D-49
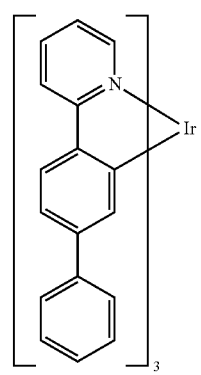
D-50
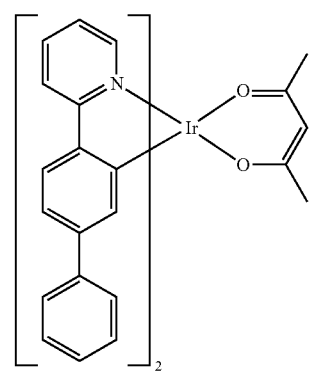
D-51
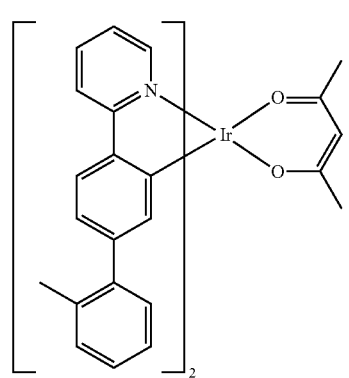
D-52
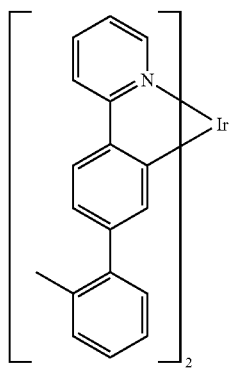
D-53
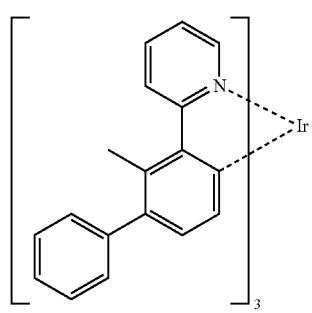
D-54
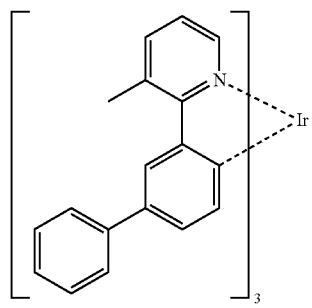
D-55
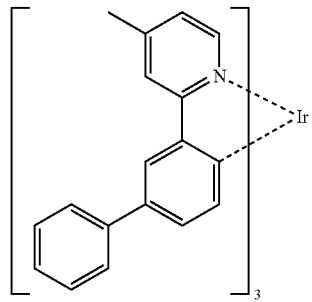
D-56
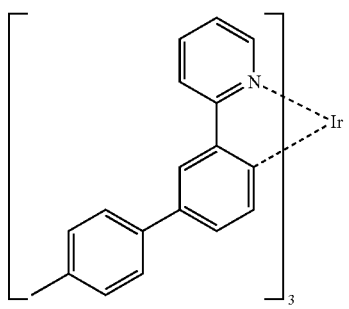

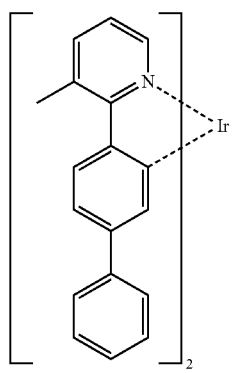 D-57
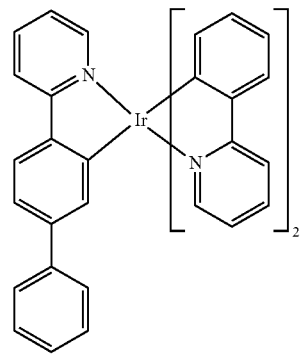 D-61
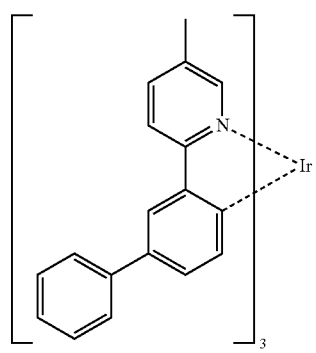 D-58
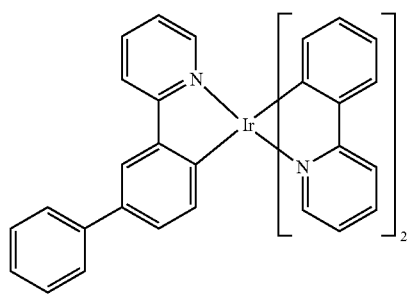 D-62
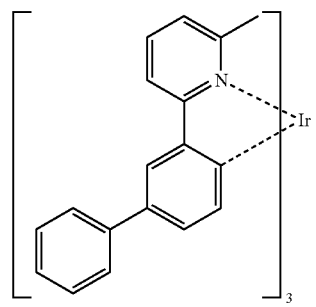 D-59
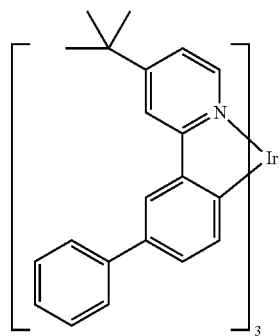 D-63
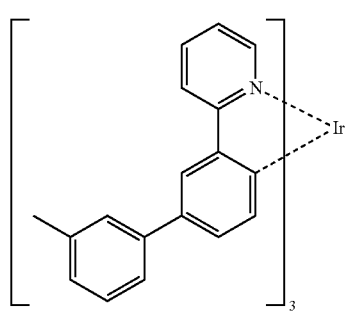 D-60
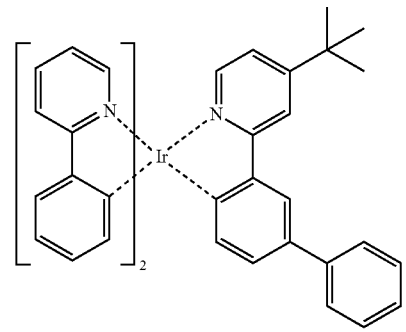 D-64

D-65 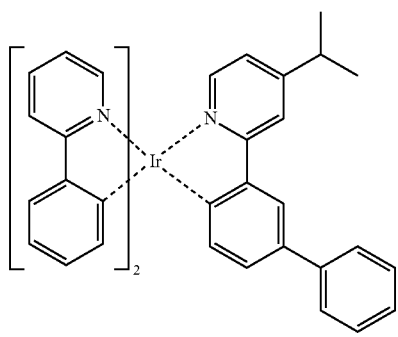
D-69 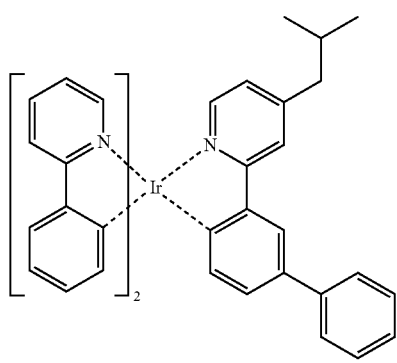
D-66 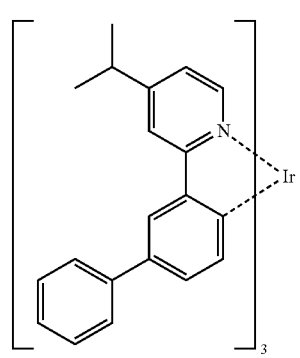
D-70 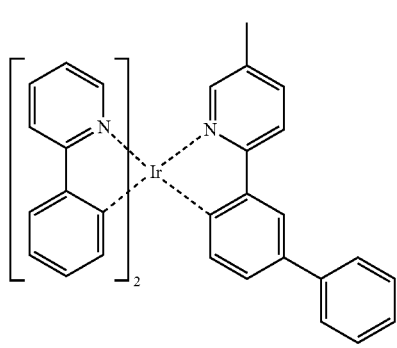
D-67 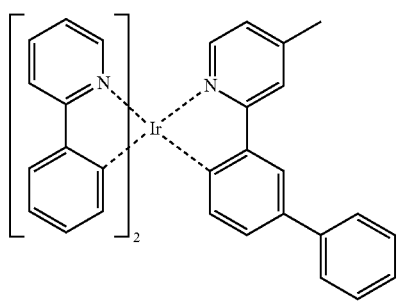
D-71 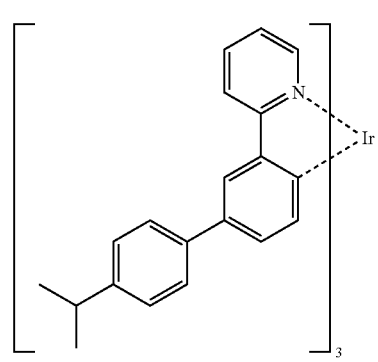
D-68 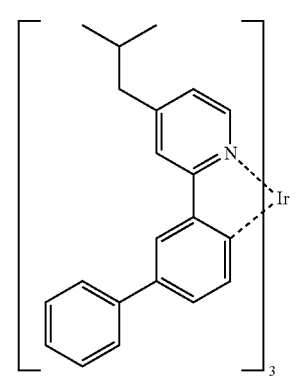
D-72 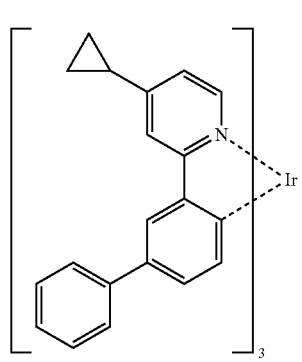

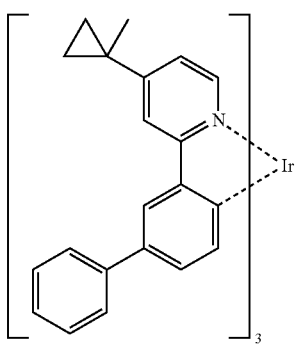 D-73
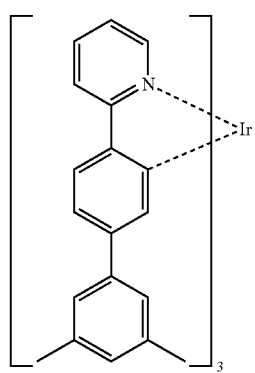 D-77
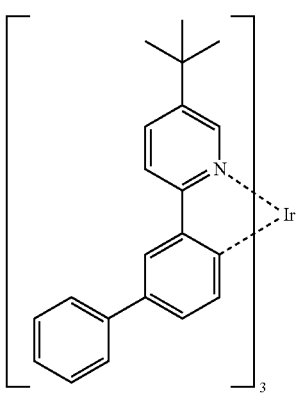 D-74
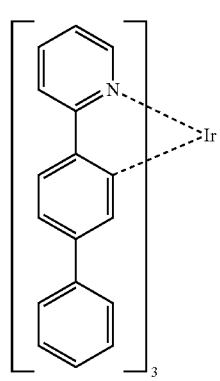 D-78
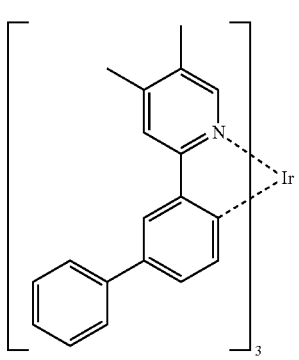 D-75
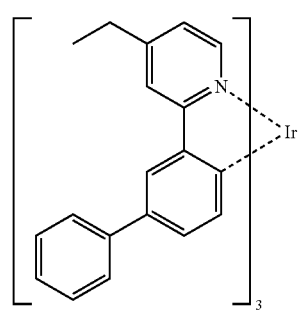 D-79
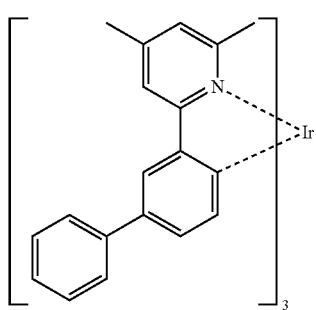 D-76
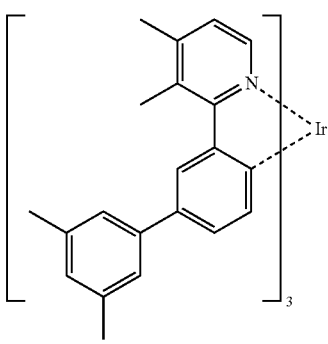 D-80

D-81 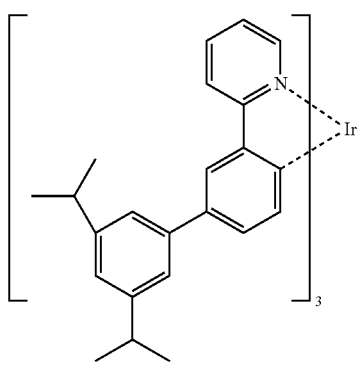
D-82 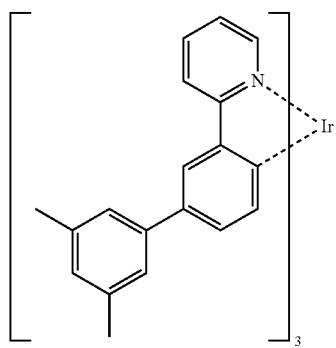
D-83 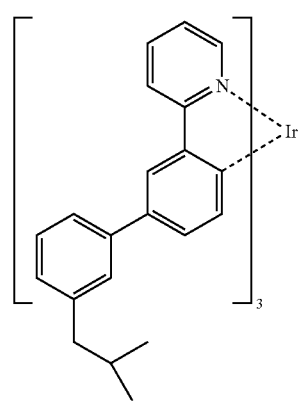
D-84 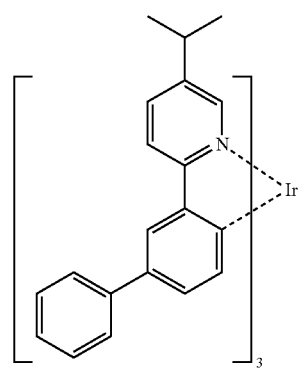
D-85 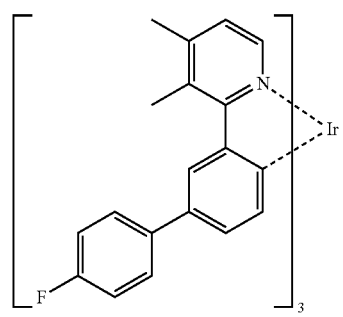
D-86 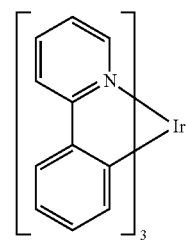
D-87 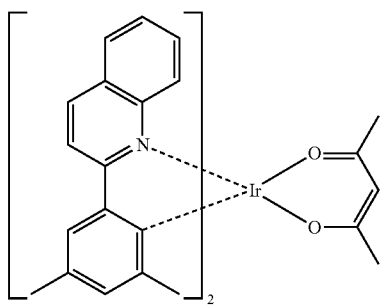
D-88 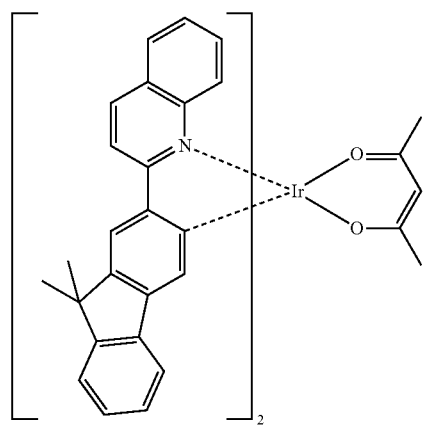
D-89 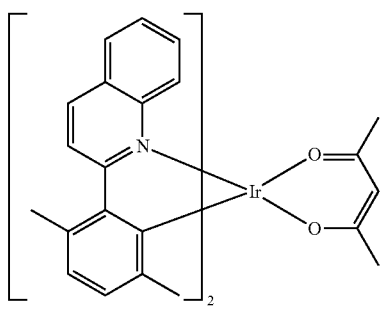

D-90 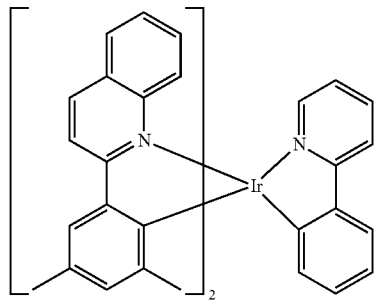
D-94 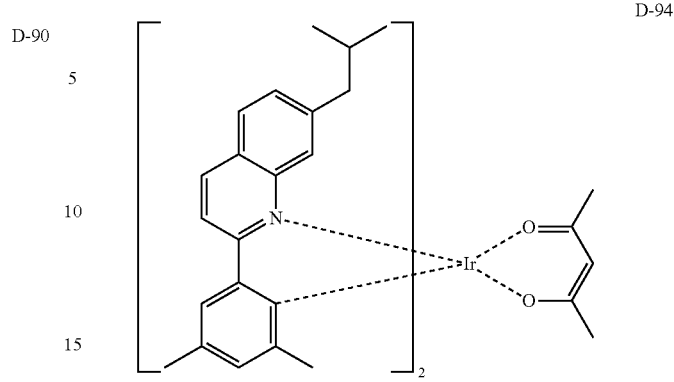
D-91 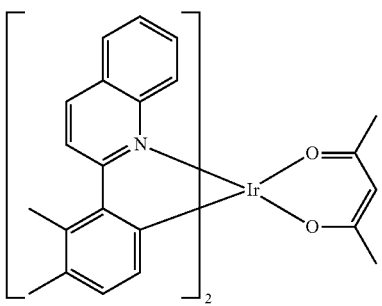
D-95 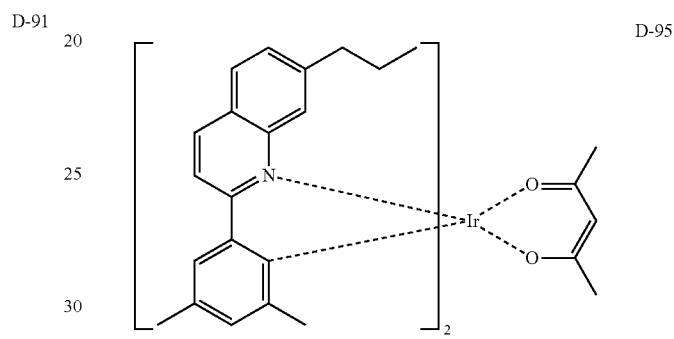
D-92 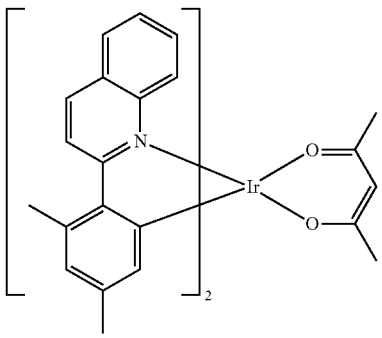
D-96 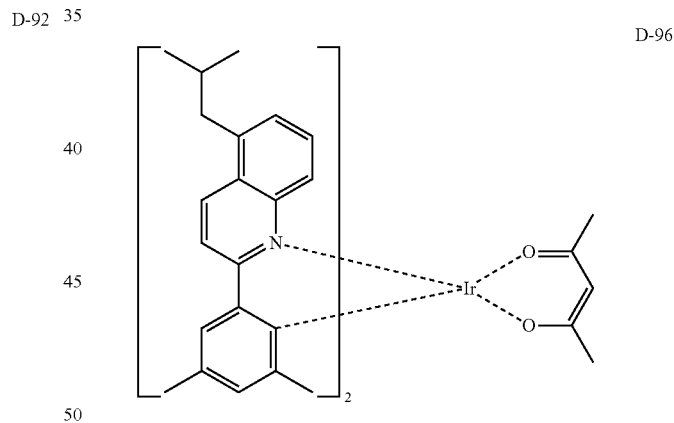
D-93 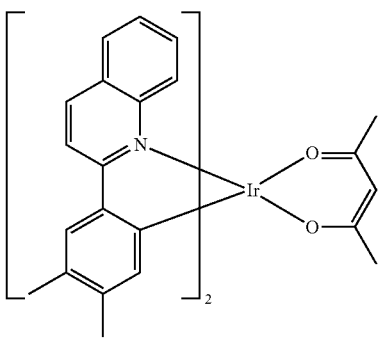
D-97 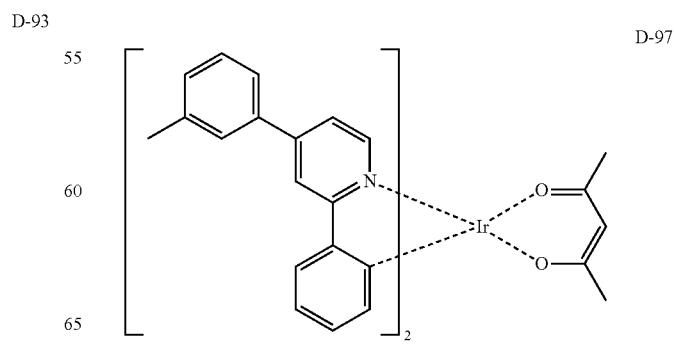

D-98
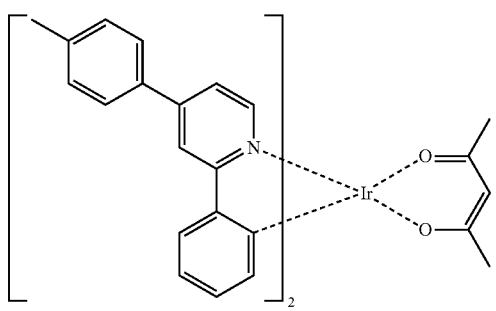
D-99
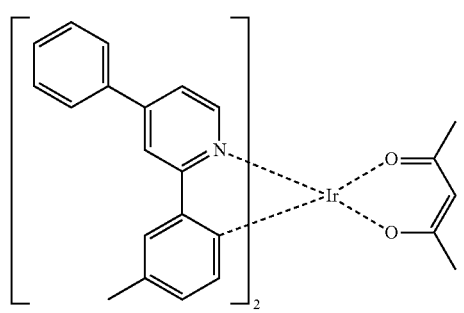
D-100
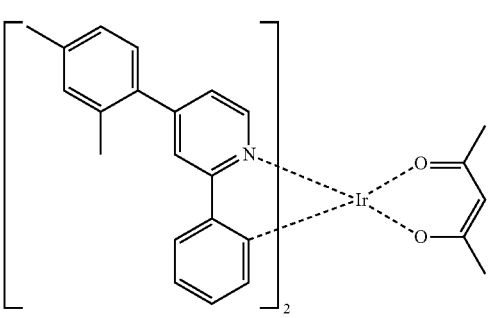
D-101
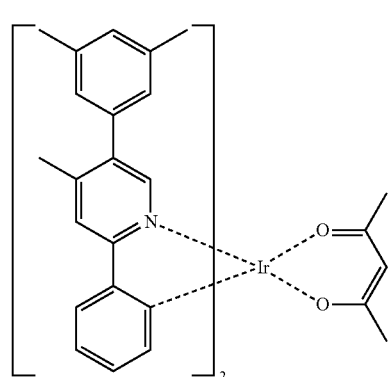
D-102
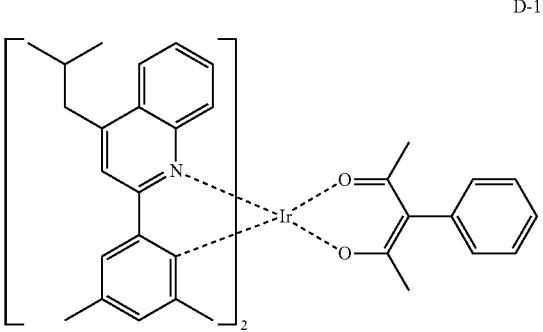
D-103
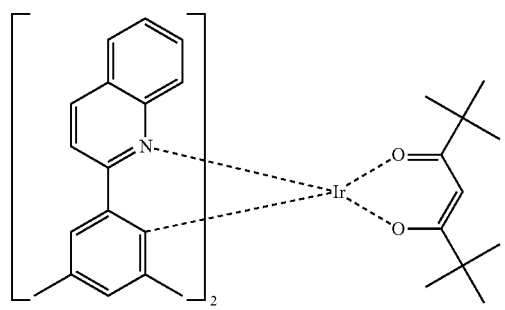
D-104
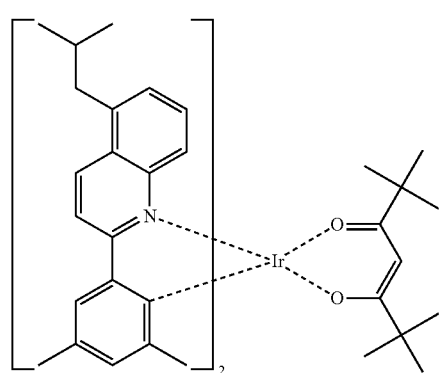
D-105
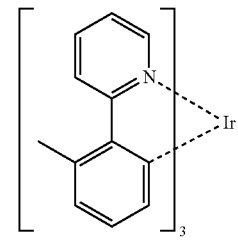
D-106
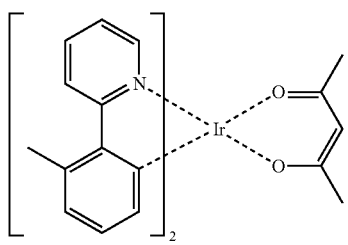
D-107
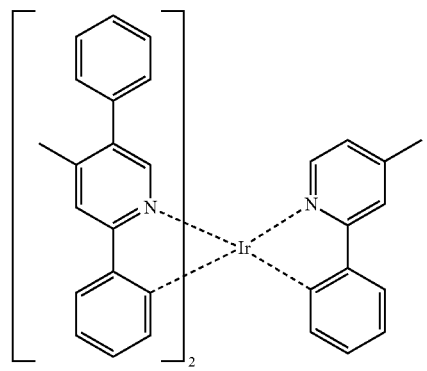

D-108
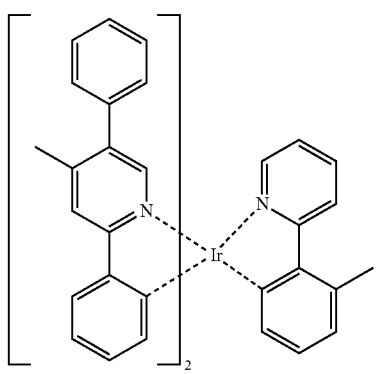
D-109
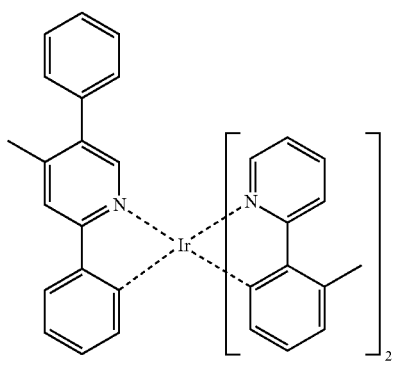
D-110
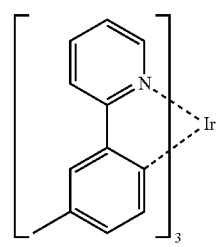
D-111
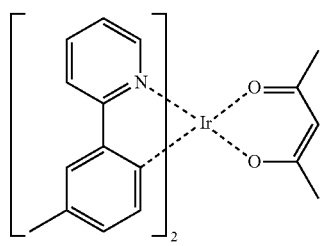
D-112
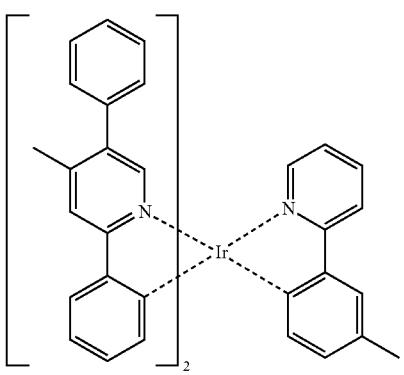
D-113
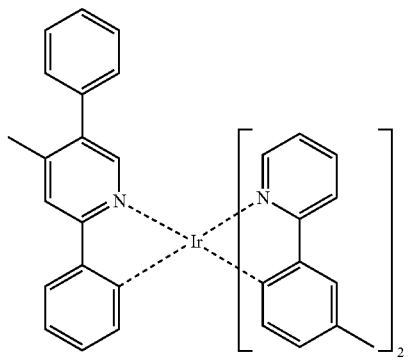
D-114
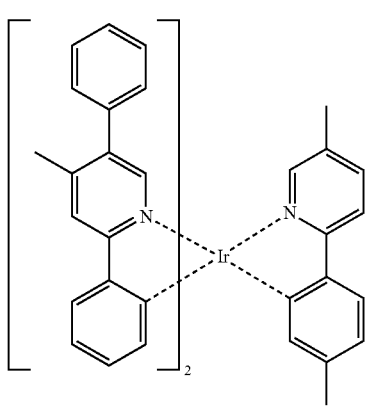
D-115
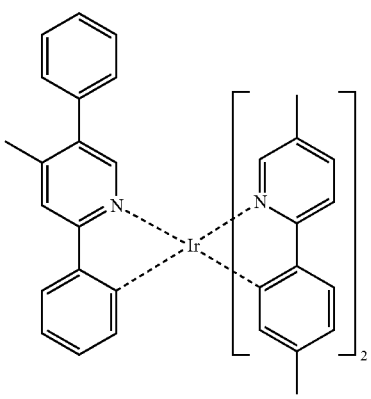
D-116
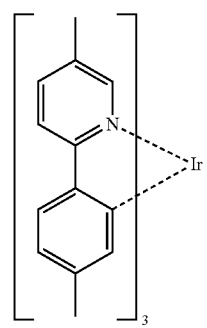

D-117
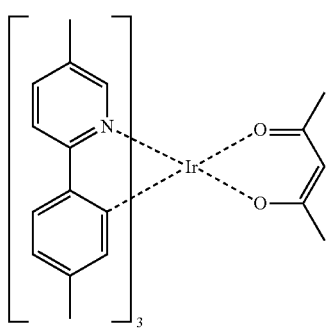
D-118
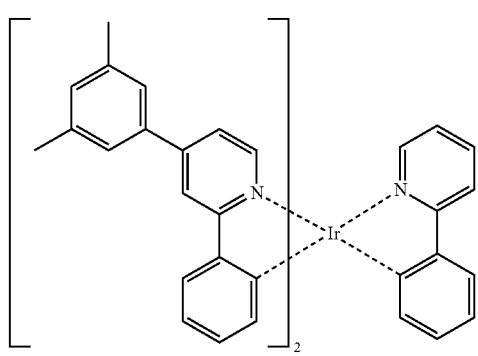
D-119
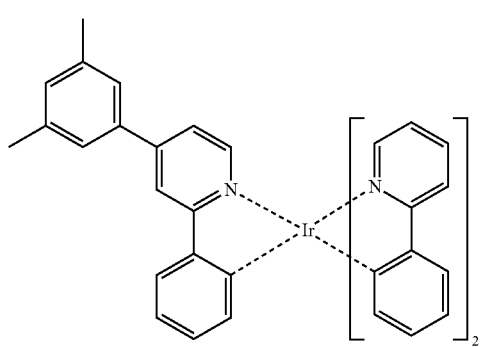
D-120
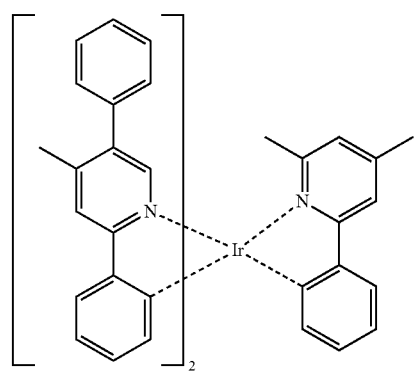
D-121
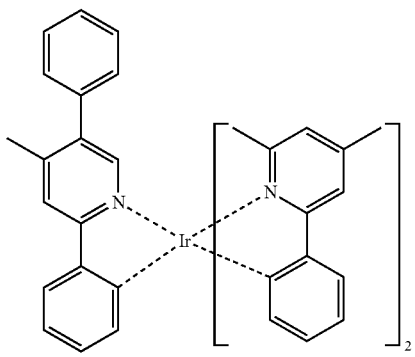
D-122
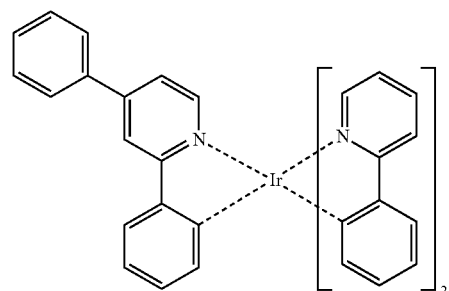
D-123
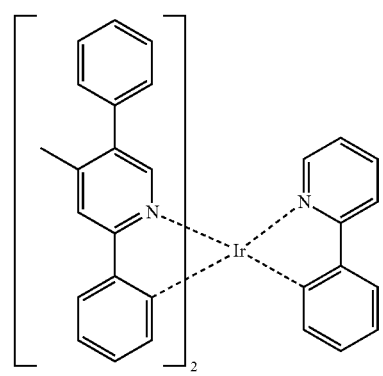
D-124
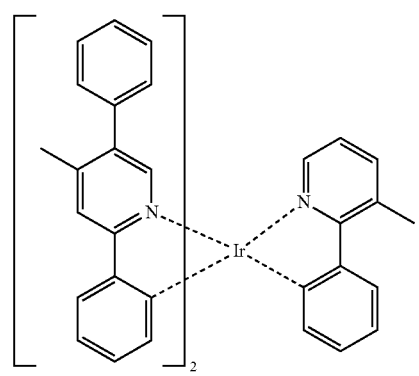

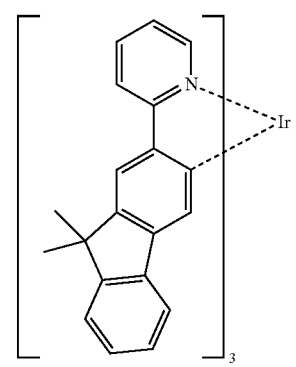 D-125
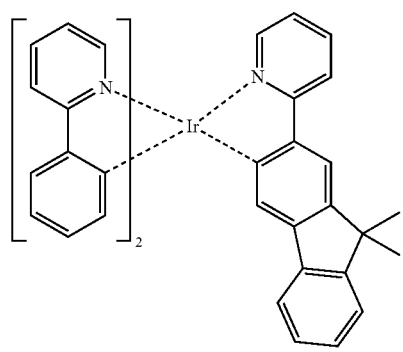 D-126
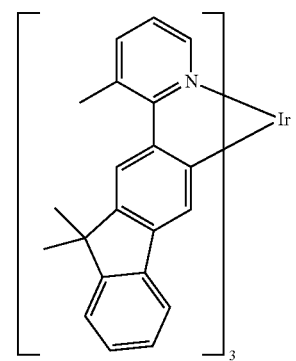 D-127
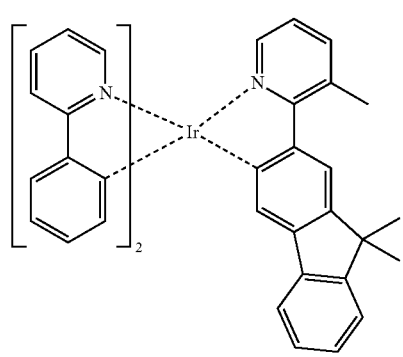 D-128
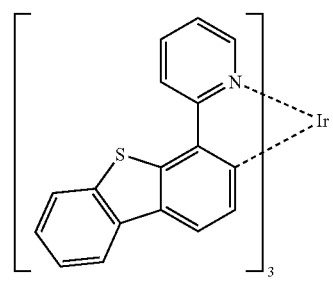 D-129
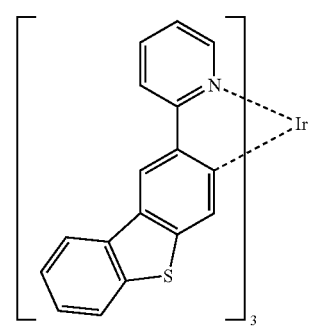 D-130
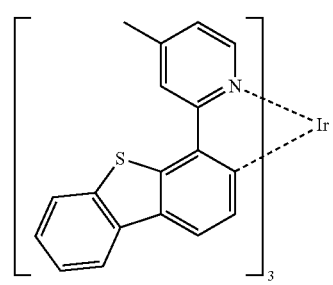 D-131
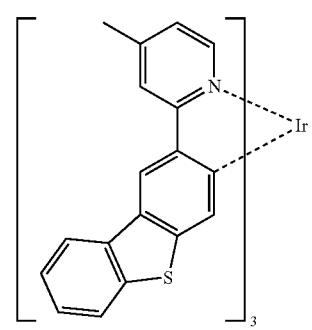 D-132
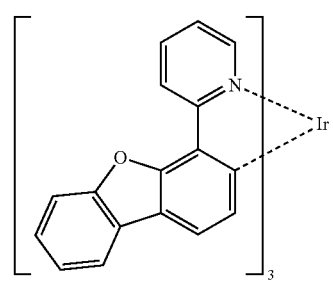 D-133

D-134
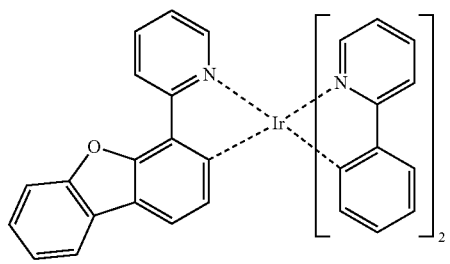
D-135
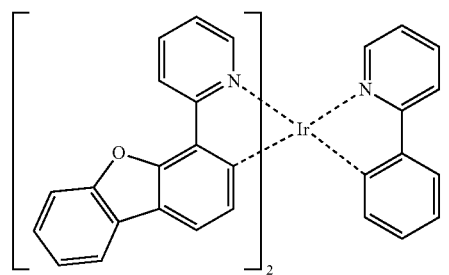
D-136
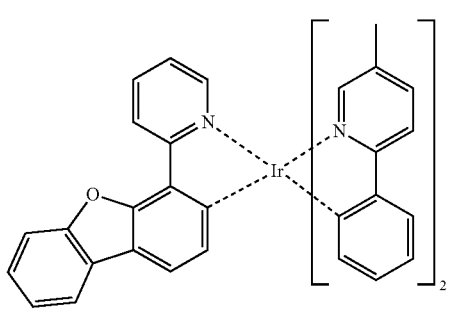
D-137
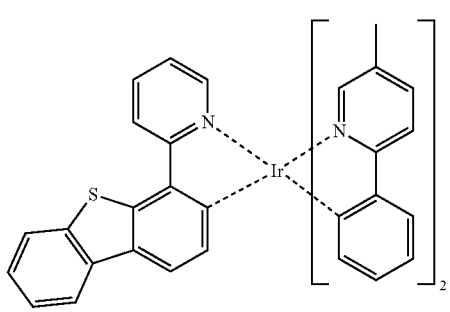
D-138
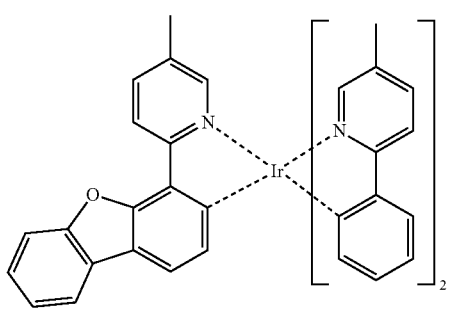
D-139
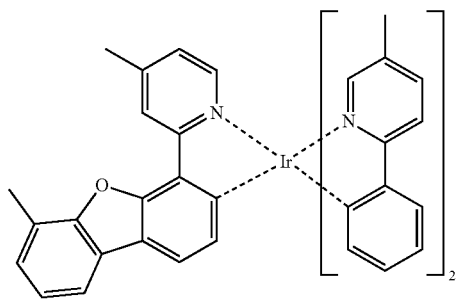
D-140
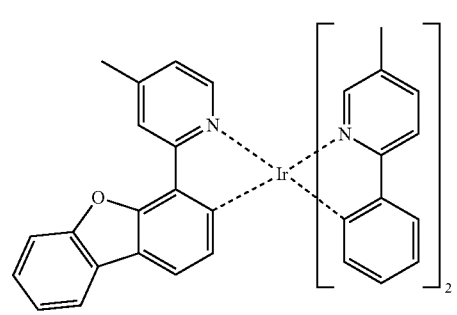
D-141
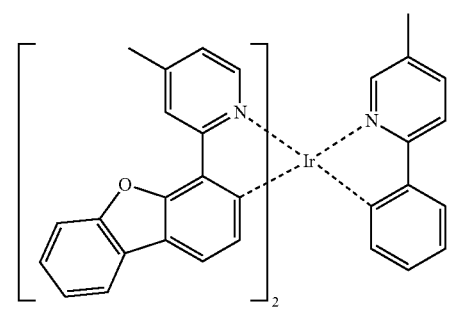
D-142
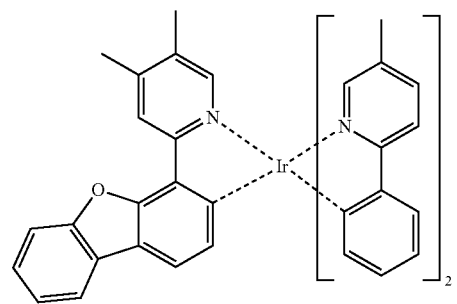
D-143
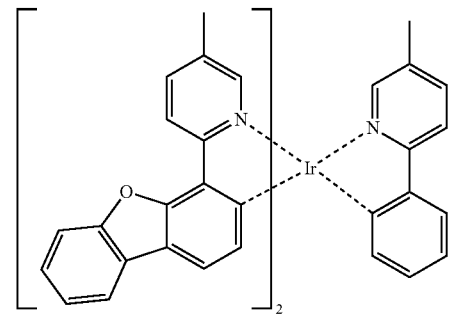

D-144
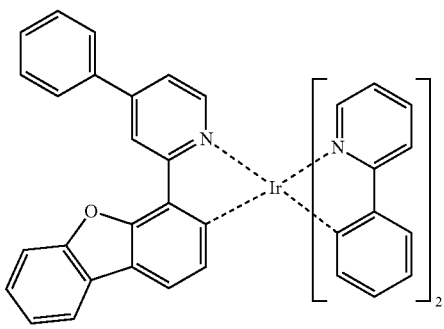
D-145
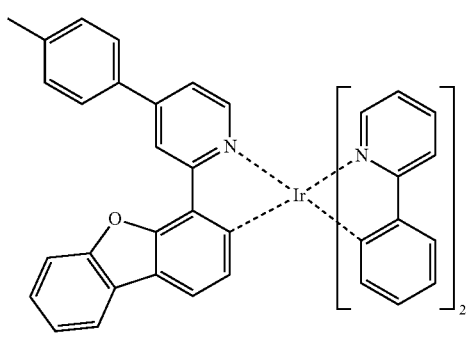
D-146
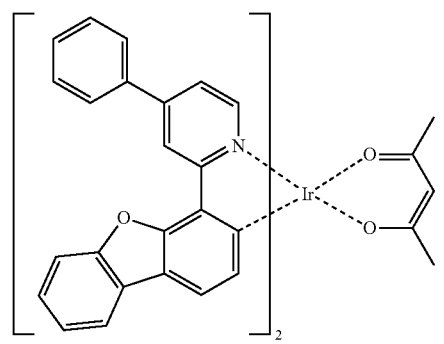
D-147
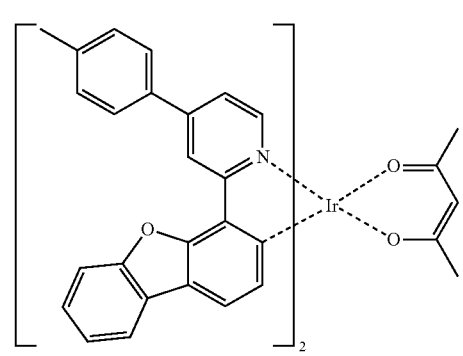
D-148
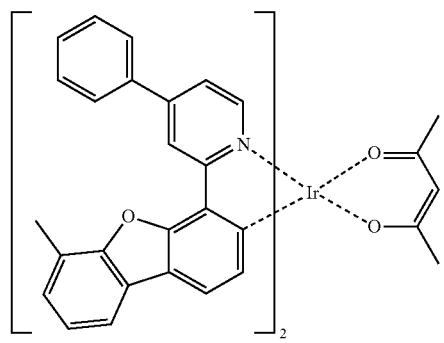
D-149
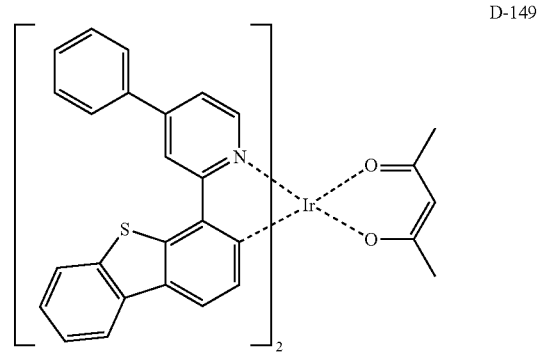
D-150
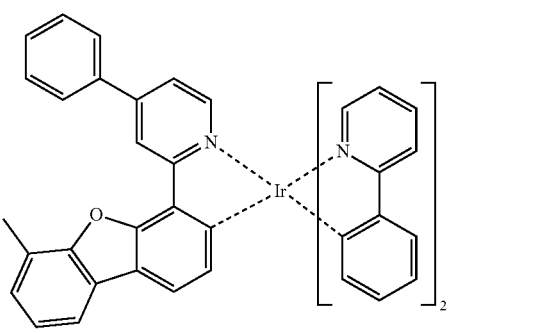
D-151
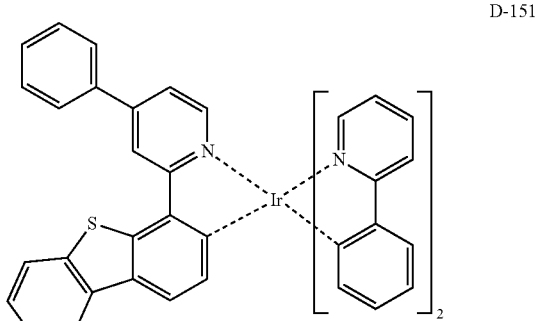
D-152
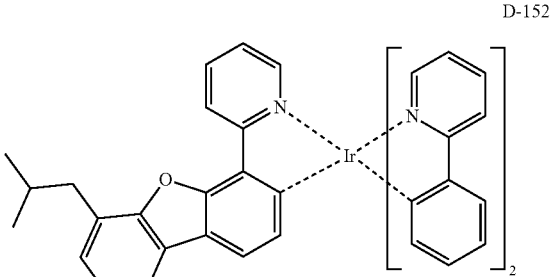

D-153
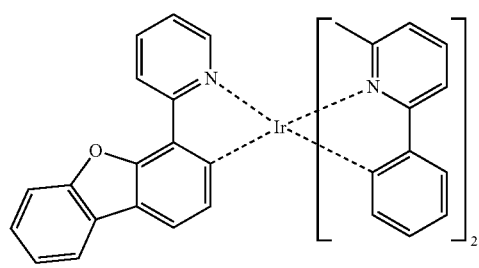
D-154
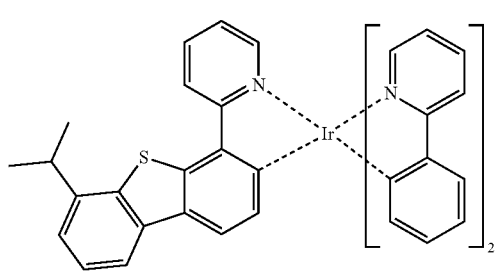
D-155
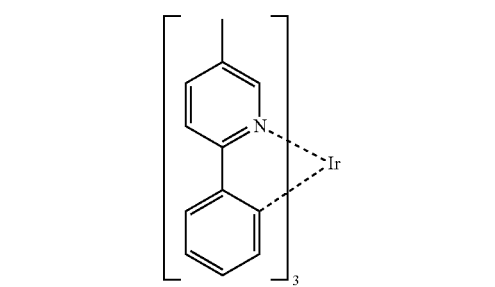
D-156
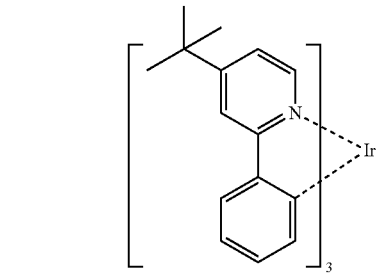
D-157
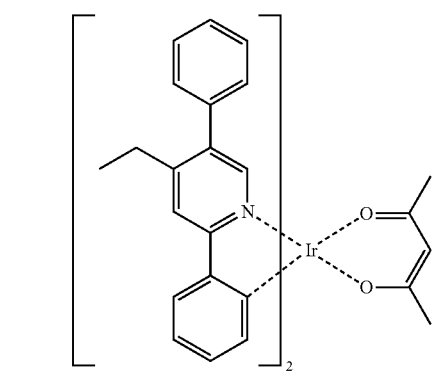
D-158
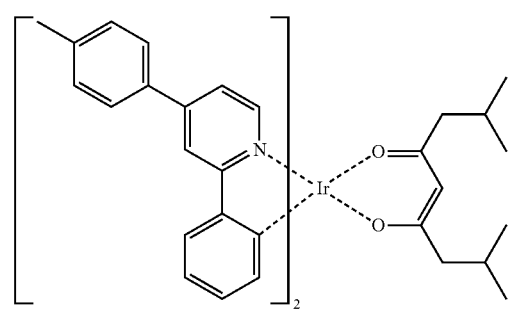
D-159
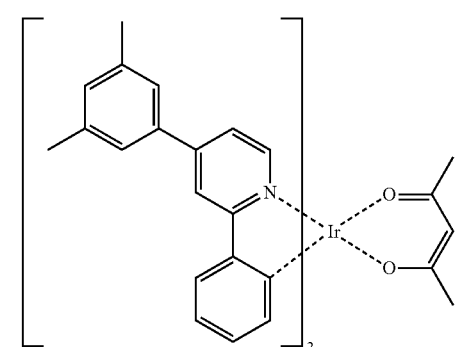
D-160
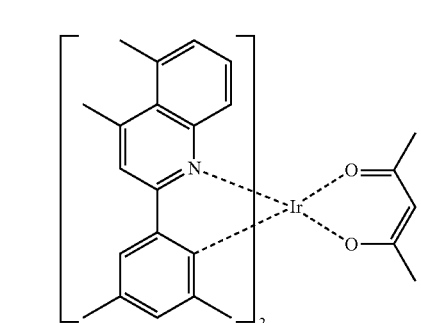
D-161
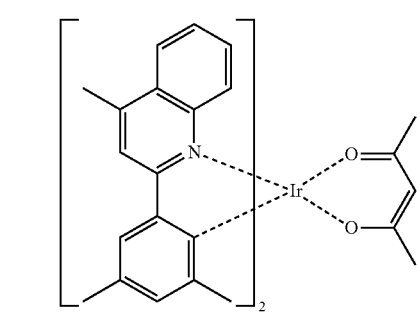
D-162
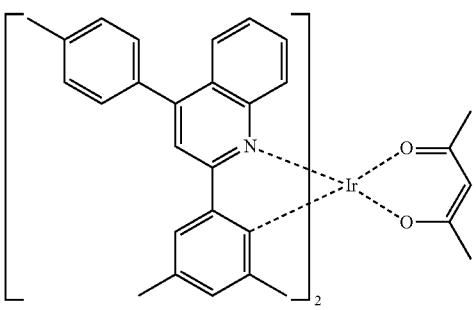

D-163 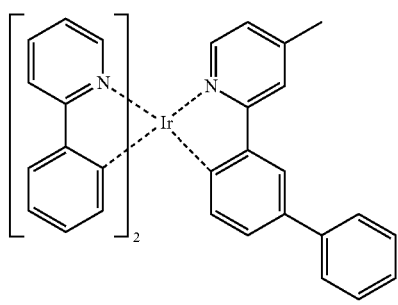
D-164 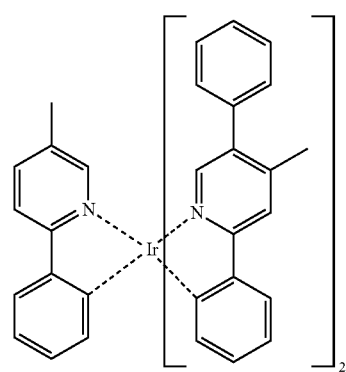
D-165 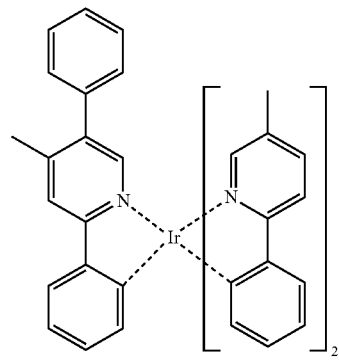
D-166 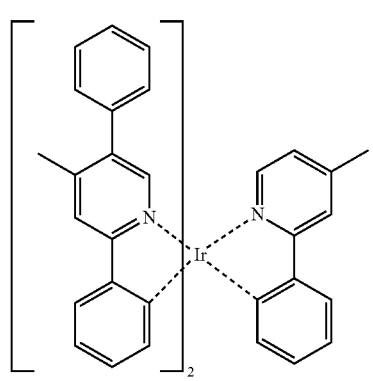
D-167 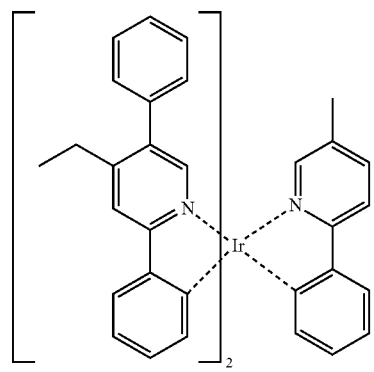
D-168 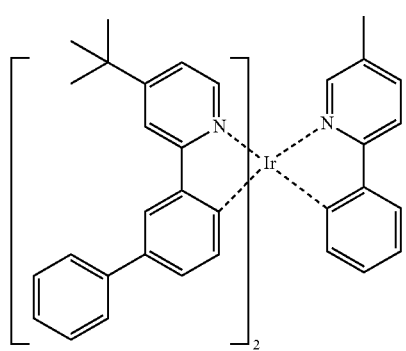
D-169 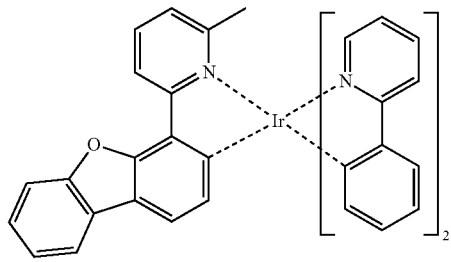
D-170 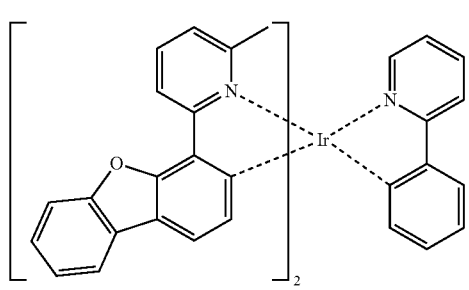
D-171 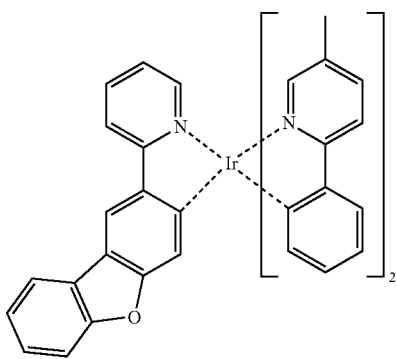

-continued
D-172
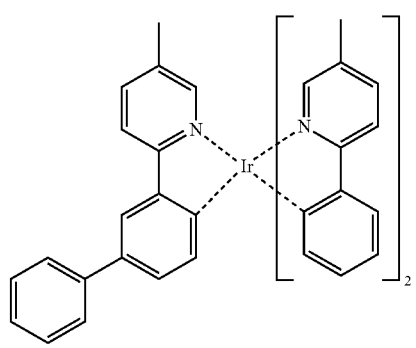
D-176
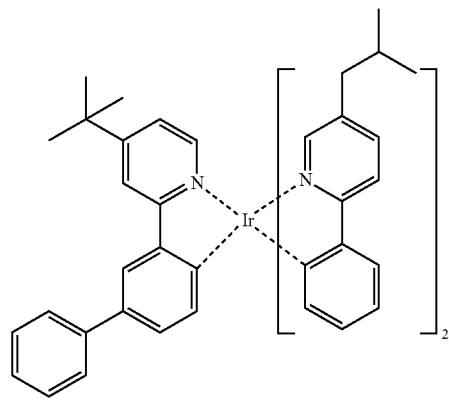
D-173
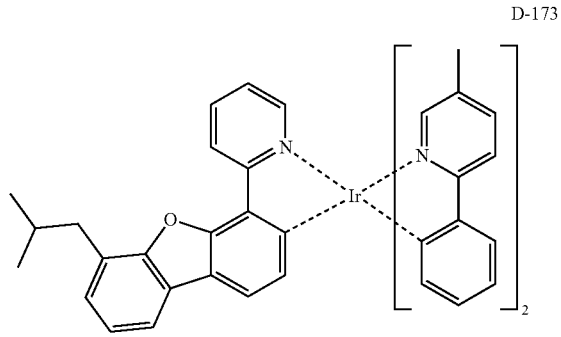
D-177
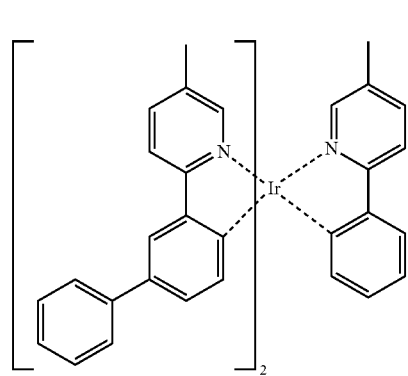
D-174
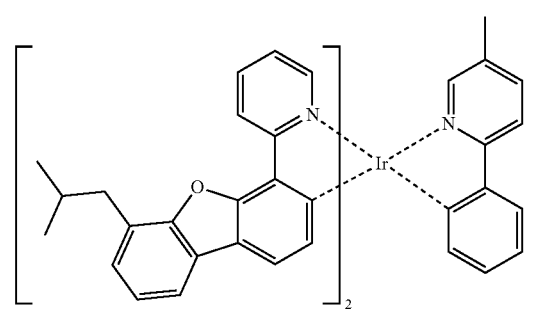
D-178
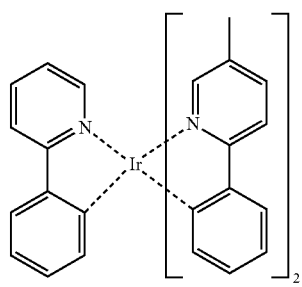
D-175
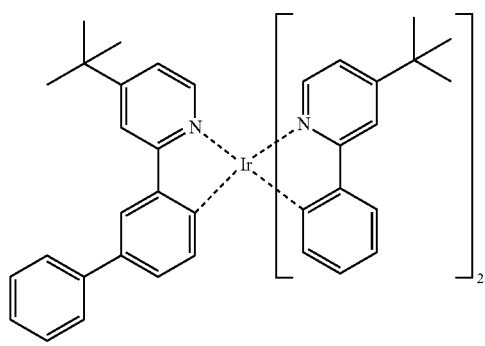
D-179
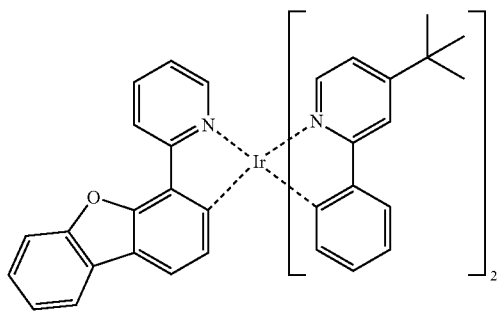

D-180
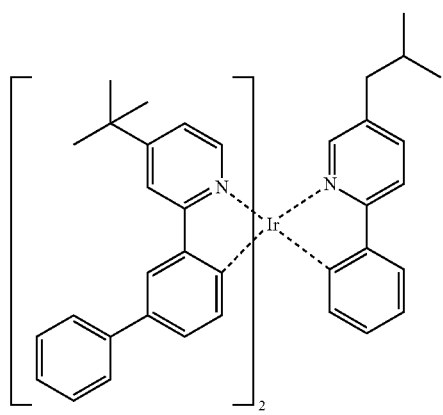
D-181
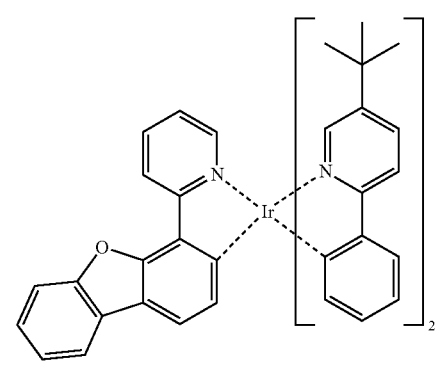
D-182
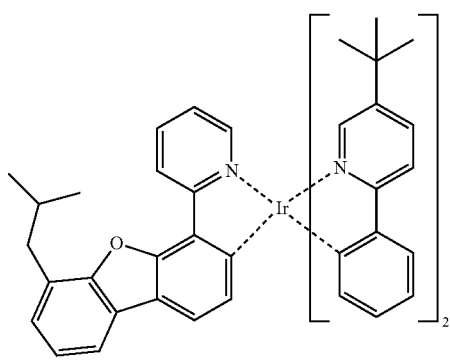
D-183
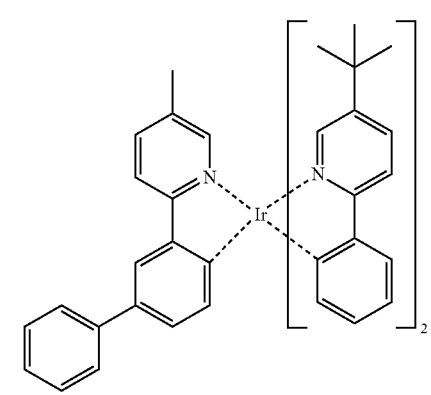
D-184
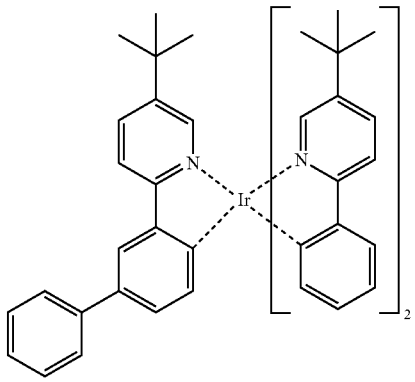
D-185
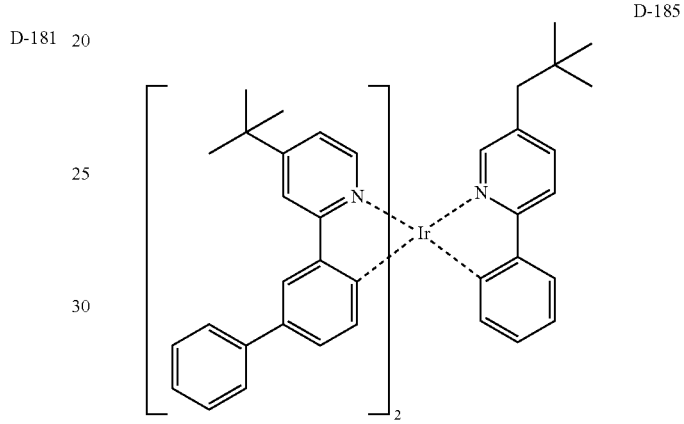
D-186
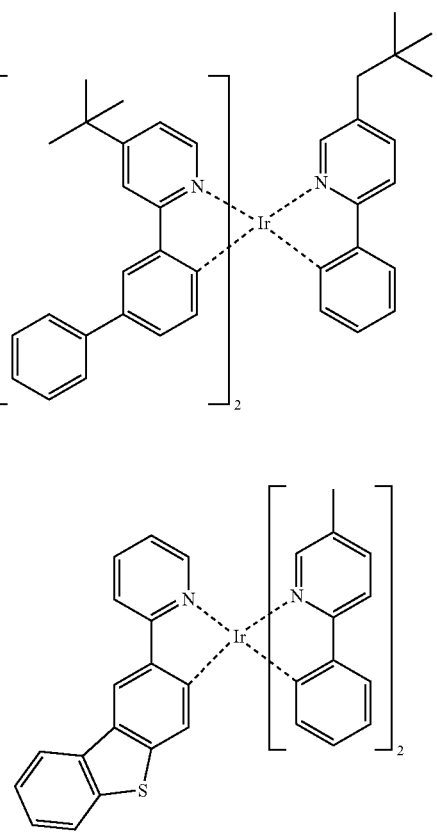
D-187
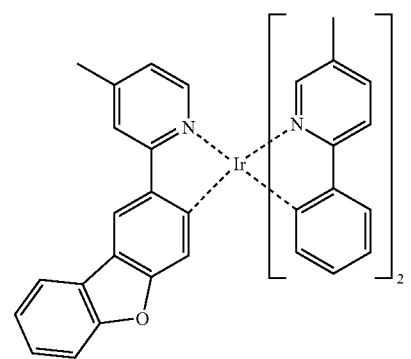

D-188
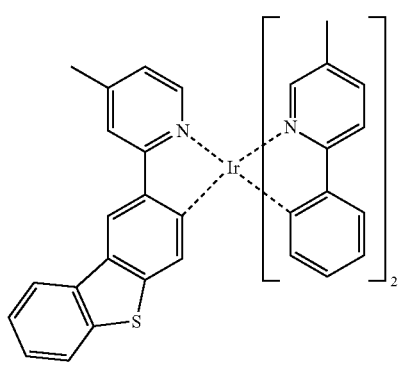
D-189
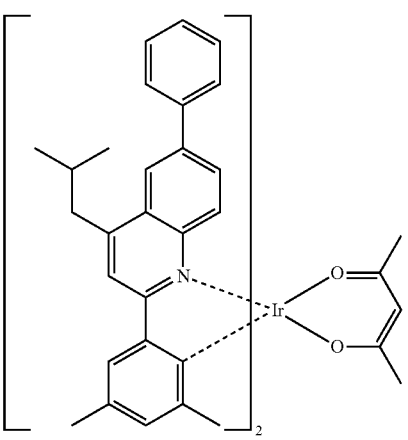
D-190
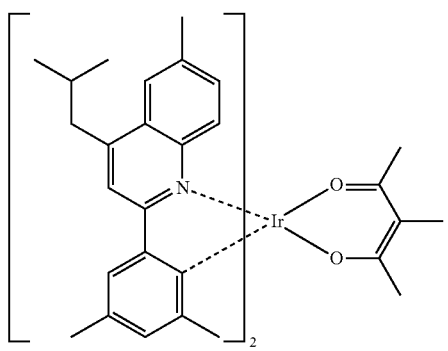
D-191
D-192
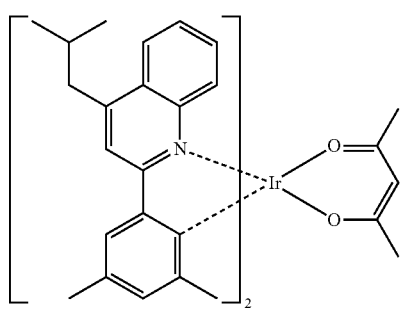
D-193
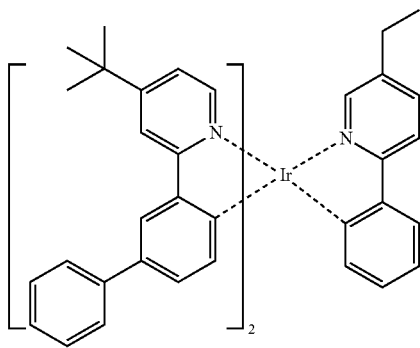
D-194
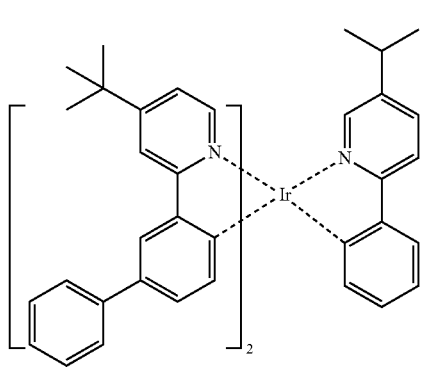
D-195
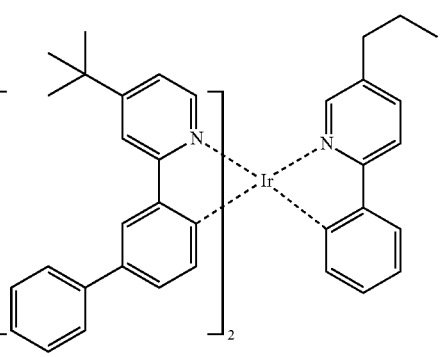

-continued

D-196
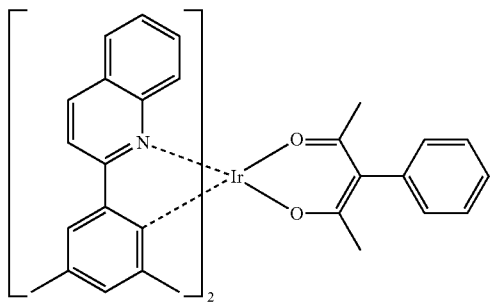

D-197
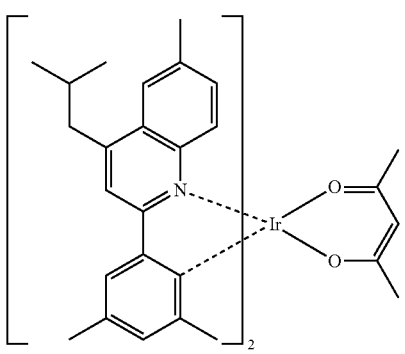

D-198
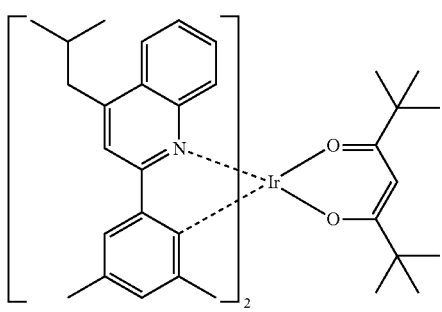

According to an additional aspect of the present disclosure, a mixture or composition for preparing an organic electroluminescent device is provided. The mixture or composition comprises the compound of the present disclosure. The mixture or composition may be used for preparing a light-emitting layer or a hole transport layer of an organic electroluminescent device. The mixture or composition for preparing a light-emitting layer of an organic electroluminescent device may be a mixture or composition for preparing a phosphorescent or fluorescent light-emitting layer, and specifically a phosphorescent red light-emitting layer of an organic electroluminescent device. Where the compound of the present disclosure is comprised in the mixture or composition for preparing a hole transport layer of an organic electroluminescent device, it may be comprised as a hole transport material. Where the compound of the present disclosure is comprised in the mixture or composition for preparing a light-emitting layer of an organic electroluminescent device, it may be comprised as a host material. Where the compound of the present disclosure is comprised as a host material, the mixture or composition may further comprise a second host material. The weight ratio between the first host material and the second host material is in the range of 1:99 to 99:1.

The organic electroluminescent device of the present disclosure may comprise a first electrode, a second electrode, and at least one organic layer disposed between the first and second electrodes, wherein the organic layer may comprise a light-emitting layer, and the light-emitting layer may comprise the mixture or composition for an organic electroluminescent device of the present disclosure.

The organic electroluminescent device of the present disclosure may further comprise, in addition to the organic electroluminescent compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the art, besides the compound of the present disclosure. If necessary, the organic electroluminescent device of the present disclosure may further comprise a yellow- or orange-light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \le X \le 2$), $AlO_X$ ($1 \le X \le 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compound of the present disclosure, the preparation method of the compound, and the luminescent properties of the device will be explained in detail with reference to the following examples.

Example 1: Preparation of Compound A-1

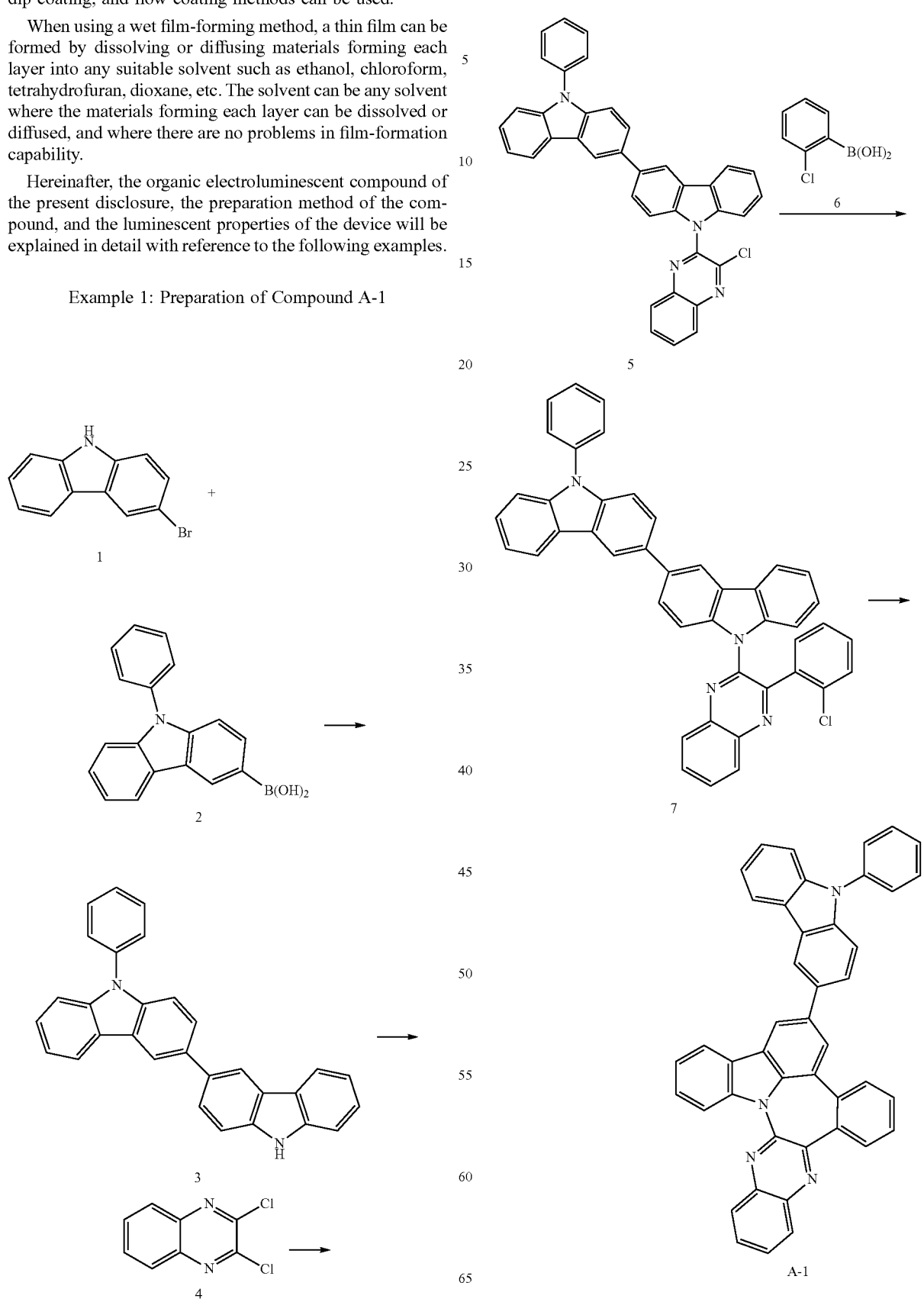

1) Preparation of Compound 3

After dissolving compound 1 (3-bromo-9H-carbazole) (20 g, 69.70 mmol), compound 2 [(9-phenyl-9H-carbazol-3-yl)boronic acid] (17.2 g, 69.70 mmol), Pd(PPh$_3$)$_4$ (2.4 g, 2.10 mmol), and Na$_2$CO$_3$ (18.5 g, 174.30 mmol) in toluene, ethanol, and H$_2$O of a flask, the mixture was under reflux at 120° C. for a day. After completion of the reaction, the mixture was extracted with ethyl acetate. The obtained organic layer was dried, and subjected to column chromatography to obtain compound 3 (12.8 g, yield: 45%).

2) Preparation of Compound 5

After dissolving compound 3 (9'-phenyl-9H,9'H-3,3'-bicarbazole) (11.8 g, 28.90 mmol) and compound 4 (7.5 g, 37.60 mmol) in dimethylformamide (DMF)(200 mL), NaH (1.8 g, 43.4 mmol, 60% in a mineral oil) was added thereto. The mixture was stirred at room temperature for 2.5 hrs, and methanol was added thereto. The resultant solid was filtered under reduced pressure, and subjected to column chromatography to obtain compound 5 (9.7 g, yield: 59%).

3) Preparation of Compound 7

After dissolving compound 5 [9-(3-chloroquinoxalin-2-yl)-9'-phenyl-9H,9'H-3,3'-bicarbazole] (18 g, 31.5 mmol), compound 6 (2-chlorophenyl)boronic acid (6 g, 32.0 mmol), Pd(PPh$_3$)$_4$ (1.83 g, 1.6 mmol), and Na$_2$CO$_3$ (10 g, 94 mmol) in toluene, ethanol, and H$_2$O of a flask, the mixture was under reflux at 120° C. for a day. After completion of the reaction, the mixture was extracted with ethyl acetate. The obtained organic layer was dried, and subjected to column chromatography to obtain compound 7 (16 g, yield: 78%).

4) Preparation of Compound A-1

A mixture of compound 7 (15 g, 23.2 mmol), Pd(OAc)$_2$ (520 mg, 1.2 mmol), Ligand (tricyclohexyl phosphonium tetrafluoroborate)(853 mg, 2.3 mmol), Cs$_2$CO$_3$ (23 g, 70 mmol), and xylene (77 mL) was stirred under reflux for 1.5 hrs. After cooling to room temperature, distilled water was added thereto. After completion of the reaction, the mixture was extracted with ethyl acetate. The obtained organic layer was dried and subjected to column chromatography to obtain compound A-1 (8.5 g, yield: 58%).

|     | Molecular Weight (MW) | UV | PL | Melting Point (M.P) |
|-----|-----------------------|--------|--------|--------------------|
| A-1 | 610.70                | 324 nm | 496 nm | 220° C.            |

Example 2: Preparation of Compound A-63

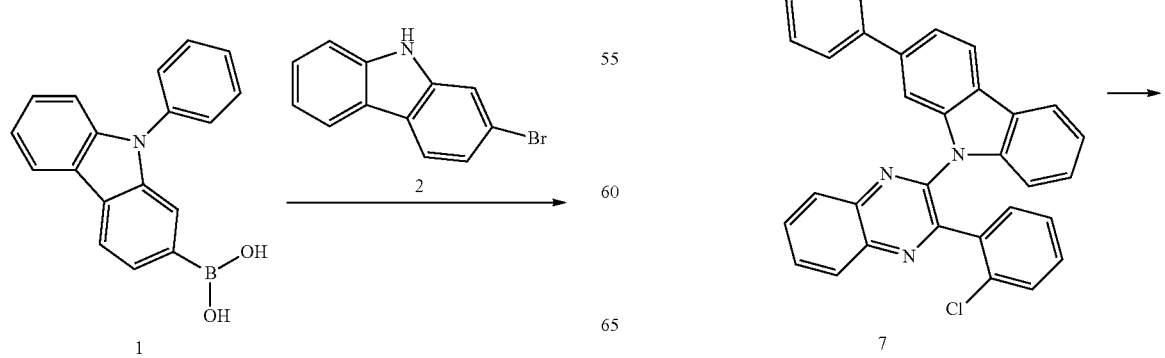

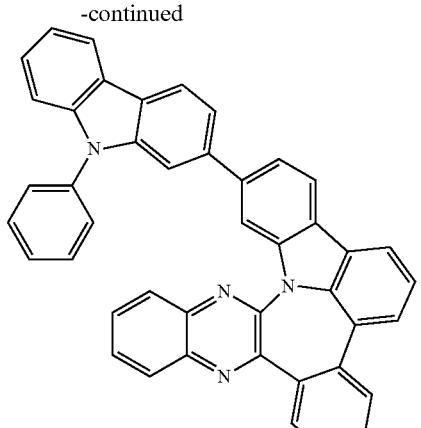

A-63

Example 3: Preparation of Compound A-62

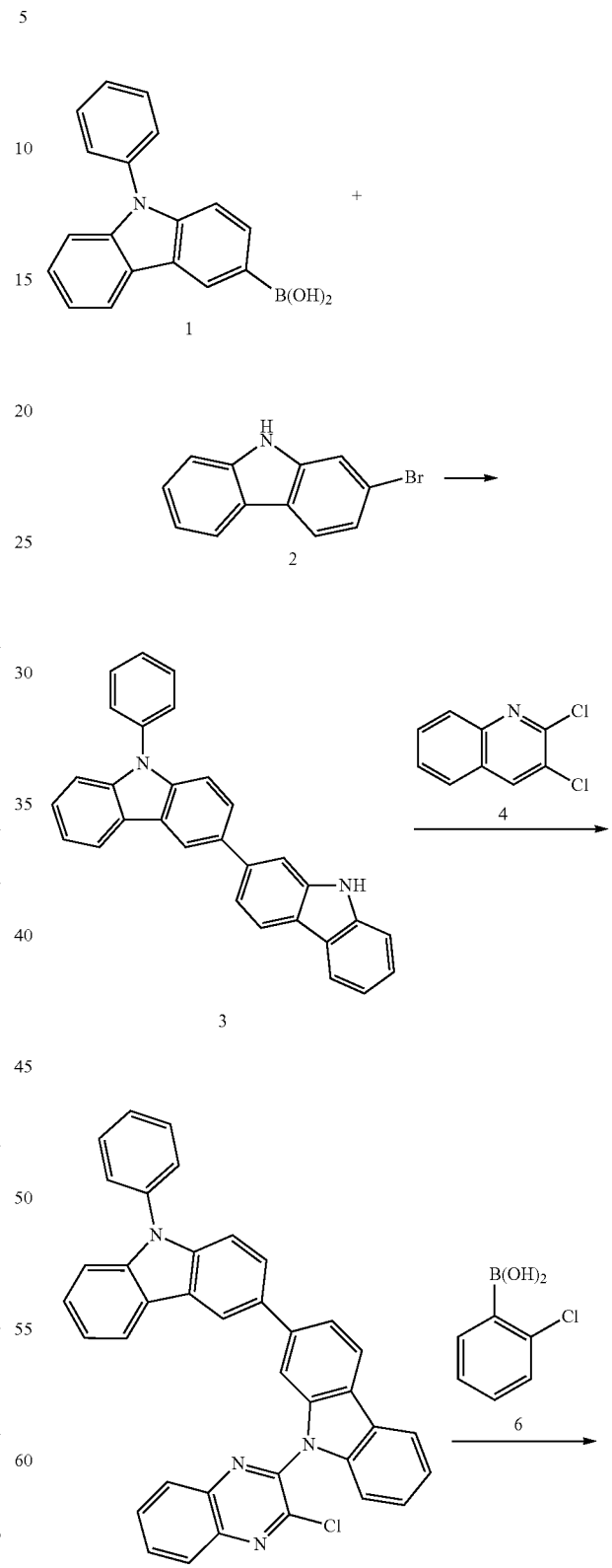

1) Preparation of Compound 3

After dissolving compound 1 (9-phenyl-9H-carbazol-2-yl)boronic acid (50 g, 174.2 mmol), compound 2 (2-bromo-9H-carbazole) (43 g, 174.2 mmol), Pd(PPh$_3$)$_4$ (10 g, 8.7 mmol), and Na$_2$CO$_3$ (54 g, 522 mmol) in toluene, ethanol, and H$_2$O of a flask, the mixture was under reflux at 120° C. for a day. After completion of the reaction, the mixture was extracted with ethyl acetate. The obtained organic layer was dried and subjected to column chromatography to obtain compound 3 (40 g, yield: 56%).

2) Preparation of Compound 5

After dissolving compound 3 (9-phenyl-9H,9'H-2,2'-bicarbazole) (40 g, 98 mmol) and compound 4 (23 g, 117 mmol) in DMF (200 mL), NaH (7.8 g, 196 mmol, 60% in a mineral oil) was added thereto. The mixture was stirred at room temperature for 2.5 hrs, and methanol was added thereto. The obtained solid was filtered under reduced pressure, and subjected to column chromatography to obtain compound 5 (30 g, yield: 54%).

3) Preparation of Compound 7

After dissolving compound 5 [9-(3-chloro quinoxalin-2-yl)-9'-phenyl-9H,9'H-2,2'-bicarbazole] (30 g, 53 mmol), compound 6 (2-chlorophenyl)boronic acid (9.8 g, 55 mmol), Pd(PPh$_3$)$_4$ (3 g, 2.6 mmol), and Na$_2$CO$_3$ (17 g, 159 mmol) in toluene, ethanol, and H$_2$O of a flask, the mixture was under reflux at 120° C. for a day. After completion of the reaction, the mixture was extracted with ethyl acetate. The obtained organic layer was dried and subjected to column chromatography to obtain compound 7 (20 g, yield: 58%).

4) Preparation of Compound A-63

A mixture of compound 7 [9-(3-(2-chlorophenyl)quinoxalin-2-yl)-9'-phenyl-9H,9'H-2,2'-bicarbazole] (20 g, 31 mmol), Pd(OAc)$_2$ (350 mg, 1.5 mmol), Ligand (tricyclohexyl phosphonium tetrafluoroborate) (1.3 mg, 3.1 mmol), Cs$_2$CO$_3$ (30 g, 90 mmol), and xylene (70 mL) was stirred under reflux for 1.5 hrs. After cooling to room temperature, distilled water was added thereto. After completion of the reaction, the mixture was extracted with ethyl acetate. The obtained organic layer was dried and subjected to column chromatography to obtain compound A-63 (6.5 g, yield: 41%).

|      | MW     | UV     | PL     | M.P     |
|------|--------|--------|--------|---------|
| A-63 | 610.70 | 344 nm | 475 nm | 289° C. |

-continued

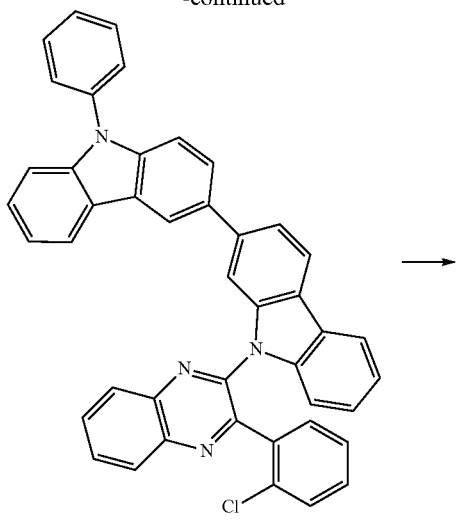

7

A-62

1) Preparation of Compound 3

After dissolving (9-phenyl-9H-carbazol-3-yl)boronic acid (50 g, 174.10 mmol), 2-bromo-9H-carbazole (43 g, 174.10 mmol), and Pd(PPh$_3$)$_4$ (6.0 g, 5.22 mmol) in toluene (870 mL), ethanol (200 mL), and H$_2$O (200 mL) of a flask, a mixture was under reflux at 120° C. for 7 hrs. After completion of the reaction, the mixture was extracted with ethyl acetate. The obtained organic layer was dried with magnesium sulfate to remove the remaining moisture, and subjected to column chromatography to obtain compound 3 (53.5 g, yield: 75%).

2) Preparation of Compound 5

After dissolving compound 3 (35.0 g, 85.70 mmol), 2,3-dichloroquinoxalin (25.6 g, 128.50 mmol), K$_2$CO$_3$ (17.8 g, 128.5 mmol), and 4-dimethylaminopyridine (DMAP) (5.2 g, 42.9 mmol) in DMF (430 mL) of a flask, the mixture was stirred at 90° C. for 6 hrs. After completion of the reaction, methanol and H$_2$O were added thereto. The mixture was stirred and filtered. The obtained solid was subjected to column chromatography to obtain compound 5 (33.3 g, yield: 68.1%).

3) Preparation of Compound 7

A mixture of compound 7 (15 g, 26.3 mmol), (2-chlorophenyl)boronic acid (5.0 g, 31.5 mmol), Pd(PPh$_3$)$_4$ (1.5 g, 1.32 mmol), Na$_2$CO$_3$ (8.4 g, 78.9 mmol), toluene (131 mL), ethanol (33 mL), and H$_2$O (33 mL) was stirred under reflux for 2 hrs. After cooling to room temperature, distilled water was added thereto. After completion of the reaction, the mixture was extracted with ethyl acetate. The obtained organic layer was dried with magnesium sulfate to remove the remaining moisture, and subjected to column chromatography to obtain compound 7 (17.0 g, yield: 99%).

4) Preparation of Compound A-62

A mixture of compound 7 (14.4 g, 22.3 mmol), Pd(OAc)$_2$ (250 mg, 1.11 mmol), Ligand (tricyclohexyl phosphonium tetrafluoroborate) (820 mg, 2.22 mmol), Cs$_2$CO$_3$ (21.7 g, 66.7 mmol), and xylene (120 mL) was stirred under reflux for 5 hrs. After cooling to room temperature, methanol was added thereto. The mixture was filtered, and the obtained solid was subjected to column chromatography to obtain compound A-62 (9.5 g, yield: 70%).

|  | MW | UV | PL | M.P |
|---|---|---|---|---|
| A-62 | 610.70 | 440 nm | 475 nm | 250.0° C. |

Example 4: Preparation of Compound A-117

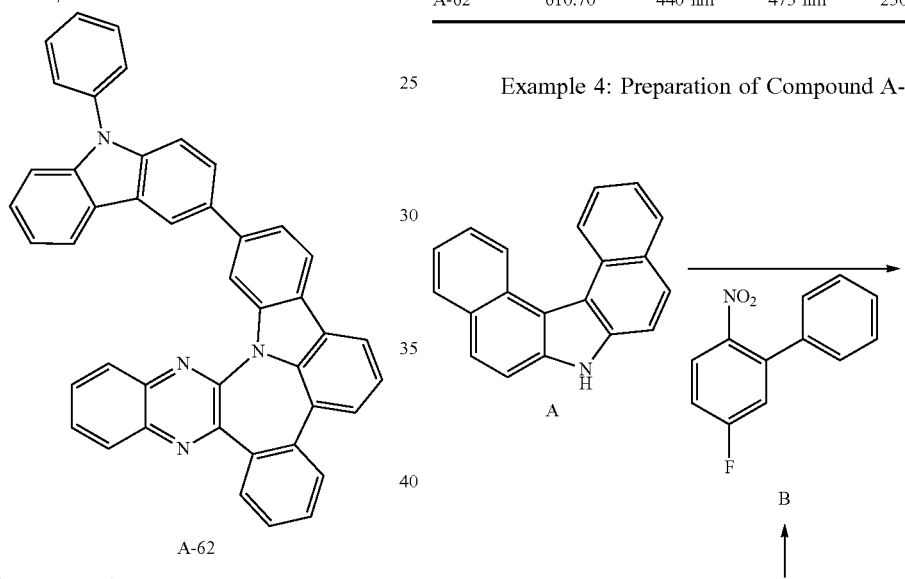

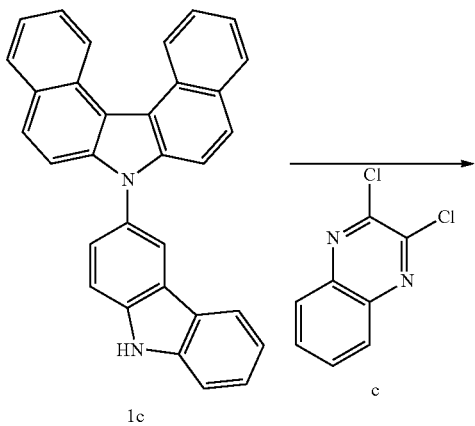

1c

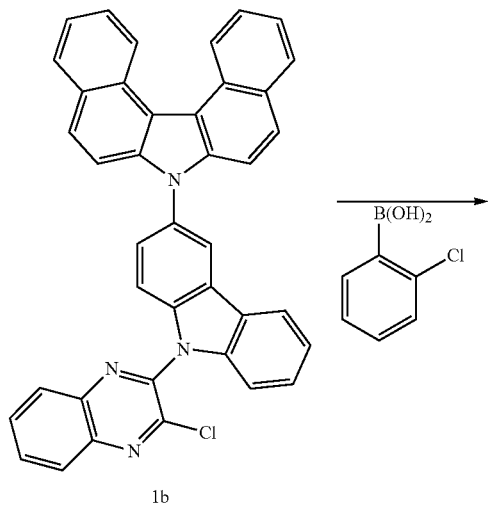

1b

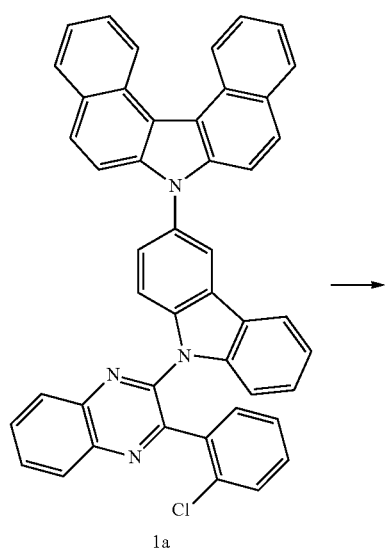

1a

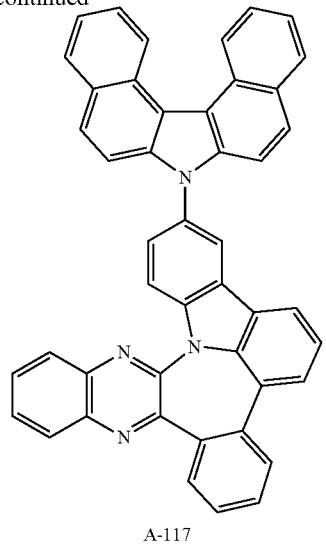

A-117

1) Preparation of Compound B

After introducing 2-bromo-4-fluoro-1-nitrobenzene (50 g, 227.3 mmol), phenylboronic acid (30.5 g, 250 mmol), Pd(PPh$_3$)$_4$ (13.1 g, 11.37 mmol), K$_2$CO$_3$ (62.8 g, 454.6 mmol), toluene (600 mL), ethanol (200 mL), and H$_2$O (200 mL) into a flask, the mixture was stirred under reflux for 6 hrs, cooled to room temperature, and extracted with ethyl acetate (EA) and distilled water. The organic layer was distilled under reduced pressure. The residue was subjected to column chromatography to obtain compound B (5-fluoro-2-nitro-1,1'-biphenyl) (49 g, yield: 99%).

2) Preparation of Compound 1d

After introducing compound A (34.5 g, 128.9 mmol), compound B (5-fluoro-2-nitro-1,1'-biphenyl) (28 g, 128.9 mmol), NaH (6.7 g, 167.6 mmol), and DMF (600 mL) into a flask, the mixture was stirred at 75° C. for 2 hrs. After cooling to room temperature, methanol (1 L) and purified water were added thereto. The mixture was filtered, and the obtained solid was dried under reduced pressure to obtain compound 1d [7-(6-nitro-[1,1'-biphenyl]-3-yl)-7H-dibenzo[c,g]carbazole] (52 g, yield: 86.8%).

3) Preparation of Compound 1c

After introducing compound 1d (52 g, 111.9 mmol), PPh$_3$ (88 g, 335.8 mmol), and 1,2-dichlorobenzene (500 mL) into a flask, the mixture was stirred. The mixture was then stirred under reflux for 6 hrs, and distilled off 1,2-dichlorobenzene. The residue was subjected to column chromatography to obtain compound 1c [7-(9H-carbazol-3-yl)-7H-dibenzo[c,g]carbazole] (39 g, yield: 75.9%).

4) Preparation of Compound 1b

After introducing compound 1c [7-(9H-carbazol-3-yl)-7H-dibenzo[c,g]carbazole] (15 g, 34.68 mmol), compound C [2,3-dichloroquinoxalin] (7.6 g, 38.15 mmol), 4-dimethylaminopyridine (2.1 g, 17.34 mmol), K$_2$CO$_3$ (4.8 g, 34.88 mmol), and DMF (200 mL) into a flask, the mixture was stirred. The mixture was then stirred under reflux for 3 hrs, and cooled to room temperature. After adding methanol (400 mL) and purified water, the mixture was filtered. The solid was dried, and subjected to column chromatography to obtain compound 1b [7-(9-(3-chloroquinoxalin-2-yl)-9H-carbazol-3-yl)-7H-dibenzo[c,g]carbazole] (17.7 g, yield: 85.8%).

5) Preparation of Compound 1a

After introducing compound 1b (17.7 g), 2-chloro-phenylboronic acid (4.7 g, 29.74 mmol), Pd(PPh$_3$)$_4$ (1.7 g, 1.487 mmol), K$_2$CO$_3$ (8.2 g, 59.48 mmol), purified water (30 mL), toluene (100 mL), and ethanol (30 mL) into a flask, the mixture was stirred. The mixture was then stirred under reflux for 4 hrs. After cooling to room temperature, the mixture was extracted with EA and purified water. The obtained organic layer was concentrated under reduced pressure. The residue was subjected to column chromatography to obtain compound 1a [7-(9-(3-(2-chlorophenyl)quinoxalin-2-yl)-9H-carbazol-3-yl)-7H-dibenzo[c,g]carbazole] (15.3 g, yield 76.6%).

6) Preparation of Compound A-117

After introducing compound 1a (14.3 g), Pd(OAc)$_2$ (0.48 g, 2.13 mmol), tricyclohexyl phosphonium tetrafluoroborate (1.57 g, 4.26 mmol), Cs$_2$CO$_3$ (20.8 g, 63.9 mmol), and o-xylene (100 mL) into a flask, the mixture was stirred. The mixture was then stirred under reflux for 2 hrs. After cooling to room temperature, the mixture was extracted with EA and purified water. The organic layer was concentrated under reduced pressure. The residue was subjected to column chromatography to obtain compound A-117 (6.5 g, yield: 48%).

| | MW | UV | PL | M.P |
|---|---|---|---|---|
| A-117 | 634.73 | 442 | 477 | 300.1° C. |

[Device Example 1] OLED Using the Compound of the Present Disclosure

OLED was produced using the organic electroluminescent compound of the present disclosure as follows. A transparent electrode indium tin oxide (ITO) thin film (10 Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was then introduced into another cell of said vacuum vapor depositing apparatus, and evaporated by applying electric current to the cell, thereby forming a second hole injection layer having a thickness of 5 nm on the first hole injection layer. HT-1 was introduced into one cell of the vacuum vapor depositing apparatus, and evaporated by applying electric current to the cell, thereby forming a first hole transport layer having a thickness of 10 nm on the second hole injection layer. HT-3 was introduced into another cell of the vacuum vapor depositing apparatus, and evaporated by applying electric current to the cell, thereby forming a second hole transport layer having a thickness of 60 nm on the first hole transport layer. Thereafter, compound A-1 was introduced into one cell of the vacuum vapor depositing apparatus as a host, and compound D-96 was introduced into another cell as a dopant. The two materials were evaporated at different rates, so that the dopant was deposited in a doping amount of 3 wt % based on the total amount of the host and dopant to form a light-emitting layer having a thickness of 40 nm on the hole transport layer. ET-1 and EI-1 were introduced into two cells of the vacuum vapor depositing apparatus, respectively, and evaporated at a 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce an OLED. The produced OLED showed a red emission having a luminance of 1,000 cd/m$^2$, and a current efficiency of 30.4 cd/A at a driving voltage of 3.6V. The minimum time taken to be reduced to 95% of the luminance at 5,000 nit was 63 hours.

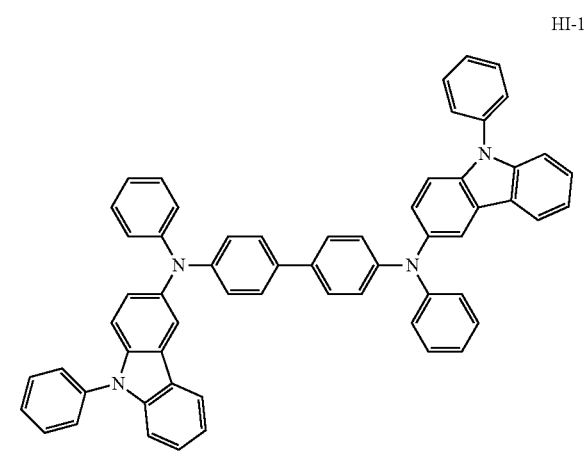

HI-1

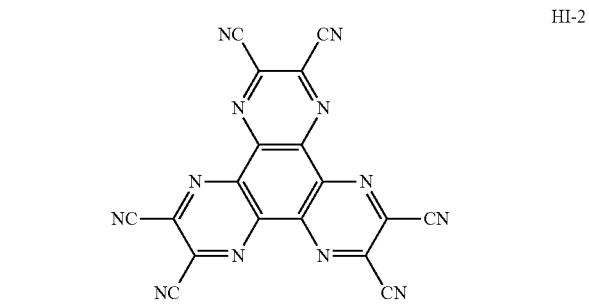

HI-2

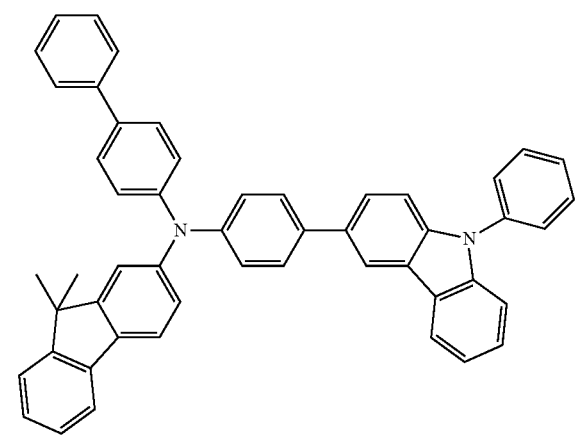

HT-1

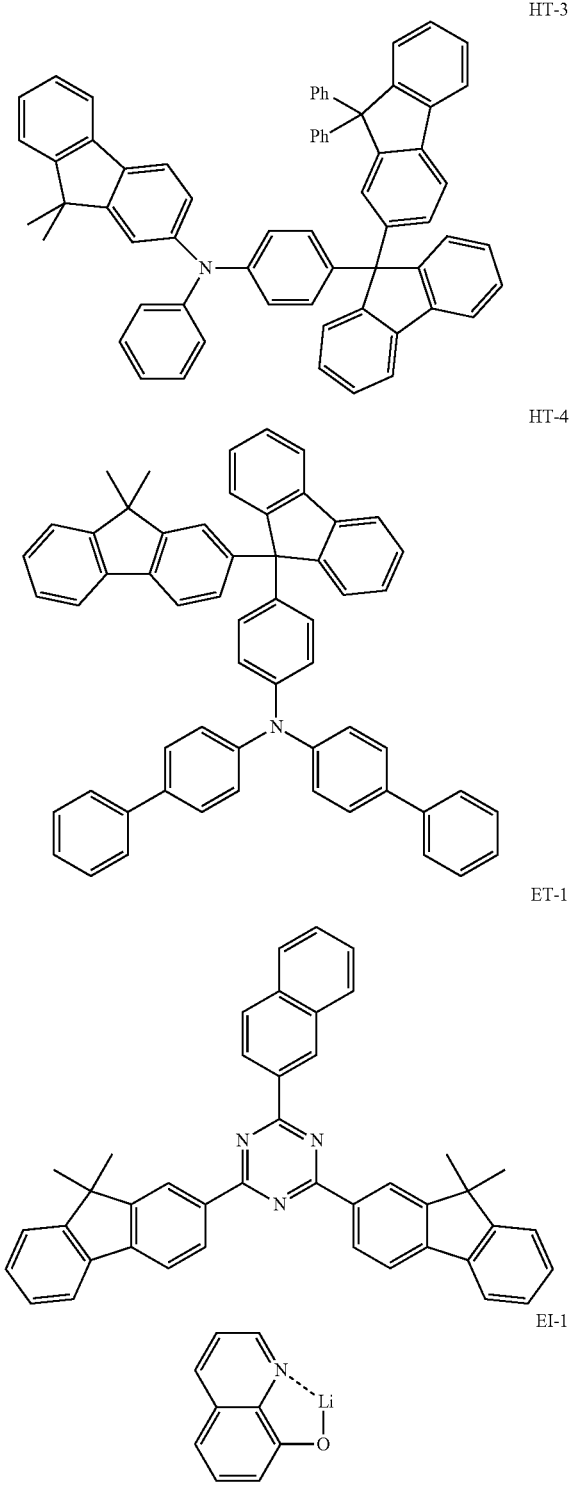

cd/m², and a current efficiency of 28.7 cd/A at a driving voltage of 4.0 V. The minimum time taken to be reduced to 95% of the luminance at 5,000 nit was 9 hours.

[Device Example 3] OLED Using the Compound of the Present Disclosure

OLED was produced in the same manner as in Device Example 1, except that compound A-63 was used as a host of the light-emitting material. The produced OLED showed a red emission having a luminance of 1,000 cd/m², and a current efficiency of 25.8 cd/A at a driving voltage of 3.7 V. The minimum time taken to be reduced to 95% of the luminance at 5,000 nit was 11 hours.

[Device Example 4] OLED Using the Compound of the Present Disclosure

OLED was produced in the same manner as in Device Example 1, except that compound A-62 was used as a host of the light-emitting material. The produced OLED showed a red emission having a luminance of 1,000 cd/m², and a current efficiency of 29.0 cd/A at a driving voltage of 3.5 V. The minimum time taken to be reduced to 95% of the luminance at 5,000 nit was 33 hours.

[Comparative Example 1] OLED Using a Conventional Compound

OLED was produced in the same manner as in Device Example 1, except that compound X shown below was used as a host of the light-emitting material. The produced OLED showed a red emission having a luminance of 1,000 cd/m², and a current efficiency of 14.3 cd/A at a driving voltage of 10 V. The minimum time taken to be reduced to 95% of the luminance at 5,000 nit was 0 hour.

Compound X

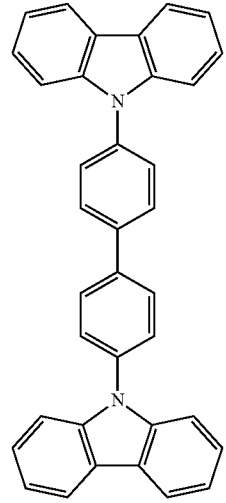

[Device Example 2] OLED Using the Compound of the Present Disclosure

OLED was produced in the same manner as in Device Example 1, except that compound A-117 was used as a host of the light-emitting material, and HT-4 was used for a second hole transport layer instead of HT-3. The produced OLED showed a red emission having a luminance of 1,000

The prior art's compounds such as those of formulae A and B shown above do not have appropriate HOMO level, LUMO level, and triplet energy for a phosphorescent red-emitting host material of an organic electroluminescent device. Therefore, when such compound is used for a phosphorescent red-emitting host material, the organic electroluminescent device shows poor characteristics such as poor luminous efficiency, short lifespan, and high driving voltage. The compounds having a fused structure such as formula A above have poor solubility, and thus cannot be used in a preparation process for a mass production. Although the compounds having formula B have good solubility, they have low triplet energy resulting in poor efficiency, and low thermal-stability. However, as shown in the working examples of the present disclosure, the organic electroluminescent compound of the present disclosure has lower driving voltage, better luminous efficiency, and longer lifespan than conventional organic electroluminescent compounds. The device comprising the organic electroluminescent compound of the present disclosure shows excellent luminous efficiency, in particular, excellent current/power efficiencies, and good color purity, thermal-stability, and solubility.

The invention claimed is:

1. An organic electroluminescent compound represented by the following formula 1:

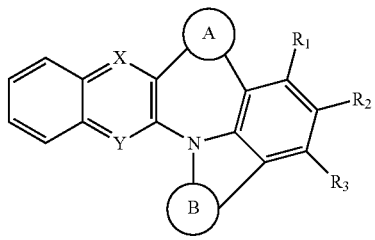

(1)

wherein ring A and ring B, each independently, represent any one of the following formulae 2-1 to 2-3:

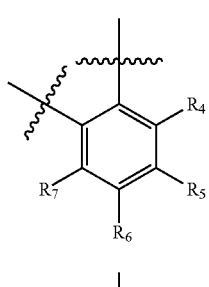

(2-1)

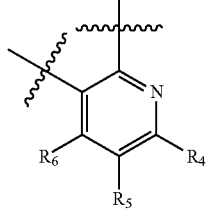

(2-2)

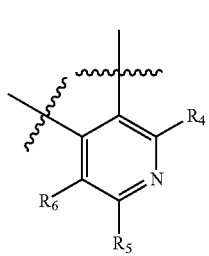

(2-3)

X and Y, each independently, represent —$CR_8$— or —N—; provided that both X and Y are not —$CR_8$—, simultaneously;

$R_1$ to $R_8$, each independently, represent hydrogen, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted benzene ring or a substituted or unsubstituted naphthalene ring; and the heteroaryl of the substituted or unsubstituted 3- to 30-membered heteroaryl contains at least one hetero atom selected from N, O and S.

2. The organic electroluminescent compound according to claim 1, wherein the substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino and the substituted alkylarylamino in $R_1$ to $R_8$, each independently, are at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein X and Y, each independently, represent —$CR_8$— or —N—; provided that both X and Y are not —$CR_8$—, simultaneously;

ring A and ring B, each independently, represent any one of the following formulae 2-1 to 2-3:

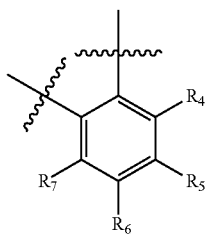

(2-1)

(2-2)
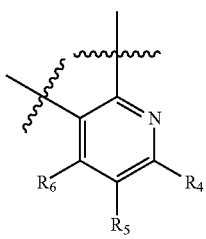

(2-3)
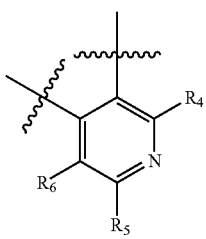

R₁ to R₈, each independently, represent hydrogen, a substituted or unsubstituted (C6-C20)aryl, a substituted or unsubstituted 5- to 25-membered heteroaryl, or a substituted or unsubstituted di(C6-C20)arylamino; or may be linked to an adjacent substituent(s) to form a substituted or unsubstituted benzene ring or a substituted or unsubstituted naphthalene ring.

4. The organic electroluminescent compound according to claim 1, wherein X and Y, each independently, represent —CR₈— or —N—; provided that both X and Y are not —CR₈—, simultaneously;

ring A and ring B, each independently, represent any one of the following formulae 2-1 to 2-3:

(2-1)
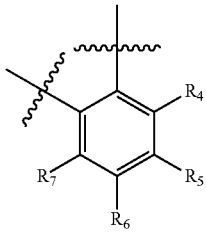

(2-2)
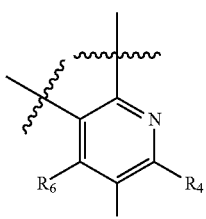

(2-3)
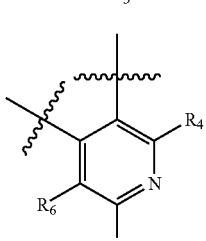

R₁ to R₇, each independently, represent hydrogen; a (C6-C20)aryl unsubstituted or substituted with a (C1-C6)alkyl, a 5- to 20-membered heteroaryl or a di(C6-C12)arylamino; or a 5- to 20-membered heteroaryl unsubstituted or substituted with a (C1-C6)alkyl, a (C6-C12)aryl or a di(C6-C12)arylamino; or may be linked to an adjacent substituent(s) to form a substituted or unsubstituted benzene ring or a substituted or unsubstituted naphthalene ring; provided that R₁ to R₇ are not hydrogen, simultaneously; and R₈ represents hydrogen or a (C1-C6)alkyl.

5. The organic electroluminescent compound according to claim 1, wherein

R₁ to R₇, each independently, represent hydrogen, a (C1-C20)alkyl, or any one of the following formulae 3-1 to 3-6; or may be linked to an adjacent substituent(s) to form a benzene ring unsubstituted or substituted with a (C1-C6)alkyl, or a naphthalene ring unsubstituted or substituted with a (C1-C6)alkyl; provided that R₁ to R₇ are not hydrogen, simultaneously; and R₈ represents hydrogen or a (C1-C6)alkyl;

(3-1)
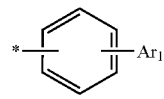

(3-2)
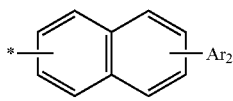

(3-3)
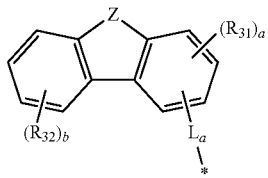

(3-4)
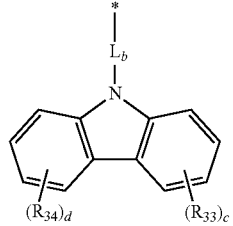

(3-5)
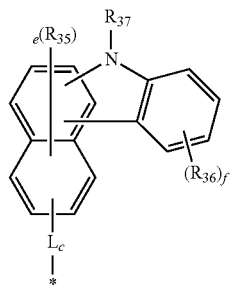

(3-6)

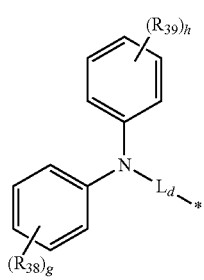

wherein,
Ar₁ and Ar₂, each independently, represent hydrogen, a substituted or unsubstituted (C1-C30)alkyl, or a substituted or unsubstituted (C6-C30)aryl; provided that Ar₁ and Ar₂ are not fluorenyl;
$L_a$, $L_b$, $L_c$, and $L_d$, each independently, represent a single bond, a substituted or unsubstituted (C6-C30)arylene, or a substituted or unsubstituted 3- to 30-membered heteroarylene;
Z represents —S—, —O—, —NR₁₁—, or —CR₁₂R₁₃—;
R₁₁ to R₁₃, each independently, represent hydrogen, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, or a substituted or unsubstituted 3- to 7-membered heterocycloalkyl; or may be linked to an adjacent substituent(s) to form a substituted or unsubstituted 3- to 30-membered, mono- or polycyclic, alicyclic or aromatic ring;
R₃₁ to R₃₉, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted 3- to 7-membered heterocycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted 3- to 30-membered, mono- or polycyclic, alicyclic or aromatic ring, whose carbon atom(s) may be replaced with at least one hetero atom selected from nitrogen, oxygen, and sulfur;
the heteroaryl(ene) and heterocycloalkyl, each independently, contain at least one hetero atom selected from nitrogen, oxygen, and sulfur;
a represents an integer of 1 to 3;
b to d and f, each independently, represent an integer of 1 to 4;
e, g, and h, each independently, represent an integer of 1 to 5; and
where a, b, c, d, e, f, g, or h is integers of 2 or more, each of R₃₁, R₃₂, R₃₃, R₃₄, R₃₅, R₃₆, R₃₇, R₃₈, or R₃₉ may be the same or different.

6. The organic electroluminescent compound according to claim 5, wherein at least one of R₁ to R₇ is selected from formulae 3-3 to 3-5, and Z of formula 3-3 represents —NR₁₁—.

7. The organic electroluminescent compound according to claim 1, wherein the compound represented by formula 1 is selected from the group consisting of:

A-1

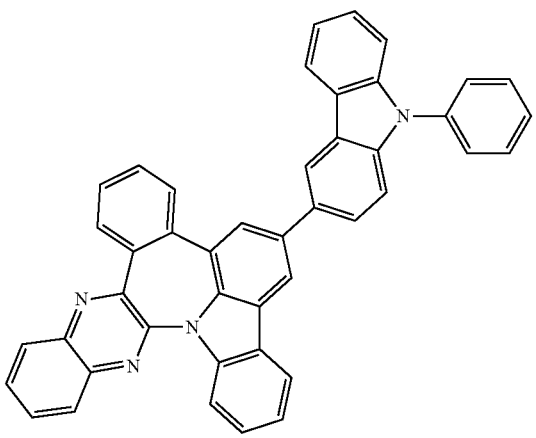

A-2

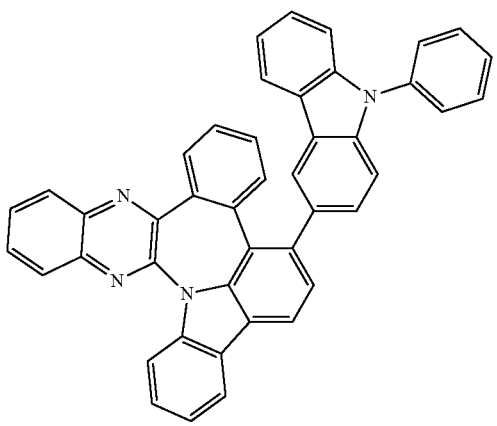

A-3

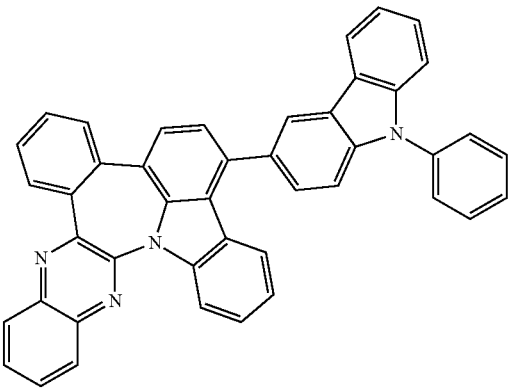

A-4
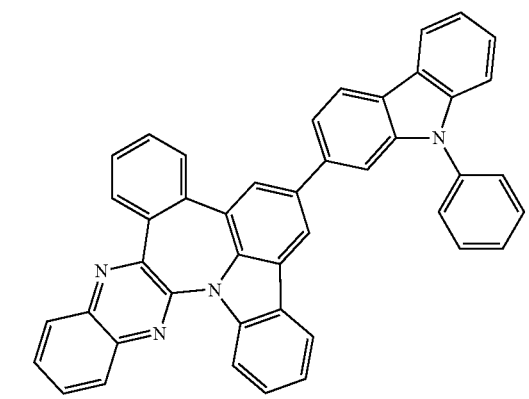
A-5
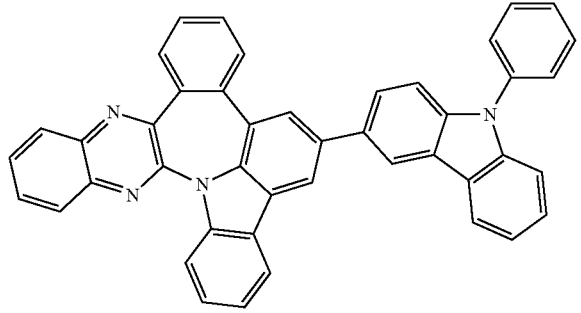
A-6
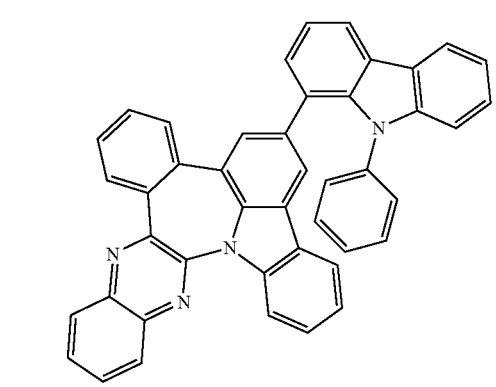
A-7
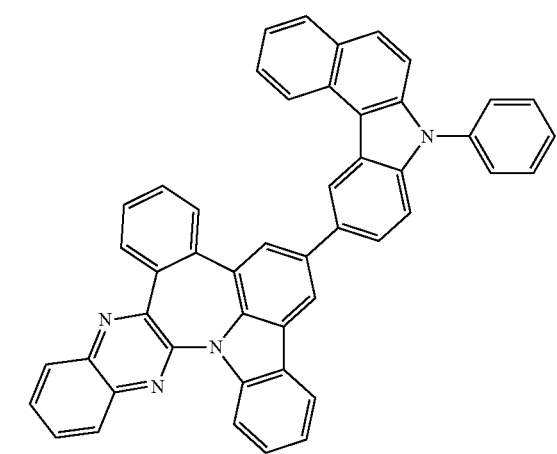
A-8
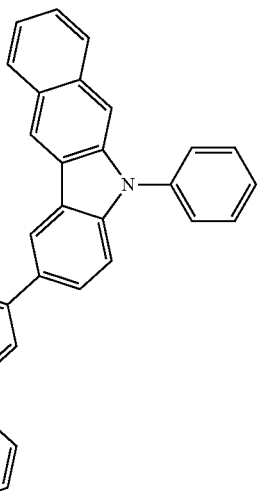
A-9
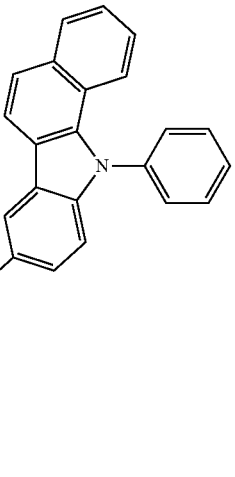
A-10
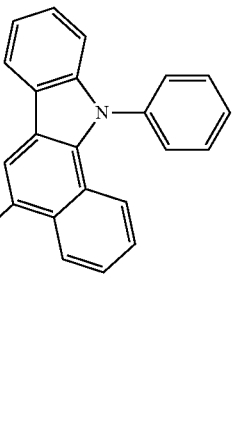

A-11
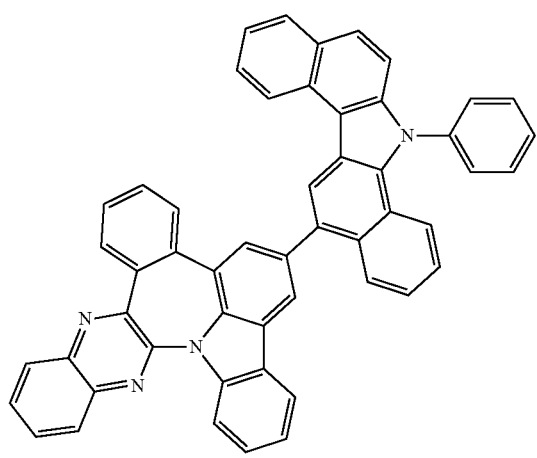
A-12
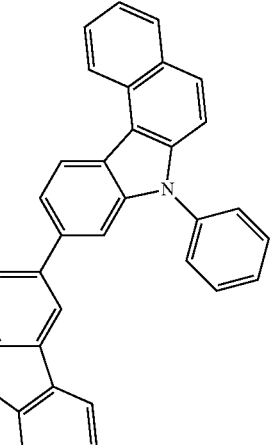
A-13
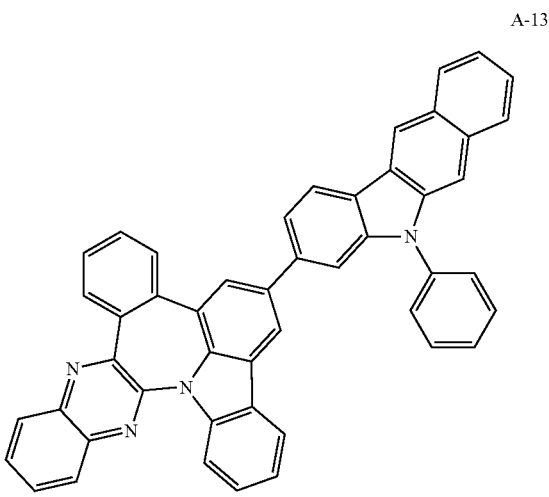
A-14
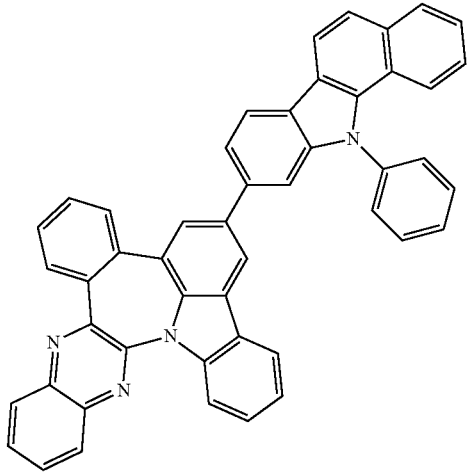
A-15
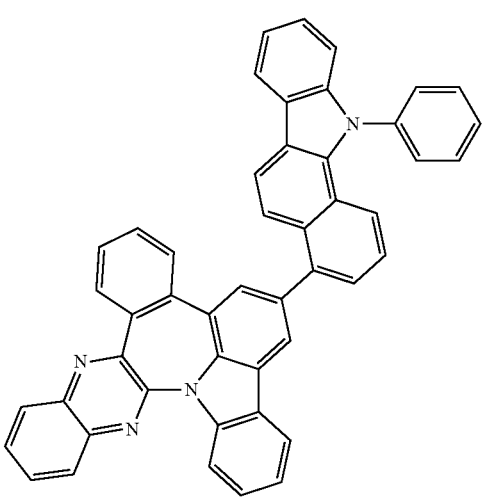
A-16
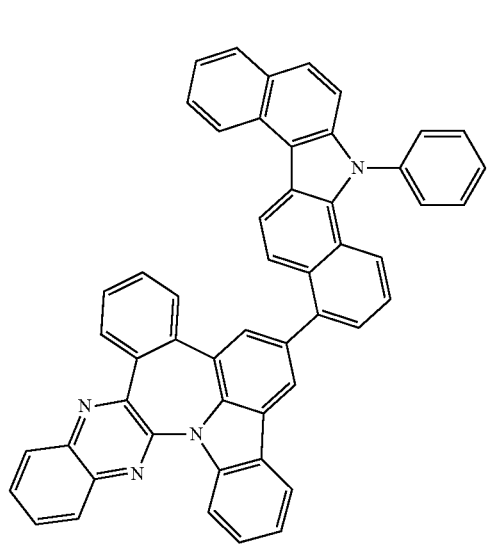

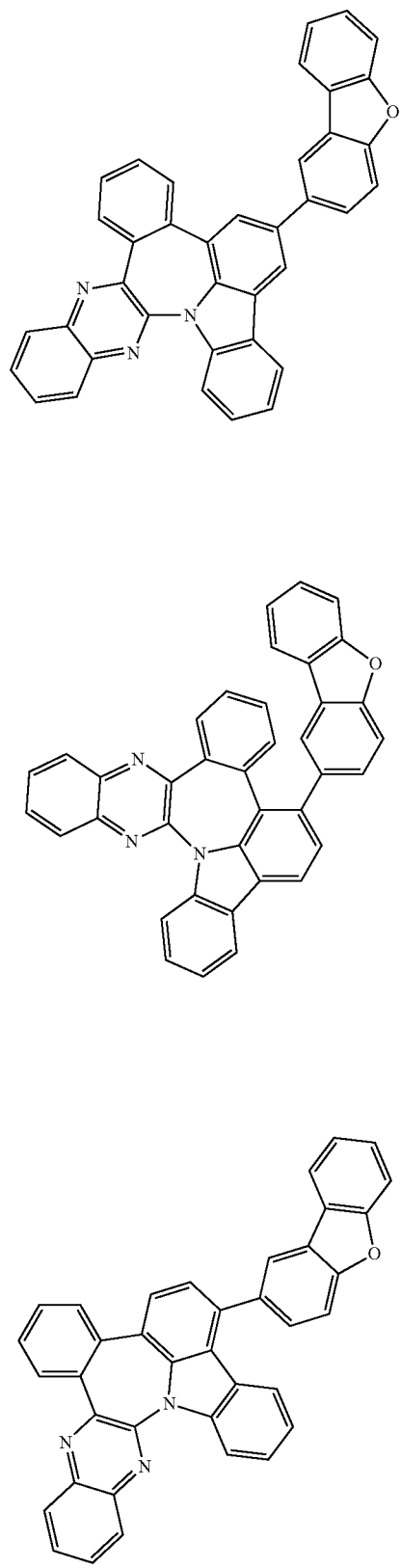
A-17
A-18
A-19
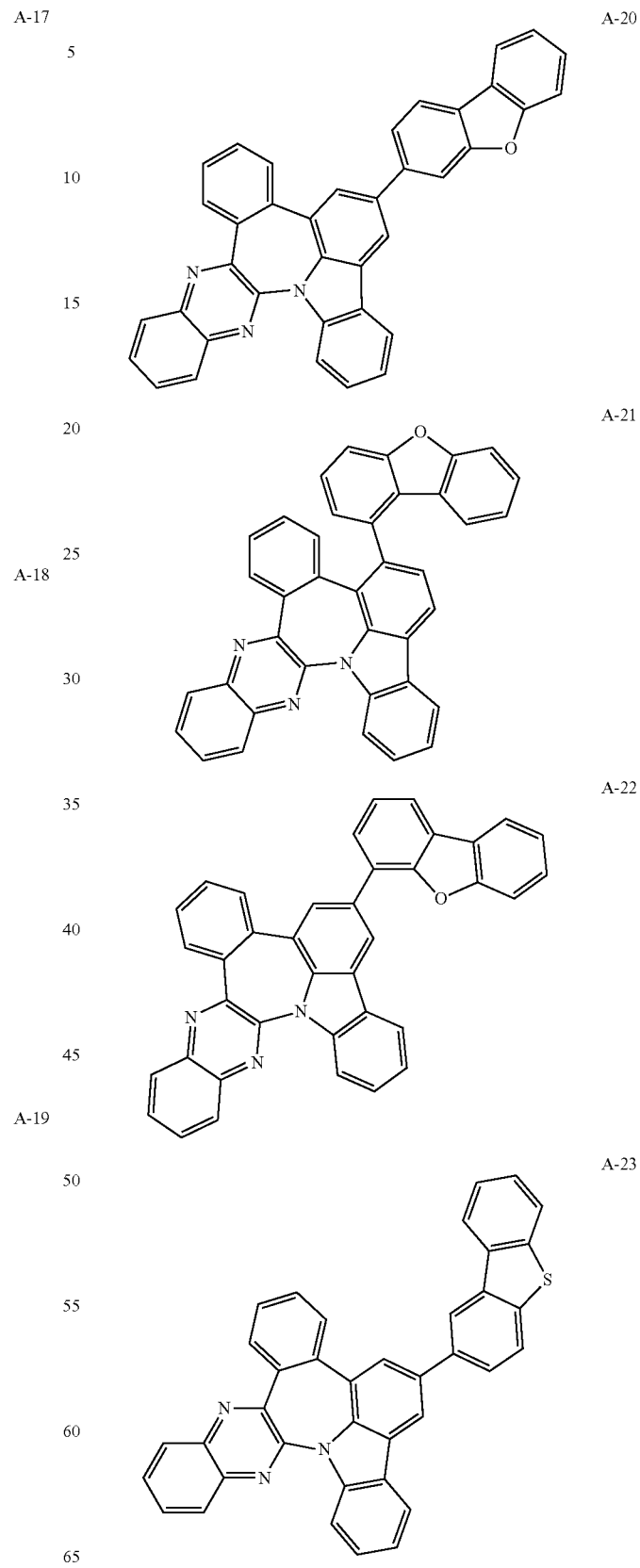
A-20
A-21
A-22
A-23

A-24
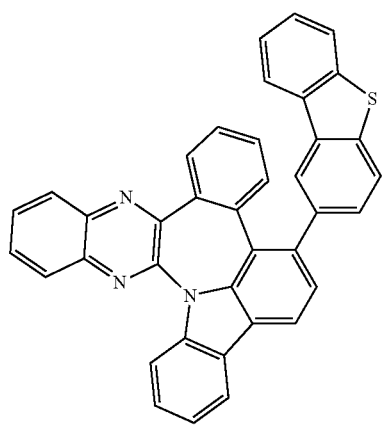
A-25
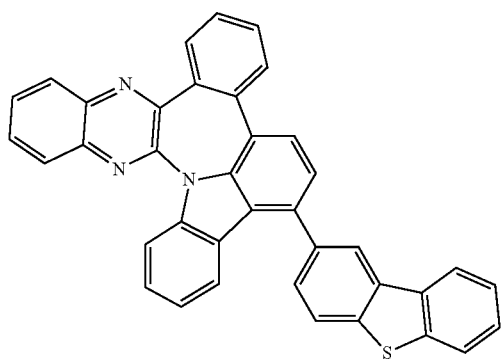
A-26
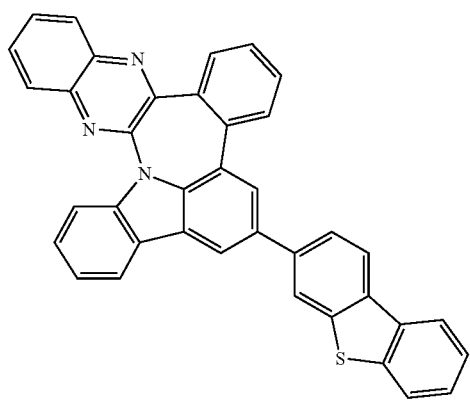
A-27
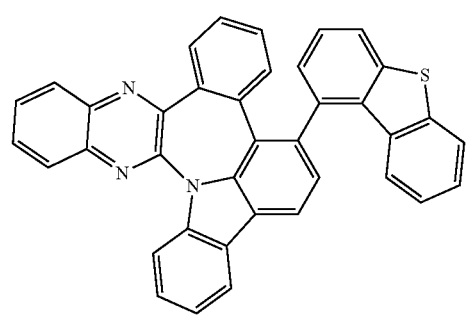
A-28
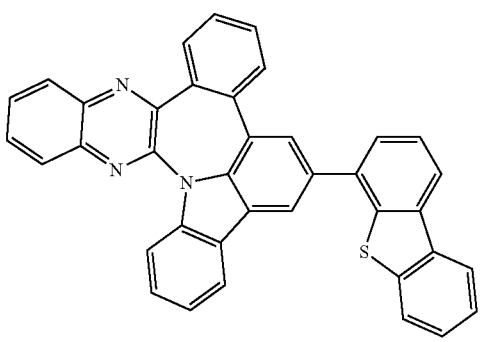
A-29
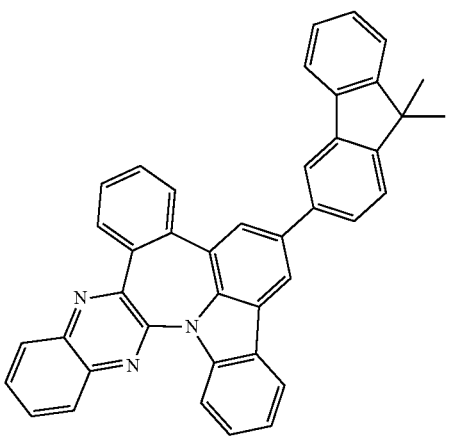
A-30
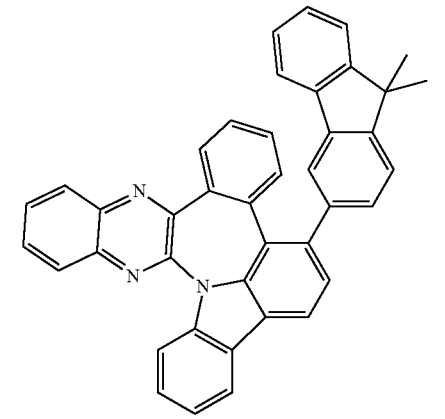
A-31
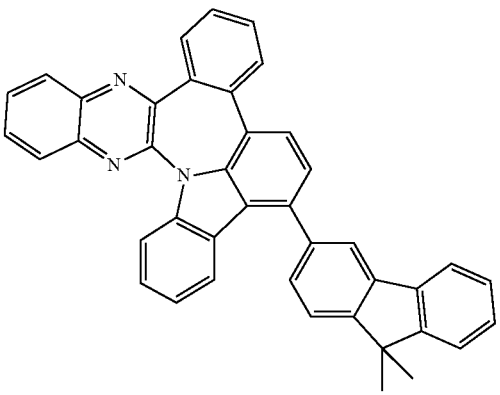

-continued
A-32
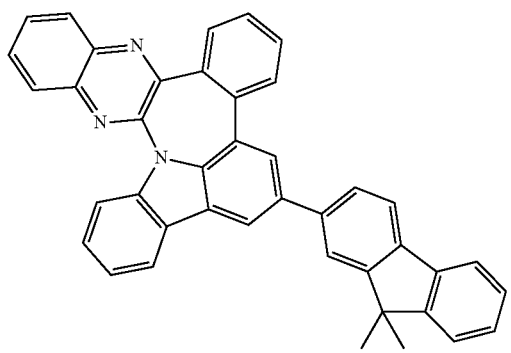
A-33
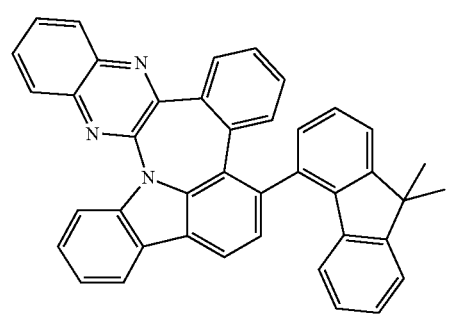
A-34
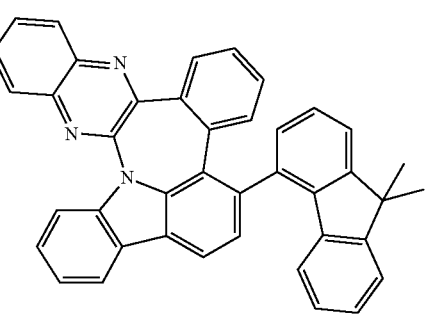
A-35
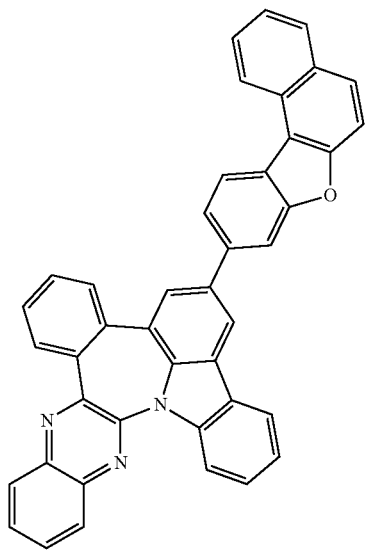
A-36
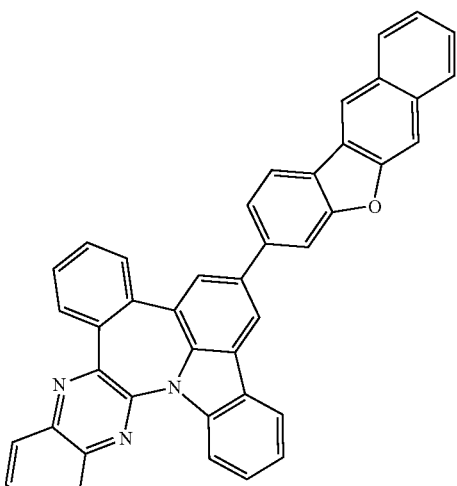
A-37
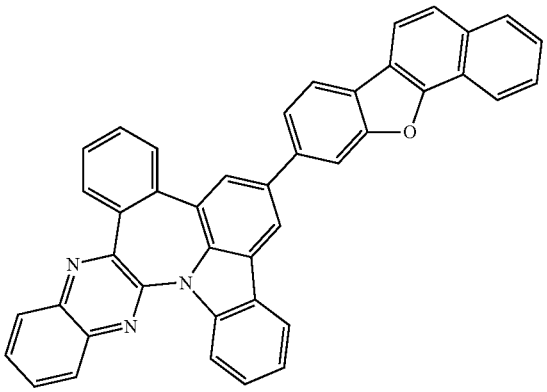
A-38
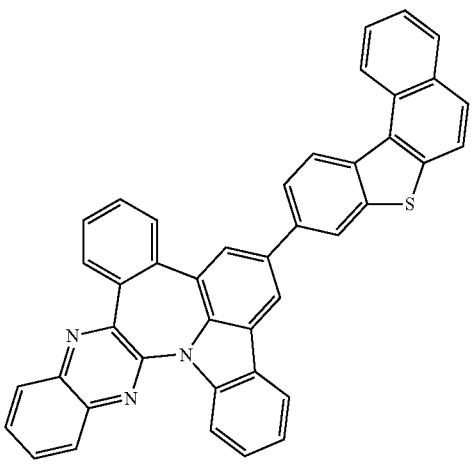

A-39
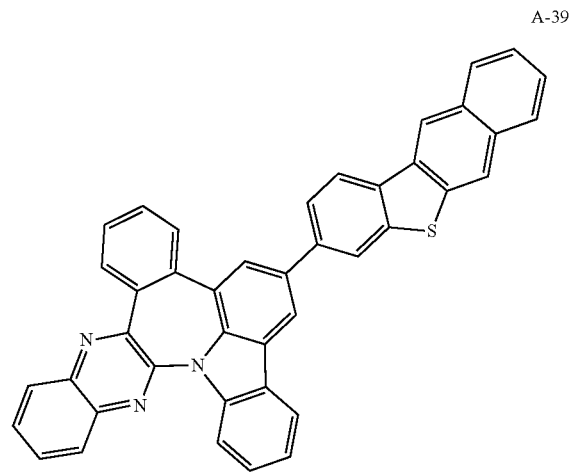
A-40
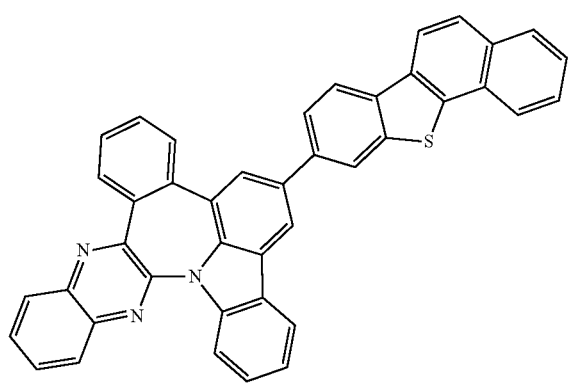
A-41
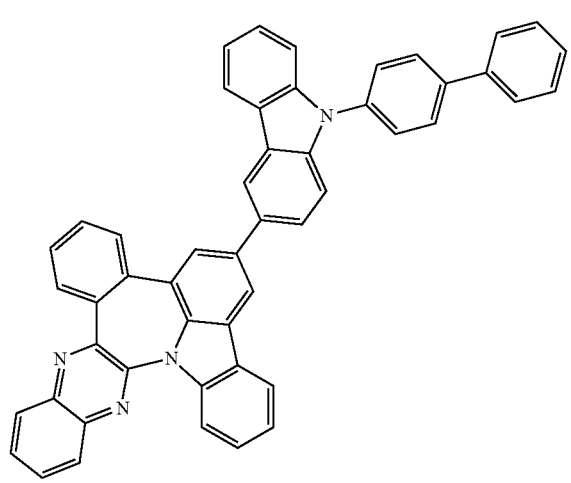
A-42
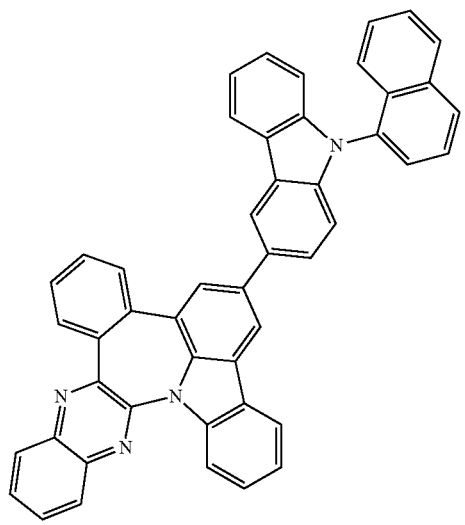
A-43
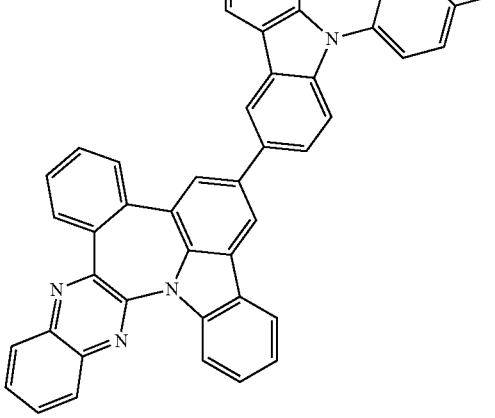
A-44
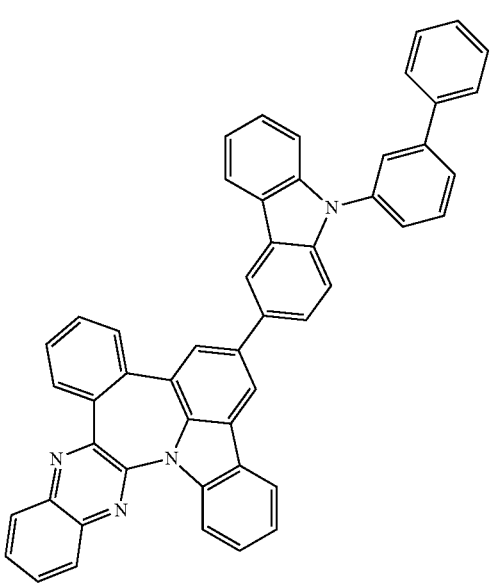

A-45
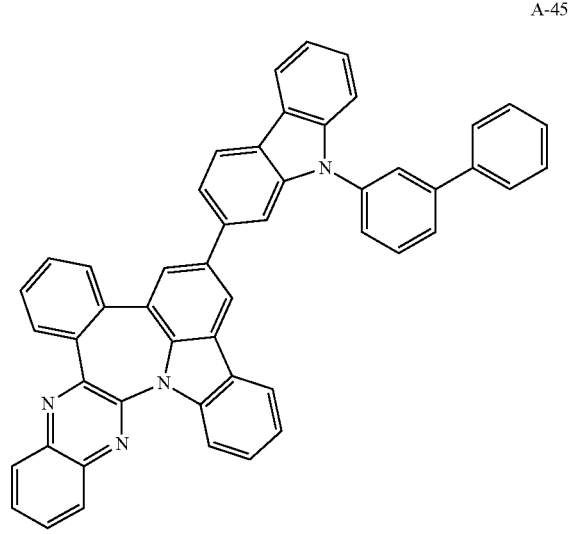
A-46
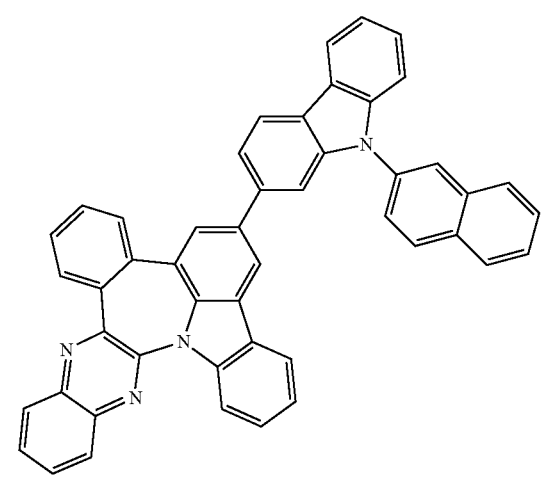
A-47
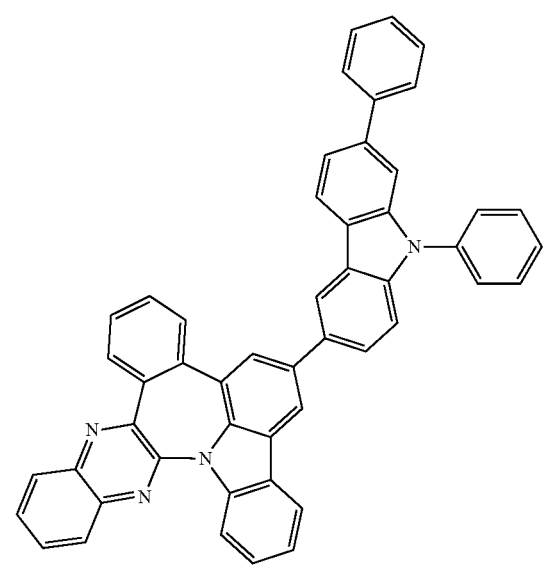
A-48
A-49
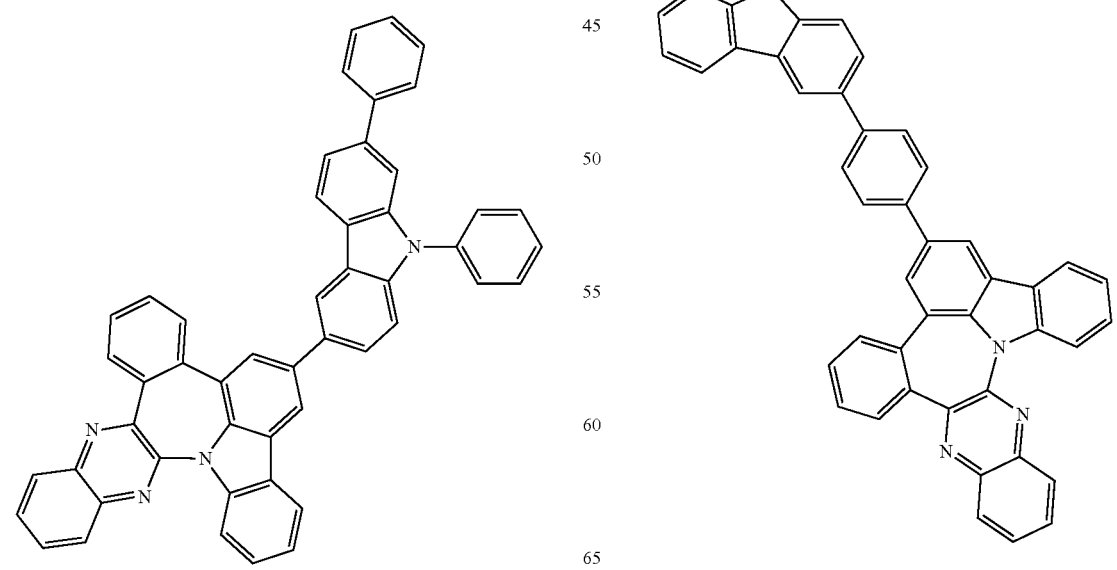

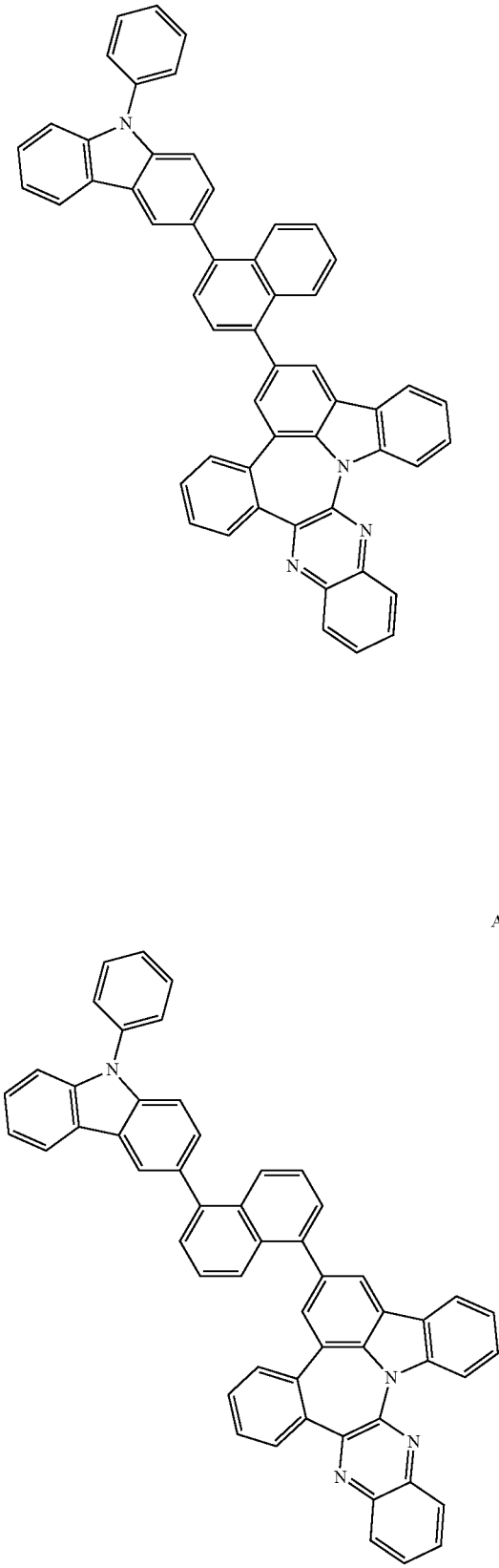
A-50
A-51
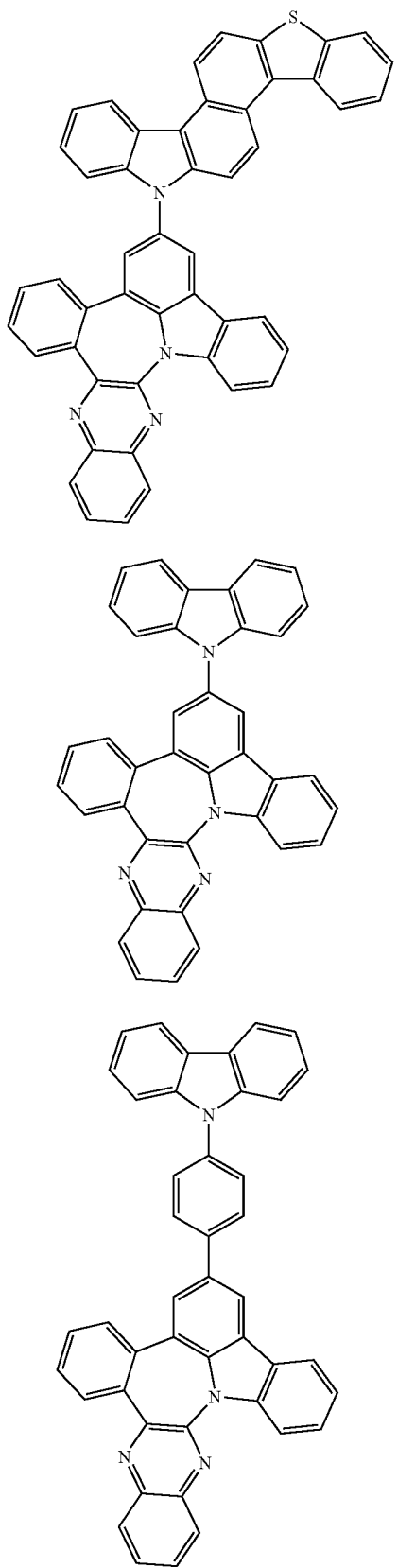
A52
A-53
A-54

-continued
A-55
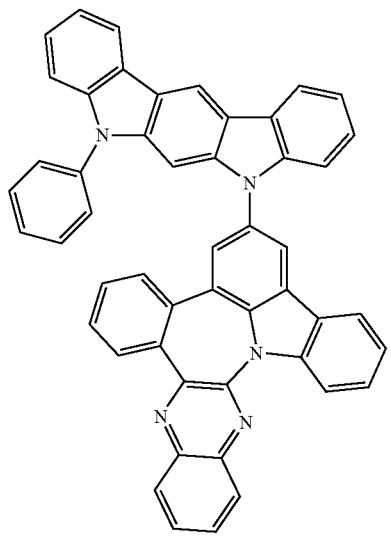
A-56
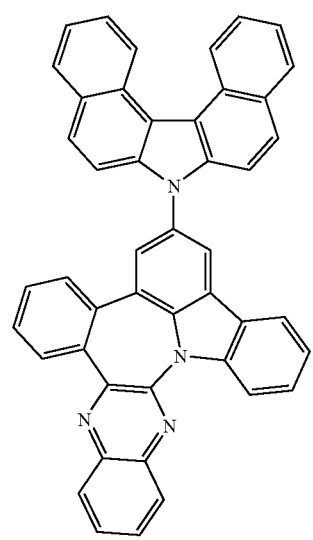
A-57
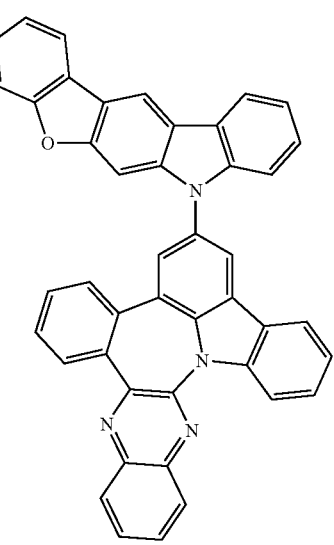
-continued
A-58
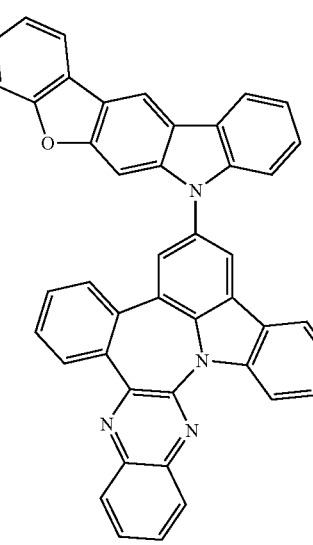
A-59
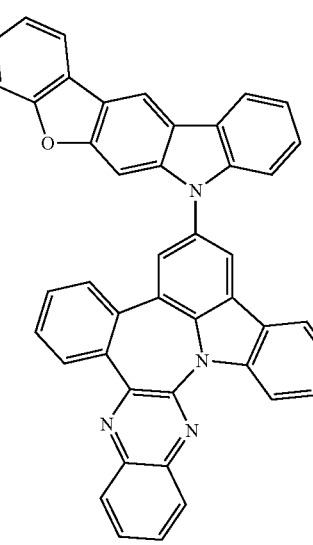

A-60
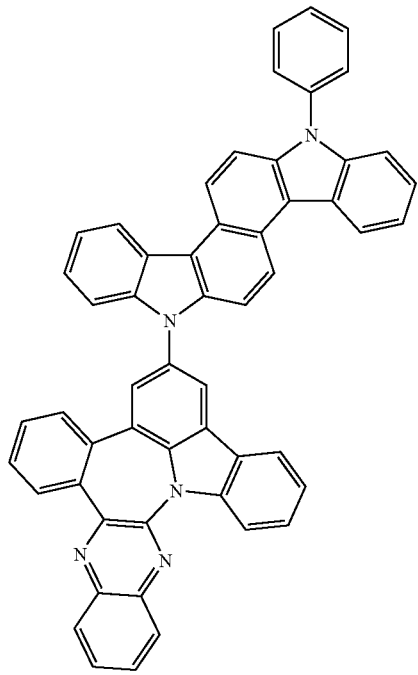
A-61
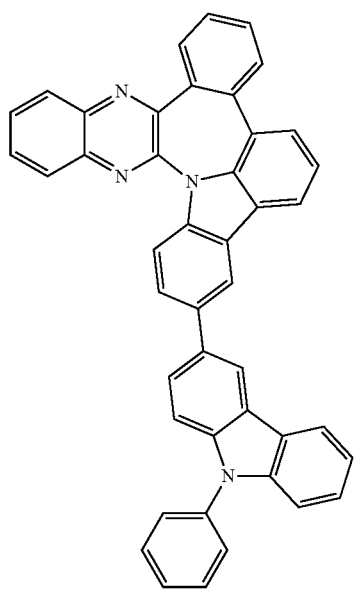
A-62
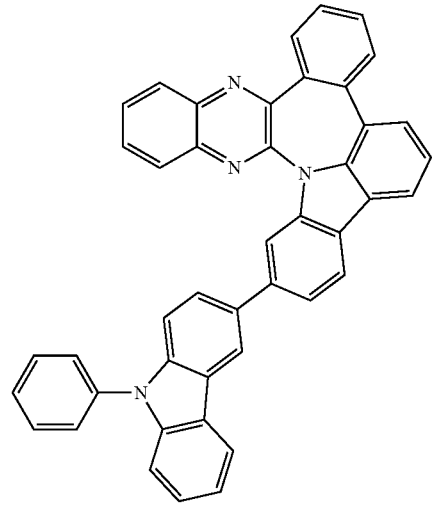
A-63
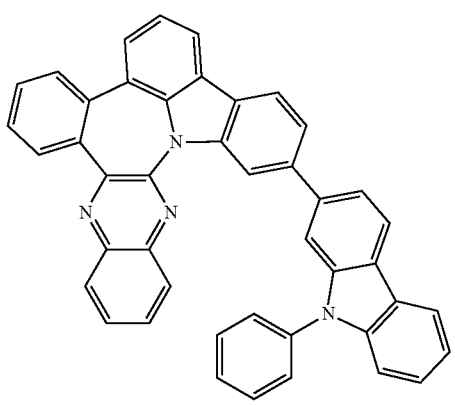
A-64
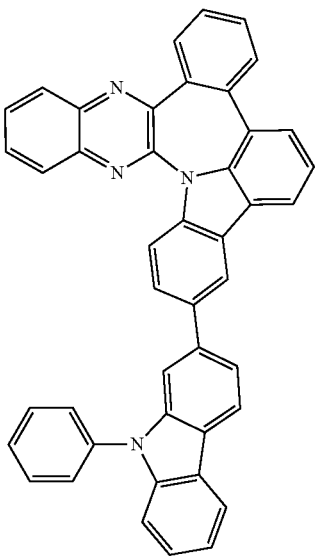

-continued
A-65
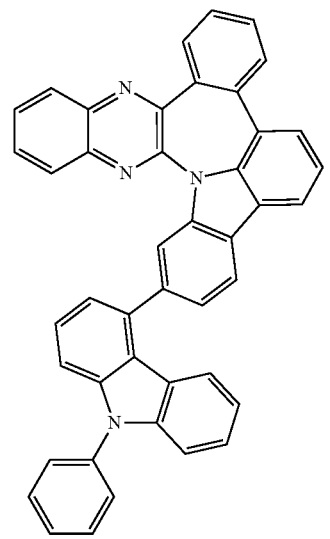
A-66
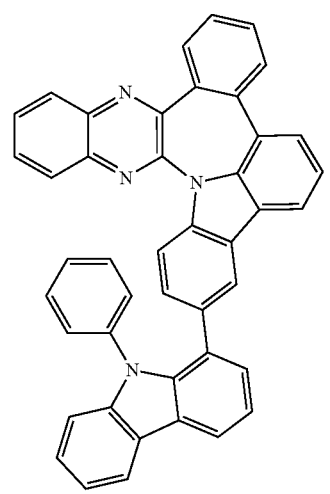
A-67
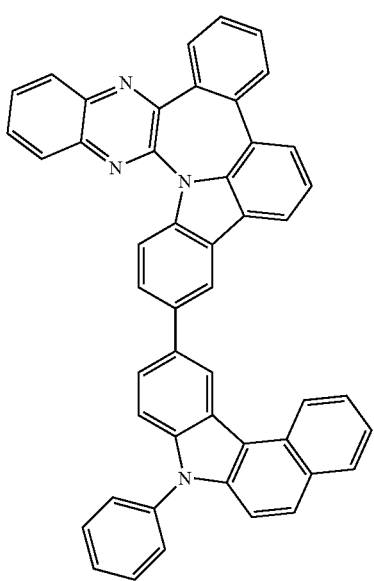
-continued
A-68
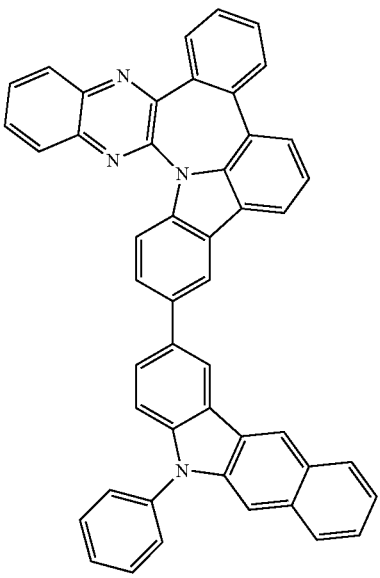
A-69
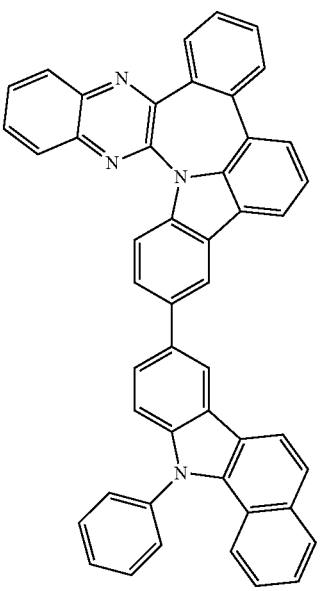

A-70
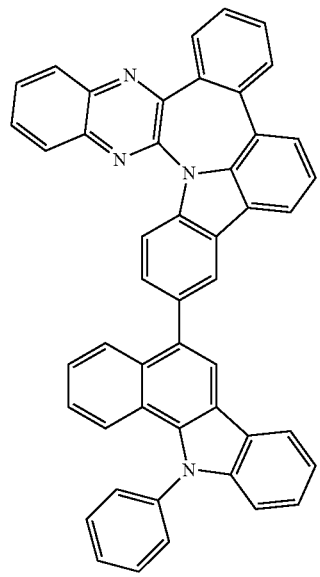
A-71
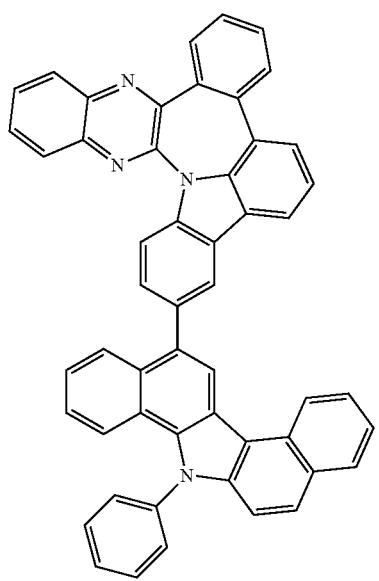
A72
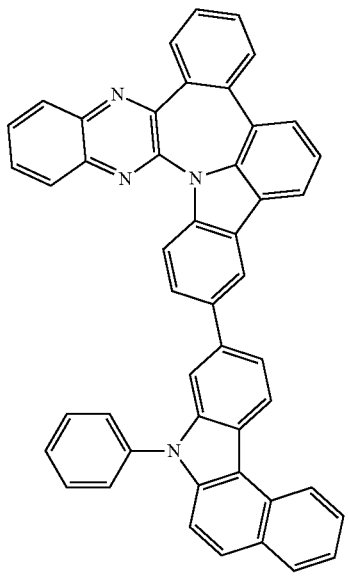
A-73
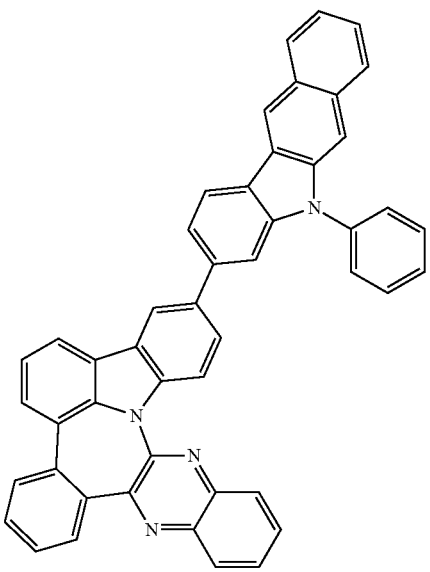
A-74
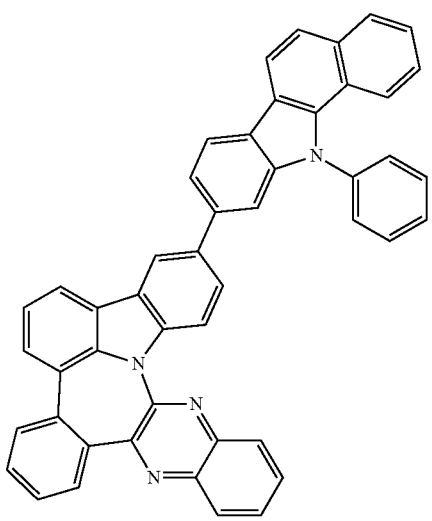

A-75
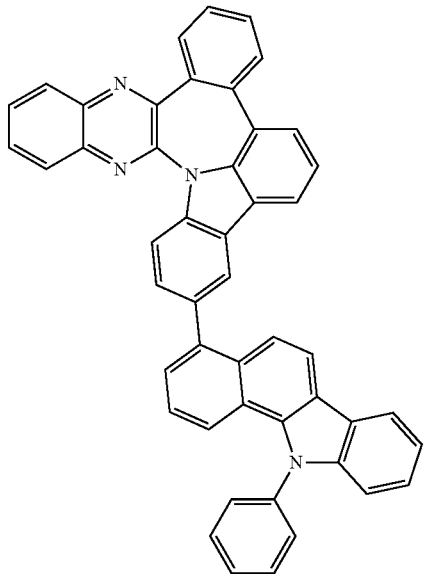
A-76
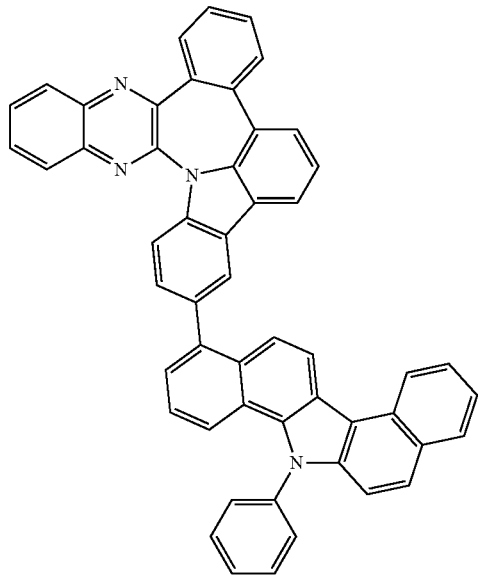
A-77
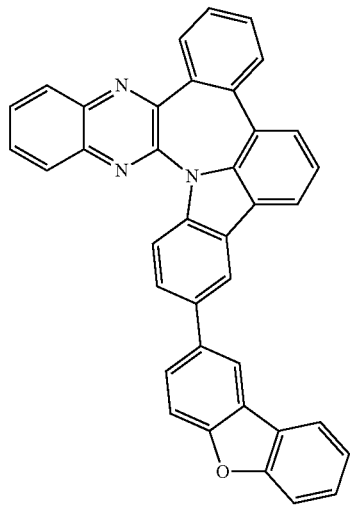
A-78
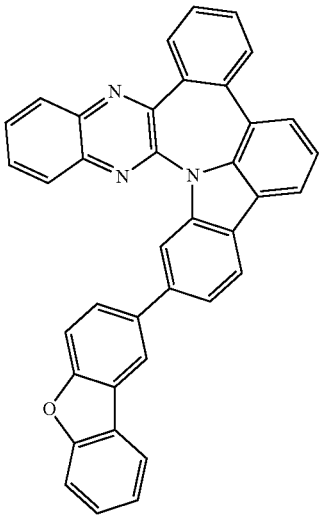
A-79
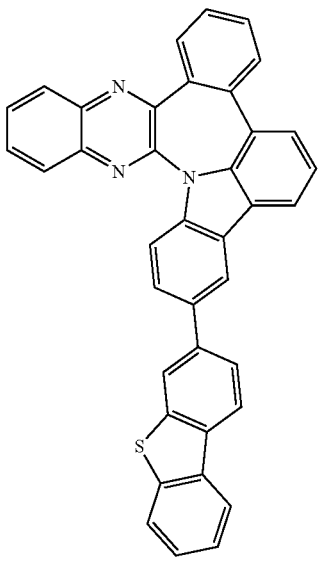
A-80
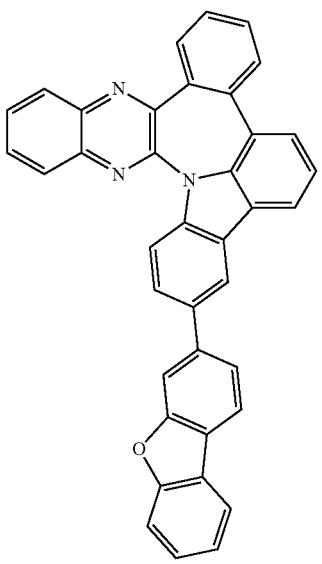

A-81
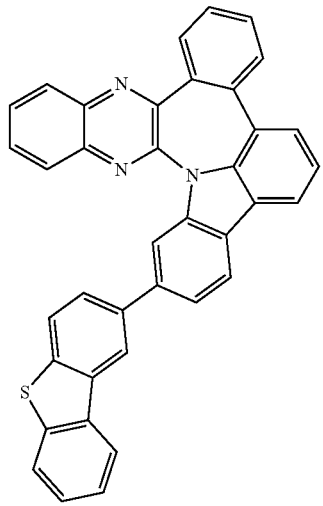
A-82
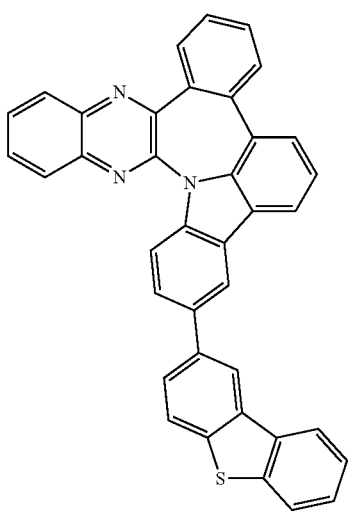
A-83
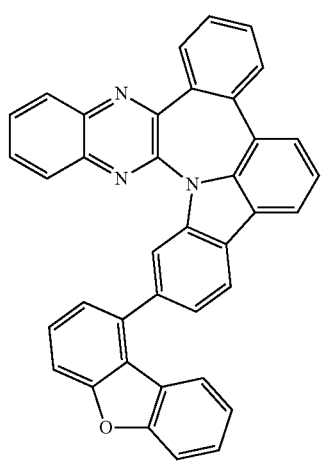
A-84
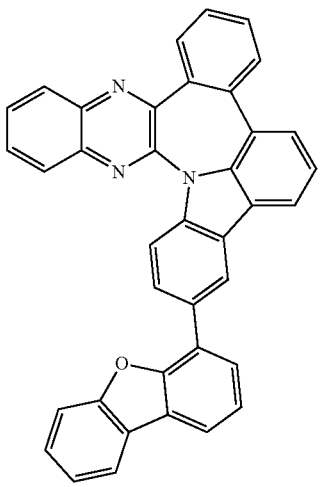
A-85
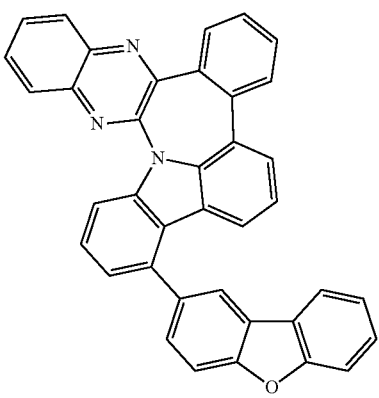
A-86
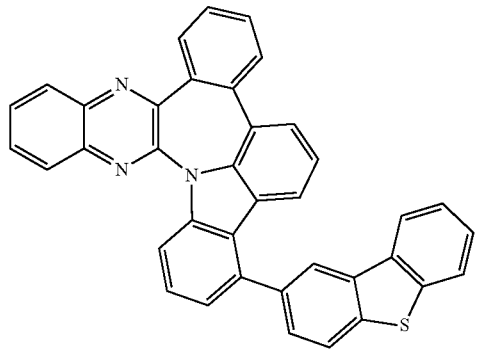

A-87 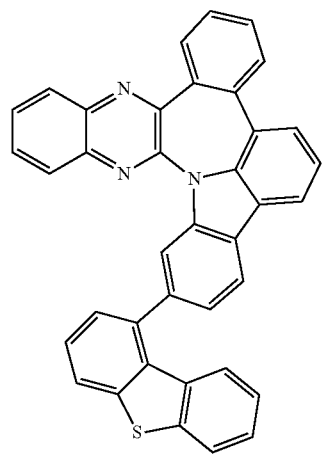
A-90 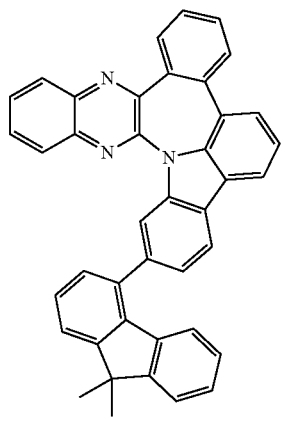
A-88 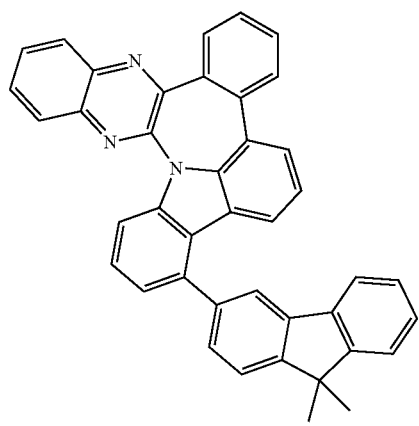
A-91 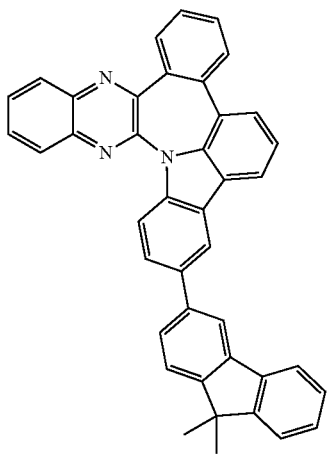
A-89 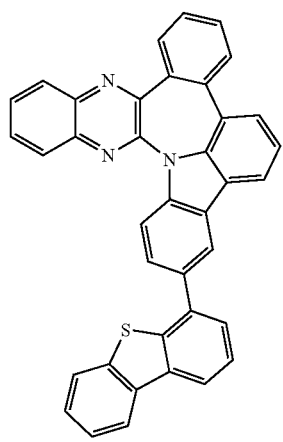
A-92 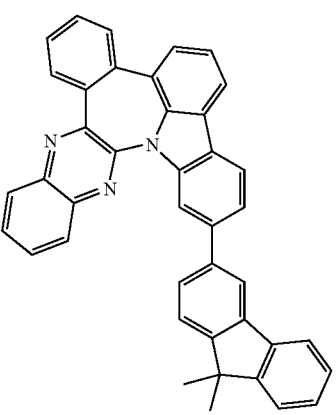

A-93
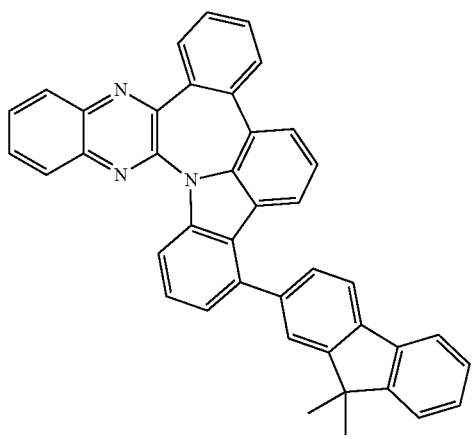
A-96
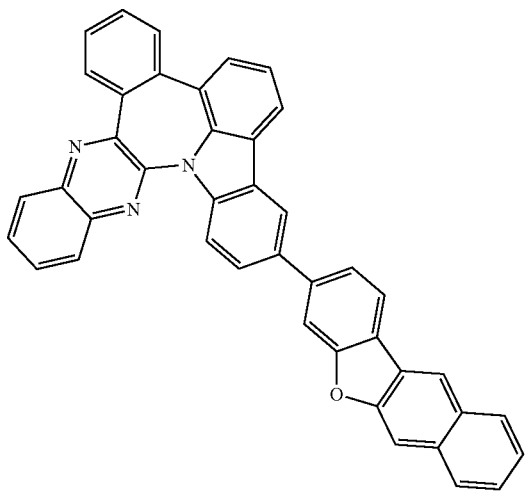
A-94
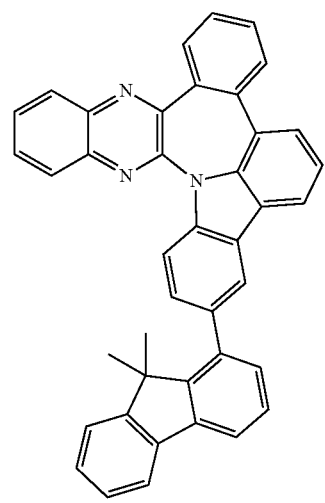
A-97
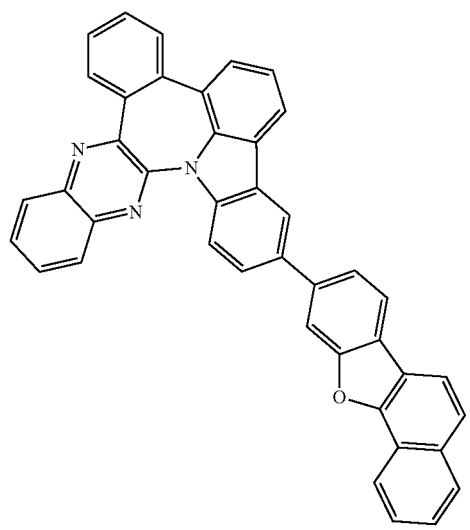
A-95
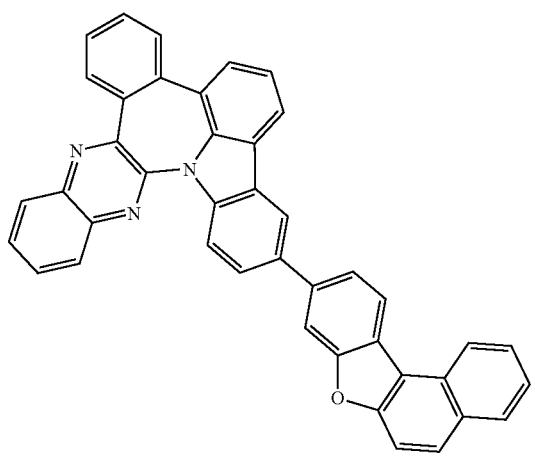
A-98
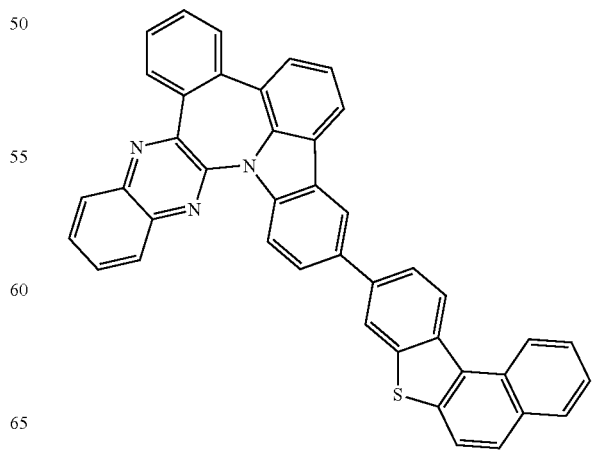

-continued
A-99
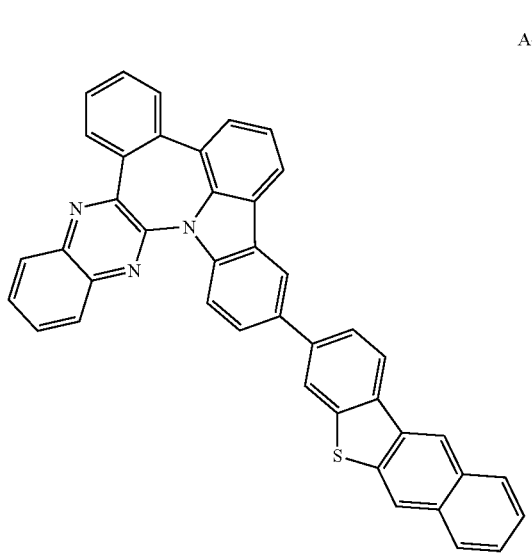
-continued
A-101
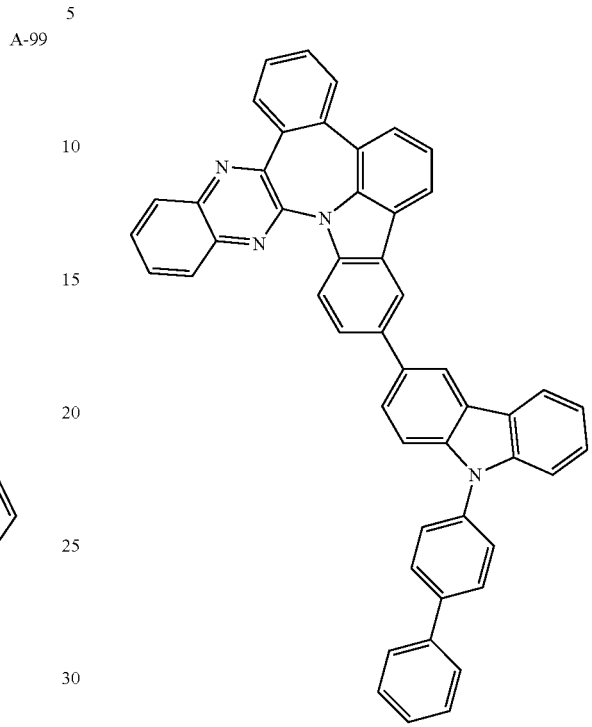
A-100
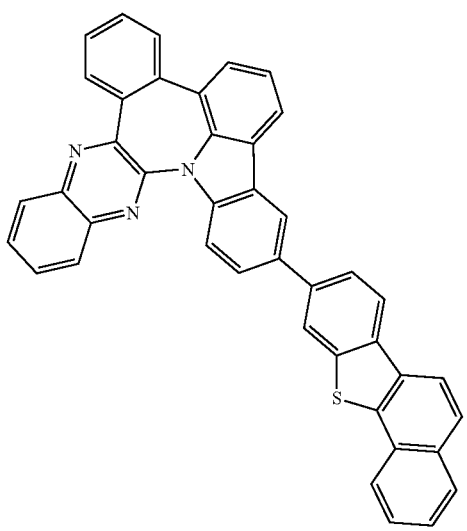
A-102
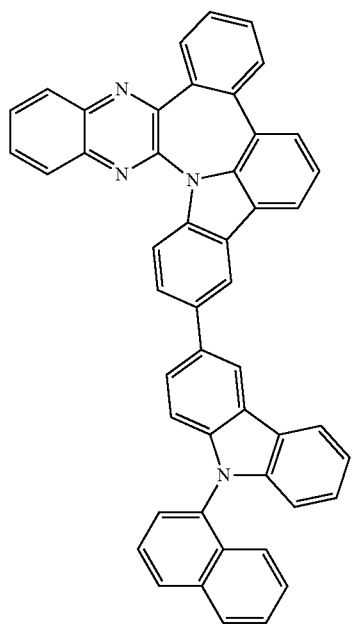

-continued
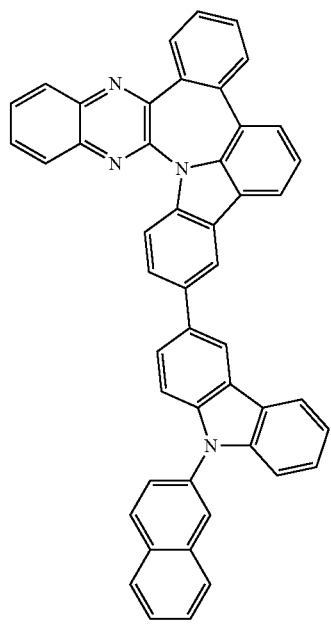
A-103
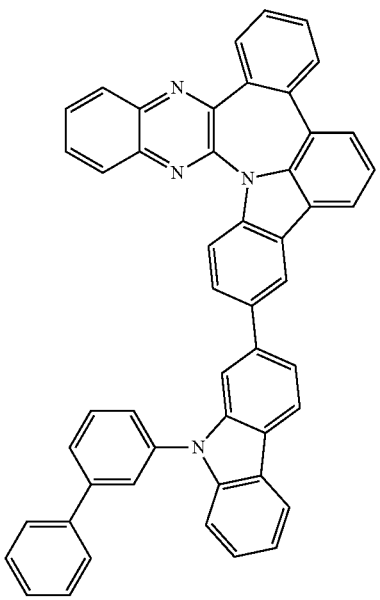
A-105
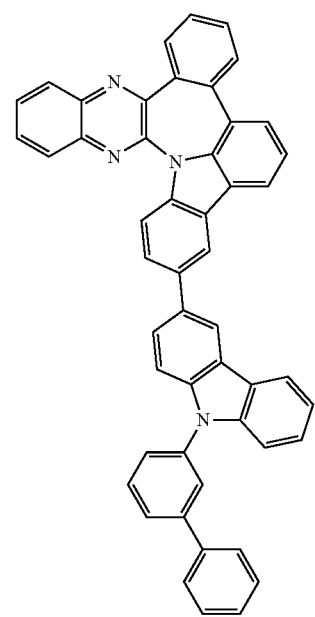
A-104
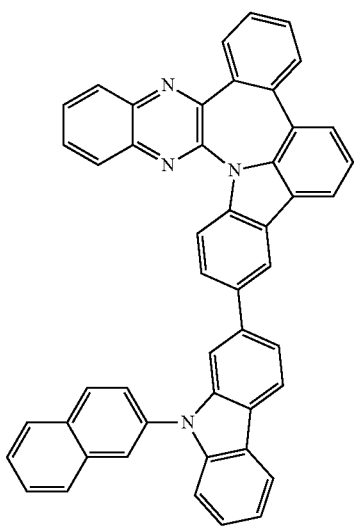
A-106

-continued
A-107
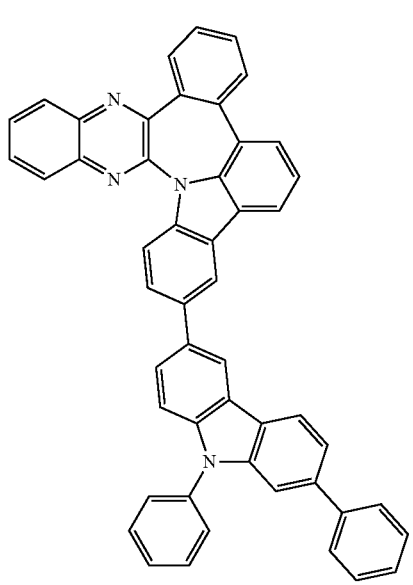
A-108
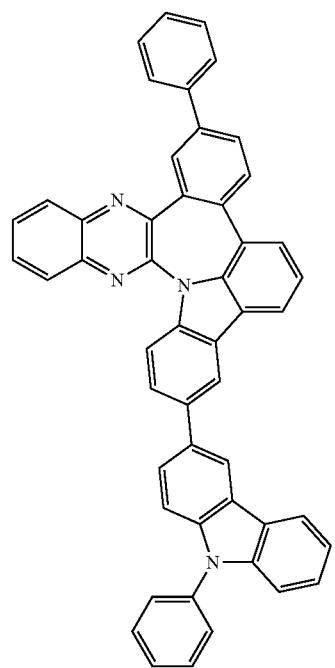
-continued
A-109
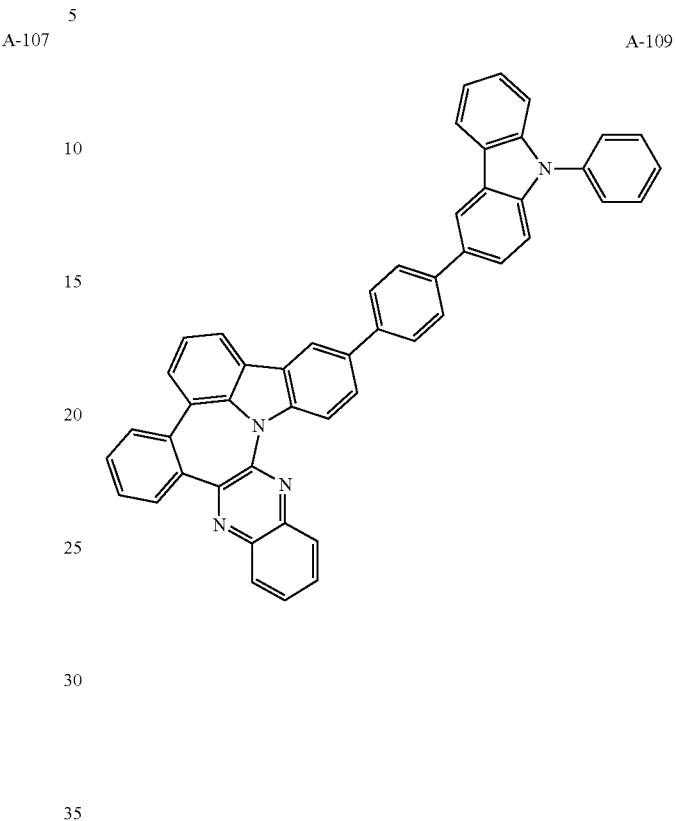
A-110
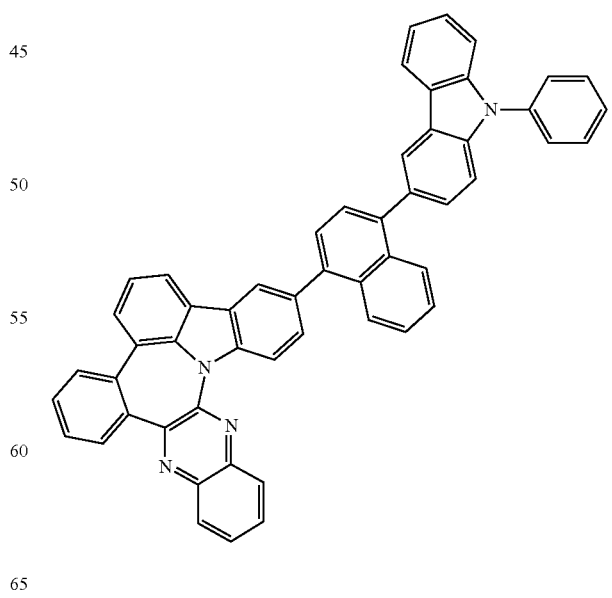

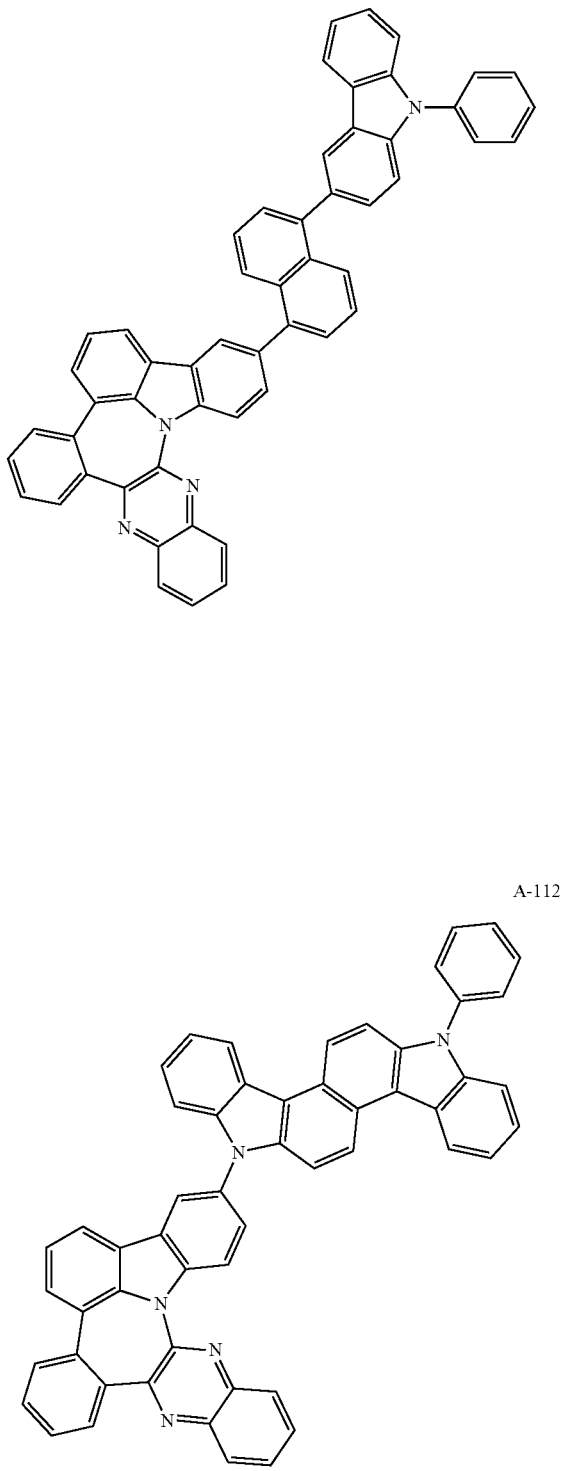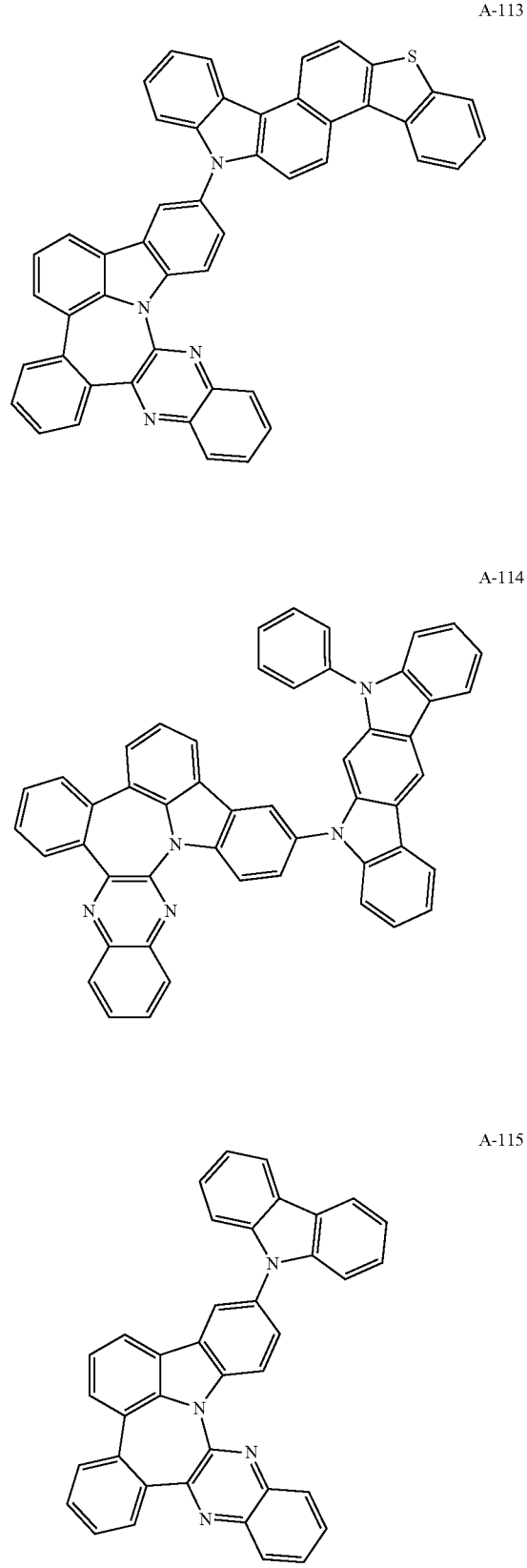

-continued
A-116
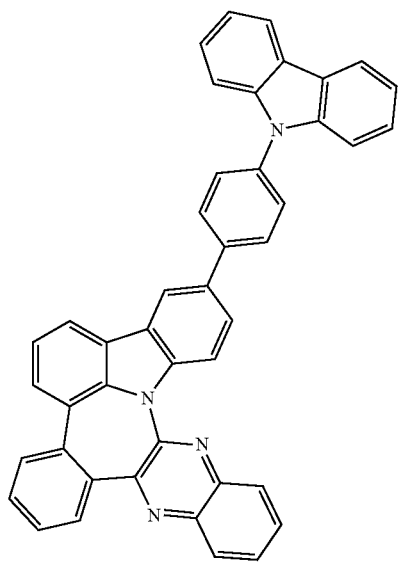
A-117
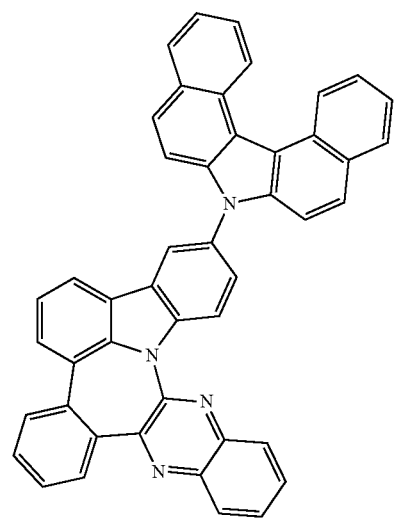
A-118
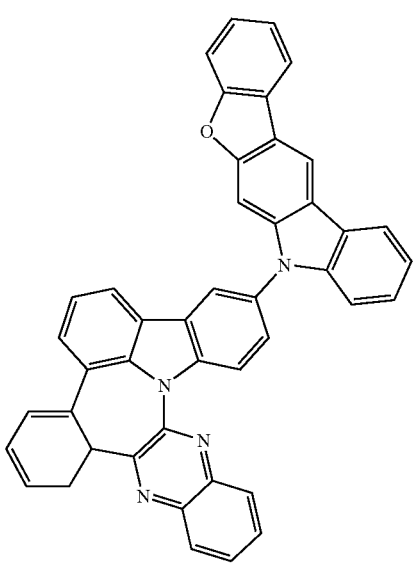
-continued
A-119
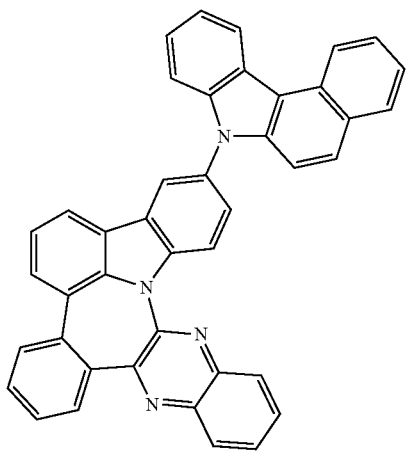
A-120
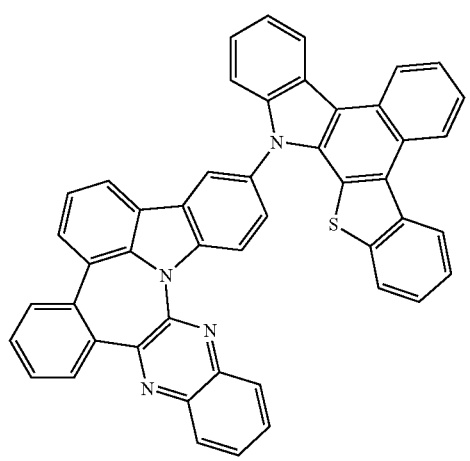
A-121
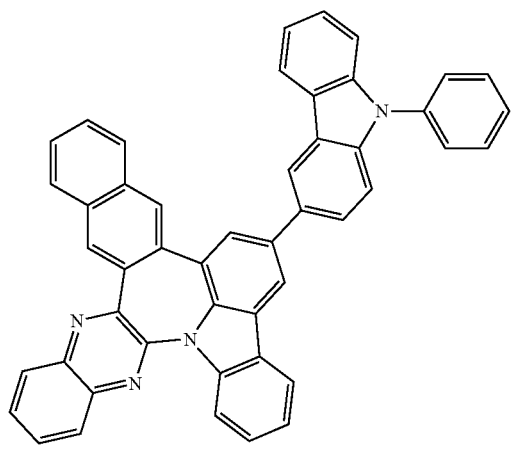

A-122
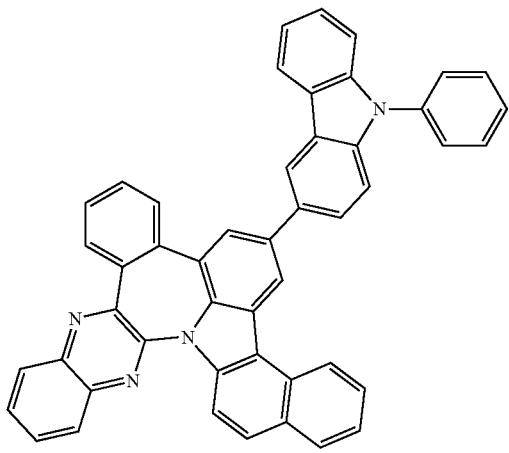
A-125
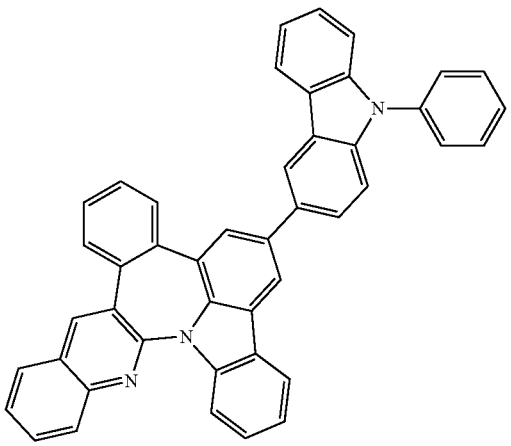
A-123
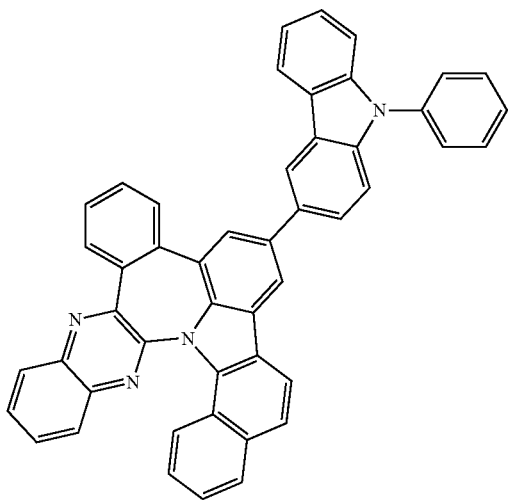
A-126
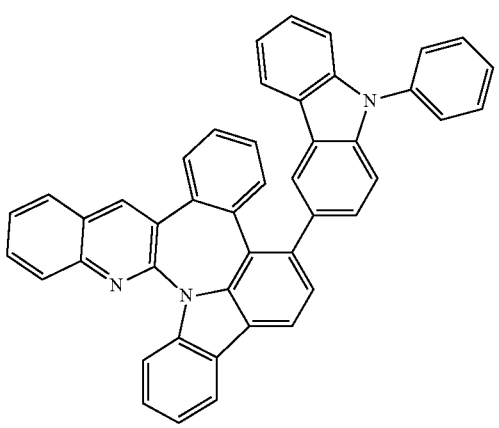
A-124
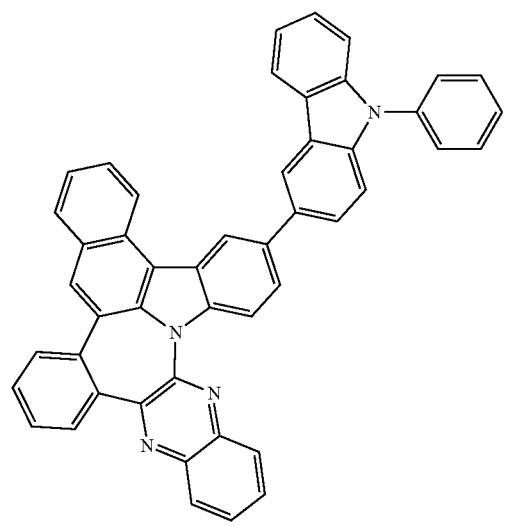
A-127
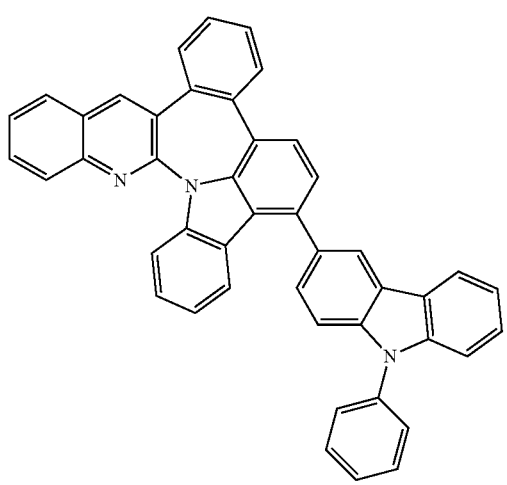

-continued
A-128
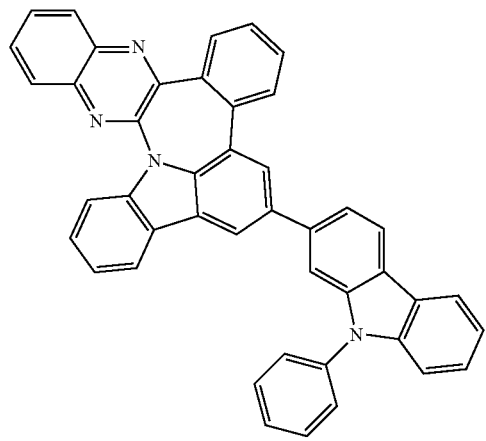
A-129
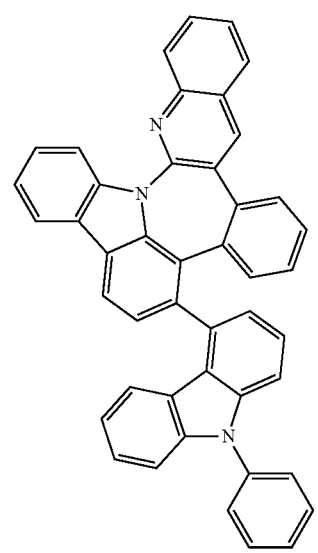
A-130
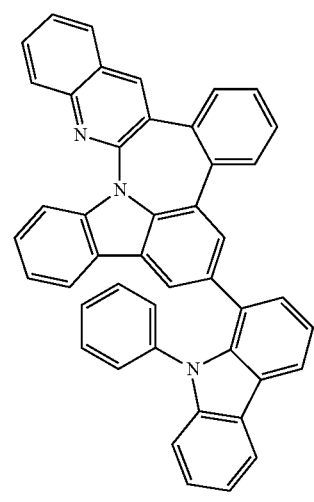
-continued
A-131
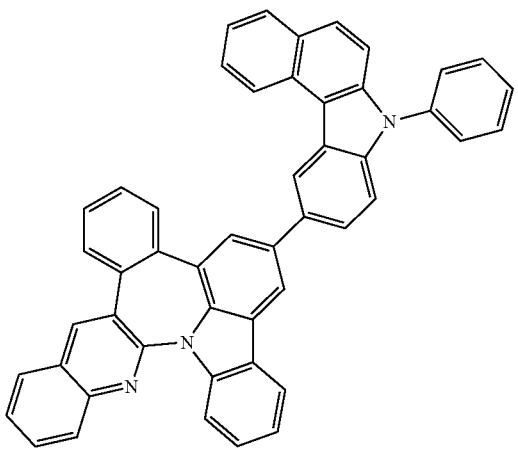
A-132
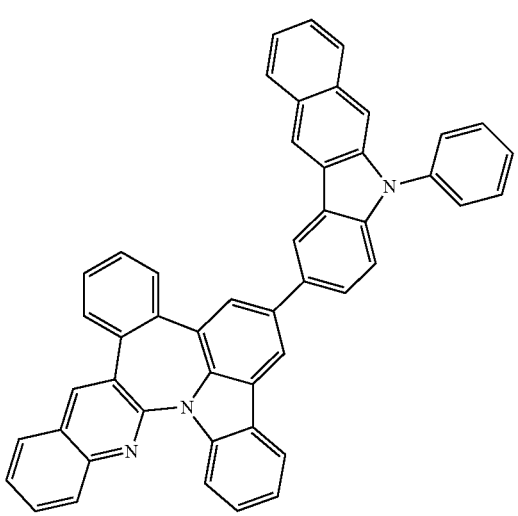
A-133
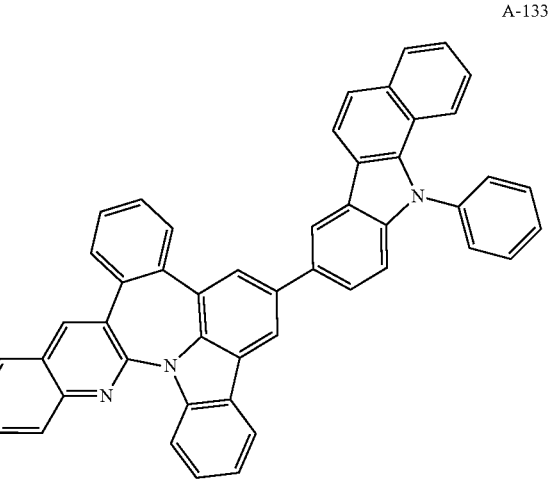

A-134
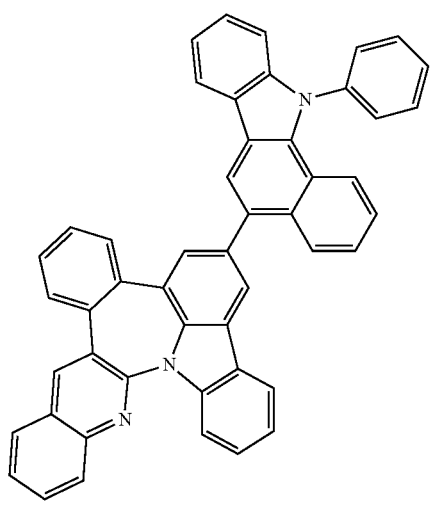
A-135
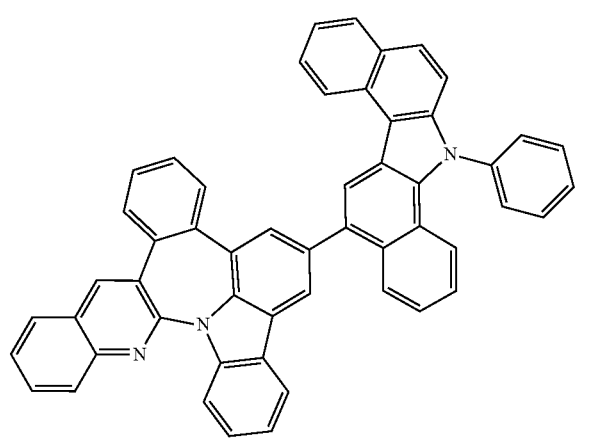
A-136
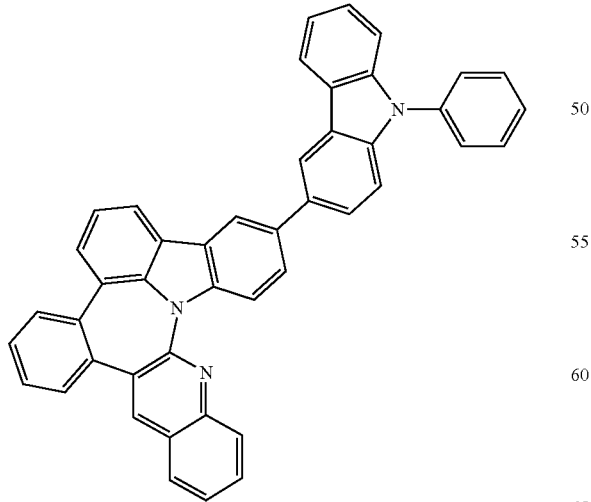
A-137
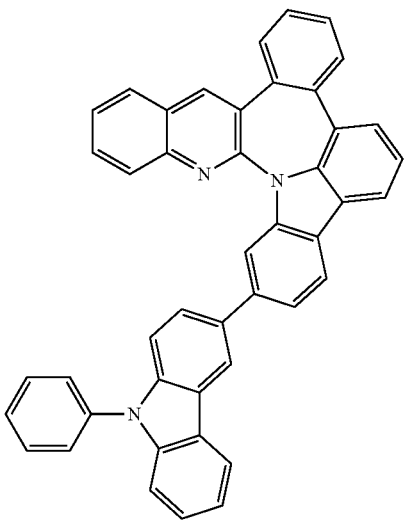
A-138
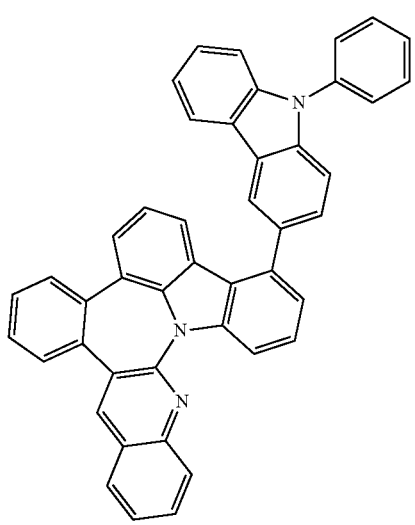
A-139
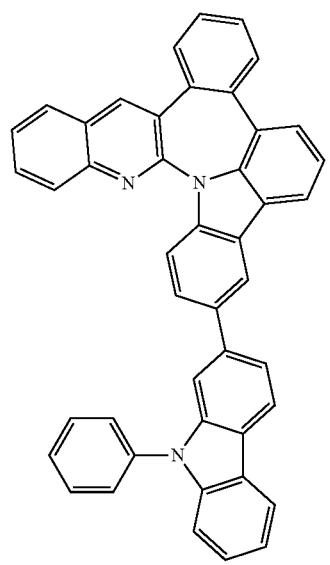

A-140
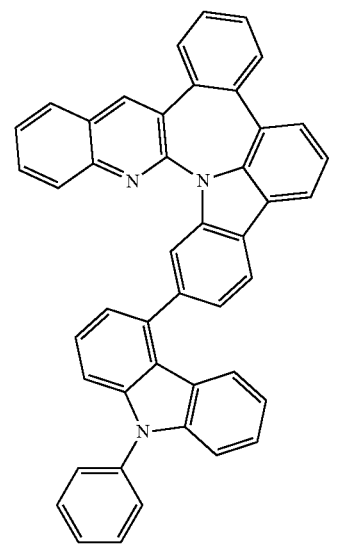
A-141
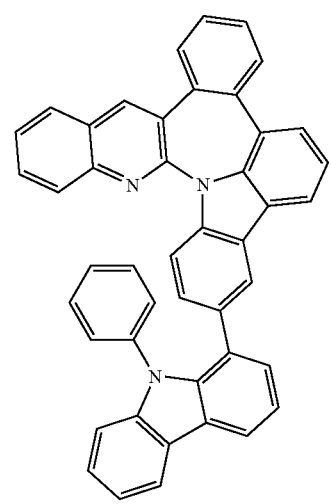
A-142
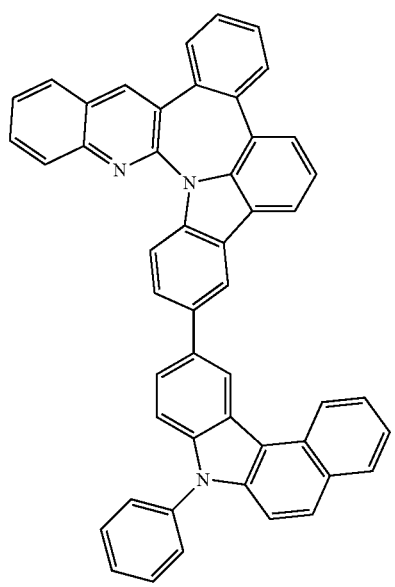
A-143
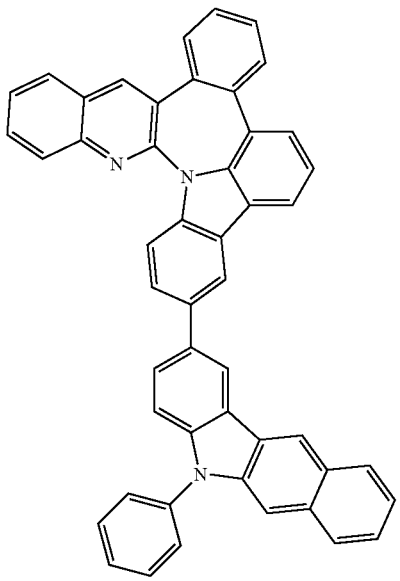
A-144
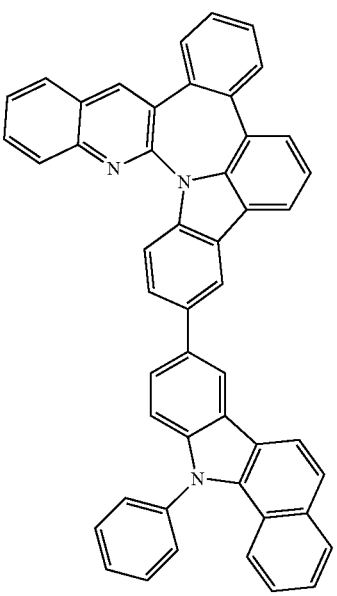

-continued
A-145
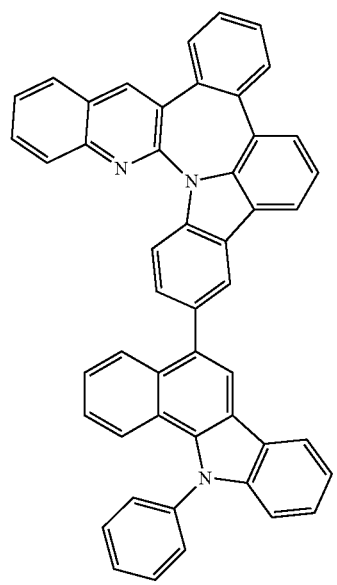
A-146
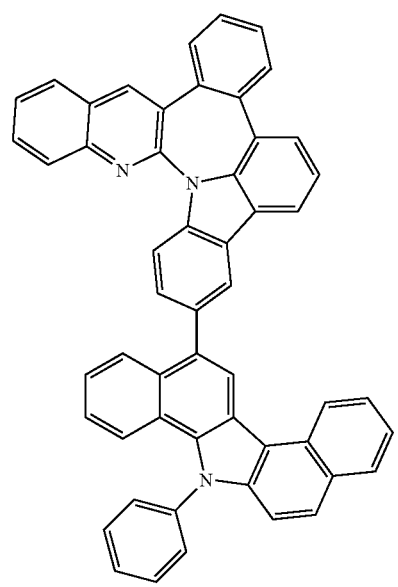
A-147
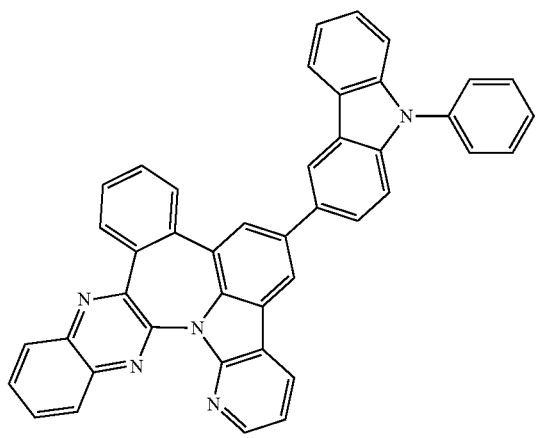
-continued
A-148
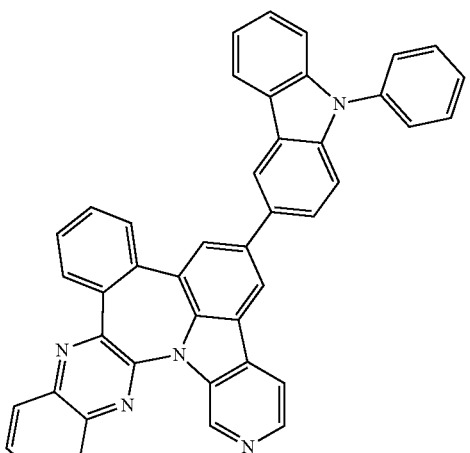
A-149
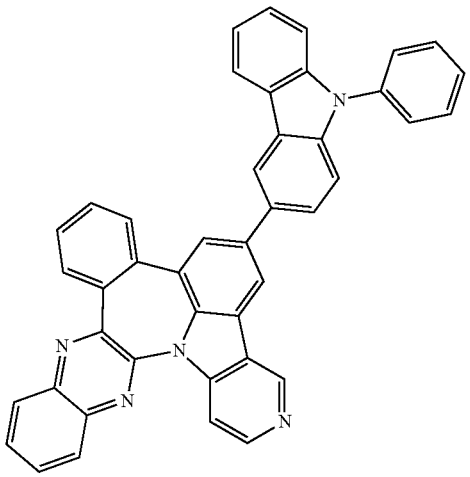
A-150
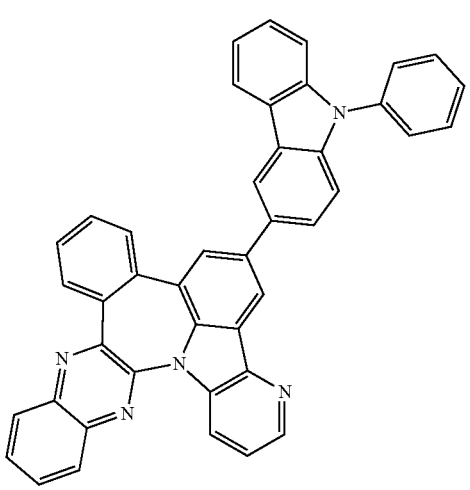

-continued
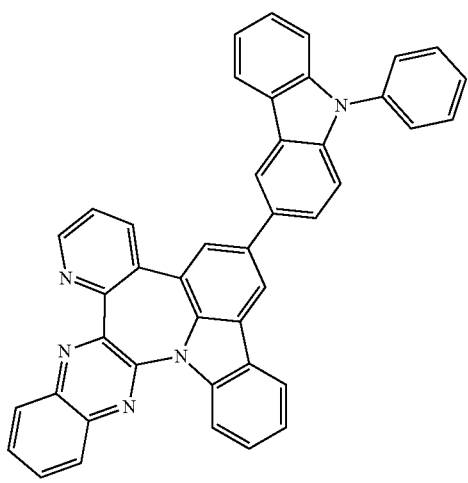
A-151
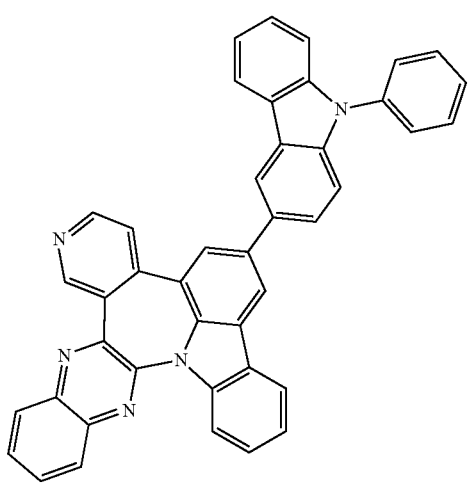
A-152
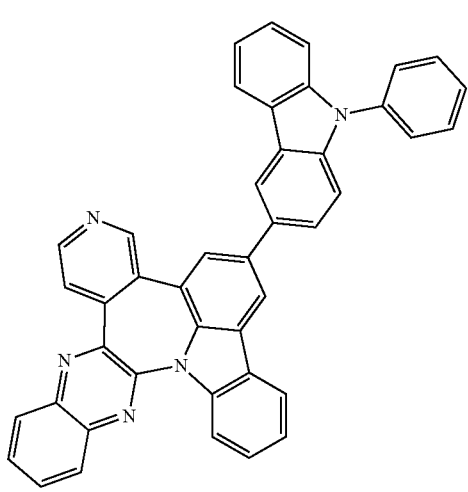
A-153
-continued
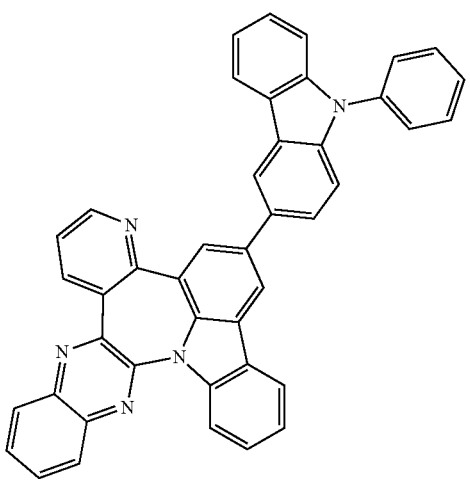
A-154
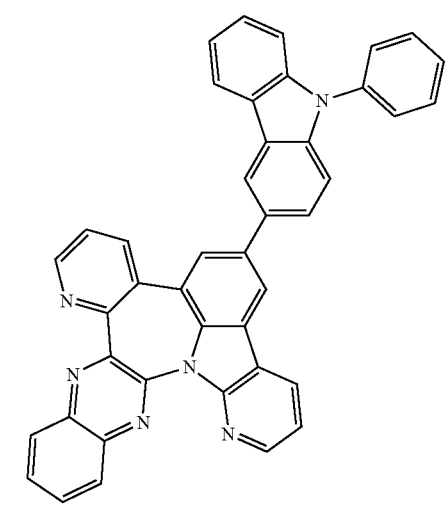
A-155
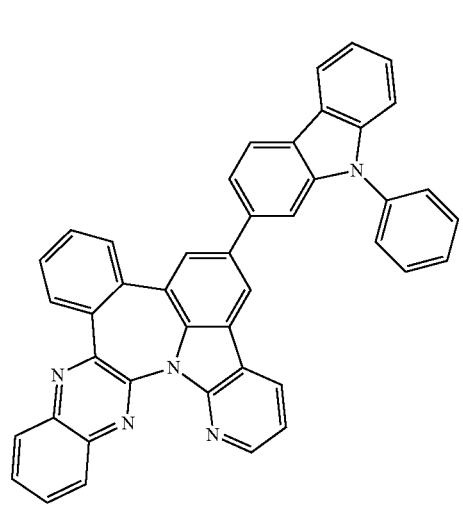
A-156

A-157
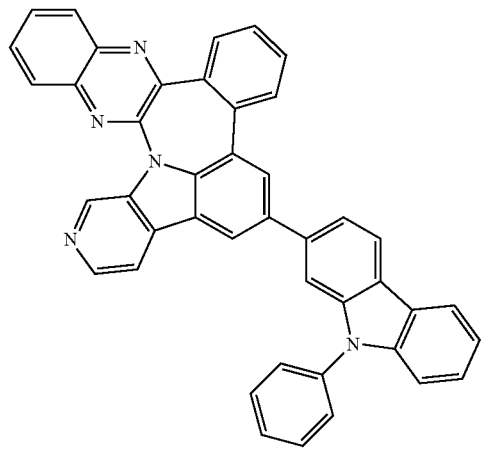
A-158
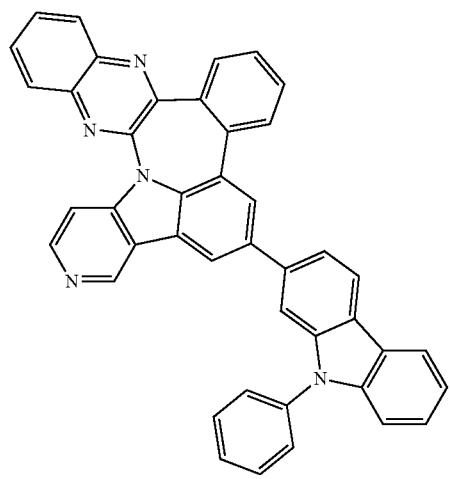
A-159
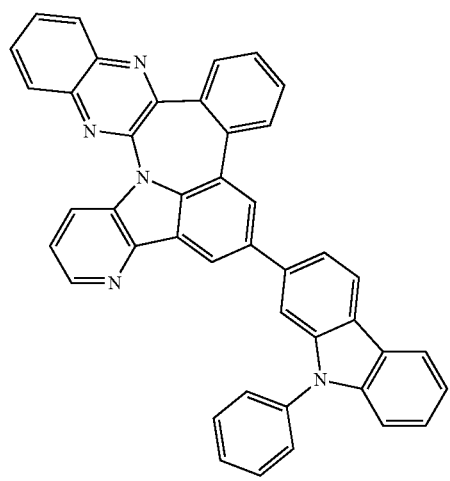
A-160
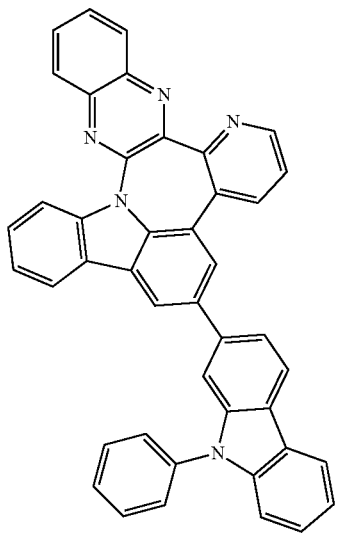
A-161
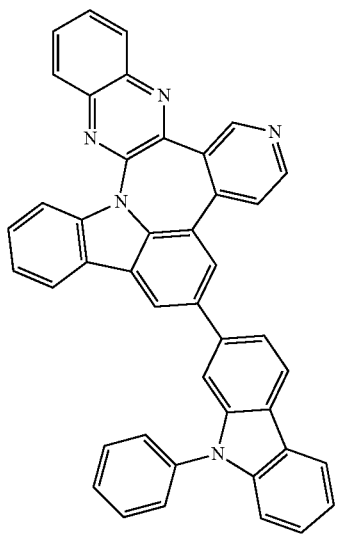
A-162
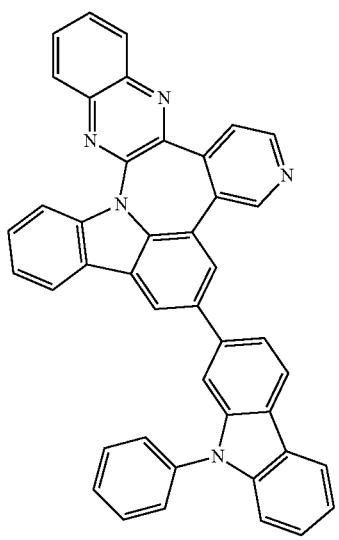

A-163
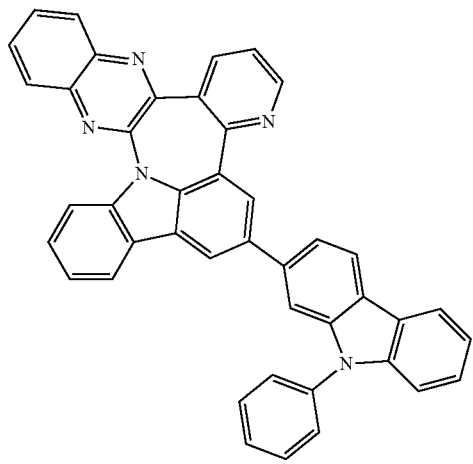
A-166
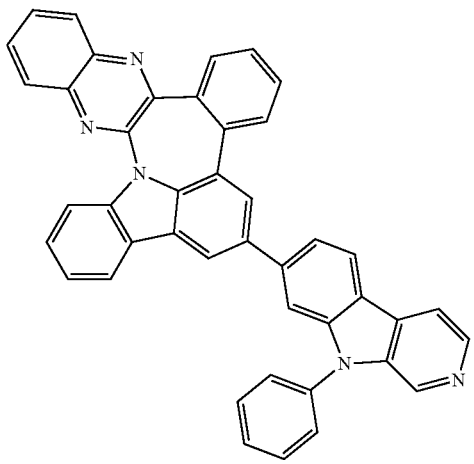
A-164
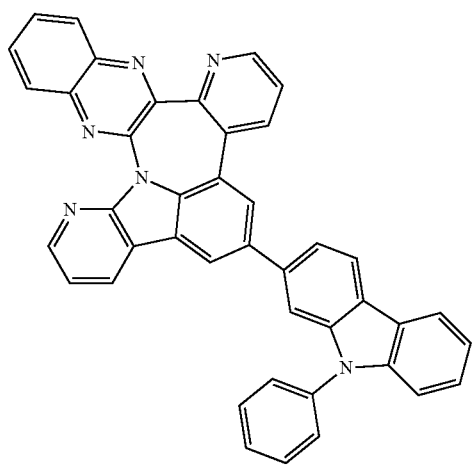
A-167
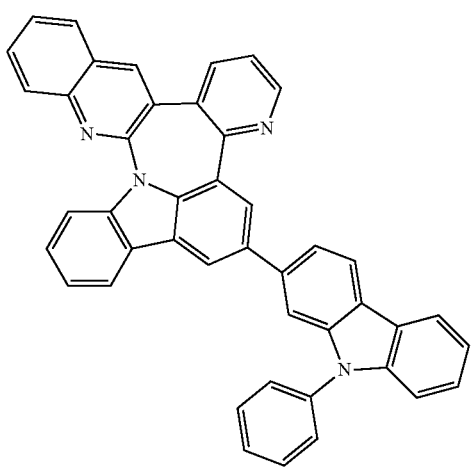
A-165
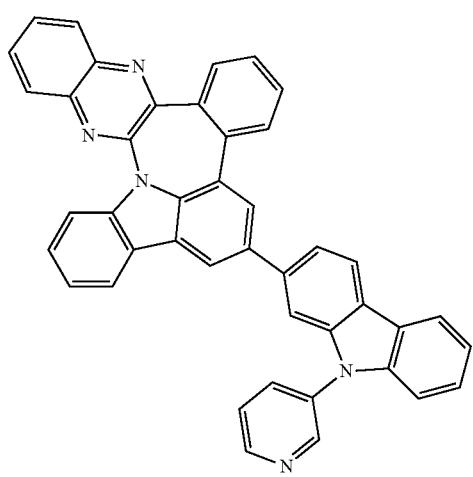
A-168
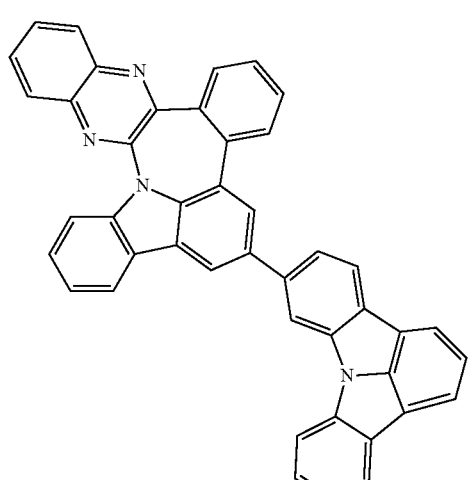

237
-continued
A-169
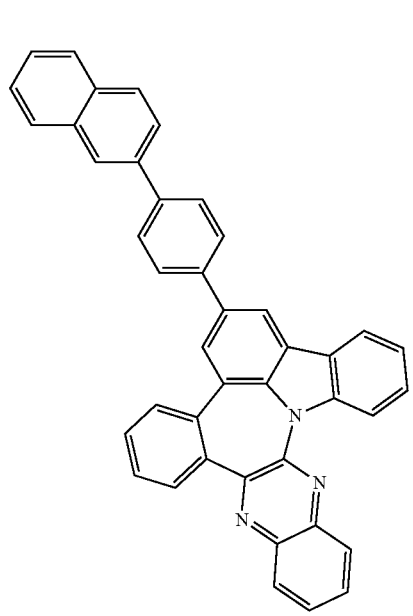
A-170
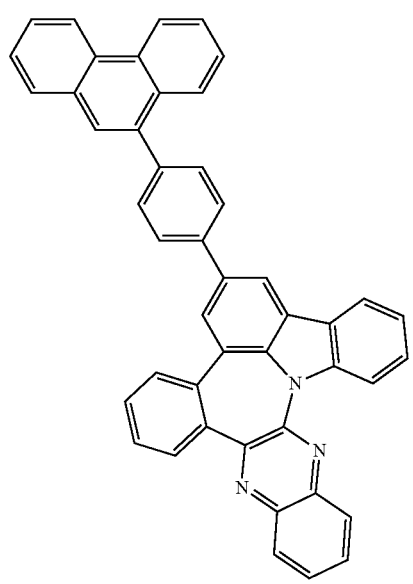
238
-continued
A-171
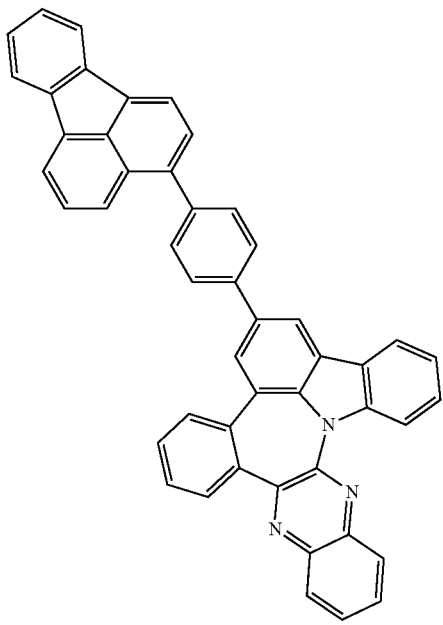
A-172
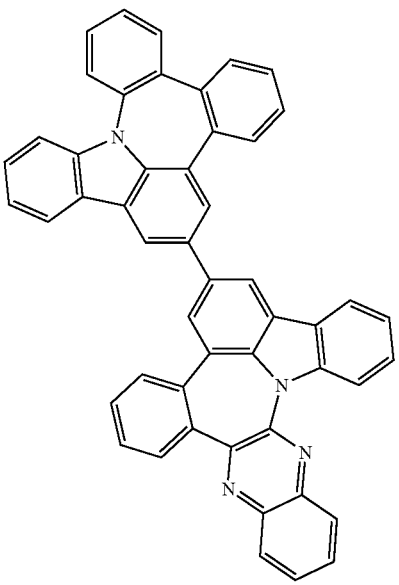

-continued
A-173
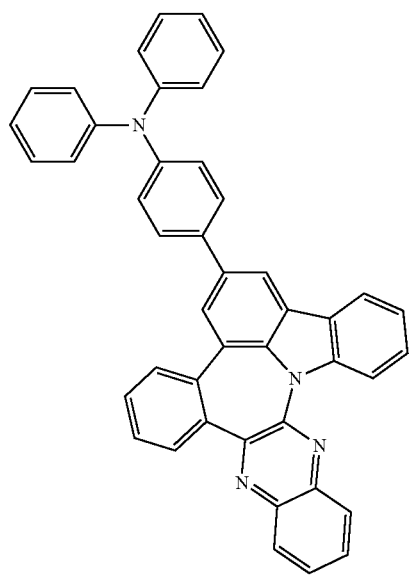
A-174
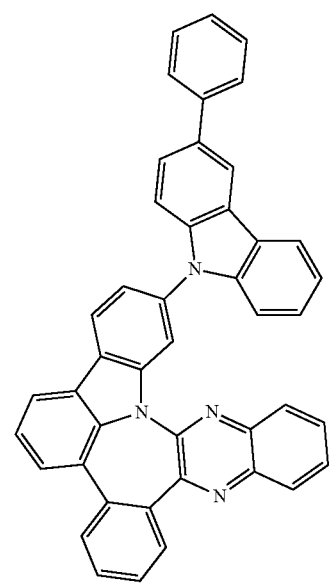
A-175
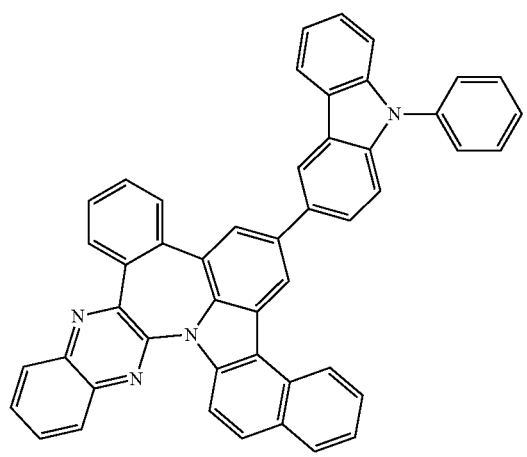
-continued
A-176
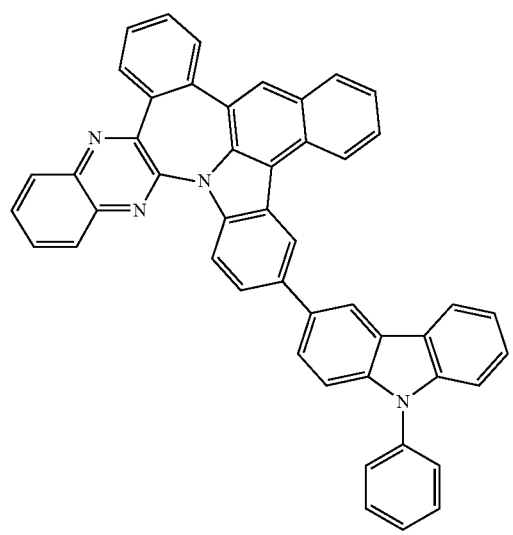
A-177
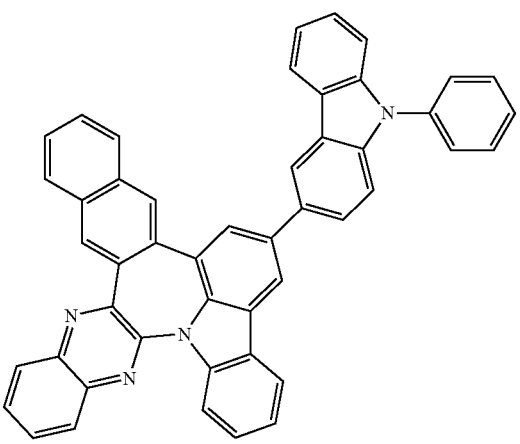
A-178
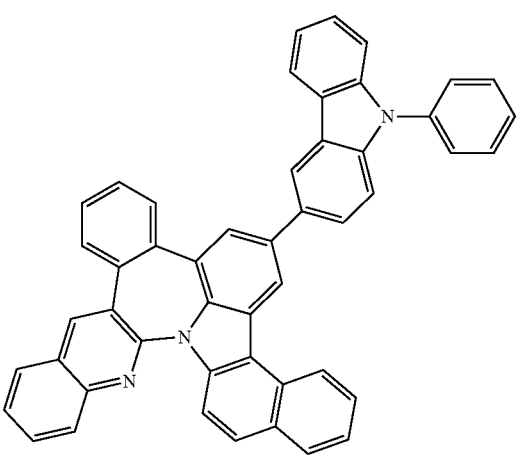

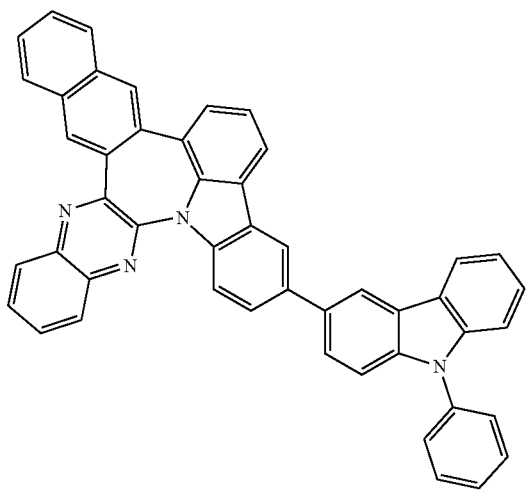
A-179
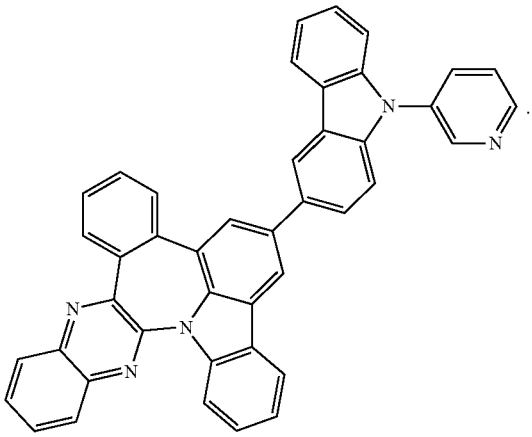
A-180
8. An organic electroluminescent device comprising the organic electroluminescent compound according to claim 1.
* * * * *